(12) United States Patent
Gangopadhyay et al.

(10) Patent No.: US 8,835,428 B2
(45) Date of Patent: Sep. 16, 2014

(54) DIACYLGLYCEROL ACYLTRANSFERASE INHIBITORS

(75) Inventors: Ashok Kumar Gangopadhyay, Mumbai (IN); Kishorkumar Shivajirao Kadam, Mumbai (IN); Ravindra Dnyandev Jadhav, Mumbai (IN); Hitesh Mistry, Mumbai (IN); Rajiv Sharma, Mumbai (IN)

(73) Assignee: Piramal Enterprises Limited, Mumbai (IN)

( * ) Notice: Subject to any disclaimer, the term of this patent is extended or adjusted under 35 U.S.C. 154(b) by 0 days.

(21) Appl. No.: 13/034,192

(22) Filed: Feb. 24, 2011

(65) Prior Publication Data

US 2011/0196002 A1 Aug. 11, 2011

Related U.S. Application Data

(63) Continuation of application No. PCT/IB2009/053708, filed on Aug. 24, 2009.

(60) Provisional application No. 61/091,498, filed on Aug. 25, 2008.

(51) Int. Cl.
| | |
|---|---|
| *C07D 261/14* | (2006.01) |
| *C07D 417/12* | (2006.01) |
| *C07D 417/14* | (2006.01) |
| *C07D 277/56* | (2006.01) |
| *A61K 31/422* | (2006.01) |
| *A61K 31/427* | (2006.01) |
| *C07D 271/06* | (2006.01) |
| *C07D 413/12* | (2006.01) |
| *C07D 413/14* | (2006.01) |
| *A61K 31/42* | (2006.01) |
| *A61K 31/4245* | (2006.01) |
| *A61K 31/426* | (2006.01) |
| *C07D 261/18* | (2006.01) |
| *A61K 31/428* | (2006.01) |
| *C07D 261/08* | (2006.01) |
| *A61K 31/4439* | (2006.01) |

(52) U.S. Cl.
CPC ............ *C07D 417/12* (2013.01); *C07D 277/56* (2013.01); *A61K 31/422* (2013.01); *A61K 31/427* (2013.01); *C07D 271/06* (2013.01); *C07D 413/12* (2013.01); *C07D 413/14* (2013.01); *A61K 31/42* (2013.01); *A61K 31/4245* (2013.01); *A61K 31/426* (2013.01); *C07D 261/18* (2013.01); *A61K 31/428* (2013.01); *C07D 261/08* (2013.01); *A61K 31/4439* (2013.01)
USPC ........ 514/229.2; 514/367; 514/378; 548/161; 548/248

(58) Field of Classification Search
None
See application file for complete search history.

(56) References Cited

U.S. PATENT DOCUMENTS

| | | | |
|---|---|---|---|
| 2002/0133023 A1* | 9/2002 | Nagarajan et al. | 548/236 |
| 2005/0272784 A1* | 12/2005 | Li et al. | 514/364 |
| 2006/0211697 A1* | 9/2006 | Huang et al. | 514/247 |

FOREIGN PATENT DOCUMENTS

| | | | |
|---|---|---|---|
| WO | WO 2007/138304 A1 | 6/2007 | |
| WO | WO 2007/138311 A1 | 12/2007 | |
| WO | WO 2007/141502 A1 | 12/2007 | |
| WO | WO 2007/141517 A1 | 12/2007 | |

OTHER PUBLICATIONS

Byrn et al., Solid-State Chemistry of Drugs (2nd Ed. 1999) (pp. 233-247, 234).*

* cited by examiner

*Primary Examiner* — Alicia L Otton
(74) *Attorney, Agent, or Firm* — Ladas & Parry LLP

(57) ABSTRACT

The present invention relates to isoxazole, thiazole and oxidiazole derivatives, processes for their preparation, pharmaceutical compositions containing them and their use as medicaments, in particular to the use of these compounds in the prevention and treatment of diseases or disorders mediated by diacylglycerol acyltransferase (DGAT), particularly DGAT1.

15 Claims, No Drawings

DIACYLGLYCEROL ACYLTRANSFERASE INHIBITORS

CROSS REFERENCE TO RELATED APPLICATION

This application is a continuation of PCT/IB2009/053708 filed Aug. 24, 2009, which claims priority to U.S. Provisional Application 61/091,498, filed on Aug. 25, 2008, which is incorporated herein by reference in its entirety.

FIELD OF THE INVENTION

The present invention relates to novel heterocyclic compounds, processes for their preparation, pharmaceutical compositions containing them and their use as medicaments, in particular to the use of these compounds in the prevention and treatment of diseases or disorders mediated by diacylglycerol acyltransferase (DGAT), particularly DGAT1.

BACKGROUND OF THE INVENTION

Obesity, generally defined as a body mass index (BMI) of more than 30 kilogram per square meter (Kg/m$^2$), is a major health problem throughout the world. It is a risk factor for hypertension, diabetes and cardiovascular disease. Obesity is viewed as an energy storage disorder, resulting when energy input exceeds energy output. Most of the excess calories are stored as fat (more than 95% of fat is triglyceride) in the adipose tissue leading to obesity, and when stored in non-adipose tissue it leads to insulin resistance. Hence, inhibition of triglyceride synthesis represents a potential therapeutic strategy for human obesity and type 2 diabetes.

Metabolic syndrome, also known as Syndrome-X, is characterized by increased body weight, altered glucose homeostasis with insulin resistance, elevated plasma triglyceride levels and low-density lipoprotein-cholesterol, high blood pressure, and increased risk of cardiovascular morbidity and mortality. The prevalence of metabolic syndrome has risen dramatically in the US and rest of the world. In the US, metabolic syndrome affects roughly 25% of adults over the age of 20 years and up to 45% of the population over the age of 50 years (JAMA, 287, 356-359 (2002). The currently available therapies for addressing the disorders associated with metabolic syndrome are far from satisfactory.

A key enzyme in the synthesis of triglycerides is acylCoA: diacylglycerol acyltransferase (DGAT). Genes for two DGAT enzymes, DGAT1 and DGAT2 have been identified. Both DGAT1 and DGAT2 are highly expressed in tissues that are active in triglyceride synthesis such as white adipose tissue (WAT), intestine, liver, skeletal muscle and mammary gland (Proc. Natl. Acad. Sciences U.S.A, 95, 13018-13023 (1998); J. Biol. Chem., 276, 38870-38876 (2001)).

Studies in experimental animals suggest that inhibiting or reducing the activity of the DGAT1 enzyme results in resistance to the development of obesity, diabetes and associated complications. DGAT1 knockout studies in mice have shown that these mice are viable and resistant to obesity (Nat. Genet., 25, 87-90 (2000)), whereas DGAT2 knockout mice die soon after birth as there is no stored form of energy source due to lack of adipose tissues (J. Biol. Chem. 279, 11767-11776 (2004)). In contrast to DGAT2 knockout mice, DGAT1 knockout mice are viable and are resistant to diet-induced obesity and steatosis. In addition, these mice are more sensitive to insulin and leptin (J. Clin. Invest. 109, 1049-1055 (2002)). Heterozygous DGAT1 knockout mice are also resistant to obesity (Thromb. Vasc. Biol., 25, 482-486 (2005); Nutr. Metab (Lond.), 3, 10 (2006)). These studies together suggest that DGAT2 plays a fundamental role in triglyceride synthesis and is essential for survival, whereas DGAT1 contributes to triglyceride synthesis and plays an important role in regulating energy metabolism.

Additional studies with DGAT1 antisense oligonucleotides indicate that inhibition of DGAT1 results in decrease in blood glucose in ob/ob mice. Thus, resistance to obesity due to increased energy expenditure and reduced energy absorption along with an apparent improvement in insulin sensitivity associated with DGAT1 deficiency suggests that inhibition of DGAT1 could be a potential treatment strategy for addressing metabolic syndrome.

Hence, there has been an increased urge among pharmaceutical companies to develop novel therapies for treating metabolic disorders associated with syndrome-X. One target that has received much attention for treatment of metabolic syndrome is the DGAT1 enzyme (Trends Cardiovasc. Medicine, 10, 188-192 (2000); Curr. Drug Targets Immune Endocr. Metabol. Disorders, 3, 263-270 (2003)).

The following patent publications describe compounds that inhibit DGAT1 activity: WO2004/100881 and WO2006/044775 describe biphenyl-4-yl-carbonyl amino acid derivatives, WO2004/047755 describes fused bicyclic nitrogen-containing heterocycles, WO2006/019020 describes substituted ureas, WO2007/016538 describes biphenyl sulfonamides, WO2006/082952 describes amide derivatives, WO2006/134317 describes oxadiazole derivatives and WO2006/019020 describes substituted ureas.

US2004/0224997 and WO2006/113919 describe aryl alkyl acid, and JP2004-67635 describes thiazoleamido substituted phenyl compounds.

WO1995/014683 describes isoxazoline and isoxazole derivatives as antagonists of the platelet glycoprotein IIb/IIIa fibrinogen receptor complex for the treatment of thromboembolic disorders.

WO2007/024922 describes nitrogen containing heteroaryl compounds as immunosuppressant useful in the treatment or prevention of diseases or disorders mediated by lymphocyte interactions.

SUMMARY OF THE INVENTION

According to one aspect of the present invention, there is provided a compound of formula (I) (as described herein below).

According to another aspect of the present invention, there is provided a compound of formula (I) for use as a medicament.

According to another aspect of the present invention, there is provided a compound of formula (I) for use in the inhibition of DGAT1 activity, in particular for use in the prevention or treatment of diseases or disorders mediated by DGAT1.

According to yet another aspect of the present invention, there is provided a compound of formula (I) for use in the prevention or treatment of diabetes mellitus.

According to yet another aspect of the present invention, there is provided a compound of formula (I) for use in the prevention or treatment of obesity.

According to yet another aspect of the present invention, there is provided a compound of formula (I) for use in the prevention or treatment of insulin resistance.

According to yet another aspect of the present invention, there is provided a compound of formula (I) for use in the prevention or treatment of impaired glucose tolerance.

According to another aspect of the present invention, there is provided a process for the preparation of a compound of formula (I).

According to another aspect of the present invention, there is provided a pharmaceutical composition, comprising a compound of the formula (I) in association with a pharmaceutically acceptable excipient or carrier.

According to another aspect of the present invention, there is provided a process for the preparation of a pharmaceutical composition, comprising bringing a compound of formula (I) into association with a pharmaceutically acceptable excipient or carrier.

According to yet another aspect of the present invention, there is provided a method for the treatment of a disease or disorder mediated by DGAT1 in a subject in need of such treatment, comprising administering to the subject a therapeutically effective amount of a compound of formula (I) or a pharmaceutically acceptable salt thereof.

According to yet another aspect of the present invention, there is provided a method, for the treatment of obesity, diabetes, insulin resistance or impaired glucose tolerance in a subject in need of such treatment, comprising administering to the subject a therapeutically effective amount of a compound of formula (I) or a pharmaceutically acceptable salt thereof.

These and other objectives and advantages of the present invention will be apparent to those skilled in the art from the following description.

DETAILED DESCRIPTION OF THE INVENTION

The present invention provides a compound of formula (I),

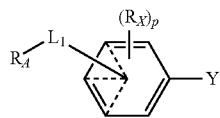

(I)

or a pharmaceutically acceptable salt, solvate or prodrug, including all stereoisomers and/or tautomers thereof, wherein, --- dotted line represents the variable attachment of -$L_1$-$R_A$ to the specified carbon atoms of the phenyl ring, $R_A$ is cycloalkyl, alkylaryl, aryl, heteroaryl or heterocycle;

$R_X$ is H, halogen, —CN, —$OR_1$, —S(=O)$_m R_1$, —$OCOR_1$, —$SCOR_1$, —$NR_1R_2$, —$NR_1COR_2$, —$NR_1COOR_2$, —$NR_1SO_2R_2$, —$NR_1CONR_2$, —$COR_1$, —$COOR_1$, —$CONR_1R_2$, alkyl, alkenyl, alkynyl, cycloalkyl, alkylcycloalkyl, aryl, alkylaryl, alkylheteroaryl, heterocycle or heteroaryl;

$R_1$ and $R_2$ are independently selected from H, alkyl, alkenyl, alkynyl, cycloalkyl, alkylcycloalkyl, aryl, alkylaryl, alkylheteroaryl, heterocycle and heteroaryl;

$L_1$ is —O—, —$NR_3(CR_4R_5)_a NR_3$—, —$(CR_4R_5)_b NR_3$—, —$SO_2NH$— or —$SO_2NHCONH$—;

$R_3$ is H, —$COR_1$, —$COOR_1$, —$CONR_1R_2$, alkyl, alkenyl, alkynyl, cycloalkyl or alkylcycloalkyl;

$R_4$ and $R_5$ are independently selected from H, —$OR_6$, —$COOR_6$, —$CONR_6R_7$, alkyl, alkenyl, alkynyl, cycloalkyl, alkylcycloalkyl, aryl, heteroaryl, alkylaryl, alkylheteroaryl and alkylheterocycle;

or $R_4$ and $R_5$ together are =O; =S or =$NR_8$;

$R_6$ and $R_7$ are independently selected from H, alkyl, cycloalkyl and heterocycle;

Y is selected from (i), (ii) and (iii)

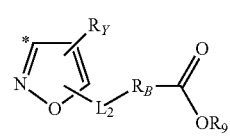

(i)

wherein, $L_2$ is —C(=O)—$NR_Z$—, —C(=S)—$NR_Z$—, —C(=$NR_8$)—$NR_Z$—, —C($SR_9$)=N—, —C(=O), —C(=S) or —$SO_2NR_Z$—;

$R_Z$ is —H, —$COR_1$, —$COOR_1$, —$CONR_1R_2$, alkyl, alkenyl, alkynyl, cycloalkyl or alkylcycloalkyl;

$R_8$ is —H, —$OR_9$, —$COR_9$, —$COOR_9$, —$CONR_8R_7$, —$SO_2R_9$ or —$SO_2NR_6R_7$;

$R_9$ is absent or is selected from H, alkyl, alkenyl, alkynyl, cycloalkyl, alkylcycloalkyl, aryl, alkylaryl, alkylheteroaryl, heterocycle and heteroaryl;

$R_B$ is —($CR_{10}R_{11}$)$_c$— or —($NR_{12}$)($CR_{10}R_{11}$)$_c$; wherein c is an integer from 1 to 3;

or $OR_9$, C(O), $R_B$ and $L_2$; or $R_B$ and $L_2$; or $R_B$, C(O) and $OR_9$ together form a 5 to 7-membered ring selected from cycloalkyl, aryl, heteroaryl and heterocycle;

$R_{10}$, $R_{11}$ and $R_{12}$ are independently selected from H and the groups alkyl, alkenyl, alkynyl, cycloalkyl, alkylcycloalkyl, aryl, alkylaryl, alkylheteroaryl, heterocycle and heteroaryl;

or $R_{12}$ and $R_{10}$ or $R_{11}$ together with the respective N and C atoms to which they are attached, form a 3 to 6 membered heterocyclic or heteroaryl ring;

or $R_{10}$ and $R_{11}$ of —($CR_{10}R_{11}$)$_c$ wherein c is the integer 1 together with the C atom to which they are attached form a 3 to 6-membered cycloalkyl ring;

or $R_{10}$ and $R_{11}$ of —($CR_{10}R_{11}$)$_c$ wherein c is the integer 1 together with the C atom to which they are attached form alkenylene;

$R_Y$ is —H, halogen, —CN, —$OR_1$, —S(=O)$_m R_1$, —$OCOR_1$, —$SCOR_1$, —$NR_1R_2$, —$NR_1COR_2$, —$NR_1COOR_2$, —$NR_1SO_2R_2$, —$NR_1CONR_2$, —$COR_1$, —$COOR_1$, —$CONR_1R_2$, alkyl, alkenyl, alkynyl, cycloalkyl, alkylcycloalkyl, aryl, alkylaryl, alkylheteroaryl or heteroaryl;

with the proviso that when $L_1$ is —($CR_4R_5$)$_b NR_3$—, $L_2$ is —C(=O)—$NR_Z$— and $R_B$ is —($CR_{10}R_{11}$)$_c$, then (a) c is the integer 1 and (b) $R_A$ is heteroaryl or heterocycle, wherein the heteroaryl or heterocycle is selected from indolyl, isoindolyl, indolizinyl, benzofuranyl, benzothienyl, quinolinyl, isoquinolinyl, benzopyranyl, indazolyl, benzimidazolyl, benzothiazolyl, coumarinyl, benzoisothiazolyl, benzodioxolyl, benzoxazolyl, benzoisoxazolyl, quinoxalinyl, quinazolinyl, phthalazinyl, pteridinyl, cinnolinyl, chromonyl, pyrrolopyridyl, furopyridinyl, purinyl, benzothiadiazolyl, benzooxadiazolyl, benzotriazolyl, acridinyl, benzothiadiazolyl, benzotriazinyl, carbazolyl, dibenzofuranyl, dibenzothienyl, phenanthridinyl and xanthenyl; and wherein the heteroaryl or heterocycle is optionally substituted with one or more groups selected from halogen, oxo, thio, nitro, —CN, —$OR_1$, —S(=O)$_m R_1$, —S(=O)$_{1-2}$ $NR_1R_2$, —$OCOR_1$, —$SCOR_1$, —$NR_1R_2$, —$NR_1COR_2$, —$NR_1COOR_2$, —$NR_1SOR_2$, —$NR_1SO_2R_2$, —$NR_1CONR_1R_2$, —$COR_1$, —$COOR_1$, —$CONR_1R_2$, alkyl, alkenyl, alkynyl, cycloalkyl, alkylcycloalkyl, aryl, alkylaryl, heterocyclyl, alkylheterocyclyl, heteroaryl and alkylheteroaryl; wherein $R_1$ and $R_2$ are independently selected from H, alkyl, alkenyl, alkynyl, cycloalkyl, alkylcycloalkyl, aryl, alkylaryl, heterocyclyl, alkylheterocyclyl, heteroaryl and alkylheteroaryl;

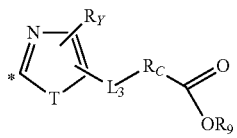

(ii)

wherein,

T is —O— or —S—;

$L_3$ is —C(=O)—$NR_Z$—, —C(=S)—$NR_Z$— or —C(=$NR_8$)—$NR_Z$—;

$R_C$ is —$(CR_{10}R_{11})_d$— or —$(NR_{12})(CR_{10}R_{11})_d$;

d is an integer from 1 to 3;

$R_8$, $R_9$, $R_{10}$, $R_{11}$, $R_{12}$, $R_Y$ and $R_Z$ are as defined above;

or $R_c$, C(O), $OR_9$ and $L_3$; or $R_c$, and $L_3$; or $R_c$, C(O), and $OR_9$ together form a 5 to 7-membered cycloalkyl, aryl, heteroaryl or heterocycle;

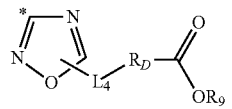

(iii)

wherein, $L_4$ is absent or is selected from —C(=O)—$NR_Z$—, —C(=S)—$NR_Z$—, —C(=$NR_8$)—$NR_Z$—, —C(=O)— and —C(=S);

$R_D$ is —$(CR_{10}R_{11})_e$— or —$(NR_{12})(CR_{10}R_{11})_e$;

e is 0 or an integer from 1 to 3;

$R_8$, $R_9$, $R_{10}$, $R_{11}$, $R_{12}$ and $R_Z$ are as defined above;

or $R_D$, C(O), $OR_9$ and $L_4$; or $R_D$ and $L_4$; or $R_D$, C(O), and $OR_9$, together form a 5 to 7-membered cycloalkyl, aryl, heteroaryl or heterocycle;

a is an integer from 1 to 5;

b is 0 or an integer from 1 to 5;

m is 0 or an integer from 1 to 2;

p is an integer from 1 to 4;

* indicates the point of attachment.

DEFINITIONS

Listed below are definitions, which apply to the terms as they are used throughout the specification (unless they are otherwise limited in specific instances), either individually or as part of a larger group.

It will be understood that "substitution" or "substituted with" includes the implicit proviso that such substitution is in accordance with permitted valence of the substituted atom and the substituent, as well as represents a stable compound, which does not readily undergo transformation such as by rearrangement, cyclization, elimination, etc.

The term "halogen" denotes an atom selected from F, Cl, Br and I.

As used herein, the term "alkyl" refers to a saturated aliphatic group, including straight or branched-chain alkyl groups containing 1 to 10 carbon atoms, suitably 1 to 6 carbon atoms, preferably 1 to 4 carbon atoms. Furthermore, unless stated otherwise, the term "alkyl" includes unsubstituted alkyl groups, as well as alkyl groups, which are substituted by one or more different substituents. Examples of alkyl groups include but are not limited to methyl, ethyl, propyl, butyl, pentyl, hexyl, heptyl, octyl, nonyl, decyl, isopropyl, isobutyl, 1-methylbutyl, isopentyl, neopentyl, 2,2-dimethylbutyl, 2-methylpentyl, 3-methylpentyl, isohexyl, 2,3,4-trimethylhexyl, isodecyl, sec-butyl, tert-butyl and the like. The "alkyl" may optionally be substituted with one or more groups selected from halogen, oxo, thio, nitro, —CN, —$OR_1$, —$S(=O)_mR_1$, —$S(=O)_{1-2}NR_1R_2$, —$OCOR_1$, —$SCOR_1$, —$NR_1R_2$, —$NR_1COR_2$, —$NR_1COOR_2$, —$NR_1SOR_2$, —$NR_1SO_2R_2$, —$NR_1CONR_1R_2$, —$COR_1$, —$COOR_1$, —$CONR_1R_2$, alkyl, alkenyl, alkynyl, cycloalkyl, alkylcycloalkyl, aryl, alkylaryl, heterocyclyl, alkylheterocyclyl, heteroaryl and alkylheteroaryl; wherein $R_1$ and $R_2$ are independently selected from H, alkyl, alkenyl, alkynyl, cycloalkyl, alkylcycloalkyl, aryl, alkylaryl, heterocyclyl, alkylheterocyclyl, heteroaryl and alkylheteroaryl. The alkyl chain may optionally be interrupted with one or more heteroatoms selected from N, O and S.

The term "haloalkyl" as used herein refers to radicals wherein any one or more of the alkyl carbon atoms are substituted with one or more halogen. Examples of haloalkyl include, but are not limited to trifluoromethyl and trichloromethyl.

The term "alkenyl" refers to an unsaturated, branched or straight chain alkyl group having from 2 to 10 carbon atoms, suitably 2 to 6 carbon atoms, preferably 2 to 4 carbon atoms, and at least one carbon-carbon double bond (two adjacent $sp^2$ carbon atoms). Depending on the placement of double bond and substituents if any, the geometry of the double bond may be entgegen (E), or zusammen (Z), cis or trans. Examples of alkenyl include but are not limited to ethenyl, propenyl, pent-2-enyl, vinyl, allyl, 2-propenyl, crotyl, 2-isopentenyl, 2-(butadienyl), 2,4-pentadienyl, 3-(1,4-pentadienyl), cis-2-butenyl, trans-2-butenyl, 2-methyl-2-propenyl, and the like. The "alkenyl" may optionally be substituted with one or more groups selected from halogen, oxo, thio, nitro, —CN, —$OR_1$, —$S(=O)_mR_1$, —$S(=O)_{1-2}NR_1R_2$, —$OCOR_1$, —$SCOR_1$, —$NR_1R_2$, —$NR_1COR_2$, —$NR_1COOR_2$, —$NR_1SOR_2$, —$NR_1SO_2R_2$, —$NR_1CONR_1R_2$, —$COR_1$, —$COOR_1$, —$CONR_1R_2$, alkyl, alkenyl, alkynyl, cycloalkyl, alkylcycloalkyl, aryl, alkylaryl, heterocyclyl, alkylheterocyclyl, heteroaryl and alkylheteroaryl; wherein $R_1$ and $R_2$ are independently selected from H, alkyl, alkenyl, alkynyl, cycloalkyl, alkylcycloalkyl, aryl, alkylaryl, heterocyclyl, alkylheterocyclyl, heteroaryl and alkylheteroaryl. The alkenyl chain may optionally be interrupted with one or more heteroatoms selected from N, O and S.

The term "alkynyl" refers to an unsaturated, branched or straight chain alkyl group having from 2 to 10 carbon atoms, suitably 2 to 6 carbon atoms, preferably 2 to 4 carbon atoms, and at least one carbon-carbon triple bond (two adjacent sp carbon atoms). Examples of alkynyl include but are not limited to ethynyl, 1-propynyl, 3-propynyl, 3-butynyl, 3-phenyl-2-propynyl, 3-(2'-fluorophenyl)-2-propynyl, 3-methyl(5-phenyl)-4-pentynyl, 2-hydroxy-2-propynyl, 2-methyl-2-propynyl, 2-propenyl, 4-hydroxy-3-butynyl, 3-(3-fluorophenyl)-2-propynyl and the like. The "alkynyl" may optionally be substituted with one or more groups selected from halogen, oxo, thio, nitro, —CN, —$OR_1$, —$S(=O)_mR_1$, —$S(=O)_{1-2}NR_1R_2$, —$OCOR_1$, —$SCOR_1$, —$NR_1R_2$, —$NR_1COR_2$, —$NR_1COOR_2$, —$NR_1SOR_2$, —$NR_1SO_2R_2$, —$NR_1CONR_1R_2$, —$COR_1$, —$COOR_1$, —$CONR_1R_2$, alkyl, alkenyl, alkynyl, cycloalkyl, alkylcycloalkyl, aryl, alkylaryl, heterocyclyl, alkylheterocyclyl, heteroaryl and alkylheteroaryl; wherein $R_1$ and $R_2$ are independently selected from H, alkyl, alkenyl, alkynyl, cycloalkyl, alkylcycloalkyl, aryl, alkylaryl, heterocyclyl, alkylheterocyclyl, heteroaryl and alkylheteroaryl. The alkynyl chain may optionally be interrupted with one or more heteroatoms selected from N, O and S.

The term "alkoxy" refers to —O-alkyl, where alkyl is as defined above.

The term "cycloalkyl" refers to a saturated or partially unsaturated cyclic hydrocarbon group including a mono-, bi- or poly-cyclic ring system and including a total of 3 to 20 ring carbon atoms. Examples of cycloalkyl include but are not limited to cyclopropyl, cyclobutyl, cyclopentyl, cyclohexyl, adamantyl, [3,3,0]bicyclooctanyl-, [4,4,0]bicyclodecanyl, indene, dihydroindene and the like. The "cycloalkyl" may be optionally substituted with one or more groups selected from halogen, oxo, thio, nitro, —CN, —OR$_1$, —S(=O)$_m$R$_1$, —S(=O)$_{1-2}$NR$_1$R$_2$, —OCOR$_1$, —SCOR$_1$, —NR$_1$R$_2$, —NR$_1$COR$_2$, —NR$_1$COOR$_2$, —NR$_1$SOR$_2$, —NR$_1$SO$_2$R$_2$, —NR$_1$CONR$_1$R$_2$, —COR$_1$, —COOR$_1$, —CONR$_1$R$_2$, alkyl, alkenyl, alkynyl, cycloalkyl, alkylcycloalkyl, aryl, alkylaryl, heterocyclyl, alkylheterocyclyl, heteroaryl and alkylheteroaryl; wherein R$_1$ and R$_2$ are independently selected from H, alkyl, alkenyl, alkynyl, cycloalkyl, alkylcycloalkyl, aryl, alkylaryl, heterocyclyl, alkylheterocyclyl, heteroaryl and alkylheteroaryl.

The term "alkylcycloalkyl" refers to a cycloalkyl group bonded through an alkyl group, wherein the terms "alkyl" and "cycloalkyl" are as defined herein above.

The term "aryl" refers to a monocyclic or polycyclic hydrocarbon group having up to 20 ring carbon atoms, preferably up to 10 ring carbon atoms, in which at least one carbocyclic ring is present that has a conjugated π electron system. Examples of aryl include but are not limited to phenyl, naphthyl, biphenyl, fluorenyl, anthracenyl, and the like. The "aryl" may be optionally substituted with one or more groups, which may be the same or different, selected from halogen, nitro, —CN, —OR$_1$, —S(=O)$_m$R$_1$, —S(=O)$_{1-2}$NR$_1$R$_2$, —OCOR$_1$, —SCOR$_1$, —NR$_1$R$_2$, —NR$_1$COR$_2$, —NR$_1$COOR$_2$, —NR$_1$SOR$_2$, —NR$_1$SO$_2$R$_2$, —NR$_1$CONR$_1$R$_2$, —COR$_1$, —COOR$_1$, —CONR$_1$R$_2$, alkyl, haloalkyl, alkenyl, alkynyl, cycloalkyl, alkylcycloalkyl, aryl, alkylaryl, heterocyclyl, alkylheterocyclyl, heteroaryl and alkylheteroaryl; wherein R$_1$ and R$_2$ are independently selected from H, alkyl, haloalkyl, alkenyl, alkynyl, cycloalkyl, alkylcycloalkyl, aryl, alkylaryl, heterocyclyl, alkylheterocyclyl, heteroaryl and alkylheteroaryl.

The term "alkylaryl" refers to an aryl group bonded through an alkyl, wherein the terms "alkyl" and "aryl" are as defined herein above. Examples of alkylaryl include but not limited to benzyl, 1-naphthyl ethyl, 1-phenyl ethyl and the like.

The term "heterocyclyl" or "heterocycle" refers to a saturated or partially unsaturated monocyclic or polycyclic ring system containing 5 to 20 ring atoms of which 1, 2, 3 or 4 are identical or different heteroatoms selected from N, O and S. The "heterocyclyl" or "heterocycle" may, for example, have 1 or 2 oxygen atoms and/or 1 or 2 sulfur atoms and/or 1 to 4 nitrogen atoms in the ring. Also included within the scope of the term, "heterocyclyl" or "heterocycle" is a group in which a non-aromatic heteroatom-containing ring is fused to one or more aromatic rings. The "heterocyclyl" or "heterocycle" preferably is a 5- or 6-membered ring. The ring heteroatoms can be present in any position with respect to each other provided that the resulting "heterocyclyl" or "heterocycle" is stable. Examples of "heterocyclyl" or "heterocycle" include but are not limited to: azocinyl, chromanyl, decahydroquinolinyl, furazanyl, imidazolidinyl, indolinyl, isobenzofuranyl, isoindolinyl, isooxazolinyl, morpholinyl, octahydroisoquinolinyl, oxazolidinyl, piperidinyl, piperazinyl, pyranyl, benzopyranyl, pyrazolinyl, pyrazolidinyl, pyrrolidinyl, pyrrolinyl, 4H-quinolizinyl, dioxolyl, tetrahydrofuranyl, benzodioxolyl, tetrahydroisoquinolinyl, tetrahydroquinolinyl, 6H-1,2,5-thiadiazinyl and xanthenyl. The "heterocyclyl" or "heterocycle" may be optionally substituted with one or more groups selected from halogen, oxo, thio, nitro, —CN, —OR$_1$, —S(=O)$_m$R$_1$, —S(=O)$_{1-2}$NR$_1$R$_2$, —OCOR$_1$, —SCOR$_1$, —NR$_1$R$_2$, —NR$_1$COR$_2$, —NR$_1$COOR$_2$, —NR$_1$SOR$_2$, —NR$_1$SO$_2$R$_2$, —NR$_1$CONR$_1$R$_2$, —COR$_1$, —COOR$_1$, —CONR$_1$R$_2$, alkyl, alkenyl, alkynyl, cycloalkyl, alkylcycloalkyl, aryl, alkylaryl, heterocyclyl, alkylheterocyclyl, heteroaryl and alkylheteroaryl; wherein R$_1$ and R$_2$ are independently selected from H, alkyl, alkenyl, alkynyl, cycloalkyl, alkylcycloalkyl, aryl, alkylaryl, heterocyclyl, alkylheterocyclyl, heteroaryl and alkylheteroaryl.

The term "alkylheterocycle" refers to a heterocycle group bonded through an alkyl, wherein the terms "alkyl" and "heterocycle" are as defined herein above.

The term "heteroaryl" as used herein refers to an aromatic heterocyclic ring system containing 5 to 20 ring atoms, suitably 5 to 10 ring atoms, which may be a single ring (monocyclic) or multiple rings (bicyclic, tricyclic or polycyclic) fused together or linked covalently. Preferably, "heteroaryl" is a 5- to 6-membered ring. The rings may contain from 1 to 4 heteroatoms selected from N, O and S, wherein the N or S atom is optionally oxidized, or the N atom is optionally quarternized. Any suitable ring position of the heteroaryl moiety may be covalently linked to the defined chemical structure. Examples of heteroaryl include but are not limited to: furan, thiophene, pyrrolyl, pyrazolyl, imidazolyl, oxazolyl, cinnolinyl, isoxazolyl, thiazolyl, isothiazolyl, 1H-tetrazolyl, oxadiazolyl, triazolyl, pyridyl, pyrimidinyl, pyrazinyl, pyridazinyl, benzoxazolyl, benzisoxazolyl; benzothiazolyl, benzofuranyl, benzothienyl, benzotriazinyl, phthalazinyl, thianthrene, dibenzofuranyl, dibenzothienyl, benzimidazolyl, indolyl, isoindolyl, indazolyl, quinolinyl, isoquinolinyl, quinazolinyl, quinoxalinyl, purinyl, pteridinyl, 9H-carbazolyl, α-carboline, indolizinyl, benzoisothiazolyl, benzoxazolyl, pyrrolopyridyl, furopyridinyl, purinyl, benzothiadiazolyl, benzooxadiazolyl, benzotriazolyl, benzotriadiazolyl, carbazolyl, dibenzothienyl, acridinyl, and the like. The "heteroaryl" may be optionally substituted with one or more groups selected from halogen, oxo, thio, nitro, —CN, —OR$_1$, —S(=O)$_m$R$_1$, —S(=O)$_{1-2}$NR$_1$R$_2$, —OCOR$_1$, —SCOR$_1$, —NR$_1$R$_2$, —NR$_1$COR$_2$, —NR$_1$COOR$_2$, —NR$_1$SOR$_2$, —NR$_1$SO$_2$R$_2$, —NR$_1$CONR$_1$R$_2$, —COR$_1$, —COOR$_1$, —CONR$_1$R$_2$, alkyl, alkenyl, alkynyl, cycloalkyl, alkylcycloalkyl, aryl, alkylaryl, heterocyclyl, alkylheterocyclyl, heteroaryl and alkylheteroaryl; wherein R$_1$ and R$_2$ are independently selected from H, —(CR$_{10}$R$_{11}$)$_c$—COOR$_{10}$, alkyl, alkenyl, alkynyl, cycloalkyl, alkylcycloalkyl, aryl, alkylaryl, heterocyclyl, alkylheterocyclyl, heteroaryl and alkylheteroaryl and R$_{10}$ and R$_{11}$ are independently selected from H and alkyl and c is an integer from 1 to 3.

The term "alkylheteroaryl" refers to a heteroaryl group bonded through an alkyl, wherein the terms "alkyl" and "heteroaryl" are as defined herein above.

The term "pharmaceutically acceptable salts" refers to the non-toxic, inorganic and organic acid addition salts and base addition salts of compounds of the present invention.

As used herein, the term "solvate" preferably refers to a compound formed by the interaction of a solute (in this invention, a compound of formula I or a salt thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water. Examples for suitable solvates are the mono- or dihydrates or alcoholates of the compounds according to the invention.

As used herein the term "prodrug" refers to a compound that is a drug precursor, which, following administration into or onto the body, releases the drug in vivo via a chemical or physiological process, e.g., a prodrug on being brought to physiological pH or through an enzyme action is converted to the desired drug form. Various forms of prodrugs are known in the art and further information is discussed in Pro-drugs as Novel Delivery Systems, Vol. 14, ACS Symposium Series (T. Higuchi and W. Stella), Bioreversible Carriers in Drug Design, Pergamon Press, 1987 (Ed. E. B. Roche, American Pharmaceutical Association) and Design of Prodrugs, Elsevier 1985, (edited by H. Bundgaard).

As used herein, the term "stereoisomer" is a general term used for all isomers of individual compounds that differ only in the orientation of their atoms in space. The term stereoisomer includes mirror image isomers (enantiomers), mixtures of mirror image isomers (racemates, racemic mixtures), geometric (cis/trans or E/Z) isomers, and isomers of compounds with more than one chiral center that are not mirror images of one another (diastereoisomers). The compounds of the present invention may have asymmetric centers and occur as racemates, racemic mixtures, individual diastereoisomers, or enantiomers, or may exist as geometric isomers, with all isomeric forms of said compounds being included in the present invention.

As used herein, the term "tautomer" refers to the coexistence of two (or more) compounds that differ from each other only in the position of one (or more) mobile atoms and in electron distribution, for example, keto-enol tautomers.

As used herein, the terms "treatment" and "therapy" and the like refer to alleviate, slow the progression, prophylaxis, attenuation or cure of existing disease (e.g., diabetes or obesity). "Prevention", as used herein, refers to delaying, slowing, inhibiting, reducing or ameliorating the onset of disease (e.g., diabetes or insulin resistance).

Compounds of the present invention can also include all isotopes of atoms occurring in the intermediates or final compounds. Isotopes include those atoms having the same atomic number but different mass numbers. For example, isotopes of hydrogen include tritium and deuterium.

EMBODIMENTS

In one embodiment, the present invention provides a compound of formula (Iaa),

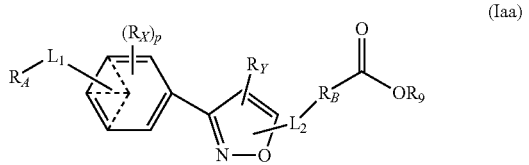

(Iaa)

or a pharmaceutically acceptable salt, solvate or prodrug, including all stereoisomers and tautomers thereof, wherein,
- - - dotted line represents the variable attachment of $-L_1-R_A$ to the specified carbon atoms of the phenyl ring, $R_A$ is cycloalkyl, aryl, alkylaryl, heteroaryl or heterocycle;

$R_X$ and $R_Y$ are independently selected from H, halogen, —CN, —$OR_1$, —$S(=O)_mR_1$, —$OCOR_1$, —$SCOR_1$, —$NR_1R_2$, —$NR_1COR_2$, —$NR_1COOR_2$, —$NR_1SO_2R_2$, —$NR_1CONR_2$, —$COR_1$, —$COOR_1$, —$CONR_1R_2$, alkyl, alkenyl, alkynyl, cycloalkyl, alkylcycloalkyl, aryl, alkylaryl, alkylheteroaryl, heterocycle and heteroaryl;

$L_1$ is —O—, —$NR_3(CR_4R_5)_aNR_3$—, —$(CR_4R_5)_bNR_3$—, —$SO_2NH$—, —$CH_2NR_3C(O)NR_3$— or —$SO_2NHCONH$—;

$L_2$ is —$C(=O)$—, —$C(=O)$—$NR_Z$—, —$C(=S)$—$NR_Z$—, —$C(=NR_8)$—$NR_Z$—, —$C(SR_9)=N$— or —$SO_2NR_Z$—;

$R_B$ is —$(CR_{10}R_{11})_c$— or —$(NR_{12})(CR_{10}R_{11})_c$, wherein c is the integer from 1 to 3;

$R_9$ is absent or is selected from H, alkyl, alkenyl, alkynyl, cycloalkyl, aryl, alkylcycloalkyl, alkylaryl, alkylheteroaryl, heterocycle and heteroaryl;

or $R_B$, C(O), $OR_9$ and $L_2$; or $R_B$ and $L_2$; or $R_B$, C(O) and $OR_9$ together form a 5 to 7-membered ring selected from cycloalkyl, aryl, heteroaryl and heterocycle;

$R_1$ and $R_2$ are independently selected from H, alkyl, alkenyl, alkynyl, cycloalkyl, alkylcycloalkyl, aryl, alkylaryl, alkylheteroaryl, heterocycle and heteroaryl;

$R_3$ is —H, —$COR_1$, —$COOR_1$, —$CONR_1R_2$, alkyl, alkenyl, alkynyl, cycloalkyl or alkylcycloalkyl;

$R_4$ and $R_5$ are independently selected from —H, —$OR_6$, —$COOR_6$, —$CONR_6R_7$, alkyl, alkenyl, alkynyl, cycloalkyl, alkylcycloalkyl, aryl, heteroaryl, alkylaryl, alkylheteroaryl and alkylheterocycle;

or $R_4$ and $R_5$ together are =O, =S or =$NR_8$;

$R_6$ and $R_7$ are independently selected from H, alkyl, cycloalkyl and heterocycle;

$R_Z$ is —H, —$COR_1$, —$COOR_1$, —$CONR_1R_2$, alkyl, alkenyl, alkynyl, cycloalkyl or alkylcycloalkyl;

$R_8$ is —H, —$OR_9$, —$COR_9$, —$COOR_9$, —$CONR_6R_7$, —$SO_2R_9$ or —$SO_2NR_6R_7$;

$R_{10}$, $R_{11}$ and $R_{12}$ are independently selected from H, and the groups alkyl, alkenyl, alkynyl, cycloalkyl, alkylcycloalkyl, aryl, alkylaryl, alkylheteroaryl, heterocycle and heteroaryl;

or $R_{12}$ and $R_{10}$ or $R_{11}$ together with the respective N and C atoms to which they are attached, form a 3 to 6-membered, heteroaryl or heterocyclic ring;

or $R_{10}$ and $R_{11}$ of —$(CR_{10}R_{11})_c$ wherein c is the integer 1, together with the C atom to which they are attached form a 3 to 6-membered cycloalkyl ring;

or $R_{10}$ and $R_{11}$ of —$(CR_{10}R_{11})_c$ wherein c is the integer 1 together with the C atom to which they are attached form alkenylene;

a is an integer from 1 to 5;
b is 0 or an integer from 1 to 5;
m is 0 or an integer from 1 to 2;
p is an integer from 1 to 4;

with the proviso that when $L_2$ is —$C(=O)$—$NR_Z$— $L_1$ is —$(CR_4R_5)_bNR_3$—, and $R_B$ is —$(CR_{10}R_{11})_c$, then (a) c is the integer 1 and (b) $R_A$ is heteroaryl or heterocycle wherein the heteroaryl or heterocycle is selected from indolyl, isoindolyl, indolizinyl, benzofuranyl, benzothienyl, quinolinyl, isoquinolinyl, benzopyranyl, indazolyl, benzimidazolyl, benzothiazolyl, benzoisothiazolyl, benzodioxolyl, benzoxazolyl, benzoisoxazolyl, quinoxalinyl, quinazolinyl, phthalazinyl, pteridinyl, cinnolinyl, chromonyl, coumarinyl, pyrrolopyridyl, furopyridinyl, purinyl, benzothiadiazolyl, benzooxadiazolyl, benzotriazolyl, benzothiadiazolyl, benzotriazinyl, carbazolyl, dibenzofuranyl, dibenzothienyl, acridinyl, phenanthridinyl and xanthenyl, and wherein the heteroaryl or heterocycle may be optionally substituted with one or more groups selected from halogen, oxo, thio, nitro, —CN, —OR$_1$, —S(=O)$_m$R$_1$, —S(=O)$_{1-2}$NR$_1$R$_2$, —OCOR$_1$, —SCOR$_1$, —NR$_1$R$_2$, —NR$_1$COR$_2$, —NR$_1$COOR$_2$, —NR$_1$SOR$_2$, —NR$_1$SO$_2$R$_2$, —NR$_1$CONR$_1$R$_2$, —COR$_1$, —COOR$_1$, —CONR$_1$R$_2$, alkyl, alkenyl, alkynyl, cycloalkyl, alkylcycloalkyl, aryl, alkylaryl, heterocyclyl, alkylheterocyclyl, heteroaryl and alkylheteroaryl; wherein R$_1$ and R$_2$ are independently selected from H, alkyl, alkenyl, alkynyl, cycloalkyl, alkylcycloalkyl, aryl, alkylaryl, heterocyclyl, alkylheterocyclyl, heteroaryl and alkylheteroaryl.

In yet another embodiment, the present invention provides a compound of formula (Iab),

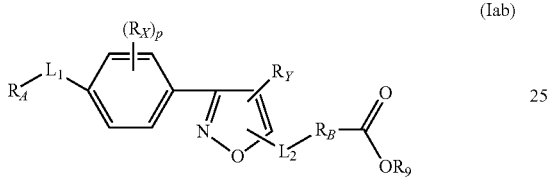

(Iab)

or a pharmaceutically acceptable salt, solvate or prodrug, including all stereoisomers and tautomers thereof, wherein, R$_A$ is cycloalkyl, alkylaryl, aryl, heteroaryl or heterocycle;

R$_X$ and R$_Y$ are independently selected from H, halogen, —CN, —OR$_1$, —S(=O)$_m$R$_1$, —OCOR$_1$, —SCOR$_1$, —NR$_1$R$_2$, —NR$_1$COR$_2$, —NR$_1$COOR$_2$, —NR$_1$SO$_2$R$_2$, —NR$_1$CONR$_2$, —COR$_1$, —COOR$_1$, —CONR$_1$R$_2$, alkyl, alkenyl, alkynyl, cycloalkyl, alkylcycloalkyl, aryl, alkylaryl, alkylheteroaryl, heterocycle and heteroaryl;

R$_1$ and R$_2$ are independently selected from H, alkyl, alkenyl, alkynyl, cycloalkyl, alkylcycloalkyl, aryl, alkylaryl, alkylheteroaryl, heterocycle and heteroaryl;

L$_1$ is —O—, —NR$_3$(CR$_4$R$_5$)$_a$NR$_3$—, —(CR$_4$R$_5$)$_b$NR$_3$—, —SO$_2$NH— or —SO$_2$NHCONH—;

R$_3$ is H, —COR$_1$, —COOR$_1$, —CONR$_1$R$_2$, alkyl, alkenyl, alkynyl, cycloalkyl or alkylcycloalkyl;

R$_4$ and R$_5$ are independently selected from H, —OR$_6$, —COOR$_6$, —CONR$_6$R$_7$, alkyl, alkenyl, alkynyl, cycloalkyl, alkylcycloalkyl, aryl, heterocyclyl, alkylaryl, alkylheteroaryl and alkylheterocycle;

or R$_4$ and R$_5$ together are =O or =S or =NR$_8$;

R$_6$ and R$_7$ are independently selected from H, alkyl, cycloalkyl and heterocycle;

L$_2$ is —C(=O)—, —C(=O)—NR$_Z$—, —C(=S)—NR$_Z$—, —C(=NR$_8$)—NR$_Z$—, —C(SR$_9$)=N— or —SO$_2$NR$_Z$—;

R$_Z$ is H, —COR$_1$, —COOR$_1$, —CONR$_1$R$_2$, alkyl, alkenyl, alkynyl, cycloalkyl or alkylcycloalkyl;

R$_8$ is H, —OR$_9$, —COR$_9$, —COOR$_9$, —CONR$_6$R$_7$, —SO$_2$R$_9$ or —SO$_2$NR$_6$R$_7$;

R$_9$ is absent or is selected from H, alkyl, alkenyl, alkynyl, cycloalkyl, aryl, alkylcycloalkyl, alkylaryl, alkylheteroaryl, heterocycle and heteroaryl;

R$_B$ is —(CR$_{10}$R$_{11}$)$_c$— or —(NR$_{12}$)(CR$_{10}$R$_{11}$)$_c$; wherein c is the integer from 1 to 3;

or R$_B$, C(O), OR$_9$ and L$_2$ or R$_B$ and L$_2$, or R$_B$, C(O) and OR$_9$, together form a 5 to 7-membered ring selected from cycloalkyl, aryl, heteroaryl or heterocycle;

R$_{10}$, R$_{11}$ and R$_{12}$ are independently selected from H, and the groups alkyl, alkenyl, alkynyl, cycloalkyl, alkylcycloalkyl, aryl, alkylaryl, alkylheteroaryl, heterocycle and heteroaryl;

or R$_{12}$ and R$_{10}$ or R$_{11}$, together with the respective N and C atoms to which they are attached, form a 3 to 6-membered heteroaryl or heterocyclic ring;

or R$_{10}$ and R$_{11}$ of —(CR$_{10}$R$_{11}$)$_c$ wherein c is the integer 1, together with the C atom to which they are attached form a 3 to 6-membered cycloalkyl ring;

or R$_{10}$ and R$_{11}$ of —(CR$_{10}$R$_{11}$)$_c$ wherein c is the integer 1 together with the C atom to which they are attached form alkenylene;

a is the integer 1;
b is 0 or an integer from 1 to 5;
m is 0 or the integer 1 or 2;
p is an integer from 1 to 4;
with the proviso that when L$_2$ is —C(=O)—NR$_Z$—, L$_1$ is —(CR$_4$R$_5$)$_b$NR$_3$—, and R$_B$ is —(CR$_{10}$R$_{11}$)$_c$, then (a) c is the integer 1 and (b) R$_A$ is heteroaryl or heterocycle, wherein the heteroaryl or heterocycle is selected from indolyl, isoindolyl, indolizinyl, benzofuranyl, benzothienyl, quinolinyl, isoquinolinyl, benzopyranyl, indazolyl, benzimidazolyl, benzothiazolyl, benzoisothiazolyl, benzodioxolyl, benzoxazolyl, benzoisoxazolyl, quinoxalinyl, quinazolinyl, phthalazinyl, pteridinyl, cinnolinyl, chromonyl, coumarinyl, pyrrolopyridyl, furopyridinyl, purinyl, benzothiadiazolyl, benzooxadiazolyl, benzotriazolyl, benzothiadiazolyl, benzotriazinyl, carbazolyl, dibenzofuranyl, dibenzothienyl, acridinyl, phenanthridinyl and xanthenyl; and wherein the heteroaryl or heterocycle is optionally substituted with one or more groups selected from halogen, oxo, thio, nitro, —CN, —OR$_1$, —S(=O)$_m$R$_1$, —S(=O)$_{1-2}$NR$_1$R$_2$, —OCOR$_1$, —SCOR$_1$, —NR$_1$R$_2$, —NR$_1$COR$_2$, —NR$_1$COOR$_2$, —NR$_1$SOR$_2$, —NR$_1$SO$_2$R$_2$, —NR$_1$CONR$_1$R$_2$, —COR$_1$, —COOR$_1$, —CONR$_1$R$_2$, alkyl, alkenyl, alkynyl, cycloalkyl, alkylcycloalkyl, aryl, alkylaryl, heterocyclyl, alkylheterocyclyl, heteroaryl and alkylheteroaryl; wherein R$_1$ and R$_2$ are independently selected from H, alkyl, alkenyl, alkynyl, cycloalkyl, alkylcycloalkyl, aryl, alkylaryl, heterocyclyl, alkylheterocyclyl, heteroaryl and alkylheteroaryl.

In a further embodiment, the present invention provides a compound of formula (Iac),

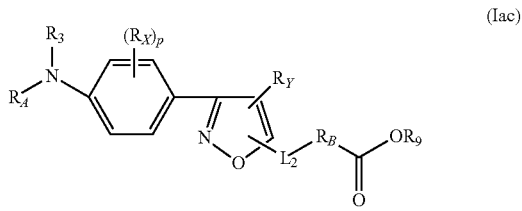

(Iac)

or a pharmaceutically acceptable salt, solvate or prodrug, including all stereoisomers thereof and tautomers thereof, wherein, R$_A$ is cycloalkyl, aryl, heteroaryl or heterocycle;

R$_X$ and R$_Y$ are independently selected from H, halogen, —CN, —OR$_1$, —S(=O)$_m$R$_1$, —OCOR$_1$, —SCOR$_1$, —NR$_1$R$_2$, —NR$_1$COR$_2$, —NR$_1$COOR$_2$, —NR$_1$SO$_2$R$_2$, —NR$_1$CONR$_2$, —COR$_1$, —COOR$_1$, —CONR$_1$R$_2$, alkyl, alkenyl, alkynyl, cycloalkyl, alkylcycloalkyl, aryl, alkylaryl, alkylheteroaryl, heterocycle and heteroaryl;

R$_1$ and R$_2$ are independently selected from H, alkyl, alkenyl, alkynyl, cycloalkyl, alkylcycloalkyl, aryl, alkylaryl, alkylheteroaryl, heterocycle and heteroaryl;

L$_2$ is —C(=O)—NR$_Z$—, —C(=S)—NR$_Z$—, —C(=NR$_8$)—NR$_Z$— or —SO$_2$NR$_Z$—;

R$_Z$ is —H, —COR$_1$, —COOR$_1$, —CONR$_1$R$_2$, alkyl, alkenyl, alkynyl, cycloalkyl or alkylcycloalkyl;

R$_8$ is H, —OR$_9$, —COR$_9$, —COOR$_9$, —CONR$_6$R$_7$, —SO$_2$R$_9$ or —SO$_2$NR$_6$R$_7$;

R$_6$ and R$_7$ are independently selected from H, alkyl, cycloalkyl and heterocycle;

R$_3$ is —H, —COR$_1$, —COOR$_1$, —CONR$_1$R$_2$, alkyl, alkenyl, alkynyl, cycloalkyl or alkylcycloalkyl;

R$_9$ is absent or is selected from H, alkyl, alkenyl, alkynyl, cycloalkyl, aryl, alkylcycloalkyl, alkylaryl, alkylheteroaryl, heterocycle and heteroaryl;

R$_B$ is —(CR$_{10}$R$_{11}$)$_c$— or —(NR$_{12}$)(CR$_{10}$R$_{11}$)$_c$; wherein c is an integer from 1 to 3;

or R$_B$, C(O), OR$_9$ and L$_2$, or R$_B$ and L$_2$ or R$_B$, C(O) and OR$_9$, together form a 5 to 7-membered ring selected from cycloalkyl, aryl, heteroaryl and heterocycle;

R$_{10}$, R$_{11}$ and R$_{12}$ are independently selected from H or the groups alkyl, alkenyl, alkynyl, cycloalkyl, alkylcycloalkyl, aryl, alkylaryl, alkylheteroaryl, heterocycle and heteroaryl;

or R$_{12}$ and R$_{10}$ or R$_{11}$ together with the respective N and C atoms to which they are attached, form a 3 to 6 membered heterocyclic or heteroaryl ring;

or R$_{10}$ and R$_{11}$ of —(CR$_{10}$R$_{11}$)$_c$ wherein c is the integer 1, together with the C atom to which they are attached form a 3 to 6-membered cycloalkyl ring;

m is 0 or an integer from 1 to 2;

p is an integer from 1 to 4;

with the proviso that when L$_2$ is —C(=O)—NR$_Z$— and R$_B$ is —(CR$_{10}$R$_{11}$)$_c$, then (a) c is the integer 1 and (b) R$_A$ is heteroaryl or heterocycle wherein the heteroaryl or heterocycle is selected from indolyl, isoindolyl, indolizinyl, benzofuranyl, benzothienyl, quinolinyl, isoquinolinyl, benzopyranyl, indazolyl, benzimidazolyl, benzothiazolyl, benzoisothiazolyl, benzodioxolyl, benzoxazolyl, benzoisoxazolyl, quinoxalinyl, quinazolinyl, phthalazinyl, pteridinyl, cinnolinyl, chromonyl, coumarinyl, pyrrolopyridyl, furopyridinyl, purinyl, benzothiadiazolyl, benzooxadiazolyl, benzotriazolyl, benzothiadiazolyl, benzotriazinyl, carbazolyl, dibenzofuranyl, dibenzothienyl, acridinyl, phenanthridinyl and xanthenyl; and wherein the heteroaryl or heterocycle is optionally substituted with one or more groups selected from halogen, oxo, thio, nitro, —CN, —OR$_1$, —S(=O)$_m$R$_1$, —S(=O)$_{1-2}$NR$_1$R$_2$, —OCOR$_1$, —SCOR$_1$, —NR$_1$R$_2$, —NR$_1$COR$_2$, —NR$_1$COOR$_2$, —NR$_1$SOR$_2$, —NR$_1$SO$_2$R$_2$, —NR$_1$CONR$_1$R$_2$, —COR$_1$, —COOR$_1$, —CONR$_1$R$_2$, alkyl, alkenyl, alkynyl, cycloalkyl, alkylcycloalkyl, aryl, alkylaryl, heterocyclyl, alkylheterocyclyl, heteroaryl and alkylheteroaryl; wherein R$_1$ and R$_2$ are independently selected from H, alkyl, alkenyl, alkynyl, cycloalkyl, alkylcycloalkyl, aryl, alkylaryl, heterocyclyl, alkylheterocyclyl, heteroaryl and alkylheteroaryl.

In a further embodiment, the present invention provides a compound of formula (Iad),

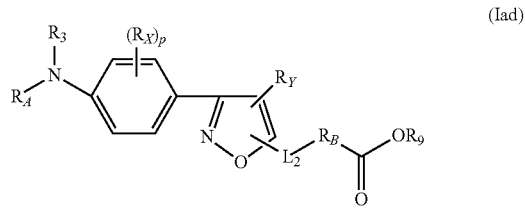

(Iad)

or a pharmaceutically acceptable salt, solvate or prodrug, including all stereoisomers thereof and tautomers thereof, wherein, R$_A$ is heteroaryl; wherein the heteroaryl is optionally substituted with one or more groups, which may be the same or different, selected from halogen, cyano, —COOR$_1$, —OR$_1$, —S(=O)$_m$R$_1$ and alkyl;

R$_X$ and R$_Y$ are independently selected from H, halogen, —CN, —OR$_1$, —S(=O)$_m$R$_1$, —NR$_1$R$_2$, —NR$_1$COR$_2$, —NR$_1$CONR$_2$, —COR$_1$, —COOR$_1$, —CONR$_1$R$_2$, alkyl, alkenyl, alkynyl, cycloalkyl and aryl;

R$_1$ and R$_2$ are independently, selected from H, alkyl and aryl;

L$_2$ is —C(=O)—NR$_Z$—, —C(=S)—NR$_Z$—, —C(=NR$_8$)—NR$_Z$— or —SO$_2$NR$_Z$—;

R$_Z$ is —H or alkyl;

R$_8$ is H, —OR$_9$, —COR$_9$, —COOR$_9$ or —CONR$_6$R$_7$;

R$_3$ is —H, or alkyl;

R$_9$ is absent or is selected from H, alkyl, alkenyl, alkynyl, cycloalkyl and aryl;

R$_B$ is —(CR$_{10}$R$_{11}$)$_c$— or —(NR$_{12}$)(CR$_{10}$R$_{11}$)$_c$; wherein c is an integer from 1 to 3;

or R$_B$, C(O), OR$_9$ and L$_2$; or R$_B$ and L$_2$; or R$_B$, C(O) and OR$_9$, together form a 5 to 7-membered ring selected from cycloalkyl, aryl, heteroaryl and heterocycle;

R$_{10}$, R$_{11}$ and R$_{12}$ are independently selected from H or the groups alkyl, alkenyl, alkynyl, cycloalkyl, alkylcycloalkyl, aryl, alkylaryl, alkylheteroaryl, heterocycle and heteroaryl;

or R$_{12}$ and R$_{10}$ or R$_{11}$ together with the respective. N and C atoms to which they are attached, form a 3 to 6 membered heterocyclic or heteroaryl ring;

or R$_{10}$ and R$_{11}$ of —(CR$_{10}$R$_{11}$)$_c$ wherein c is the integer 1, together with the C atom to which they are attached form a 3 to 6-membered cycloalkyl ring;

m is 0 or an integer from 1 to 2;

p is an integer from 1 to 4;

with the proviso that when L$_2$ is —C(=O)—NR$_Z$— and R$_B$ is —(CR$_{10}$R$_{11}$)$_c$, then (a) c is the integer 1 and (b) R$_A$ is heteroaryl or heterocycle wherein the heteroaryl or heterocycle is selected from indolyl, isoindolyl, indolizinyl, benzofuranyl, benzothienyl, indazolyl, benzimidazolyl, benzothiazolyl, benzoisothiazolyl, benzodioxolyl, benzoxazolyl, benzoisoxazolyl, pyrrolopyridyl, furopyridinyl, purinyl, benzothiadiazolyl, benzooxadiazolyl, benzotriazolyl, benzothiadiazolyl and benzotriazinyl, wherein the heteroaryl or heterocycle is optionally substituted with one or more groups selected from halogen, nitro, —CN, —OR$_1$, —S(=O)$_m$R$_1$, —S(=O)$_{1-2}$NR$_1$R$_2$, —NR$_1$R$_2$, —NR$_1$COR$_2$, —NR$_1$SOR$_2$, —NR$_1$SO$_2$R$_2$, —NR$_1$CONR$_1$R$_2$, —COR$_1$, —COOR$_1$, —CONR$_1$R$_2$ and alkyl, wherein R$_1$ and R$_2$ are independently selected from H, alkyl and aryl.

In a further embodiment, the present invention provides a compound of formula (Iae),

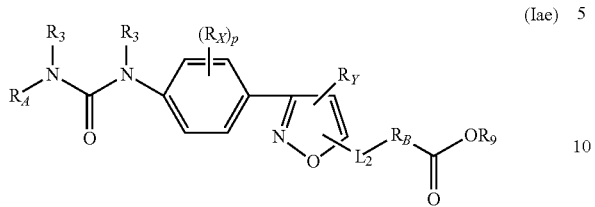

(Iae)

or a pharmaceutically acceptable salt, solvate, or prodrug, including all stereoisomers and, tautomers thereof, wherein, $R_A$ is cycloalkyl, alkylaryl, aryl, heteroaryl or heterocycle;

$R_X$ and $R_Y$ are independently selected from H, halogen, —CN, —OR$_1$, —S(=O)$_m$R$_1$, —OCOR$_1$, —SCOR$_1$, —NR$_1$R$_2$, —NR$_1$COR$_2$, —NR$_1$COOR$_2$, —NR$_1$SO$_2$R$_2$, —NR$_1$CONR$_2$, —COR$_1$, —COOR$_1$, —CONR$_1$R$_2$, alkyl, alkenyl, alkynyl, cycloalkyl, alkylcycloalkyl, aryl, alkylaryl, alkylheteroaryl, heterocycle and heteroaryl;

$R_1$ and $R_2$ are independently selected from H, alkyl, alkenyl, alkynyl, cycloalkyl, alkylcycloalkyl, aryl, alkylaryl, alkylheteroaryl, heterocycle and heteroaryl;

$R_3$ is H, —COR$_1$, —COOR$_1$, —CONR$_1$R$_2$, alkyl, alkenyl, alkynyl, cycloalkyl or alkylcycloalkyl;

$L_2$ is —C(=O)—, —C(=O)—NR$_Z$—, —C(=S)—NR$_Z$—, —C(=NR$_8$)—NR$_Z$—, —C(SR$_9$)=N— or —SO$_2$NR$_Z$—;

$R_Z$ is H, —COR$_1$, —COOR$_1$, —CONR$_1$R$_2$, alkyl, alkenyl, alkynyl, cycloalkyl or alkylcycloalkyl;

$R_8$ is H, —OR$_9$, —COR$_9$, —COOR$_9$, —CONR$_6$R$_7$, —SO$_2$R$_9$ or —SO$_2$NR$_6$R$_7$;

$R_6$ and $R_7$ are independently selected from H, alkyl, cycloalkyl and heterocycle;

$R_9$ is —H, alkyl, alkenyl, alkynyl, cycloalkyl, aryl, alkylcycloalkyl, alkylaryl, alkylheteroaryl, heterocycle or heteroaryl;

$R_B$ is —(CR$_{10}$R$_{11}$)$_c$— or —(NR$_{12}$)(CR$_{10}$R$_{11}$)$_c$; wherein c is the integer from 1 to 3;

or $R_B$, C(O), OR$_9$ and L$_2$; or $R_B$ and L$_2$; or $R_B$, C(O) and OR$_9$, together form a 5 to 7-membered ring selected from cycloalkyl, aryl, heteroaryl and heterocycle;

$R_{10}$, $R_{11}$ and $R_{12}$ are independently selected from —H, and the groups alkyl, alkenyl, alkynyl, cycloalkyl, alkylcycloalkyl, aryl, alkylaryl, alkylheteroaryl, heterocycle and heteroaryl;

or $R_{12}$ and $R_{10}$ or $R_{11}$ together with the respective N and C atoms to which they are attached, form a 3 to 6 membered heterocyclic or heteroaryl ring;

or $R_{10}$ and $R_{11}$ of —(CR$_{10}$R$_{11}$)$_c$ wherein c is the integer 1, together with the C atom to which they are attached form a 3 to 6-membered cycloalkyl ring;

or $R_{10}$ and $R_{11}$ of —(CR$_{10}$R$_{11}$)$_c$ wherein c is the integer 1 together with the C atom to which they are attached form alkenylene;

m is 0 or the integer 1 or 2;

p is an integer from 1 to 4.

In a further embodiment, the present invention provides a compound of formula (Iaf),

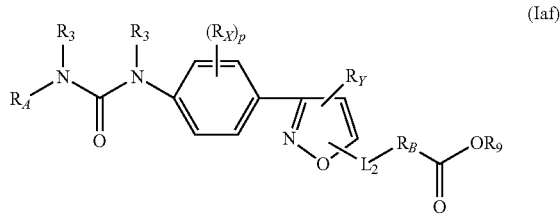

(Iaf)

or a pharmaceutically acceptable salt, solvate, or prodrug, including all stereoisomers and tautomers thereof, wherein, $R_A$ is cycloalkyl, alkylaryl, aryl, heteroaryl or heterocycle; wherein the cycloalkyl, alkylaryl, aryl, heteroaryl or heterocyclyl is optionally substituted with one or more groups, which may be the same or different, selected from halogen, —CN, —COOR$_1$, —OR$_1$, —S(=O)$_m$R$_1$, alkyl, haloalkyl, cycloalkyl, aryl and heteroaryl;

$R_X$ and $R_Y$ are independently selected from H, halogen, —CN, —OR$_1$, —S(=O)$_m$R$_1$, —NR$_1$R$_2$, —NR$_1$COR$_2$, —NR$_1$SO$_2$R$_2$, —NR$_1$CONR$_2$, —COR$_1$, —COOR$_1$, —CONR$_1$R$_2$, alkyl, alkenyl, alkynyl, cycloalkyl or aryl;

$R_1$ and $R_2$ are independently selected from H, alkyl, haloalkyl, alkenyl, alkynyl, cycloalkyl or aryl;

$R_3$ is H, or alkyl;

$L_2$ is —C(=O)—, —C(=O)—NR$_Z$—, —C(=S)—NR$_Z$—, —C(=NR$_8$)—NR$_Z$—, —C(SR$_9$)=N— or —SO$_2$NR$_Z$—;

$R_Z$ is H, alkyl, alkenyl, alkynyl, cycloalkyl or alkylcycloalkyl;

$R_8$ is H, —OR$_9$, —COR$_9$, —COOR$_9$, —CONR$_6$R$_7$, —SO$_2$R$_9$ or —SO$_2$NR$_6$R$_7$;

$R_6$ and $R_7$ are independently selected from H, alkyl, cycloalkyl and heterocycle;

$R_9$ is —H, alkyl, alkenyl, alkynyl, cycloalkyl, aryl, alkylcycloalkyl, alkylaryl, alkylheteroaryl, heterocycle or heteroaryl;

$R_B$ is —(CR$_{10}$R$_{11}$)$_c$— or —(NR$_{12}$)(CR$_{10}$R$_{11}$)$_c$; wherein c is an integer from 1 to 3;

or $R_B$, C(O), OR$_9$ and L$_2$; or $R_B$ and L$_2$; or $R_B$, C(O) and OR$_9$, together form a 5 to 7-membered ring selected from cycloalkyl, aryl, heteroaryl and heterocycle;

$R_{10}$, $R_{11}$ and $R_{12}$ are independently selected from —H, and the groups alkyl, alkenyl, alkynyl, cycloalkyl, alkylcycloalkyl, aryl, alkylaryl, alkylheteroaryl, heterocycle and heteroaryl wherein the alkyl, alkenyl, alkynyl, cycloalkyl, alkylcycloalkyl, aryl, alkylaryl, alkylheteroaryl, heterocycle and heteroaryl is optionally substituted with OH;

or $R_{12}$ and $R_{10}$ or $R_{11}$ together with the respective N and C atoms to which they are attached, form a 3 to 6 membered heterocyclic or heteroaryl ring;

or $R_{10}$ and $R_{11}$ of —(CR$_{10}$R$_{11}$)$_c$ wherein c is the integer 1, together with the C atom to which they are attached form a 3 to 6-membered cycloalkyl ring;

or $R_{10}$ and $R_{11}$ of —(CR$_{10}$R$_{11}$)$_c$ wherein c is the integer 1 together with the C atom to which they are attached form alkenylene;

m is 0 or the integer 1 or 2;

p is an integer from 1 to 4.

In a further embodiment, the present invention provides a compound of formula (Iag), (Iag)

or a pharmaceutically acceptable salt, solvate, or prodrug, including all stereoisomers and tautomers thereof,
wherein,
- $R_A$ is cycloalkyl, alkylaryl, aryl, heteroaryl or heterocycle; wherein the cycloalkyl, alkylaryl, aryl, heteroaryl or heterocyclyl are optionally substituted with one or more groups, which may be the same or different, selected from halogen, cyano, —COOR$_1$, —OR$_1$, —S(=O)$_m$R$_1$, alkyl, haloalkyl, cycloalkyl, aryl and heteroaryl;
- $R_X$ and $R_Y$ are independently selected from H, halogen, —CN, —OR$_1$, —NR$_1$R$_2$, —COR$_1$, —COOR$_1$, —CONR$_1$R$_2$, alkyl, alkenyl, alkynyl, cycloalkyl or aryl;
- $R_1$ and $R_2$ are independently selected from H and alkyl;
- $R_3$ is H or alkyl;
- $L_2$ is —C(=O)—, —C(=O)—NR$_Z$—, —C(=S)—NR$_Z$—, —C(=NR$_8$)—NR$_Z$—, —C(SR$_9$)=N— or —SO$_2$NR$_Z$—;
- $R_Z$ is H, alkyl, alkenyl, alkynyl, cycloalkyl or alkylcycloalkyl;
- $R_8$ is H, —OR$_9$, —COR$_9$, —COOR$_9$, —CONR$_6$R$_7$, —SO$_2$R$_9$ or —SO$_2$NR$_6$R$_7$;
- $R_9$ is —H, alkyl, alkenyl, alkynyl, cycloalkyl, aryl, alkylcycloalkyl, alkylaryl, alkylheteroaryl, heterocycle or heteroaryl;
- $R_B$ is —(CR$_{10}$R$_{11}$)$_c$— or —(NR$_{12}$)(CR$_{10}$R$_{11}$)$_c$; wherein c is an integer from 1 to 3;
- $R_{10}$, $R_{11}$ and $R_{12}$ are independently selected from —H, and the groups alkyl, aryl, alkylaryl, wherein the alkyl, aryl and alkylaryl are optionally substituted with OH;
- or $R_{12}$ and $R_{10}$ or $R_{11}$ together with the respective N and C atoms to which they are attached, form a 3 to 6 membered heterocyclic or heteroaryl ring;
- or $R_{10}$ and $R_{11}$ of —(CR$_{10}$R$_{11}$)$_c$ wherein c is the integer 1, together with the C atom to which they are attached form a 3 to 6-membered cycloalkyl ring;
- or $R_{10}$ and $R_{11}$ of —(CR$_{10}$R$_{11}$)$_c$ wherein c is the integer 1 together with the C atom to which they are attached form alkenylene;
- m is 0 or the integer 1 or 2;
- p is an integer from 1 to 4.

In yet another embodiment, the present invention provides a compound of formula (Iah), (Iah)

or a pharmaceutically acceptable salt, solvate or prodrug, including all stereoisomers and tautomers thereof, wherein,
- $R_A$ is cycloalkyl, alkylaryl, aryl, heteroaryl or heterocycle, wherein the cycloalkyl, alkylaryl, aryl, heteroaryl or heterocycle are optionally substituted with one or more groups, which may be the same or different, selected from halogen, cyano, —COOR$_1$, —OR$_1$, —S(=O)$_m$R$_1$, alkyl, haloalkyl, cycloalkyl, aryl and heteroaryl; wherein R$_1$ is hydrogen, alkyl, haloalkyl; alkenyl, alkynyl, cycloalkyl or aryl;
- $R_X$ and $R_Y$ are independently selected from H, halogen, alkyl and aryl;
- $L_1$ is —NH(C=O)NH—, —NH— or —(CO)NR$_3$—, wherein R$_3$ is H or alkyl;
- $L_2$ is —C(=O), —C(=O)—NR$_Z$—, —C(=S)—NR$_Z$—, —C(=NR$_8$)—NR$_Z$—, —C(SR$_9$)=N— or —SO$_2$NR$_Z$—;
- $R_Z$ is H or alkyl; $R_8$ is —OR$_9$, wherein R$_9$ is absent or is selected from H and alkyl;
- $R_B$ is —(CR$_{10}$R$_{11}$)$_c$; or —(NR$_{12}$)(CR$_{10}$R$_{11}$)$_c$; wherein c is an integer from 1 to 3;
- or $R_B$, C(O), OR$_9$ and L$_2$; or R$_B$ and L$_2$ or R$_B$; C(O) and OR$_9$, together form a 5 to 7-membered ring selected from cycloalkyl, aryl, heteroaryl or heterocycle, wherein the cycloalkyl, aryl, heteroaryl or heterocycle are optionally substituted with one or more groups selected from halogen, —CN, —OR$_1$, —S(=O)$_m$R$_1$, —OCOR$_1$, —SCOR$_1$, —NR$_1$R$_2$, —NR$_1$COR$_2$, —NR$_1$COOR$_2$, —NR$_1$SO$_2$R$_2$, —NR$_1$CONR$_2$, —COR$_1$, —COOR$_1$, —CONR$_1$R$_2$, alkyl, alkenyl, alkynyl, cycloalkyl and alkylcycloalkyl;
wherein R$_2$ is hydrogen, alkyl, haloalkyl, alkenyl, alkynyl, cycloalkyl or aryl;
- $R_{10}$, $R_{11}$ and $R_{12}$ are independently selected from H, alkyl, and aryl, wherein the alkyl or aryl is optionally substituted with OH or alkoxy;
- or $R_{12}$ and $R_{10}$ or $R_{11}$ together with the respective N and C atoms to which they are attached, together form a heterocyclic ring such as pyrrolidine ring;
- or $R_{10}$ and $R_{11}$ of —CR$_{10}$R$_{11}$ together with the C atom to which they are attached form a 3 to 6-membered cycloalkyl ring such as cyclopentyl ring;
- or $R_{10}$ and $R_{11}$ of —(CR$_{10}$R$_{11}$)$_c$ wherein c is the integer 1 together with the C atom to which they are attached form alkenylene;
- m is 0 or the integer 1 or 2;
- p is an integer from 1 to 4;
with the proviso that when $L_1$ is —NH—, $L_2$ is —C(=O)—NR$_Z$— and
- $R_B$ is —CR$_{10}$R$_{11}$ then $R_A$ is heteroaryl or heterocycle selected from indolyl, isoindolyl, indolizinyl, benzofuranyl, benzothienyl, quinolinyl, isoquinolinyl, benzopyranyl, indazolyl, benzimidazolyl, benzothiazolyl, benzoisothiazolyl, benzodioxolyl, benzoxazolyl, benzoisoxazolyl, quinoxalinyl, quinazolinyl, phthalazinyl, pteridinyl, cinnolinyl, chromonyl, coumarinyl, pyrrolopyridyl, furopyridinyl, purinyl, benzothiadiazolyl, benzooxadiazolyl, benzotriazolyl, benzothiadiazolyl, benzotriazinyl, carbazolyl, dibenzofuranyl, dibenzothienyl, acridinyl, phenanthridinyl and xanthenyl; and wherein the heteroaryl or heterocycle is optionally substituted with one or more groups selected from halogen, oxo, thio, nitro, —CN, —$OR_1$, —$S(=O)_mR_1$, —$S(=O)_{1-2}NR_1R_2$, —$OCOR_1$, —$SCOR_1$, —$NR_1R_2$, —$NR_1COR_2$, —$NR_1COOR_2$, —$NR_1SOR_2$, —$NR_1SO_2R_2$, —$NR_1CONR_1R_2$, —$COR_1$, —$COOR_1$, —$CONR_1R_2$, alkyl, alkenyl, alkynyl, cycloalkyl, alkylcycloalkyl, aryl, alkylaryl, heterocyclyl, alkylheterocyclyl, heteroaryl and alkylheteroaryl; wherein $R_1$ and $R_2$ are independently selected from H, alkyl, alkenyl, alkynyl, cycloalkyl, alkylcycloalkyl, aryl, alkylaryl, heterocyclyl, alkylheterocyclyl, heteroaryl and alkylheteroaryl.

In yet another embodiment, the present invention provides a compound of formula (Iai),

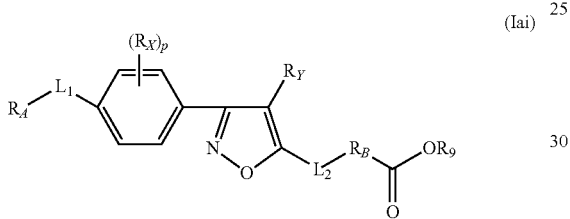

(Iai)

or a pharmaceutically acceptable salt, solvate or prodrug, including all stereoisomers and tautomers thereof, wherein, $R_A$ is cycloalkyl, alkylaryl, aryl, heteroaryl or heterocycle; wherein the cycloalkyl, alkylaryl, aryl, heteroaryl or heterocycle are optionally substituted with one or more groups, which may be the same or different, selected from cyano, halogen, —$OR_1$; —$COOR_1$, —$S(=O)_m R_1$, alkyl, haloalkyl, cycloalkyl, aryl and heteroaryl; $R_1$ is hydrogen, alkyl, haloalkyl, alkenyl, alkynyl; cycloalkyl or aryl;

$R_X$ and $R_Y$ are independently H, halogen, alkyl or aryl;

$L_1$ is —NH(C=O)NH—, —NH— or —(CO)$NR_3$—, wherein $R_3$ is H or alkyl;

$L_2$ is —C(=O)—, —C(=O)—$NR_Z$—, —C(=S)—$NR_Z$—, —C(=$NR_8$)—$NR_Z$—, —C($SR_9$)=N— or —$SO_2NR_Z$—;

$R_Z$ is H or alkyl; $R_8$ is —$OR_9$, wherein $R_9$ is absent or is selected from H or alkyl;

$R_B$ is —$(CR_{10}R_{11})_c$ or —$(NR_{12})(CR_{10}R_{11})_c$; wherein c is an integer from 1 to 3;

or $R_B$, C(O), $OR_9$ and $L_2$; or $R_B$ and $L_2$ or $R_B$; C(O) and $OR_9$, together form a 5 to 7-membered ring selected from cycloalkyl, aryl, heteroaryl or heterocycle, wherein the cycloalkyl, aryl, heteroaryl or heterocycle are optionally substituted with one or more groups selected from halogen, —CN, —$OR_1$, —$S(=O)_mR_1$, —$OCOR_1$, —$SCOR_1$, —$NR_1R_2$, —$NR_1COR_2$, —$NR_1COOR_2$, —$NR_1SO_2R_2$, —$NR_1CONR_2$, —$COR_1$, —$COOR_1$, —$CONR_1R_2$, alkyl, alkenyl, alkynyl, cycloalkyl and alkylcycloalkyl;

wherein $R_2$ is hydrogen, alkyl, haloalkyl, alkenyl, alkynyl, cycloalkyl or aryl;

$R_{10}$, $R_{11}$ and $R_{12}$ are independently selected from H, alkyl, —$COOR_1$ and aryl, wherein the alkyl or aryl is optionally substituted with OH or alkoxy;

or $R_{12}$ and $R_{10}$ or $R_{11}$ together with the respective N and C atoms to which they are attached, together form a heterocyclic ring such as pyrrolidine ring;

or $R_{10}$ and $R_{11}$ of —$CR_{10}R_{11}$ together with the C atom to which they are attached form a 3 to 6-membered cycloalkyl ring such as cyclopentyl ring;

to or $R_{10}$ and $R_{11}$ of —$(CR_{10}R_{11})_c$ wherein c is the integer 1 together with the C atom to which they are attached form alkenylene;

m is 0 or the integer 1 or 2;

p is an integer from 1 to 4;

with the proviso that when $L_1$ is —NH—, $L_2$ is —C(=O)—$NR_Z$— and $R_B$ is —$CR_{10}R_{11}$ then $R_A$ is heteroaryl or heterocycle selected from indolyl, isoindolyl, indolizinyl, benzofuranyl, benzothienyl, quinolinyl, isoquinolinyl, benzopyranyl, indazolyl, benzimidazolyl, benzothiazolyl, benzoisothiazolyl, benzodioxolyl, benzoxazolyl, benzoisoxazolyl, quinoxalinyl, quinazolinyl, phthalazinyl, pteridinyl, cinnolinyl, chromonyl, coumarinyl, pyrrolopyridyl, furopyridinyl, purinyl, benzothiadiazolyl, benzooxadiazolyl, benzotriazolyl, benzothiadiazolyl, benzotriazinyl, carbazolyl, dibenzofuranyl, dibenzothienyl, acridinyl, phenanthridinyl and xanthenyl; and wherein the heteroaryl or heterocycle is optionally substituted with one or more groups selected from halogen, oxo, thio, nitro, —CN, —$OR_1$, —$S(=O)_mR_1$, —$S(=O)_{1-2}NR_1R_2$, $OCOR_1$, —$SCOR_1$, —$NR_1R_2$, —$NR_1COR_2$, —$NR_1COOR_2$, —$NR_1SOR_2$, —$NR_1SO_2R_2$, —$NR_1CONR_1R_2$, —$COR_1$, —$COOR_1$, —$CONR_1R_2$, alkyl, alkenyl, alkynyl, cycloalkyl, alkylcycloalkyl, aryl, alkylaryl, heterocyclyl, alkylheterocyclyl, heteroaryl and alkylheteroaryl; wherein $R_1$ and $R_2$ are independently selected from H, alkyl, alkenyl, alkynyl, cycloalkyl, alkylcycloalkyl, aryl, alkylaryl, heterocyclyl, alkylheterocyclyl, heteroaryl and alkylheteroaryl.

In yet another embodiment, the present invention provides a compound of formula (Iaj),

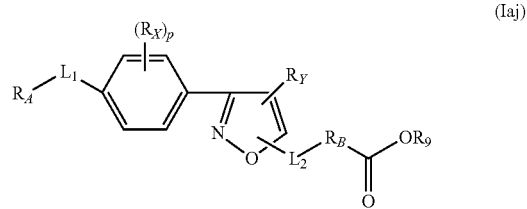

(Iaj)

or a pharmaceutically acceptable salt, solvate or prodrug thereof, including all stereoisomers and tautomers thereof, wherein, $R_A$ is cycloalkyl, alkylaryl, aryl, heteroaryl or heterocycle; wherein the cycloalkyl, alkylaryl, aryl, heteroaryl or heterocycle are optionally substituted with one or more groups, which may be the same or different, selected from halogen, —$OR_1$, alkyl and haloalkyl; wherein $R_1$ is hydrogen or alkyl;

$R_X$ and $R_Y$ are hydrogen;

$L_1$ is —O—, —$NR_3$(C=S)$NR_3$—, —$SO_2NHCONH$—, —$SO_2NH$—, —$NR_3(CO)_2NR_3$—, wherein $R_3$ is H or alkyl;

$L_2$ is —C(=O)—, —C(=O)—$NR_Z$—, —C(=S)—$NR_Z$—, —C(=$NR_8$)—$NR_Z$— or —$SO_2NR_Z$—;

$R_Z$ is H; $R_8$ is —$OR_9$, wherein $R_9$ is H or alkyl;

$R_B$ is —$CR_{10}R_{11}$; or —$(NR_{12})(CR_{10}R_{11})_c$; wherein c is an integer from 1 to 3;

or $R_B$, C(O), $OR_9$ and $L_2$; or $R_B$ and $L_2$; or $R_B$, C(O) and $OR_9$, together form a 5 to 7-membered ring selected from cycloalkyl, aryl, heteroaryl or heterocycle, wherein the cycloalkyl, aryl, heteroaryl or heterocycle are optionally substituted with one or more groups selected from halogen, —CN, —$OR_1$, —S(=O)$_mR_1$, —$OCOR_1$, —$SCOR_1$, —$NR_1R_2$, —$NR_1COR_2$, —$NR_1COOR_2$, —$NR_1SO_2R_2$, —$NR_1CONR_2$, —$COR_1$, —$COOR_1$, —$CONR_1R_2$, alkyl, alkenyl, alkynyl, cycloalkyl and alkylcycloalkyl;

$R_{10}$, $R_{11}$ and $R_{12}$ are independently selected from H and alkyl;

or $R_{12}$ and $R_{10}$ or $R_{11}$ together with the respective N and C atoms to which they are attached, together form a heterocyclic ring such as pyrrolidine ring;

m is 0 or the integer 1 or 2;

p is an integer from 1 to 4.

In yet another embodiment, the present invention provides a compound of formula (Ib),

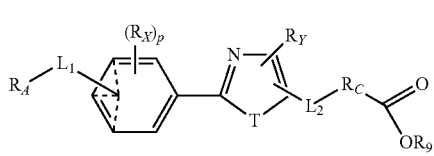

(Ib)

or a pharmaceutically acceptable salt solvate or prodrug, including all stereoisomers and tautomers thereof,
wherein, --- dotted line represents the variable attachment of -$L_1$-$R_A$ to the specified carbon atoms of the phenyl ring, $R_A$ is cycloalkyl, alkylaryl, aryl, heteroaryl or heterocycle;

$R_X$ and $R_Y$ are independently selected from H, halogen, —CN, —$OR_1$, —S(=O)$_mR_1$, —$OCOR_1$, —$SCOR_1$, —$NR_1R_2$, —$NR_1COR_2$, —$NR_1COOR_2$, —$NR_1SO_2R_2$, —$NR_1CONR_2$, —$COR_1$, —$COOR_1$, —$CONR_1R_2$, alkyl, alkenyl, alkynyl, cycloalkyl, alkylcycloalkyl, aryl, alkylaryl, alkylheteroaryl, heterocycle and heteroaryl;

$R_1$ and $R_2$ are independently selected from H, alkyl, alkenyl, alkynyl, cycloalkyl, alkylcycloalkyl, aryl, alkylaryl, alkylheteroaryl, heterocycle and heteroaryl;

$L_1$ is —$NR_3(CR_4R_5)_aNR_3$—, —$(CR_4R_5)_bNR_3$— or —$SO_2NH$;

$R_3$ is H, —$COR_1$, —$COOR_1$, —$CONR_1R_2$, alkyl, alkenyl, alkynyl, cycloalkyl or alkylcycloalkyl;

$R_4$ and $R_5$ are independently selected from H, —$OR_6$, —$COOR_6$, —$CONR_6R_7$, alkyl, alkenyl, alkynyl, cycloalkyl, alkylcycloalkyl, aryl, heteroaryl, alkylaryl, alkylheteroaryl and alkylheterocycle;

or $R_4$ and $R_5$ together are =O, =S or =$NR_8$;

$R_6$ and $R_7$ are independently selected from H, alkyl, cycloalkyl and heterocycle;

T is O or S;

$L_3$ is —C(=O)—$NR_Z$—, —C(=S)—$NR_Z$— or —C(=$NR_8$)—$NR_Z$—;

$R_Z$ is H, —$COR_1$, —$COOR_1$, —$CONR_1R_2$, alkyl, alkenyl, alkynyl, cycloalkyl or alkylcycloalkyl;

$R_8$ is H, —$OR_9$, —$COR_9$, —$COOR_9$, —$CONR_6R_7$, —$SO_2R_9$ or —$SO_2NR_6R_7$;

$R_9$ is H, alkyl, alkenyl, alkynyl, cycloalkyl, aryl, alkylcycloalkyl, alkylaryl, alkylheteroaryl, heterocycle or heteroaryl;

$R_C$ is —$(CR_{10}R_{11})_d$— or $(NR_{12})(CR_{10}R_{11})_d$;

d is an integer from 1 to 3;

or $R_c$, C(O), $OR_9$ and $L_3$; or $R_C$ and $L_3$; or $R_c$, C(O) and $OR_9$, together form a 5 to 7-membered cycloalkyl, aryl, heteroaryl or heterocycle;

$R_{10}$, $R_{11}$ and $R_{12}$ are independently selected from H and the groups alkyl, alkenyl, alkynyl, cycloalkyl, alkylcycloalkyl, aryl, alkylaryl, alkylheteroaryl, heterocycle and heteroaryl;

or $R_{12}$ and $R_{10}$ or $R_{11}$ together with the respective N and C atoms to which they are attached, form a 3 to 6 membered heterocyclic or heteroaryl ring;

or $R_{10}$ and $R_{11}$ of —$(CR_{10}R_{11})_c$ wherein c is the integer 1, together with the C atom to which they are attached form a 3 to 6-membered cycloalkyl ring;

a is an integer from 1 to 5;

b is 0 or an integer from 1 to 5;

m is 0 or the integer 1 or 2;

p is an integer from 1 to 4.

In yet another embodiment, the present invention provides a compound of formula (Ic)

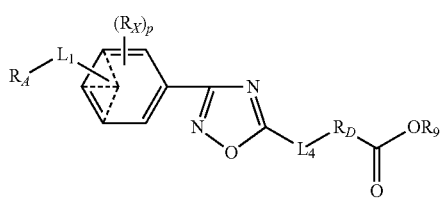

(Ic)

or a pharmaceutically acceptable salt, solvate or prodrug, including all stereoisomers and tautomers thereof,
wherein, --- dotted line represents the variable attachment of -$L_1$-$R_A$ to the specified carbon atoms of the phenyl ring, $R_A$ is cycloalkyl, alkylaryl, aryl, heteroaryl or heterocycle;

$R_X$ is selected from H, halogen, —CN, —$OR_1$, —S(=O)$_m$ $R_1$, —$OCOR_1$, —$SCOR_1$, —$NR_1R_2$, —$NR_1COR_2$, —$NR_1COOR_2$, —$NR_1SO_2R_2$, —$NR_1CONR_2$, —$COR_1$, —$COOR_1$, —$CONR_1R_2$, alkyl, alkenyl, alkynyl, cycloalkyl, alkylcycloalkyl, aryl, alkylaryl, alkylheteroaryl, heterocycle and heteroaryl;

$R_1$ and $R_2$ are independently selected from H, alkyl, alkenyl, alkynyl, cycloalkyl, alkylcycloalkyl, aryl, alkylaryl, alkylheteroaryl, heterocycle and heteroaryl;

$L_1$ is —$NR_3(CR_4R_5)_aNR_3$—, —$(CR_4R_5)_bNR_3$—, —$SO_2NH$— or —$SO_2NHCONH$—;

$R_3$ is H, —$COR_1$, —$COOR_1$, —$CONR_1R_2$, alkyl, alkenyl, alkynyl, cycloalkyl or alkylcycloalkyl;

$R_4$ and $R_5$ are independently selected from H, —$OR_6$, —$COOR_6$, —$CONR_6R_7$, alkyl, alkenyl, alkynyl, cycloalkyl, alkylcycloalkyl, aryl, heteroaryl, alkylaryl, alkylheteroaryl and alkylheterocycle;

or $R_4$ and $R_5$ together are =O, =S or =$NR_8$;

$R_6$ and $R_7$ are independently selected from H, alkyl, cycloalkyl and heterocycle;

$L_4$ is absent or is selected from —C(=O)—$NR_Z$—, —C(=S)—$NR_Z$—, —C(=$NR_8$)—$NR_Z$—, —C(=O)— and —C(=S)—;

$R_Z$ is H, $COR_1$, $COOR_1$, $CONR_1R_2$, alkyl, alkenyl, alkynyl, cycloalkyl or alkylcycloalkyl;

$R_8$ is H, $-OR_9$, $-COR_9$, $-COOR_9$, $-CONR_6R_7$, $-SO_2R_9$ or $-SO_2NR_6R_7$;

$R_9$ is H, alkyl, alkenyl, alkynyl, cycloalkyl, aryl, alkylcycloalkyl, alkylaryl, alkylheteroaryl, heterocycle or heteroaryl;

$R_D$ is $-(CR_{10}R_{11})_e-$ or $-(NR_{12})(CR_{10}R_{11})_e$; wherein e is an integer from 1 to 3;

or $R_D$, C(O), $OR_9$ and $L_4$; or $R_D$ and $L_4$; or $R_D$, C(O) and $OR_9$, together form a 5 to 7-membered cycloalkyl, aryl, heteroaryl or heterocycle;

$R_{10}$, $R_{11}$ and $R_{12}$ are independently selected from H and the groups alkyl, alkenyl, alkynyl, cycloalkyl, alkylcycloalkyl, aryl, alkylaryl, alkylheteroaryl, heterocycle and heteroaryl;

or $R_{12}$ and $R_{10}$ or $R_{11}$ together with the respective N and C atoms to which they are attached, form a 3 to 6 membered heterocyclic or heteroaryl ring;

or $R_{10}$ and $R_{11}$ of $-(CR_{10}R_{11})_c$ wherein c is the integer 1, together with the C atom to which they are attached form a 3 to 6-membered cycloalkyl ring;

a is an integer from 1 to 5;
b is 0 or an integer from 1 to 5;
m is 0 or an integer from 1 to 2;
p is an integer from 1 to 4.

In one embodiment of a compound of formula (I), the 5 to 7-membered ring formed from $R_B$, C(O), $OR_9$ and $L_2$; or $R_B$ and $L_2$ in formula (Iaa-Iaj), is a substituted 5-7-membered heterocyclic ring of the formula

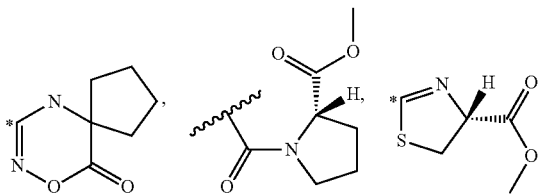

and the like.

In one aspect of the present invention, there is provided a compound of formula (I), (Iaa), (Iab), (Iac), (Iad), (Iae), (Iaf), (Iag), (Iah), (Iai), (Iaj), (Ib) or (Ic) above for use in the prevention or treatment of diseases or disorders mediated by DGAT1.

Representative compounds of the present invention include any of the following compounds or their pharmaceutically acceptable salts, solvates and/or prodrugs, as well as stereoisomers and tautomers thereof. However, the present invention is not limited to these compounds alone.

(S)-2-({3-[4-(6-Fluoro-benzothiazol-2-ylamino)-phenyl]-isoxazole-5-carbonyl}-amino)-3-methyl-butyric acid methyl ester;

(S)-2-({3-[4-(6-Fluoro-benzothiazol-2-ylamino)-phenyl]-isoxazole-5-carbothioyl}-amino)-3-methyl-butyric acid methyl ester;

(S)-2-({3-[4-(6-Fluoro-benzothiazol-2-ylamino)-phenyl]-N-hydroxy-isoxazole-5-carboximidoyl}-amino)-3-methyl-butyric acid methyl ester;

(S)-2-({3-[4-(6-Fluoro-benzothiazol-2-ylamino)-phenyl]-N-hydroxy-isoxazole-5-carboximidoyl}-amino)-3-methyl-butyric acid;

(S)-2-({3-[4-(6-Fluoro-benzothiazol-2-ylamino)-phenyl]-isoxazole-5-carbonyl}-amino)-3-hydroxy-propionic acid methyl ester;

(S)-2-({3-[4-(6-Fluoro-benzothiazol-2-ylamino)-phenyl]-isoxazole-5-carbonyl}-amino)-3-hydroxy-propionic acid;

(S)-2-{3-[4-(6-Fluoro-benzothiazol-2-ylamino)-phenyl]-isoxazol-5-yl}-4,5-dihydro-thiazole-4-carboxylic acid methyl ester;

(S)-2-({3-[4-(6-Fluoro-benzothiazol-2-ylamino)-phenyl]-isoxazole-5-carbonyl}-amino)-3-methoxy-propionic acid methyl ester;

(S)-2-({3-[4-(6-Fluoro-benzothiazol-2-ylamino)-phenyl]-isoxazole-5-carbonyl}-amino)-3-methoxy-propionic acid;

(S)-2-({3-[4-(6-Fluoro-benzothiazol-2-ylamino)-phenyl]-isoxazole-5-carbothioyl}-amino)-3-methoxy-propionic acid methyl ester;

(S)-2-({3-[4-(6-Fluoro-benzothiazol-2-ylamino)-phenyl]-isoxazole-5-carbothioyl}-amino)-3-methoxy-propionic acid;

(S)-2-({3-[4-(6-Fluoro-benzothiazol-2-ylamino)-phenyl]-N-hydroxy-isoxazole-5-carboximidoyl}-amino)-3-methoxy-propionic acid methyl ester;

(S)-2-({3-[4-(6-Fluoro-benzothiazol-2-ylamino)-phenyl]-N-hydroxy-isoxazole-5-carboximidoyl}-amino)-3-methoxy-propionic acid;

(S)-1-{3-[4-(6-Fluoro-benzothiazol-2-ylamino)-phenyl]-isoxazole-5-carbonyl}-pyrrolidine-2-carboxylic acid methyl ester;

(S)-1-{3-[4-(6-Fluoro-benzothiazol-2-ylamino)-phenyl]-isoxazole-5-carbonyl}-pyrrolidine-2-carboxylic acid;

(S)-2-({3-[3-(6-Fluoro-benzothiazol-2-ylamino)-phenyl]-isoxazole-5-carbonyl}-amino)-3-methyl-butyric acid methyl ester;

(S)-2-({3-[3-(6-Fluoro-benzothiazol-2-ylamino)-phenyl]-isoxazole-5-carbonyl}-amino)-3-methyl-butyric acid;

(S)-2-({3-[3-(6-Fluoro-benzothiazol-2-ylamino)-phenyl]-isoxazole-5-carbothioyl}-amino)-3-methyl-butyric acid methyl ester;

(S)-2-({3-[3-(6-Fluoro-benzothiazol-2-ylamino)-phenyl]-isoxazole-5-carbothioyl}-amino)-3-methyl-butyric acid;

(S)-2-({3-[3-(6-Fluoro-benzothiazol-2-ylamino)-phenyl]-N-hydroxy-isoxazole-5-carboximidoyl}-amino)-3-methyl-butyric acid methyl ester;

(S)-2-({3-[3-(6-Fluoro-benzothiazol-2-ylamino)-phenyl]-N-hydroxy-isoxazole-5-carboximidoyl}-amino)-3-methyl-butyric acid;

(S)-2-({3-[3-(6-Fluoro-benzothiazol-2-ylamino)-phenyl]-isoxazole-5-carbonyl}-amino)-3-methoxy-propionic acid methyl ester;

(S)-2-({3-[3-(6-Fluoro-benzothiazol-2-ylamino)-phenyl]-isoxazole-5-carbonyl}-amino)-3-methoxy-propionic acid;

(S)-2-({3-[3-(6-Fluoro-benzothiazol-2-ylamino)-phenyl]-isoxazole-5-carbothioyl}-amino)-3-methoxy-propionic acid methyl ester;

(S)-2-({3-[3-(6-Fluoro-benzothiazol-2-ylamino)-phenyl]-isoxazole-5-carbothioyl}-amino)-3-methoxy-propionic acid;

(S)-2-({3-[3-(6-Fluoro-benzothiazol-2-ylamino)-phenyl]-N-hydroxy-isoxazole-5-carboximidoyl}-amino)-3-methoxy-propionic acid methyl ester;

(S)-2-({3-[3-(6-Fluoro-benzothiazol-2-ylamino)-phenyl]-N-hydroxy-isoxazole-5-carboximidoyl}-amino)-3-methoxy-propionic acid;

(S)-1-{3-[3-(6-Fluoro-benzothiazol-2-ylamino)-phenyl]-isoxazole-5-carbonyl}-pyrrolidine-2-carboxylic acid methyl ester;

(S)-1-{3-[3-(6-Fluoro-benzothiazol-2-ylamino)-phenyl]-isoxazole-5-carbonyl}-pyrrolidine-2-carboxylic acid;

(S)-1-{3-[3-(6-Fluoro-benzothiazol-2-ylamino)-phenyl]-isoxazole-5-carbothioyl}-pyrrolidine-2-carboxylic acid methyl ester;
(S)-1-{3-[3-(6-Fluoro-benzothiazol-2-ylamino)-phenyl]-isoxazole-5-carbothioyl}-pyrrolidine-2-carboxylic acid;
(R)-2-({3-[4-(6-Fluoro-benzothiazol-2-ylamino)-phenyl]-isoxazole-5-carbonyl}-amino)-3-methyl-butyric acid methyl ester;
(R)-2-({3-[4-(6-Fluoro-benzothiazol-2-ylamino)-phenyl]-isoxazole-5-carbothioyl}-amino)-3-methyl-butyric acid methyl ester;
(R)-2-({3-[4-(6-Fluoro-benzothiazol-2-ylamino)-phenyl]-N-hydroxy-isoxazole-5-carboximidoyl}-amino)-3-methyl-butyric acid methyl ester;
(R)-2-({3-[4-(6-Fluoro-benzothiazol-2-ylamino)-phenyl]-N-hydroxy-isoxazole-5-carboximidoyl}-amino)-3-methyl-butyric acid;
(R)-2-({3-[4-(6-Fluoro-benzothiazol-2-ylamino)-phenyl] isoxazole-5-carbonyl}-amino)-3-methyl-butyric acid;
(R)-2-({3-[4-(6-Fluoro-benzothiazol-2-ylamino)-phenyl]-isoxazole-5-carbothioyl}-amino)-3-methyl-butyric acid;
(S)-2-({3-[4-(6-Fluoro-benzothiazol-2-ylamino)-phenyl]-isoxazole-5-carbonyl}-amino)-3-methyl-butyric acid;
(S)-2-({3-[4-(6-Fluoro-benzothiazol-2-ylamino)-phenyl]-isoxazole-5-carbothioyl}-amino)-3-methyl-butyric acid;
(S)-2-({3-[4-(6-Fluoro-benzothiazol-2-ylamino)-phenyl]-isoxazole-5-carbonyl}-amino)-4-methyl-pentanoic acid methyl ester;
(S)-2-({3-[4-(6-Fluoro-benzothiazol-2-ylamino)-phenyl]-isoxazole-5-carbonyl}-amino)-4-methyl-pentanoic acid;
(S)-2-({3-[4-(6-Fluoro-benzothiazol-2-ylamino)-phenyl]-isoxazole-5-carbothioyl}-amino)-4-methyl-pentanoic acid methyl ester;
(S)-2-({3-[4-(6-Fluoro-benzothiazol-2-ylamino)-phenyl]-isoxazole-5-carbothioyl}-amino)-4-methyl-pentanoic acid;
(S)-2-({3-[4-(6-Fluoro-benzothiazol-2-ylamino)-phenyl]-N-hydroxy-isoxazole-5-carboximidoyl}-amino)-4-methyl-pentanoic acid methyl ester;
(S)-2-({3-[4-(6-Fluoro-benzothiazol-2-ylamino)-phenyl]-N-hydroxy-isoxazole-5-carboximidoyl}-amino)-4-methyl-pentanoic acid;
(S)-({3-[4-(6-Fluoro-benzothiazol-2-ylamino)-phenyl]-isoxazole-5-carbonyl}-amino)-phenyl-acetic acid methyl ester;
(S)-({3-[4-(6-Fluoro-benzothiazol-2-ylamino)-phenyl]-isoxazole-5-carbonyl}-amino)-phenyl-acetic acid;
(S)-({3-[4-(6-Fluoro-benzothiazol-2-ylamino)-phenyl]-isoxazole-5-carbothioyl}-amino)-phenyl-acetic acid methyl ester;
(S)-({3-[4-(6-Fluoro-benzothiazol-2-ylamino)-phenyl]-isoxazole-5-carbothioyl}-amino)-phenyl-acetic acid;
(S)-({3-[4-(6-Fluoro-benzothiazol-2-ylamino)-phenyl]-N-hydroxy-isoxazole-5-carboximidoyl}-amino)-phenyl-acetic acid methyl ester;
(S)-({3-[4-(6-Fluoro-benzothiazol-2-ylamino)-phenyl]-N-hydroxy-isoxazole-5-carboximidoyl}-amino)-phenyl-acetic acid;
({3-[4-(6-Fluoro-benzothiazol-2-ylamino)-phenyl]-isoxazole-5-carbonyl}-amino)-acetic acid methyl ester;
({3-[4-(6-Fluoro-benzothiazol-2-ylamino)-phenyl]-isoxazole-5-carbonyl}-amino)-acetic acid;
({3-[4-(6-Fluoro-benzothiazol-2-ylamino)-phenyl]-isoxazole-5-carbothioyl}-amino)-acetic acid methyl ester;
({3-[4-(6-Fluoro-benzothiazol-2-ylamino)-phenyl]-isoxazole-5-carbothioyl}-amino)-acetic acid;
1-({3-[4-(6-Fluoro-benzothiazol-2-ylamino)-phenyl]-isoxazole-5-carbonyl}-amino)-cyclopentanecarboxylic acid methyl ester;
1-({3-[4-(6-Fluoro-benzothiazol-2-ylamino)-phenyl]-isoxazole-5-carbonyl}-amino)-cyclopentanecarboxylic acid;
1-({3-[4-(6-Fluoro-benzothiazol-2-ylamino)-phenyl]-isoxazole-5-carbothioyl}-amino)-cyclopentanecarboxylic acid methyl ester;
1-({3-[4-(6-Fluoro-benzothiazol-2-ylamino)-phenyl]-isoxazole-5-carbothioyl}-amino)-cyclopentanecarboxylic acid;
1-({3-[4-(6-Fluoro-benzothiazol-2-ylamino)-phenyl]-N-hydroxy-isoxazole-5-carboximidoyl}-amino)-cyclopentanecarboxylic acid;
7-{3-[4-(6-Fluoro-benzothiazol-2-ylamino)-phenyl]-isoxazole-5-yl}-9-oxa-6,8-diaza-spiro[4,5]dec-7-en-10-one;
(S)-2-({3-[4-(6-Fluoro-benzothiazol-2-ylamino)-phenyl]-5-phenyl-isoxazole-4-carbonyl}-amino)-3-methyl-butyric acid methyl ester;
(S)-2-({3-[4-(6-Fluoro-benzothiazol-2-ylamino)-phenyl]-5-phenyl-isoxazole-4-carbonyl}-amino)-3-methyl-butyric acid;
(S)-2-({3-[4-(6-Fluoro-benzothiazol-2-ylamino)-phenyl]-5-phenyl-isoxazole-4-carbonyl}-amino)-3-methoxy-propionic acid methyl ester;
(S)-2-({3-[4-(6-Fluoro-benzothiazol-2-ylamino)-phenyl]-5-phenyl-isoxazole-4-carbonyl}-amino)-3-methoxy-propionic acid;
(S)-2-({3-[4-(6-Fluoro-benzothiazol-2-ylamino)-phenyl]-5-phenyl-isoxazole-4-carbothioyl}-amino)-3-methyl-butyric acid methyl ester;
(S)-2-({3-[4-(6-Fluoro-benzothiazol-2-ylamino)-phenyl]-5-phenyl-isoxazole-4-carbothioyl}-amino)-3-methyl-butyric acid;
(S)-2-({3-[4-(6-Fluoro-benzothiazol-2-ylamino)-phenyl]-5-phenyl-isoxazole-4-carbothioyl}-amino)-3-methoxy-propionic acid methyl ester;
(S)-2-({3-[4-(6-Fluoro-benzthiazol-2-ylamino)-phenyl]-5-phenyl-isoxazole-4-carbothioyl}-amino)-3-methoxy-propionic acid;
(S)-3-Methyl-2-({3-[4-(3-phenyl-ureido)-phenyl]-isoxazole-5-carbonyl}-amino)-butyric acid methyl ester;
(S)-3-Methyl-2-({3-[4-(3-phenyl-ureido)-phenyl]-isoxazole-5-carbonyl}-amino)-butyric acid;
(S)-3-Methyl-2-({3-[4-(3-phenyl-ureido)-phenyl]-isoxazole-5-carbonyl}-amino)-pentanoic acid methyl ester;
(S)-3-Methyl-2-({3-[4-(3-phenyl-ureido)-phenyl]-isoxazole-5-carbonyl}-amino)-pentanoic acid;
(S)-2-({3-[4-(3-cyclohexyl-ureido)-phenyl]-isoxazole-5-carbonyl}-amino)-3-methyl-butyric acid methyl ester;
(S)-2-({3-[4-(3-cyclohexyl-ureido)-phenyl]-isoxazole-5-carbonyl}-amino)-3-methyl-butyric acid;
(S)-2-({3-[4-(3-cyclohexyl-ureido)-phenyl]-isoxazole-5-carbonyl}-amino)-4-methyl-pentanoic acid methyl ester;
(S)-2-({3-[4-(3-cyclohexyl-ureido)-phenyl]-isoxazole-5-carbonyl}-amino)-4-methyl-pentanoic acid;
(S)-2-[(3-{4-[3-(4-Fluoro-phenyl)-ureido]-phenyl}-isoxazole-5-carbonyl)-amino]-3-methyl-butyric acid methyl ester;
(S)-2-[(3-{4-[3-(4-Fluoro-phenyl)-ureido]-phenyl}-isoxazole-5-carbonyl)-amino]-3-methyl-butyric acid;
(S)-2-[(3-{4-[3-(4-Fluoro-phenyl)-ureido]-phenyl}-isoxazole-5-carbonyl)-amino]-4-methyl-pentanoic acid methyl ester;
(S)-2-[(3-{4-[3-(4-Fluoro-phenyl)-ureido]-phenyl}-isoxazole-5-carbonyl)-amino]-4-methyl-pentanoic acid;

(S)-3-Methyl-2-({4-phenyl-3-[4-(3-phenyl-ureido)-phenyl]-isoxazole-5-carbonyl}-amino)-butyric acid methyl ester;
(S)-3-Methyl-2-({4-phenyl-3-[4-(3-phenyl-ureido)-phenyl]-isoxazole-5-carbonyl}-amino)-butyric acid;
(S)-4-Methyl-2-({4-phenyl-3-[4-(3-phenyl-ureido)-phenyl]-isoxazole-5-carbonyl}-amino)-pentanoic acid methyl ester;
(S)-4-Methyl-2-({4-phenyl-3-[4-(3-phenyl-ureido)-phenyl]-isoxazole-5-carbonyl}-amino)-pentanoic acid;
(S)-2-[(3-{4-[3-(4-Fluoro-phenyl)-ureido]-phenyl}-4-phenyl-isoxazole-5-carbonyl)-amino]-3-methyl-butyric acid methyl ester;
(S)-2-[(3-{4-[3-(4-Fluoro-phenyl)-ureido]-phenyl}-4-phenyl-isoxazole-5-carbonyl)-amino]-3-methyl-butyric acid;
(S)-2-({3-[4-(6-Fluoro-benzothiazol-2-ylamino)-phenyl]-4-phenyl-isoxazole-5-carbonyl}-amino)-4-methyl-pentanoic acid methyl ester;
(S)-2-({3-[4-(6-Fluoro-benzothiazol-2-ylamino)-phenyl]-4-phenyl-isoxazole-5-carbonyl}-amino)-4-methyl-pentanoic acid;
(S)-2-[3-{3-Fluoro-4-[3-(4-fluoro-phenyl)-ureido]-phenyl}-isoxazole-5-carbonyl)-amino]-3-methyl-butyric acid methyl ester;
(S)-2-[3-{3-Fluoro-4-[3-(4-fluoro-phenyl)-ureido]-phenyl}-isoxazole-5-carbonyl)-amino]-3-methyl-butyric acid;
2-(3-(4-(3-(2,6-Difluorophenyl)ureido)-3-methylphenyl) isoxazole-5-carboxamido)-3-methylbutanoic acid;
Methyl 2-(3-(4-(3-(2,6-difluorophenyl)ureido)-3-methylphenyl)isoxazole-5-carboxamido)-4-methylpentanoate;
2-(3-(4-(3-(2,6-Difluorophenyl)ureido)-3-methylphenyl) isoxazole-5-carboxamido)-4-methylpentanoic acid;
Methyl 2-(3-(4-(3-(2,6-difluorophenyl)ureido)-3-methylphenyl)isoxazole-5-carboxamido)propanoate;
2-(3-(4-(3-(2,6-Difluorophenyl)ureido)-3-methylphenyl) isoxazole-5-carboxamido)propanoic acid;
2-(3-(4-(3-(2,4-Difluorophenyl)ureido)-3-methylphenyl) isoxazole-5-carboxamido)-3-methylbutanoic acid;
2-(3-(4-(3-(2,4-Difluorophenyl)ureido)phenyl)-1,2,4-oxadiazole-5-carboxamido)-3-methylbutanoic acid;
2-[(3-{4-[3-(2-Fluoro-phenyl)ureido]-phenyl}-isoxazole-5-carbonyl)-amino]-3-methyl-butyric acid methyl ester;
2-(3-(4-(3-(2-Fluorophenyl)ureido)phenyl)isoxazole-5-carboxamido)-3-methylbutanoic acid;
Methyl 2-(3-(4-(3-benzylureido)phenyl)isoxazole-5-carboxamido)-3-methylbutanoate;
2-(3-(4-(3-Benzylureido)phenyl)isoxazole-5-carboxamido)-3-methylbutanoic acid;
Methyl 2-(3-(4-(3-benzylureido)phenyl)isoxazole-5-carboxamido)-4-methylpentanoate;
2-(3-(4-(3-Benzylureido)phenyl)isoxazole-5-carboxamido)-4-methyl pentanoic acid;
Methyl 2-(3-(4-(3-(2,4-difluorophenyl)ureido)phenyl)isoxazole-5-carboxamido)-3-methylbutanoate;
2-(3-(4-(3-(2,4-Difluorophenyl)ureido)phenyl)isoxazole-5-carboxamido)-3-methylbutanoic acid;
Methyl 2-(3-(4-(3-(2,4-difluorophenyl)ureido)phenyl)isoxazole-5-carboxamido)-4-methylpentanoate;
2-(3-(4-(3-(2,4-Difluorophenyl)ureido)phenyl)isoxazole-5-carboxamido)-4-methylpentanoic acid;
Methyl 2-(3-(4-(3-(4-fluorophenyl)ureido)phenyl)isoxazole-5-carboxamido)propanoate;
2-(3-(4-(3-(4-Fluorophenyl)ureido)phenyl)isoxazole-5-carboxamido)propanoic acid;
Methyl 2-(3-(4-(3-(4-fluorophenyl)ureido)phenyl)isoxazole-5-carboxamido)-2-methylpropanoate;
2-(3-(4-(3-(4-fluorophenyl)ureido)phenyl)isoxazole-5-carboxamido-2-methylpropanoic acid;
Methyl 1-(3-(4-(3-(4-fluorophenyl)ureido)phenyl)isoxazole-5-carboxamido) cyclopentanecarboxylate;
1-(3-(4-(3-(4-Fluorophenyl)ureido)phenyl)isoxazole-5-carboxamido) cyclopentanecarboxylic acid;
Methyl 2-methyl-2-(3-(4-(3-phenylureido)phenyl)isoxazole-5-carboxamido)propanoate;
2-methyl-2-(3-(4-(3-phenylureido)phenyl)isoxazole-5-carboxamido) propanoic acid;
Methyl 2-(3-(4-(3-(2,6-difluorophenyl)ureido)phenyl)isoxazole-5-carboxamido)-3-methylbutanoate;
2-(3-(4-(3-(2,6-difluorophenyl)ureido)phenyl)isoxazole-5-carboxamido)-3-methylbutanoic acid;
Methyl 3-methyl-2-(3-(4-(3-p-tolylureido)phenyl)isoxazole-5-carboxamido) butanoate;
3-Methyl-2-(3-(4-(3-p-tolylureido)phenyl)isoxazole-5-carboxamido) butanoic acid;
Methyl 2-(3-(4-(3-(4-methoxyphenyl)ureido)phenyl)isoxazole-5-carboxamido)-3-methylbutanoate;
2-(3-(4-(3-(4-methoxyphenyl)ureido)phenyl)isoxazole-5-carboxamido)-3-methylbutanoic acid;
(S)-methyl 2-(3-(4-(3-(3,4-difluorophenyl)ureido)phenyl) isoxazole-5-carboxamido)-3-methylbutanoate;
(S)-2-(3-(4-(3-(3,4-difluorophenyl)ureido)phenyl)isoxazole-5-carboxamido)-3-methylbutanoic acid;
Methyl 2-(3-(5-(3-(4-fluorophenyl)ureido)-2-methylphenyl) isoxazole-5-carboxamido)-4-methylpentanoate;
2-(3-(5-(3-(4-fluorophenyl)ureido)-2-methylphenyl)isoxazole-5-carboxamido)-4-methylpentanoic acid;
Methyl 2-(3-(4-(3-(4-fluorophenyl)ureido)-2-methylphenyl) isoxazole-5-carboxamido)-3-methylbutanoate;
2-(3-(4-(3-(4-fluorophenyl)ureido)-2-methylphenyl)isoxazole-5-carboxamido)-3-methylbutanoic acid;
Methyl 2-(3-(4-(3-(2-fluorophenyl)ureido)-2-methylphenyl) isoxazole-5-carboxamido)-3-methylbutanoate;
2-(3-(4-(3-(2-Fluorophenyl)ureido)-2-methylphenyl)isoxazole-5-carboxamido)-3-methylbutanoic acid;
Methyl 2-(3-(4-(3-(2,4-difluorophenyl)ureido)-2-methylphenyl)isoxazole-5-carboxamido)-3-methylbutanoate;
2-(3-(4-(3-(2,4-difluorophenyl)ureido)-2-methylphenyl) isoxazole-5-carboxamido)-3-methylbutanoic acid;
Methyl 2-(3-(4-(3-(2,4-difluorophenyl)ureido)-2-methylphenyl)isoxazole-5-carboxamido)-4-methylpentanoate;
2-(3-(4-(3-(2,4-difluorophenyl)ureido)-2-methylphenyl) isoxazole-5-carboxamido)-4-methylpentanoic acid;
(S)-Methyl 2-(3-(4-(3-(2,4-Difluorophenyl)ureido)-2-fluorophenyl)isoxazole-5-carboxamido)-3-methylbutanoate;
(S)-2-(3-(4-(3-(2,4-difluorophenyl)ureido)-2-fluorophenyl) isoxazole-5-carboxamido)-3-methylbutanoic acid;
(S)-methyl 2-(3-(2-fluoro-4-(3-(2-fluorophenyl)ureido)phenyl)isoxazole-5-carboxamido)-3-methylbutanoate;
(S)-2-(3-(2-Fluoro-4-(3-(2-fluorophenyl)ureido)phenyl) isoxazole-5-carboxamido)-3-methylbutanoic acid;
(S)-Methyl 2-(3-(2-fluoro-4-(3-(4-fluorophenyl)ureido)phenyl)isoxazole-5-carboxamido)-3-methylbutanoate;
(S)-2-(3-(2-fluoro-4-(3-(4-fluorophenyl)ureido)phenyl) isoxazole-5-carboxamido)-3-methylbutanoic acid;
Methyl 2-(3-(3-fluoro-4-(3-(2-fluorophenyl)ureido)phenyl) isoxazole-5-carboxamido)-3-methylbutanoate;
2-(3-(3-fluoro-4-(3-(2-fluorophenyl)ureido)phenyl)isoxazole-5-carboxamido)-3-methylbutanoic acid;
Methyl 2-(3-(4-(3-(2,4-difluorophenyl)ureido)-3-fluorophenyl)isoxazole-5-carboxamido)-3-methylbutanoate;
2-(3-(4-(3-(2,4-Difluorophenyl)ureido)-3-fluorophenyl) isoxazole-5-carboxamido)-3-methylbutanoic acid;
Methyl 2-(3-(4-(3-(3-fluorophenyl)ureido)phenyl)isoxazole-5-carboxamido)-3-methylbutanoate;

2-(3-(4-(3-(3-fluorophenyl)ureido)phenyl)isoxazole-5-carboxamido)-3-methylbutanoic acid;
Methyl 3-methyl-2-(3-(4-(3-o-tolylureido)phenyl)isoxazole-5-carboxamido) butanoate;
3-methyl-2-(3-(4-(3-o-tolylureido)phenyl)isoxazole-5-carboxamido) butanoic acid;
Methyl 2-(3-(4-(3-(2-fluoro-5-methylphenyl)ureido)phenyl) isoxazole-5-carboxamido)-3-methylbutanoate;
2-(3-(4-(3-(2-fluoro-5-methylphenyl)ureido)phenyl)isoxazole-5-carboxamido)-3-methylbutanoic acid;
Methyl 2-(3-(4-(3-(4-butylphenyl) ureido)phenyl)isoxazole-5-carboxamido)-3-methylbutanoate;
2-(3-(4-(3-(4-butylphenyl)ureido)phenyl)isoxazole-5-carboxamido)-3-methylbutanoic acid;
Methyl 2-(3-(4-(3-(3,5-difluorophenyl)ureido)phenyl)isoxazole-5-carboxamido)-3-methylbutanoate;
2-(3-(4-(3-(3,5-difluorophenyl)ureido)phenyl)isoxazole-5-carboxamido)-3-methylbutanoic acid;
Methyl 2-(3-(4-(3-(3-chloro-4-fluorophenyl)ureido)phenyl) isoxazole-5-carboxamido)-3-methylbutanoate;
2-(3-(4-(3-(3-chloro-4-fluorophenyl)ureido)phenyl)isoxazole-5-carboxamido)-3-methylbutanoic acid;
(S)-methyl 3-methyl-2-(3-(4-(3-(2-(trifluoromethyl)phenyl) ureido)phenyl)isoxazole-5-carboxamido)butanoate;
(S)-3-methyl-2-(3-(4-(3-(2-(trifluoromethyl)phenyl)ureido) phenyl)isoxazole-5-carboxamido)butanoic acid;
(S)-Methyl 2-(3-(4-(3-(2,5-dimethoxyphenyl)ureido)phenyl)isoxazole-5-carboxamido)-3-methylbutanoate;
(S)-2-(3-(4-(3-(2,5-Dimethoxyphenyl)ureido)phenyl)isoxazole-5-carboxamido)-3-methylbutanoic acid;
(S)-2-(3-(4-(3-(3,5-difluorophenyl)ureido)phenyl)isoxazole-5-carboxamido)-3-methylbutanoic acid;
(S)-methyl 2-(3-(4-(3-(2,4-dimethoxyphenyl)ureido)phenyl) isoxazole-5-carboxamido)-3-methylbutanoate;
(S)-2-(3-(4-(3-(2,4-dimethoxyphenyl)ureido)phenyl)isoxazole-5-carboxamido)-3-methylbutanoic acid;
(S)-methyl 2-(3-(4-(3-(2,4-dimethylphenyl)ureido)phenyl) isoxazole-5-carboxamido)-3-methylbutanoate;
(S)-2-(3-(4-(3-(2,4-dimethylphenyl)ureido)phenyl)isoxazole-5-carboxamido)-3-methylbutanoic acid;
(S)-methyl 2-(3-(4-(3-(3,4-dimethylphenyl)ureido)phenyl) isoxazole-5-carboxamido)-3-methylbutanoate;
(S)-2-(3-(4-(3-(3,4-dimethylphenyl)ureido)phenyl)isoxazole-5-carboxamido)-3-methylbutanoic acid;
(S)-Methyl 2-(3-(4-(3-(2-chloro-6-methylphenyl)ureido) phenyl)isoxazole-5-carboxamido)-3-methylbutanoate;
(S)-2-(3-(4-(3-(2-Chloro-6-methylphenyl)ureido)phenyl) isoxazole-5-carboxamido)-3-methylbutanoic acid;
(S)-Methyl 2-(3-(4-(3-benzo[d][1,3]dioxol-5-ylureido)phenyl)isoxazole-5-carboxamido)-3-methylbutanoate;
(S)-2-(3-(4-(3-benzo[d][1,3]dioxol-5-ylureido)phenyl)isoxazole-5-carboxamido)-3-methylbutanoic acid;
(S)-Methyl 2-(3-(4-(3-(4-chlorophenyl)ureido)phenyl)isoxazole-5-carboxamido)-3-methylbutanoate;
(S)-2-(3-(4-(3-(4-Chlorophenyl)ureido)phenyl)isoxazole-5-carboxamido)-3-methylbutanoic acid;
(S)-Methyl 2-(3-(4-(3-(2,3-dihydro-1H-inden-5-yl)ureido) phenyl)isoxazole-5-carboxamido)-3-methylbutanoate;
(S)-2-(3-(4-(3-(2,3-Dihydro-1H-inden-5-yl)ureido)phenyl) isoxazole-5-carboxamido)-3-methylbutanoic acid;
(S)-Methyl 2-(3-(4-(3-(3-chloro-2-fluorophenyl)ureido)phenyl)isoxazole-5-carboxamido)-3-methylbutanoate;
(S)-2-(3-(4-(3-(3-Chloro-2-fluorophenyl)ureido)phenyl) isoxazole-5-carboxamido)-3-methylbutanoic acid;
(S)-Methyl 2-(3-(4-(3-(2-methoxyphenyl)ureido)phenyl) isoxazole-5-carboxamido)-3-methylbutanoate;
(S)-2-(3-(4-(3-(2-Methoxyphenyl)ureido)phenyl)isoxazole-5-carboxamido)-3-methylbutanoic acid;
(S)-Methyl 3-methyl-2-(3-(4-(3-(4-(trifluoromethoxy)phenyl)ureido)phenyl)isoxazole-5-carboxamido)butanoate;
(S)-3-Methyl-2-(3-(4-(3-(4-(trifluoromethoxy)phenyl)ureido)phenyl)isoxazole-5-carboxamido)butanoic acid;
(S)-Methyl 2-(3-(4-(3-(2-chloro-5-methylphenyl)ureido) phenyl)isoxazole-5-carboxamido)-3-methylbutanoate;
(S)-2-(3-(4-(3-(2-chloro-5-methylphenyl)ureido)phenyl) isoxazole-5-carboxamido)-3-methylbutanoic acid;
(S)-Methyl 3-methyl-2-(3-(4-(3-(2,3,4-trifluorophenyl)ureido)phenyl)isoxazole-5-carboxamido)butanoate;
(S)-3-Methyl-2-(3-(4-(3-(2,3,4-trifluorophenyl)ureido)phenyl)isoxazole-5-carboxamido)butanoic acid;
(S)-Methyl 2-(3-(4-(3-(4-chloro-2-fluorophenyl)ureido)phenyl)isoxazole-5-carboxamido)-3-methylbutanoate;
(S)-2-(3-(4-(3-(4-Chloro-2-fluorophenyl)ureido)phenyl) isoxazole-5-carboxamido)-3-methylbutanoic acid;
(S)-Methyl 2-(3-(4-(3-(5-chloro-2-methylphenyl)ureido) phenyl)isoxazole-5-carboxamido)-3-methylbutanoate;
(S)-2-(3-(4-(3-(5-chloro-2-methylphenyl)ureido)phenyl) isoxazole-5-carboxamido)-3-methylbutanoic acid;
(S)-Methyl 3-methyl-2-(3-(4-(3-(4-(methylthio)phenyl)ureido)phenyl)isoxazole-5-carboxamido)butanoate;
(S)-3-Methyl-2-(3-(4-(3-(4-(methylthio)phenyl)ureido)phenyl)isoxazole-5-carboxamido) butanoic acid;
(S)-Methyl 2-(3-(4-(3-(2,5-difluorophenyl)ureido)phenyl) isoxazole-5-carboxamido)-3-methylbutanoate;
(S)-2-(3-(4-(3-(2,5-Difluorophenyl)ureido)phenyl)isoxazole-5-carboxamido)-3-methylbutanoic acid;
(S)-Methyl 2-(3-(4-(3-(4-chloro-2-phenoxyphenyl)ureido) phenyl)isoxazole-5-carboxamido)-3-methylbutanoate;
(S)-2-(3-(4-(3-(4-chloro-2-phenoxyphenyl)ureido)phenyl) isoxazole-5-carboxamido-3-methylbutanoic acid;
(S)-Methyl 3-methyl-2-(3-(4-(3-(2-(trifluoromethoxy)phenyl) ureido)phenyl)isoxazole-5-carboxamido)butanoate;
(S)-3-Methyl-2-(3-(4-(3-(2-(trifluoromethoxy)phenyl)ureido)phenyl)isoxazole-5-carboxamido)butanoic acid;
(S)-Methyl 2-(3-(4-(3-(3,5-dimethylphenyl)ureido)phenyl) isoxazole-5-carboxamido)-3-methylbutanoate;
(S)-2-(3-(4-(3-(3,5-dimethylphenyl)ureido)phenyl)isoxazole-5-carboxamido)-3-methylbutanoic acid;
(S)-Methyl 2-(3-(4-(3-(6-chloropyridin-3-yl)ureido)phenyl) isoxazole-5-carboxamido)-3-methylbutanoate;
(S)-2-(3-(4-(3-(6-Chloropyridin-3-yl)ureido)phenyl)isoxazole-5-carboxamido)-3-methylbutanoic acid;
(S)-Methyl 2-(3-(4-(3-(3-chlorophenyl)ureido)phenyl)isoxazole-5-carboxamido)-3-methylbutanoate;
(S)-2-(3-(4-(3-(3-Chlorophenyl)ureido)phenyl)isoxazole-5-carboxamido)-3-methylbutanoic acid;
(S)-Methyl 2-(3-(4-(3-(2-chloro-5-(trifluoromethyl)phenyl) ureido)phenyl)isoxazole-5-carboxamido)-3-methylbutanoate;
(S)-2-(3-(4-(3-(2-chloro-5-(trifluoromethyl)phenyl)ureido) phenyl)isoxazole-5-carboxamido)-3-methylbutanoic acid;
(S)-Methyl 2-(3-(4-(3-(4-fluoro-2-(trifluoromethyl)phenyl) ureido)phenyl)isoxazole-5-carboxamido)-3-methylbutanoate;
(S)-2-(3-(4-(3-(4-Fluoro-2-(trifluoromethyl)phenyl)ureido) phenyl)isoxazole-5-carboxamide)-3-methylbutanoic acid;
(S)-Methyl 2-(3-(4-(3-(4-chloro-2-(trifluoromethyl)phenyl) ureido)phenyl)isoxazole-5-carboxamido)-3-methylbutanoate;
(S)-2-(3-(4-(3-(4-Chloro-2-(trifluoromethyl)phenyl)ureido) phenyl)isoxazole-5-carboxamido)-3-methylbutanoic acid;
(R)-Methyl 2-(3-(4-(3-(2-cyanophenyl)ureido)phenyl)isoxazole-5-carboxamido)-3-methylbutanoate;

(R)-2-(3-(4-(3-(3-Cyanophenyl)ureido)phenyl)isoxazole-5-carboxamido)-3-methylbutanoic acid;
(R)-Methyl 2-(3-(4-(3-(4-cyanophenyl)ureido)phenyl)isoxazole-5-carboxamido)-3-methylbutanoate;
(R)-2-(3-(4-(3-(4-Cyanophenyl)ureido)phenyl)isoxazole-5-carboxamido)-3-methylbutanoic acid;
(R)-Methyl 2-(3-(4-(3-(2-chlorophenyl)ureido)phenyl)isoxazole-5-carboxamido)-3-methylbutanoate;
(R)-2-(3-(4-(3-(2-Chlorophenyl)ureido)phenyl)isoxazole-5-carboxamido)-3-methylbutanoic acid;
(R)-Methyl 2-(3-(4-(3-(2-fluorophenyl)ureido)phenyl)isoxazole-5-carbothioamide)-3-methylbutanoate;
(R)-Methyl 3-methyl-2-(3-(4-(3-p-tolylureido)phenyl)isoxazole-5-carbothioamide) butanoate;
(R, Z)-Methyl 2-(ethylthio(3-(4-(3-(2-fluorophenyl)ureido) phenyl) isoxazol-5-yl)methyleneamino)-3-methylbutanoate;
(R,Z)-Methyl 2-(ethylthio(3-(4-(3-p-tolylureido)phenyl) isoxazol-5-yl)methyleneamino)-3-methylbutanoate;
(R, E)-2-(3-(4-(3-(2-Fluorophenyl)ureido)phenyl)-N'-hydroxyisoxazole-5-carboximidamide)-3-methylbutanoic acid;
(S)-Methyl 2-(3-(4-(3-(4-isopropylphenyl)ureido)phenyl) isoxazole-5-carboxamido)-3-methylbutanoate;
(S)-2-(3-(4-(3-(4-Isopropylphenyl)ureido)phenyl)isoxazole-5-carboxamido)-3-methylbutanoic acid;
(S)-Methyl 2-(3-(4-(3-(2-fluoro-6-(trifluoromethyl)phenyl) ureido)phenyl)isoxazole-5-carboxamido)-3-methylbutanoate;
(S)-2-(3-(4-(3-(2-Fluoro-6-(trifluoromethyl)phenyl)ureido) phenyl)isoxazole-5-carboxamido)-3-methylbutanoic acid;
(S)-Methyl 2-(3-(4-(3-(2-chloro-4-(trifluoromethyl)phenyl) ureido)phenyl)isoxazole-5-carboxamido)-3-methylbutanoate;
(S)-2-(3-(4-(3-(2-Chloro-4-(trifluoromethyl)phenyl)ureido) phenyl)isoxazole-5-carboxamido)-3-methylbutanoic acid;
(S)-Methyl 2-(3-(4-(3-(2-chloro-6-(trifluoromethyl)phenyl) ureido)phenyl)isoxazole-5-carboxamido)-3-methylbutanoate;
(S)-2-(3-(4-(3-(2-Chloro-6-(trifluoromethyl)phenyl)ureido) phenyl)isoxazole-5-carboxamido)-3-methylbutanoic acid;
(S)-Methyl 2-(3-(4-(3-(5-chloro-2-phenoxyphenyl)ureido) phenyl)isoxazole-5-carboxamido)-3-methylbutanoate;
(S)-2-(3-(4-(3-(5-Chloro-2-phenoxyphenyl)ureido)phenyl) isoxazole-5-carboxamido)-3-methylbutanoic acid;
(S)-Methyl 3-methyl-2-(3-(4-(3-(2-phenoxyphenyl)ureido) phenyl)isoxazole-5-carboxamido)butanoate;
(S)-3-Methyl-2-(3-(4-(3-(2-phenoxyphenyl)ureido)phenyl) isoxazole-5-carboxamido) butanoic acid;
(S)-Methyl 3-methyl-2-(3-(4-(3-(4-phenoxyphenyl)ureido) phenyl)isoxazole-5-carboxamido)butanoate;
(S)-3-Methyl-2-(3-(4-(3-(4-phenoxyphenyl)ureido)phenyl) isoxazole-5-carboxamido) butanoic acid;
Methyl 2-(3-(4-(3-(2-fluorophenyl)ureido)phenyl)isoxazole-5-carboxamido)-3-phenylpropanoate;
2-(3-(4-(3-(2-Fluorophenyl)ureido)phenyl)isoxazole-5-carboxamido)-3-phenylpropanoic acid;
Methyl 3-phenyl-2-(3-(4-(3-p-tolylureido)phenyl)isoxazole-5-carboxamido) propanoate;
3-Phenyl-2-(3-(4-(3-p-tolylureido)phenyl)isoxazole-5-carboxamido) propanoic acid;
Methyl 2-(3-(4-(3-(2,4-difluorophenyl)ureido)phenyl)isoxazole-5-carboxamido)-3-phenylpropanoate;
2-(3-(4-(3-(2,4-Difluorophenyl)ureido)phenyl)isoxazole-5-carboxamido)-3-phenylpropanoic acid;
Methyl 2-(3-(4-(3-(3-chloro-4-methylphenyl)ureido)phenyl) isoxazole-5-carboxamido)-3-methylbutanoate;
2-(3-(4-(3-(3-Chloro-4-methylphenyl)ureido)phenyl)isoxazole-5-carboxamido)-3-methylbutanoic acid;
Ethyl 2-(3-(4-(3-(3-fluoro-4-methylphenyl)ureido)phenyl) isoxazole-5-carboxamido)-3-methylbutanoate;
2-(3-(4-(3-(3-Fluoro-4-methylphenyl)ureido)phenyl)isoxazole-5-carboxamido)-3-methylbutanoic acid;
Methyl 2-(3-(4-(3-(5-fluoro-2-methylphenyl)ureido)phenyl) isoxazole-5-carboxamido)-3-methylbutanoate;
2-(3-(4-(3-(5-Fluoro-2-methylphenyl)ureido)phenyl)isoxazole-5-carboxamido)-3-methylbutanoic acid;
Methyl 4-(3-(4-(3-(2-fluorophenyl)ureido)phenyl)isoxazole-5-carboxamido) butanoate;
4-(3-(4-(3-(2-Fluorophenyl)ureido)phenyl)isoxazole-5-carboxamido) butanoic acid;
Methyl 4-(3-(4-(3-p-tolylureido)phenyl)isoxazole-5-carboxamido) butanoate;
4-(3-(4-(3-p-Tolylureido)phenyl)isoxazole-5-carboxamido) butanoic acid;
(R)Methyl 2-(3-(4-(3-(2-fluorophenyl)ureido)phenyl)isoxazole-5-carboxamido)-3-methylbutanoate;
(R)-2-(3-(4-(3-(2-Fluorophenyl)ureido)phenyl)isoxazole-5-carboxamido)-3-methylbutanoic acid;
(R)-Methyl 1-(3-(4-(3-(2-fluorophenyl)ureido)phenyl)isoxazole-5-carbonyl)pyrrolidine-2-carboxylate;
(R)-1-(3-(4-(3-(2-Fluorophenyl)ureido)phenyl)isoxazole-5-carbonyl)pyrrolidine-2-carboxylic acid;
(S)-Methyl 1-(3-(4-(3-(2-fluorophenyl)ureido)phenyl)isoxazole-5-carbonyl)pyrrolidine-2-carboxylate;
(S)-1-(3-(4-(3-(2-Fluorophenyl)ureido)phenyl)isoxazole-5-carbonyl)pyrrolidine-2-carboxylic acid;
Methyl 3-methyl-2-(3-(4-(3-(o-tolylsulfonyl)ureido)phenyl) isoxazole-5-carboxamido) butanoate;
3-Methyl-2-(3-(4-(3-(o-tolylsulfonyl)ureido)phenyl)isoxazole-5-carboxamido) butanoic acid;
(S)-methyl 3-methyl-2-(3-(4-(3-m-tolylureido)phenyl)isoxazole-5-carboxamido) butanoate;
(S)-3-methyl-2-(3-(4-(3-m-tolylureido)phenyl)isoxazole-5-carboxamido) butanoic acid;
(S)-methyl 2-(3-(4-(3-(3-fluorophenyl)thioureido)phenyl) isoxazole-5-carboxamido)-3-methylbutanoate;
(S)-2-(3-(4-(3-(3-fluorophenyl)thioureido)phenyl)isoxazole-5-carboxamido)-3-methylbutanoic acid;
(S)-methyl 2-(3-(4-(3-(2-fluorophenyl)thioureido)phenyl) isoxazole-5-carboxamido)-3-methylbutanoate;
(S)-2-(3-(4-(3-(2-fluorophenyl)thioureido)phenyl)isoxazole-5-carboxamido)-3-methylbutanoic acid;
(S)-Methyl 3-methyl-2-(3-(4-(3-p-tolylthioureido)phenyl) isoxazole-5-carboxamido)butanoate;
(S)-methyl 3-(4-hydroxyphenyl)-2-(3-(4-(3-p-tolylureido) phenyl)isoxazole-5-carboxamido)propanoate;
(S)-3-(4-hydroxyphenyl)-2-(3-(4-(3-p-tolylureido)phenyl) isoxazole-5-carboxamido)propanoic acid;
(S)-methyl 2-(3-(4-(3-(2-fluorophenyl)ureido)phenyl)isoxazole-5-carboxamido)-3-(4-hydroxyphenyl)propanoate;
Methyl 3-methyl-2-(3-(4-(3-(4-(trifluoromethyl)phenyl)ureido)phenyl)isoxazole-5-carboxamido)butanoate;
3-Methyl-2-(3-(4-(3-(4-(trifluoromethyl)phenyl)ureido) phenyl)isoxazole-5-carboxamido)butanoic acid;
Methyl 3-methyl-2-(3-(4-(3-(3-(trifluoromethyl)phenyl)ureido)phenyl)isoxazole-5-carboxamido)butanoate;
3-Methyl-2-(3-(4-(3-(3-(trifluoromethyl)phenyl)ureido) phenyl)isoxazole-5-carboxamido)butanoic acid;
Methyl 3-methyl-2-(3-(4-(3-pyridin-2-ylureido)phenyl) isoxazole-5-carboxamido) butanoate;
3-methyl-2-(3-(4-(3-pyridin-2-ylureido)phenyl)isoxazole-5-carboxamido)butanoic acid;

2-({3-[4-(3-{4-[5-(1-Methoxycarbonyl-2-methyl-propylcarbamoyl)-isoxazol-3-yl]-phenyl}-ureido)-phenyl]-isoxazol-5-carbonyl}-amino)-3-methyl-butyric acid methyl ester;
2-({3-[4-(3-{4-[5-(1-Carboxy-2-methyl-propylcarbamoyl)-isoxazol-3-yl]-phenyl}-ureido)-phenyl]-isoxazol-5-carbonyl}-amino)-3-methyl-butyric acid;
Methyl 4-(3-(4-(5-(1-methoxy-3-methyl-1-oxobutan-2-ylcarbamoyl) isoxazol-3-yl)phenyl)ureido)benzoate;
Methyl 2-(3-(4-(3-(4-fluoro-2-methylphenyl)ureido)phenyl) isoxazole-5-carboxamido)-3-methylbutanoate;
2-(3-(4-(3-(4-fluoro-2-methylphenyl)ureido)phenyl)isoxazole-5-carboxamido)-3-methylbutanoic acid;
Methyl 2-(3-(4-(3-(2-chloro-4-(trifluoromethoxy)phenyl)ureido)phenyl)isoxazole-5-carboxamido)-3-methylbutanoate;
2-(3-(4-(3-(2-chloro-4-(trifluoromethoxy)phenyl)ureido)phenyl)isoxazole-5-carboxamido)-3-methylbutanoic acid;
Ethyl 2-(3-(4-(3-(3-chloro-4-(trifluoromethoxy)phenyl)ureido)phenyl)isoxazole-5-carboxamido)-3-methylbutanoate;
(3-(4-(3-(3-chloro-4-(trifluoromethoxy)phenyl)ureido)phenyl)isoxazole-5-carboxamido)-3-methylbutanoic acid;
Methyl 2-(3-(4-(3-biphenyl-2-ylureido)phenyl)isoxazole-5-carboxamido)-3-methylbutanoate;
2-(3-(4-(3-biphenyl-2-ylureido)phenyl)isoxazole-5-carboxamido)-3-methylbutanoic acid;
Methyl 2-(3-(4-(3-(4-cyclohexylphenyl)ureido)phenyl)isoxazole-5-carboxamido)-3-methylbutanoate;
2-(3-(4-(3-(4-cyclohexylphenyl)ureido)phenyl)isoxazole-5-carboxamido)-3-methylbutanoic acid;
Methyl 3-methyl-2-(3-(4-(3-(2-methyl-4-(trifluoromethoxy)phenyl)ureido)phenyl) isoxazole-5-carboxamido)butanoate;
3-methyl-2-(3-(4-(3-(2-methyl-4-(trifluoromethoxy)phenyl)ureido)phenyl)isoxazole-5-carboxamido)butanoic acid;
Methyl 2-(3-(4-(4-tert-butylbenzamido)phenyl)isoxazole-5-carboxamido)-3-methylbutanoate;
2-(3-(4-(4-tert-butylbenzamido)phenyl)isoxazole-5-carboxamido)-3-methylbutanoic acid;
(S)-Methyl 2-(3-(4-(3-(2-fluorophenyl)ureido)phenyl)isoxazole-5-carboxamido)-3-hydroxypropanoate;
(S)-2-(3-(4-(3-(2-Fluorophenyl)ureido)phenyl)isoxazole-5-carboxamido)-3-hydroxypropanoic acid;
(S)-tert-butyl 2-(3-(4-(3-(2-fluorophenyl)ureido)phenyl) isoxazole-5-carboxamido)-3-methylbutanoate;
Methyl 2-(3-(4-(3-(2-fluorophenyl)ureido)phenyl)isoxazole-5-carboxamido)acrylate;
2-(3-(4-(3-(2-Fluorophenyl)ureido)phenyl)isoxazole-5-carboxamido) acrylic acid;
Methyl 2-(3-(4-(3-p-tolylureido)phenyl)isoxazole-5-carboxamido) acrylate;
2-(3-(4-(3-p-tolylureido)phenyl)isoxazole-5-carboxamido) acrylic acid;
(S)-Methyl 2-(3-(4-(3-(2-fluorophenyl)ureido)phenyl)-N-methylisoxazole-5-carboxamido)-3-methylbutanoate;
(S)-2-(3-(4-(3-(2-fluorophenyl)ureido)phenyl)-N-methyl-isoxazole-5-carboxamido)-3-methylbutanoic acid;
(S)-methyl 2-(3-(4-(3-(4-fluorophenyl)ureido)phenyl)-N-methylisoxazole-5-carboxamido)-3-methylbutanoate;
(S)-2-(3-(4-(3-(4-fluorophenyl)ureido)phenyl)-N-methyl-isoxazole-5-carboxamido)-3-methylbutanoic acid;
(S)-methyl 3-methyl-2-(N-methyl-3-(4-(3-(3-(trifluoromethyl)phenyl)ureido)phenyl) isoxazole-5-carboxamido) butanoate;
(S)-3-methyl-2-(N-methyl-3-(4-(3-(3-(trifluoromethyl)phenyl)ureido)phenyl)isoxazole-5-carboxamido)butanoic acid;
(S)-methyl 2-(3-(4-(3-cyclohexylureido)phenyl)-N-methyl-isoxazole-5-carboxamido)-3-methylbutanoate;
(S)-2-(3-(4-(3-cyclohexylureido)phenyl)-N-methylisoxazole-5-carboxamido)-3-methylbutanoic acid;
(S)-methyl 2-(3-(4-(3-(2-chlorophenyl)ureido)phenyl)-N-methylisoxazole-5-carboxamido)-3-methylbutanoate;
(S)-2-(3-(4-(3-(2-chlorophenyl)ureido)phenyl)-N-methyl-isoxazole-5-carboxamido)-3-methylbutanoic acid;
(R)-methyl 2-(3-(4-(2-fluorophenylsulfonamido)phenyl) isoxazole-5-carboxamido)-3-methylbutanoate;
(R)-Methyl 2-(3-(4-(2,6-difluorophenylsulfonamido)phenyl)isoxazole-5-carboxamido)-3-methylbutanoate;
(R)-methyl 3-methyl-2-(3-(4-(4-(trifluoromethyl)phenylsulfonamido) phenyl)isoxazole-5-carboxamido)butanoate;
(R)-3-methyl-2-(3-(4-(4-(trifluoromethyl)phenylsulfonamido)phenyl)isoxazole-5-carboxamido)butanoic acid;
(R)-2-(3-(4-(2,6-Difluorophenylsulfonamido)phenyl)isoxazole-5-carboxamido)-3-methylbutanoic acid;
(R)-2-(3-(4-(3,5-Difluorophenylsulfonamido)phenyl)isoxazole-5-carboxamido)-3-methylbutanoic acid;
Methyl 2-(3-(4-(benzyloxy)phenyl)isoxazole-5-carboxamido)-3-methylbutanoate;
2-(3-(4-(Benzyloxy)phenyl)isoxazole-5-carboxamido)-3-methylbutanoic acid;
Methyl 2-(3-(4-(4-fluorobenzyloxy)phenyl)isoxazole-5-carboxamido)-3-methylbutanoate;
2-(3-(4-(Benzyloxy)phenyl)isoxazole-5-carboxamido)-3-methylbutanoic acid;
Methyl 3-methyl-2-(3-(4-(3-(trifluoromethyl)benzyloxy) phenyl)isoxazole-5-carboxamido)butanoate;
3-Methyl-2-(3-(4-(3-(trifluoromethyl)benzyloxy)phenyl) isoxazole-5-carboxamido) butanoic acid;
Methyl 3-methyl-2-(3-(4-(4-(trifluoromethyl)benzyloxy) phenyl)isoxazole-5-carboxamido)butanoate;
3-methyl-2-(3-(4-(4-(trifluoromethyl)benzyloxy)phenyl) isoxazole-5-carboxamido) butanoic acid;
Methyl 3-methyl-2-(3-(4-(2-(trifluoromethyl)benzyloxy) phenyl)isoxazole-5-carboxamido)butanoate;
3-methyl-2-(3-(4-(2-(trifluoromethyl)benzyloxy)phenyl) isoxazole-5-carboxamido)butanoic acid;
Methyl 2-(3-(4-(2,4-difluorobenzyloxy)phenyl)isoxazole-5-carboxamido)-3-methylbutanoate;
2-(3-(4-(2,4-Difluorobenzyloxy)phenyl)isoxazole-5-carboxamido)-3-methylbutanoic acid;
Methyl 1-(3-(4-(benzyloxy)phenyl)isoxazole-5-carbonyl) pyrrolidine-2-carboxylate;
Methyl 2-(3-(4-(6-fluorobenzo[d]thiazol-2-yloxy)phenyl) isoxazole-5-carboxamido)-3-methylbutanoate;
2-(3-(4-(6-fluorobenzo[d]thiazol-2-yloxy)phenyl)isoxazole-5-carboxamido)-3-methylbutanoic acid;
Methyl 3-methyl-2-(3-(4-(2-oxo-2-(3-(trifluoromethyl)phenylamino)acetamido) phenyl)isoxazole-5-carboxamido) butanoate;
3-Methyl-2-(3-(4-(2-oxo-2-(3-(trifluoromethyl)phenylamino)acetamido)phenyl) isoxazole-5-carboxamido)butanoic acid;
Methyl 2-(3-(4-(2-(2,4-difluorophenylamino)-2-oxoacetamido)phenyl)isoxazole-5-carboxamido)-3-methylbutanoate;
2-(3-(4-(2-(2,4-difluorophenylamino)-2-oxoacetamido)phenyl)isoxazole-5-carboxamido)-3-methylbutanoic acid;
Methyl 2-(3-(4-((R)-2-hydroxy-2-phenylacetamido)phenyl) isoxazole-5-carboxamido)-3-methylbutanoate;

2-(3-(4-((R)-2-hydroxy-2-phenylacetamido)phenyl)isoxazole-5-carboxamido)-3-methylbutanoic acid;

(S)-Methyl 2-(3-(4-(3-(4-fluorophenyl)ureido)phenyl)-1,2,4-oxadiazole-5-carboxamido)-3-methylbutanoate;

(S)-2-(3-(4-(3-(4-Fluorophenyl)ureido)phenyl)-1,2,4-oxadiazole-5-carboxamido)-3-methylbutanoic acid;

(S)-Methyl 2-(3-(4-(3-(4-methoxyphenyl)ureido)phenyl)-1,2,4-oxadiazole-5-carboxamido)-3-methylbutanoate;

(S)-2-(3-(4-(3-(4-methoxyphenyl)ureido)phenyl)-1,2,4-oxadiazole-5-carboxamido)-3-methylbutanoic acid;

(S)-methyl 3-methyl-2-(3-(4-(3-p-tolylureido)phenyl)-1,2,4-oxadiazole-5-carboxamido)butanoate;

(S)-3-methyl-2-(3-(4-(3-p-tolylureido)phenyl)-1,2,4-oxadiazole-5-carboxamido) butanoic acid;

(S)-methyl 2-(3-(4-(3-(2-fluorophenyl)ureido)phenyl)-1,2,4-oxadiazole-5-carboxamido)-3-methylbutanoate;

(S)-2-(3-(4-(3-(2-Fluorophenyl)ureido)phenyl)-1,2,4-oxadiazole-5-carboxamido)-3-methylbutanoic acid;

(S)-methyl 2-(3-(4-(2,4-difluorophenylsulfonamido)phenyl)-1,2,4-oxadiazole-5-carboxamido)-3-methylbutanoate;

(S)-Methyl 3-methyl-2-(3-(4-(3-phenylureido)phenyl)-1,2,4-oxadiazole-5-carboxamido)butanoate;

(S)-methyl 2-(3-(4-(3-benzylureido)phenyl)-1,2,4-oxadiazole-5-carboxamido)-3-methylbutanoate;

(S)-Methyl 2-(3-(4-(3-(3-fluorophenyl)thioureido)phenyl)-1,2,4-oxadiazole-5-carboxamido)-3-methylbutanoate;

(S)-methyl 2-(3-(4-(3-(4-fluorophenyl)thioureido)phenyl)-1,2,4-oxadiazole-5-carboxamido)-3-methylbutanoate;

(S)-methyl 2-(3-(4-(3-(2-fluorophenyl)thioureido)phenyl)-1,2,4-oxadiazole-5-carboxamido)-3-methylbutanoate;

(S)-methyl 2-(3-(4-(3-benzylthioureido)phenyl)-1,2,4-oxadiazole-5-carboxamido)-3-methylbutanoate;

(S)-methyl 3-methyl-2-(3-(4-(3-phenylthioureido)phenyl)-1,2,4-oxadiazole-5-carboxamido)butanoate;

(S)-methyl 2-(2-(4-(3-(2,4-difluorophenyl)ureido)phenyl)thiazole-4-carboxamido)-3-methylbutanoate;

(S)-2-(2-(4-(3-(2,4-difluorophenyl)ureido)phenyl)thiazole-4-carboxamido)-3-methylbutanoic acid;

(S)-methyl 2-(2-(4-(3-(2,3-dihydro-1H-inden-5-yl)ureido)phenyl) thiazole-4-carboxamido)-3-methylbutanoate;

(S)-2-(2-(4-(3-(2,3-dihydro-1H-inden-5-yl)ureido)phenyl) thiazole-4-carboxamido)-3-methylbutanoic acid;

(S)-methyl 2-(2-(4-(3-(3,4-dimethylphenyl)ureido)phenyl) thiazole-4-carboxamido)-3-methylbutanoate;

(S)-2-(2-(4-(3-(3,4-dimethylphenyl)ureido)phenyl)thiazole-4-carboxamido)-3-methylbutanoic acid;

(S)-methyl 2-(2-(4-(3-(4-chloro-2-phenoxyphenyl)ureido) phenyl) thiazole-4-carboxamido)-3-methylbutanoate;

(S)-2-(2-(4-(3-(4-chloro-2-phenoxyphenyl)ureido)phenyl) thiazole-4-carboxamido)-3-methylbutanoic acid;

(S)-methyl 3-methyl-2-(2-(4-(3-(3-(trifluoromethyl)phenyl) ureido)phenyl)thiazole-4-carboxamido)butanoate;

(S)-3-methyl-2-(2-(4-(3-(3-(trifluoromethyl)phenyl)ureido) phenyl) thiazole-4-carboxamido) butanoic acid;

(S)-methyl 2-(2-(4-(3-(2-chlorophenyl)ureido)phenyl)thiazole-4-carboxamido)-3-methylbutanoate;

(S)-2-(2-(4-(3-(2-chlorophenyl)ureido)phenyl)thiazole-4-carboxamido)-3-methylbutanoic acid;

(S)-methyl 2-(2-(4-(3-(3,4-difluorophenyl)ureido)phenyl) thiazole-4-carboxamido)-3-methylbutanoate;

(S)-2-(2-(4-(3-(3,4-difluorophenyl)ureido)phenyl)thiazole-4-carboxamido)-3-methylbutanoic acid;

and their pharmaceutically acceptable salts and solvates.

Compounds for use in the prevention or treatment of clinical conditions associated with obesity, diabetes, insulin resistance and impaired glucose tolerance in accordance with the present, invention include:

3-[4-(6-Fluoro-benzothiazol-2-ylamino)-phenyl]-isoxazole-5-carboxylic acid ethyl ester;

3-[4-(6-Fluoro-benzothiazol-2-ylamino)-phenyl]-isoxazole-5-carboxylic acid;

3-[4-(6-Fluoro-benzothiazol-2-ylamino)-phenyl]-isoxazole-5-carboxylic acid amide;

3-[4-(6-Fluoro-benzothiazol-2-ylamino)-phenyl]-isoxazole-5-carbothioic acid amide;

3-(4-Nitro-phenyl)-5-phenyl-isoxazole-4-carboxylic acid ethyl ester;

3-(4-Amino-phenyl)-5-phenyl-isoxazole-4-carboxylic acid ethyl ester;

3-[4-(6-Fluoro-benzothiazol-2-ylamino)-phenyl]-5-phenyl-isoxazole-4-carboxylic acid ethyl ester;

3-[4-(6-Fluoro-benzothiazol-2-ylamino)-phenyl]-5-phenyl-isoxazole-4-carboxylic acid;

3-[4-(3-phenyl-ureido)-phenyl]isoxazole-5-carboxylic acid ethyl ester;

3-[4-(3-phenyl-ureido)-phenyl]-isoxazole-5-carboxylic acid;

3-[4-(3-cyclohexyl-ureido)-phenyl]-isoxazole-5-carboxylic acid ethyl ester;

3-[4-(3-cyclohexyl-ureido)-phenyl]-isoxazole-5-carboxylic acid;

3-{4-[3-(4-Fluoro-phenyl}-ureido]-phenyl)-isoxazole-5-carboxylic acid ethyl ester;

3-{-4-[3-(4-Fluoro-phenyl)-ureido]-phenyl}-isoxazole-5-carboxylic acid;

4-Phenyl-3-[4-(3-phenyl-ureido)-phenyl]-isoxazole-5-carboxylic acid ethyl ester;

4-Phenyl-3-[4-(3-phenyl-ureido)-phenyl]-isoxazole-5-carboxylic acid;

3-{4-[3-(4-Fluoro-phenyl)-ureido]-phenyl}-4-phenyl-isoxazole-5-carboxylic acid ethyl ester;

or a pharmaceutically acceptable salt, solvate and/or prodrug, as well as all stereoisomers and tautomers thereof.

According to, a further aspect of the present invention, there is provided a process for the preparation of a compound of formula (I), and its salt, solvate or prodrug.

According to further aspect of the present invention, there is provided a process for the preparation of a compound of formula (Ivi):

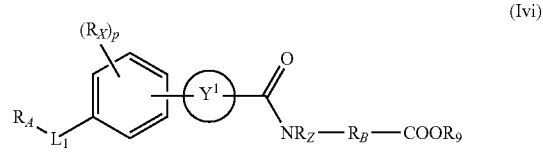

and its salt, solvate or prodrug, comprising
reacting a compound of formula (Iv)

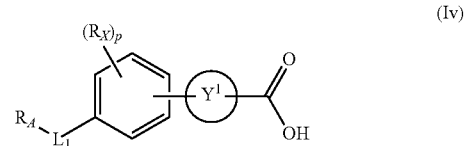

with a compound of formula $R_ZNH—R_B—COOR_9$ wherein $Y^1$ is selected from

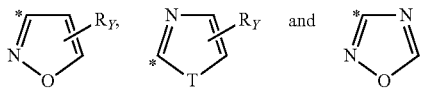

$R_A$, $L_1$, $R_X$, $R_Y$, $R_Z$, $R_B$, $R_9$ and p are as defined above in relation to formula (I), T is —O— or —S— and * indicates point of attachment to phenyl ring.

According to further aspect of the present invention, there is provided a process for the preparation of a compound of formula (Ivii)

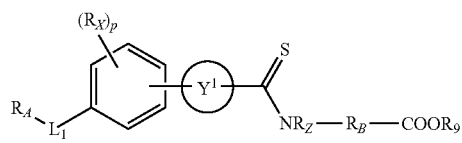

(Ivii)

and its salt, solvate or prodrug, comprising
reacting a compound of formula (Ivi)

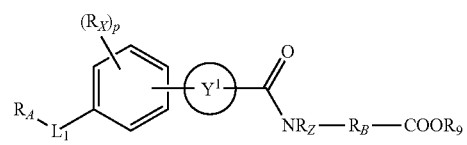

(Ivi)

with $P_2S_5$ or Lawesson's reagent
wherein $R_A$, $L_1$, $R_X$, $R_9$, $Y^1$, $R_Z$, $R_B$ and p are as defined above in relation to formula (I).

According to further aspect of the present invention, there is provided a process for the preparation of a compound of formula (Iix)

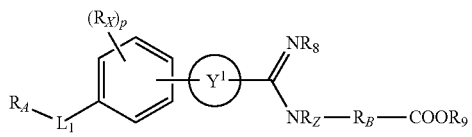

(Iix)

and its salt, solvate or prodrug, comprising
reacting a compound of formula (Ivii)

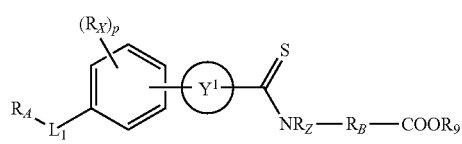

(Ivii)

with hydroxylamine hydrochloride and further treating it with compound of formula $R_9COL_g$, $R_9OCOL_g$, $R_6R_7N=C=O$, $R_9SO_2Cl$ or with a combination of carbonyldiimidazole (CDI) and $R_6R_7NH$, wherein $R_8$ is —$COR_9$, —$COOR_9$, —$CONR_6R_7$ or —$SO_2R_9$; $R_A$, $L_1$, $R_X$, $Y^1$, $R_Z$, $R_B$, $R_9$, $R_6$, $R_7$ and p have the same meanings as described herein above in relation to formula (I).

According to further aspect of the present invention, there is provided a process for the preparation of a compound of formula (Ixix)

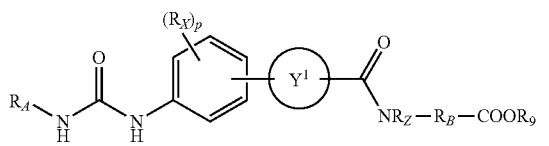

(Ixix)

and its salt, solvate or prodrug, comprising
reacting a compound of formula (Ixviii)

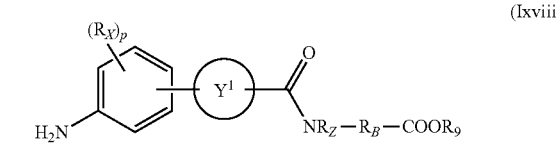

(Ixviii)

with a compound of formula $R_A—N=C=O$ or with a compound of formula $R_A—NH_2$ in presence of a coupling agent such as carbonyl diimidazole, wherein $R_X$, $R_Z$, $R_B$, $R_9$, $Y^1$ and p are as defined above in relation to formula (I).

According to further aspect of the present invention, there is provided a process for the preparation of a compound of formula (Ixxia) and (Ixxib)

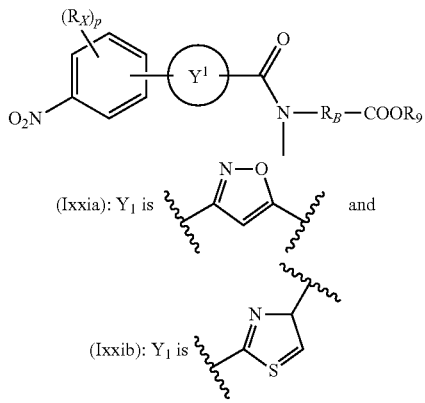

and its salt, solvate or prodrug, comprising
reacting a compound of formula (Ixviia) and (Ixviib) respectively

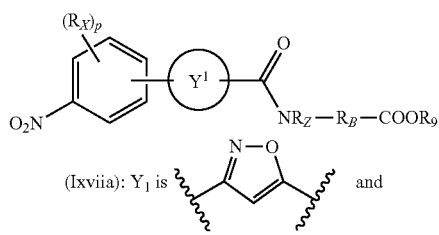

-continued (Ixviib): Y₁ is 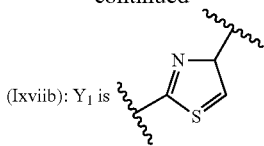

with methyl iodide, wherein $R_X$, $R_B$, $R_9$ and p are as defined above in relation to formula (I) and $R_Z$ is H.

According to further aspect of the present invention, there is provided a process for the preparation of a compound of formula (Ixviiia) and (Ixviiib)

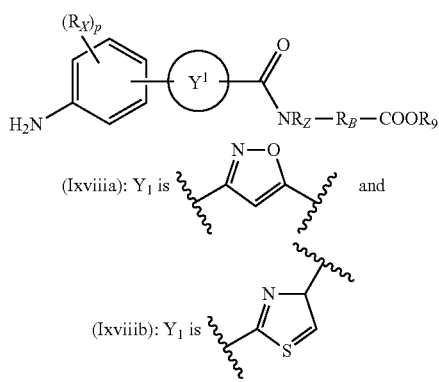

(Ixviiia): Y₁ is  and (Ixviiib): Y₁ is and its salt, solvate or prodrug, comprising
reducing a compound of formula (Ixviia) and (Ixviib) or (Ixxia) and (Ixxib) respectively, wherein $R_X$, $R_B$, $R_Z$, $R_9$ and p are as defined above in relation to formula (I) and $R_Z$ is H or methyl.

According to further aspect of the present invention, there is provided a process for the preparation of a compound of formula (Ixxviii)

(Ixxviii)
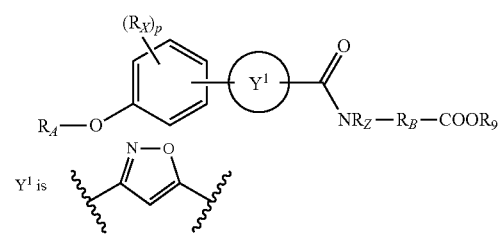

and its salt, solvate or prodrug, comprising
reacting a compound of formula (Ixxvii)

(Ixxvii)
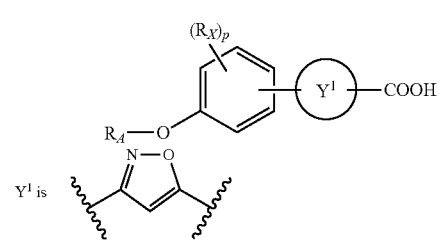

with a compound of formula $NHR_ZR_BCOOR_9$, wherein $R_X$, $R_B$, $R_Z$, $R_9$ and p are as defined above in relation to formula (I) and $R_A$ is substituted or unsubstituted alkylaryl.

According to further aspect of the present invention, there is provided a process for the preparation of a compound of formula (Ixxviii)

(Ixxviii)
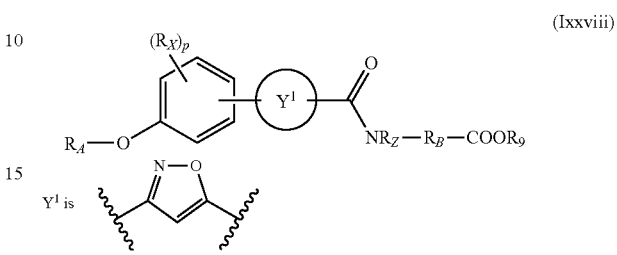

and its salt, solvate or prodrug, comprising
reacting a compound of formula (Ixxx)

(Ixxx)
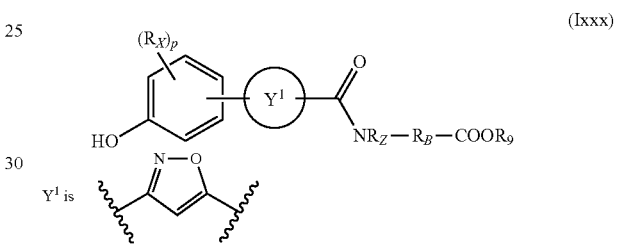

with a compound of formula $R_A$—Cl, wherein $R_X$, $R_B$, $R_Z$, $R_9$ and p are as, defined above in relation to formula (I) and $R_A$ is heteroaryl or substituted alkylaryl.

According to further aspect of the present invention, there is provided a process for the preparation of a compound of formula (Ixxxi)

(Ixxxi)
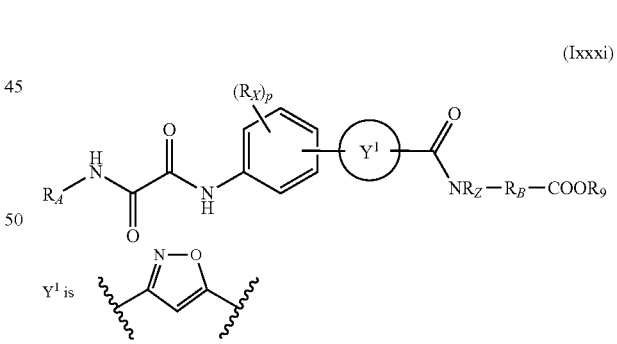

and its salt, solvate or prodrug, comprising
reacting a compound of formula (Ixviiia)

(Ixviiia)
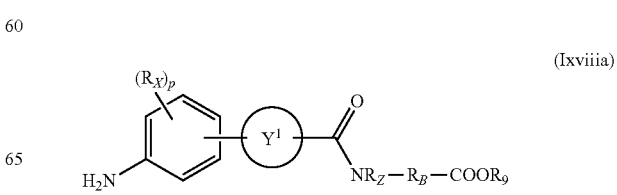

Y¹ is 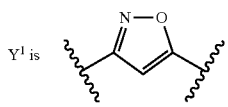

with a compound of formula R$_A$—NH$_2$ in presence of oxalyl chloride, wherein R$_A$, R$_X$, R$_Z$, R$_B$, R$_9$ and p are as defined above in relation to formula (I).

According to further aspect of the present invention, there is provided a process for the preparation of a compound of formula (lxxxiii)

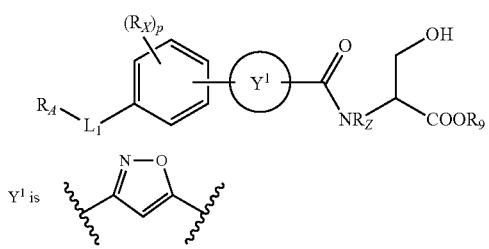
(lxxxiii)

and its salt, solvate or prodrug, comprising reacting a compound of formula (Iv)

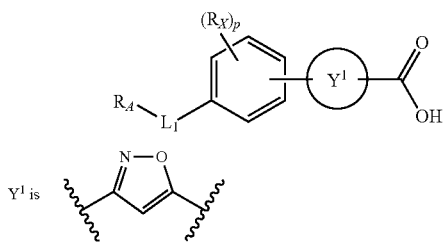
(Iv)

with a compound of formula NHR$_Z$CH(CH$_2$OH)COOR$_9$, wherein R$_A$, R$_X$, R$_Z$, R$_9$ and p are as defined above in relation to formula (I).

According to further aspect of the present invention, there is provided a process for the preparation of a compound of formula (lxxxv),

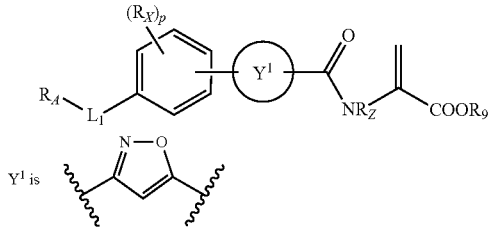
(lxxxv)

and its salt, solvate or prodrug, comprising reacting a compound of formula (lxxxiii)

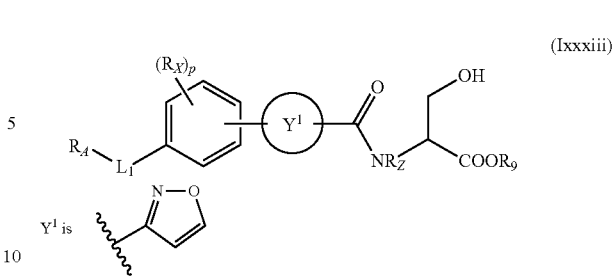
(lxxxiii)

with mesyl chloride, wherein R$_A$, R$_X$, R$_Z$, R$_9$ and p are as defined above in relation to formula (I) and L$_1$ is NHC(O)NH.

According to further aspect of the present invention, there is provided a process for the preparation of a compound of formula (lxxxv)

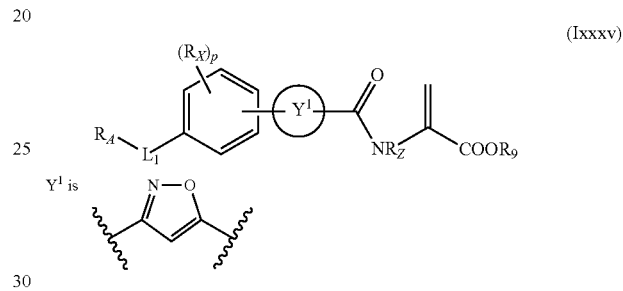
(lxxxv)

and its salt, solvate or prodrug, comprising reacting a compound of formula (lxxxix)

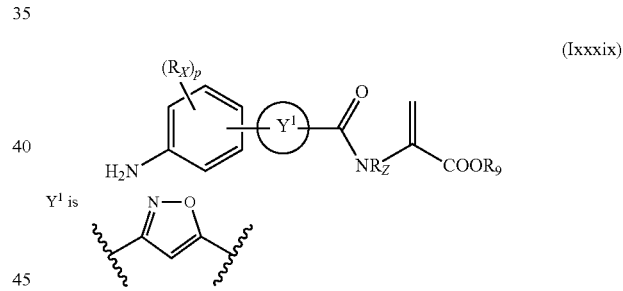
(lxxxix)

with a compound of formula R$_A$—N═C═O, wherein R$_A$, R$_X$, R$_Z$, R$_9$ and p are as defined above in relation to formula (I) and L$_1$ is NHC(O)NH.

According to further aspect of the present invention, there is provided a process for the preparation of a compound of formula (lxxxvii)

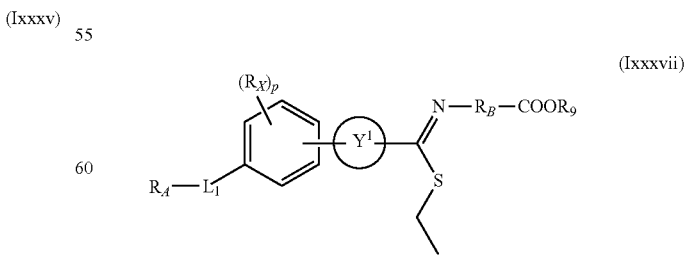
(lxxxvii)

and its salt, solvate or prodrug, comprising reacting a compound of formula (lvii)

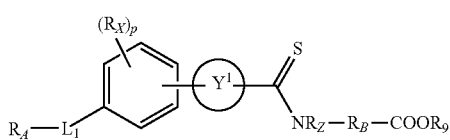

(Ivii)

with ethyl iodide, wherein $R_A$, $L_1$, $R_X$, $Y^1$, $R_Z$, $R_B$, $R_9$ and p are as defined above in relation to formula (I).

According to further aspect of the present invention, there is provided a process for the preparation of a compound of formula (lxxxviii)

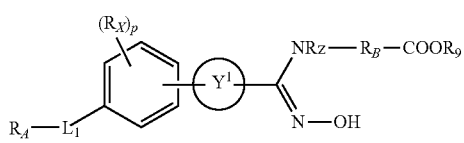

(lxxxviii)

and its salt, solvate or prodrug, comprising reacting a compound of formula (lxxxvii)

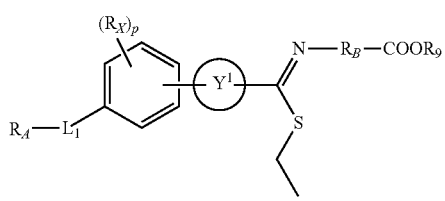

(lxxxvii)

with hydroxylamine hydrochloride, wherein $R_A$, $L_1$, $R_X$, $Y^1$, $R_Z$, $R_B$, $R_9$ and p are as defined above in relation to formula (I).

The compounds of formula (Ivi), (Ivii), (Iix) (Ixix), (Ixixa), (Ixixb), (Ixxviii); (Ixxxi), (Ixxxiii), (Ixxxv), (Ixxxvii) and (Ixxxviii) can be converted to corresponding acids by alkaline hydrolysis; optionally converting the resultant acid into salt, solvate or prodrug.

A convenient method for the synthesis of a compound of the present invention typically involves the series of steps described herein below:

The compounds of formula (I) are prepared using techniques known to one skilled in the art through the reaction sequences shown in Schemes 1-22 below with reference to specific examples. Those with skill in the art will appreciate that the specific starting compounds and reagents, such as acids, bases, solvents, etc., identified in the Schemes can be altered to prepare compounds encompassed by the present invention.

In one of the sequence of steps as shown in Scheme-1, a compound of formula (1c) may be prepared by reacting a compound of formula (1b) with HC≡C—COORp and a compound of formula 1(d) may be prepared by reacting a compound of formula (1 b) with CN—COORp, in a solvent such as toluene and in presence of a base such as triethylamine wherein $R_p$ is a suitable protecting group selected from methyl, ethyl, tert-butyl, benzyl, p-methoxybenzyl and, the like. A compound of formula (1b) may be prepared by reacting a compound of formula 1(a) with hydroxylamine hydrochloride.

The compounds of formulae (1c) and (1d) are reduced to their corresponding amine derivatives by reducing agents such as Fe and ammonium chloride in a solvent such as ethanol, tetrahydrofuran, water or mixture thereof.

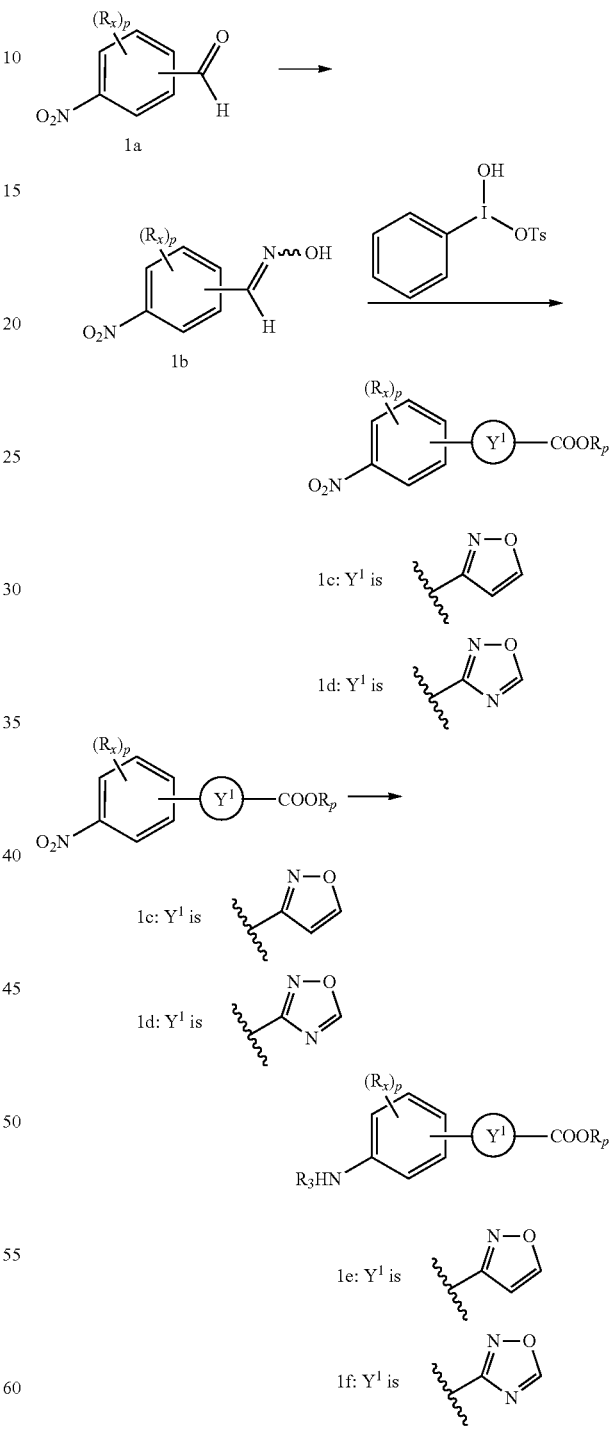

Scheme - 1

In one of the sequence of steps as shown in Scheme-2, a compound of formula (Ii) may be prepared either by reacting a compound of formula (2a) with a compound of formula $R_AL_g$ (2c), in a solvent such as ethanol or by reacting a compound of formula (2b) with a compound of formula $R_ANHR_3$ (2d), optionally in presence of a metal salt or metal complex as catalyst.

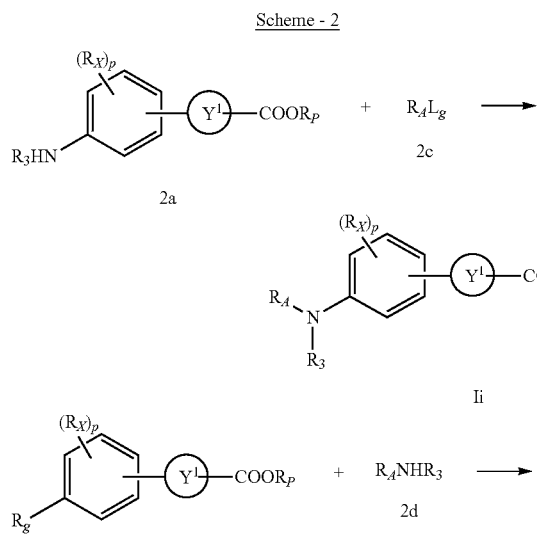

Scheme - 2

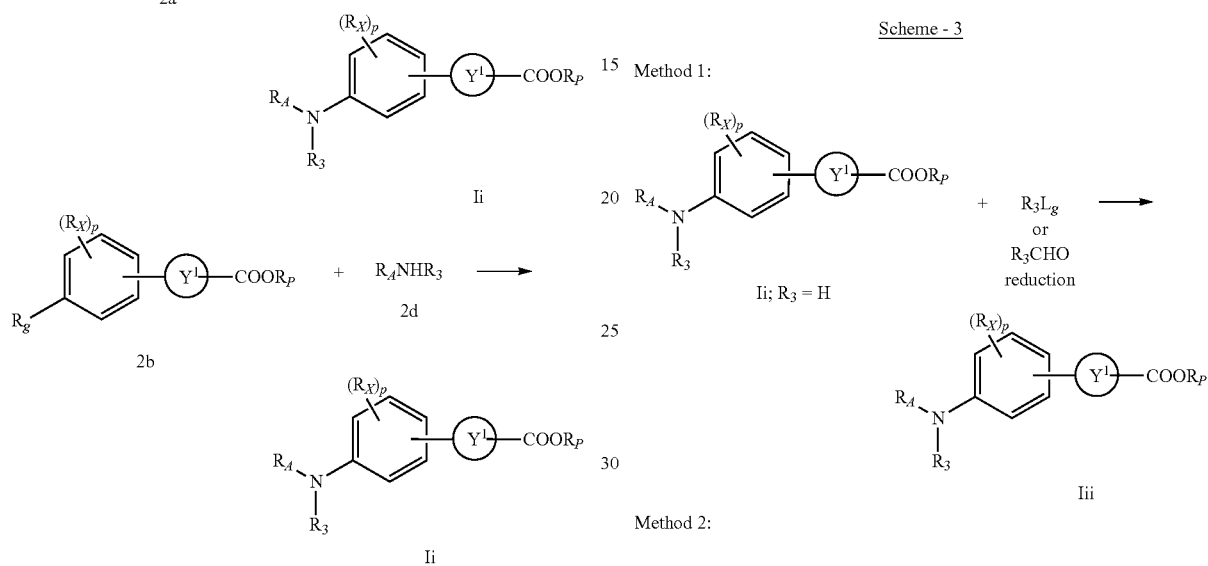

wherein,
$R_g$ is a removable group selected from halogen, triflate, boronic acid, substituted boronic acid and the like;
$L_g$ is a leaving group selected from halogen, OMes, OTs, —S(=O)$_2$Me, —S(=O)$_2$Et and the like;
$R_p$ is a suitable protecting group selected from methyl, ethyl, tert-butyl, benzyl, p-methoxybenzyl and the like;
$Y^1$ is selected from groups of the following formulae

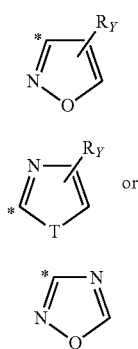

(a)

(b)

(c)

$R_A$, $R_X$, $R_Y$, $R_3$ and p have the same meanings as described herein above.
* is the point of attachment In another sequence of steps as shown in Scheme-3, a compound of formula (Iii) may be prepared by two methods.
Method 1: A compound of formula (Iii) (wherein $R_3$ is alkyl, alkenyl, alkynyl, cycloalkyl or alkylcycloalkyl) may be prepared by reacting a compound of formula (Ii) (wherein $R_3$ is H) with a compound of formula $R_3L_g$ or $R_3CHO$ (wherein $R_3$ is $C_1$-$C_{10}$ alkyl, $C_2$-$C_{10}$ alkenyl, $C_2$-$C_{10}$ alkynyl, $C_3$-$C_8$ cycloalkyl or $C_4$-$C_{10}$ alkylcycloalkyl).

Method 2: Compounds of formula (Iii) (wherein $R_3$ is —COR$_1$, —COOR$_1$ and —CONR$_1$R$_2$) may be prepared by reacting compounds of formula Ii (wherein $R_3$ is H) with compounds of formula R$_1$COCl, R$_1$OCOCl or R$_1$R$_2$NCOCl (wherein $R_3$ is —COR$_1$, —COOR$_1$ and —CONR$_1$R$_2$).

Scheme - 3

Method 1:

Method 2:

wherein,
$R_A$, $R_X$, $Y^1$, $R_P$, $L_g$, $R_1$, $R_2$ and p have the same meanings as described herein above.

In yet another sequence of steps as shown in Scheme-4, compounds of formula (Iiii) may be synthesized by any of the following methods:
i) alkylation of a compound of formula (2a) using a compound of formula $R_A$—(CR$_4$R$_5$)$_b$-L$_g$ in a solvent such as ethanol;
ii) reductive alkylation of a compound of formula (2a) using a compound of formula $R_A$—(CR$_4$R$_5$)$_{b-1}$—CHO;
iii) reacting a compound of formula (2b) with a compound of formula $R_A$—(CR$_4$R$_5$)$_b$—NHR$_3$, optionally in the presence of a metal salt or metal complex as catalyst;

Scheme - 4

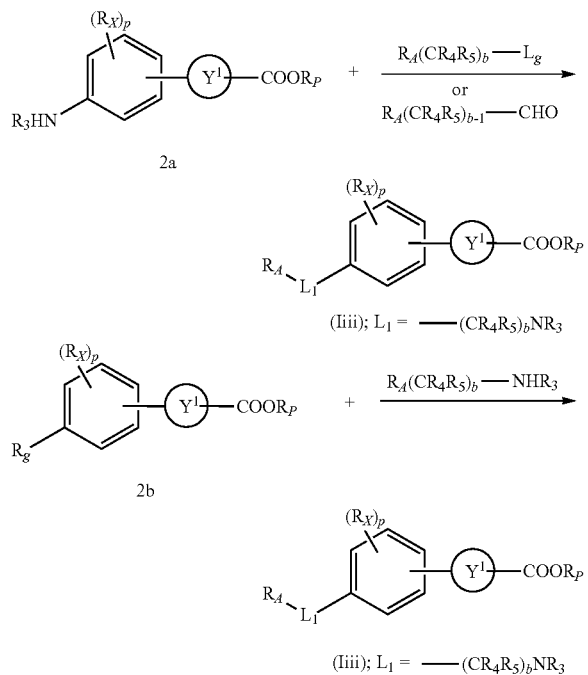

(Iiii); $L_1 = —(CR_4R_5)_b NR_3$ wherein, $L_1$ is $—(CR_4R_5)_b NR_3—$; $R_g$, $R_A$, $R_X$, $Y^1$, $R_P$, $R_3$, $L_g$, $R_4$, $R_5$, b and p have the same meanings as described herein above.

In a further sequence of steps as shown in Scheme-5, a compound of formula (Iiv) may be prepared by reacting a compound of formula (2a) either with a compound of formula $R_A N=C=T$ or sequentially with a compound of formula $R_A NR_3 H$ and a compound of formula $(C=T)Lg_2$ in a solvent such as tetrahydrofuran.

Scheme - 5

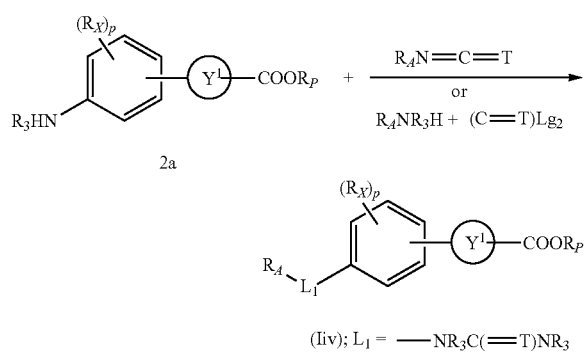

(Iiv); $L_1 = —NR_3C(=T)NR_3$ wherein, $L_1$ is $—NR_3C(=T)NR_3$; T, $R_A$, $R_X$, $Y^1$, $R_P$, $R_3$, $L_g$ and p have the same meanings as described herein above.

In a further sequence of steps as shown in Scheme-6, compounds of formula (Ii)-(Iiv) may be hydrolyzed to the corresponding acid of formula (Iv) by a standard method of hydrolysis using alkali metal hydroxide such as lithium hydroxide or mineral acid in a solvent such as tetrahydrofuran.

Scheme - 6

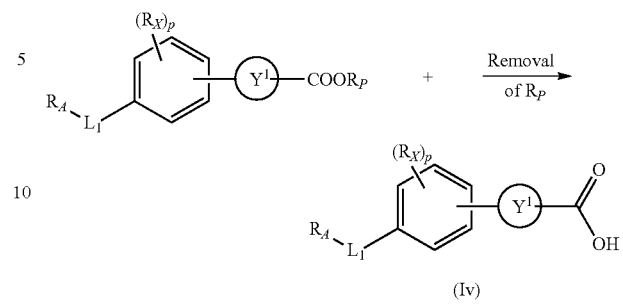

wherein, $L_1$ is NH, $NR_3$, $—(CR_4R_5)_b NR_3$ or $—NR_3C(=T)NR_3—$; T, $R_A$, $R_X$, $Y^1$, $R_P$, $R_3$, $R_4$, $R_5$, $L_g$ and p have the same meanings as described herein above.

In a further sequence of steps as shown in Scheme-7, the acid of formula (Iv) may be reacted with an amine of formula $R_Z NH—R_B—COOR_9$ by a standard amidation reaction or standard peptide coupling procedures to obtain a compound of formula (Ivi). The reaction may be performed in a solvent such as dimethyl formamide in presence of a base such as triethylamine and coupling agent such as N-Hydroxybenzotriazole and N,N'-dicyclohexylcarbodiimide.

Scheme - 7

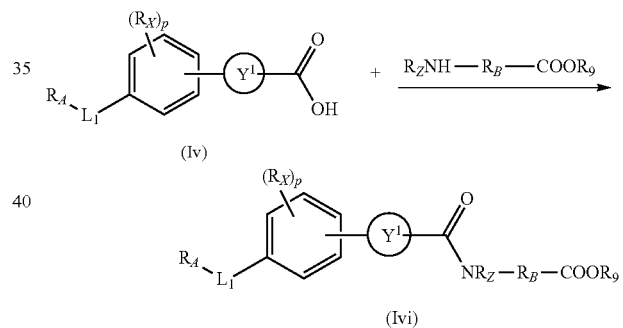

wherein, $L_1$ is NH, $NR_3$, $—(CR_4R_5)_b NR_3—$ or $—NR_3C(=T)NR_3—$; $R_A$, T, $R_X$, $Y^1$, $R_9$, $R_B$, $R_Z$, $R_3$, $R_4$, $R_5$, b and p have the same meanings as described herein above.

In yet another sequence of steps as shown in Scheme-8, a compound of formula (Ivi) (where $L_1$ is not $—NR_3C(=T)NR_3—$) may be treated with $P_2S_5$ or Lawesson's reagent in a solvent such as dioxane to obtain a compound of formula (Ivii).

Scheme-8

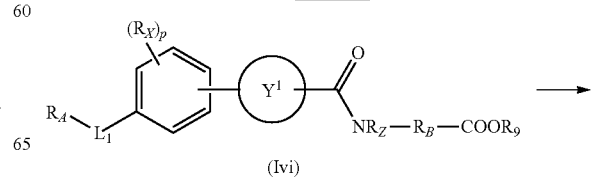

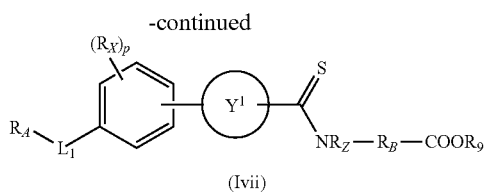

(Ivii)

wherein,
L$_1$ is NH, NR$_3$ or —C(R$_4$R$_5$)$_b$NR$_3$—; R$_A$, R$_X$, Y$^1$, R$_9$, R$_Z$, R$_B$, R$_3$, R$_4$, R$_5$, b and p have the same meanings as described herein above.

In a further sequence of steps as shown in Scheme-9, a compound of formula (Ivii) may be reacted with a compound of formula R$_{12}$NH$_2$ in a solvent such as methanol, in presence of iodomethane and a base such as sodium metal to obtain a compound of formula (Iviii) or its tautomeric forms.

Scheme-9

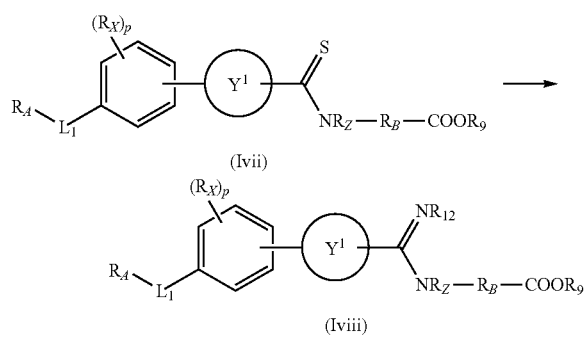

wherein;
R$_{12}$ is H or OR$_9$; L$_1$ is NH, NR$_3$ and —C(R$_4$R$_5$)$_b$NR$_3$—; R$_Z$R$_A$, R$_X$, Y$^1$, R$_9$, R$_B$, R$_3$, R$_4$, R$_5$, b and p have the same meanings as described herein above.

In a further sequence of steps as shown in Scheme-10, a compound of formula (Iviii) may be reacted with a compound of formula R$_9$COL$_g$, R$_9$OCOL$_g$, R$_6$R$_7$N═C═O, R$_9$SO$_2$Cl or with a combination of carbonyldiimidazole (CDI) and R$_6$R$_7$NH to obtain a compound of formula (Iix) or its tautomeric forms.

Scheme-10

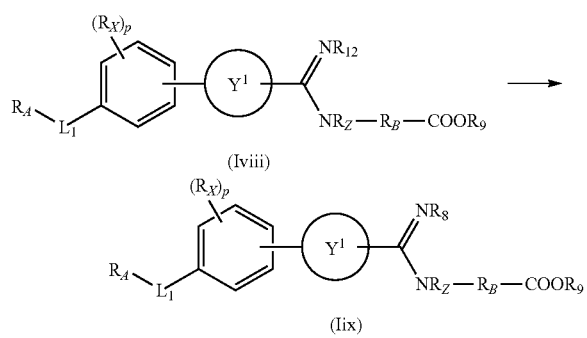

wherein,
R$_{12}$ is H; L$_1$ is NH, NR$_3$, or —C(R$_4$R$_5$)$_b$NR$_3$—; R$_8$ is —COR$_9$, —COOR$_9$, —CONR$_6$R$_7$ or —SO$_2$R$_9$; R$_Z$, R$_A$, R$_X$, Y$^1$, R$_9$, R$_B$, R$_3$, R$_4$, R$_5$, R$_6$, R$_7$, b and p have the same meanings as described herein above.

In yet another sequence of steps as shown in Scheme-11, a compound of formula (Ivi), (Ivii), (Iviii) or (Iix) may undergo a deprotection reaction in presence of a base such as lithium hydroxide in a solvent such as tetrahydrofuran to obtain a compound of formula (Ix), (Ixi), (Ixii) or (Ixiii), respectively.

Scheme-11

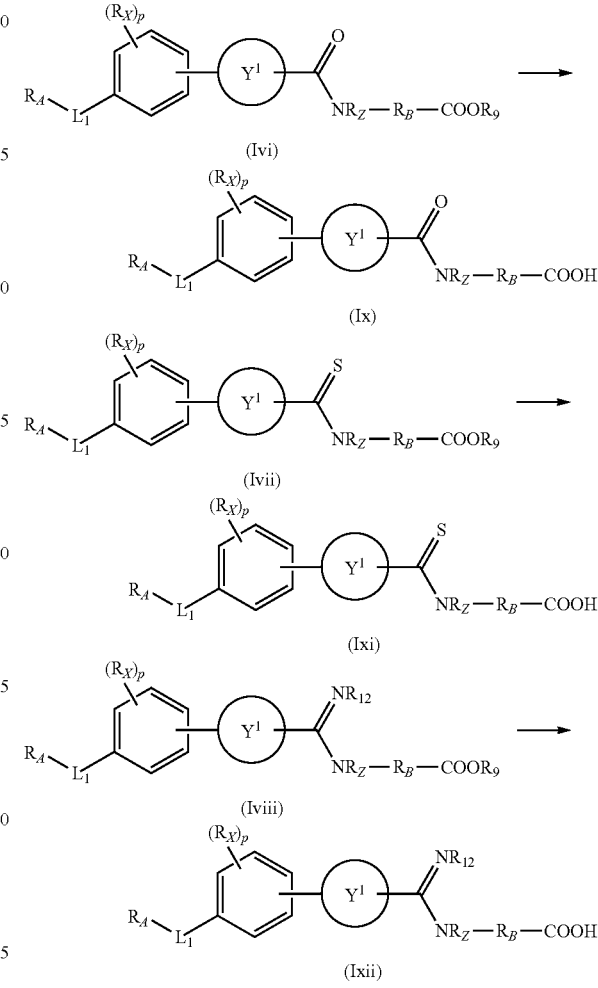

wherein,
R$_8$ is —COR$_{9a}$, —COOR$_{9a}$, —CONR$_6$R$_7$ or —SO$_2$R$_{9a}$; R$_{12}$, R$_A$, L$_1$, R$_X$, Y$^1$, R$_Z$, R$_B$, R$_6$, R$_7$ and p have the same meanings as described herein above in relation to formula (I), R$_{9a}$ is —H, alkyl, alkenyl, alkynyl, cycloalkyl, alkylcycloalkyl, aryl, alkylaryl, alkylheteroaryl, heterocycle or heteroaryl and R$_9$ is selected from methyl, ethyl, tert-butyl, benzyl, p-methoxybenzyl. The compounds of formula (lvi), (lvii), (lviii) and (lix) are converted to corresponding acids of formula (lx), (lxi), (lxii) and (lxiii) by alkaline hydrolysis; optionally converting the resultant acid into salt, solvate or prodrug.

In a further sequence of steps as shown in Scheme-12, a compound of formula (lxiv) may be reacted with a hydroxylamine hydrochloride in presence of a base such as potassium carbonate to form an oxime of formula (lxv). The oxime of formula (lxv) may be reacted with ClCOCO-OR$_p$ in a solvent such as chloroform and in presence of a base such as pyridine to obtain a compound of formula (lxvi). A compound of formula (lxvi) may be reacted with —NHR$_Z$R$_B$COOR$_9$ in a solvent such as ethanol and in presence of a base such as triethylamine to form a compound of formula (lxvii), which on further reduction forms an amine of formula (lxviii). The reduction may be performed in presence of a reducing agent such as Fe and ammonium chloride in a solvent such as ethanol, tetrahydrofuran, water or mixture thereof. The amine of formula (lxviii) may be reacted with an isocyanate of formula R$_A$—N=C=O in a solvent such as tetrahydrofuran, to form a compound of formula (lxix) wherein R$_A$, R$_X$, R$_Z$, R$_B$, R$_p$, and p are the same as defined earlier and Y$^1$ is of formula (c) (Scheme 2). A compound of formula (lxix) may be hydrolyzed in the presence of a base to form a compound of formula (lxx).

In a further sequence of steps as shown in Scheme-13, a compound of formula (Ib) may be reacted with a chlorinating agent such as N-chlorosuccinimide to, form an oxime of formula (Ig). The compound of formula (Ig) may be refluxed with compound of formula HC≡C—COOR$_p$ in a solvent such as toluene in presence a base such as triethylamine to form a compound of formula (Ixvia), wherein R$_p$ is as defined for formula 1c and R$_X$ and p are as defined for formula I.

Scheme-13

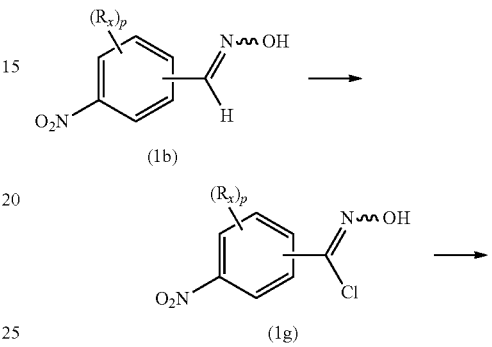

Scheme-12

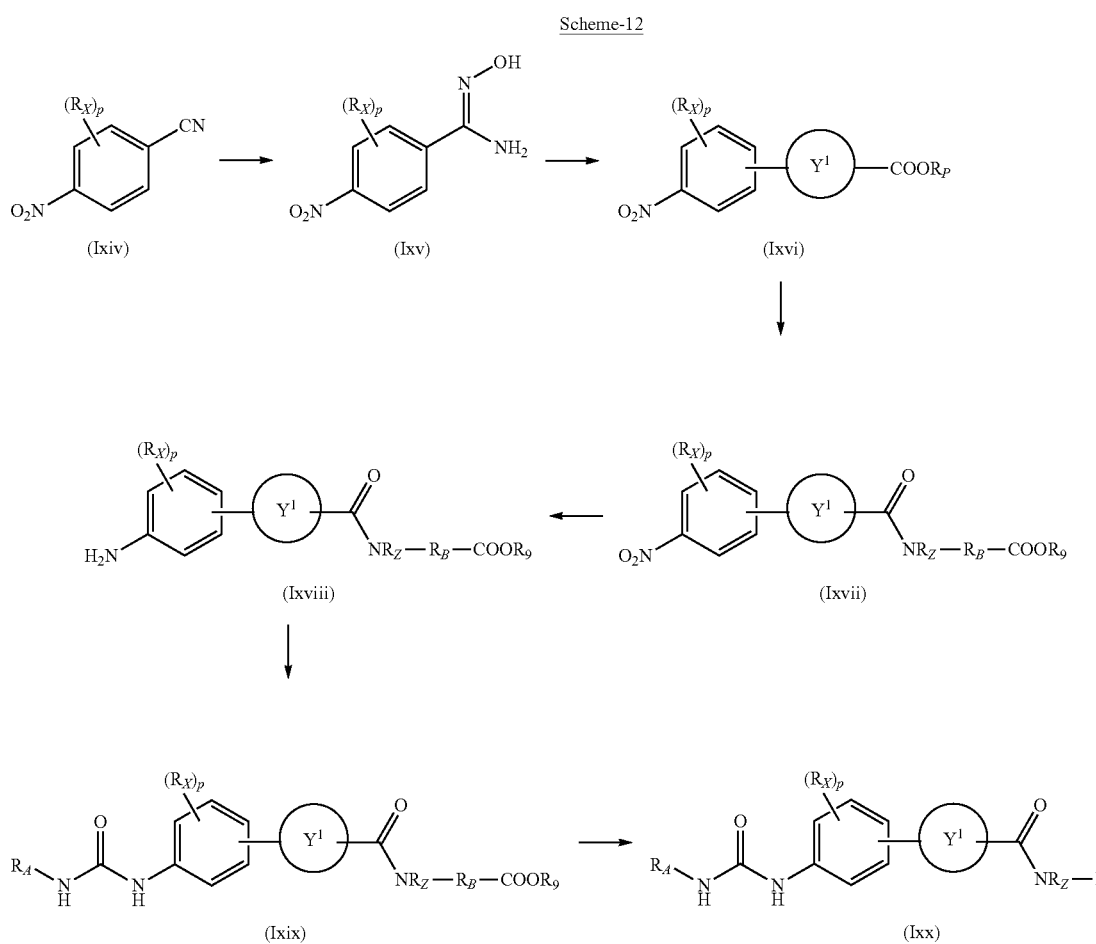

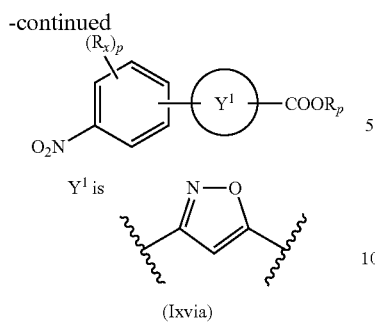

(Ixvia)

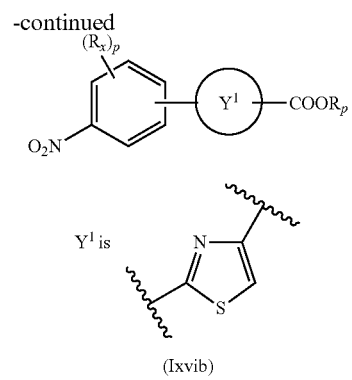

(Ixvib)

In a further sequence of steps as shown in Scheme-14, a compound of formula (Ih) may be refluxed with Lawesson's reagent in a solvent such as dioxane to form a thioamide of formula (Ii). Thioamide of formula (Ii) may be refluxed in a solvent such as ethanol with bromo ethyl pyruvate to form a compound of formula (Ixvib), wherein $R_p$ is as defined for formula 1c, (Scheme 1) and $R_X$ and p are as defined for formula I.

In a further sequence of steps as shown in Scheme-15, compounds of formula (Ixvia) and (Ixvib), (wherein $R_p$ is the same as defined for formula Ic) may be hydrolyzed in a solvent such as tetrahydrofuran in presence of a base such as sodium hydroxide or lithium hydroxide to form compounds of formula (Ixvic) and (Ixvid) respectively. The compounds of formula (Ixvic) and (Ixvid) may be reacted with a compound of formula $NHR_ZR_BCOOR_9$ in a solvent such as tetrahydrofuran, in presence of a coupling agent such as isobutyl chloroformate and a base such as N-methylmorpholine or triethylamine to form compounds of formula (Ixviia), and (Ixviib) respectively, wherein $R_Z$ is H, $R_X$, $R_B$, $R_9$ and p are as defined for formula I. The compounds of formula (Ixviia) and (Ixviib) may be reacted with methyl iodide in a solvent such as dimethylformamide in presence of base such as sodium hydride to form compounds of formula (Ixviiia) and (Ixviiib) respectively. The compounds of formula (Ixviia), (Ixviib) and (Ixxia), (Ixxib) may be reduced to form a compound of formula (Ixviiia) and (Ixviiib) respectively, wherein $R_Z$ is H or methyl, in presence of reducing agent such as Fe in presence of ammonium chloride, ethanol and water. The compounds of formula (Ixviiia) and (Ixviiib) may be reacted with, a compound of formula $R_AN=C=O$ in a solvent such as tetrahydrofuran to form compounds of formula (Ixixa) and (Ixixb) respectively, wherein $R_A$ is as defined for formula I. The compounds of formula (Ixixa) and (Ixixb) may be further hydrolyzed in presence of base such as lithium hydroxide to form compounds of formula (Ixxa) and (Ixxb) respectively, wherein $R_A$, $R_X$, $R_B$ and p are as defined for formula I, wherein $R_Z$ is H or methyl, $R_A$, $R_X$, $R_B$ and p are as defined for formula I.

Scheme-14

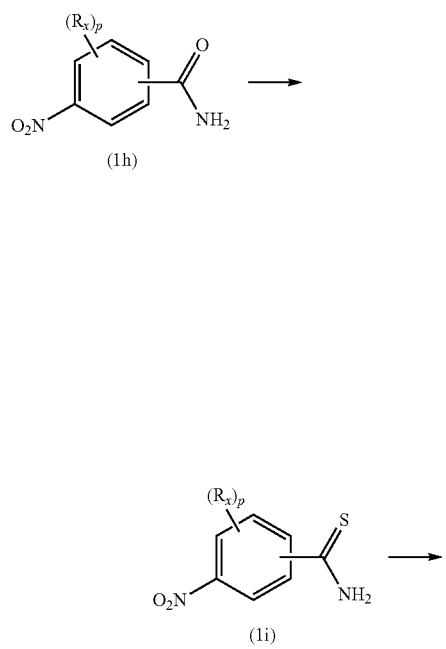

Scheme-15

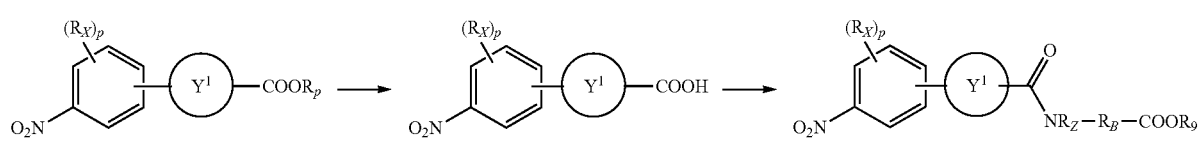

-continued
(lxvia): Y¹ is 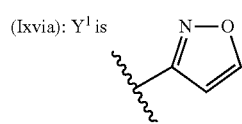
(lxvib): Y¹ is 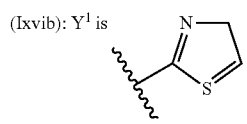
(lxvic): Y¹ is 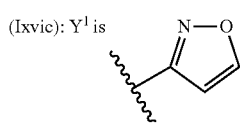
(lxvid): Y¹ is 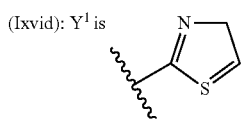
(lxviia): Y¹ is 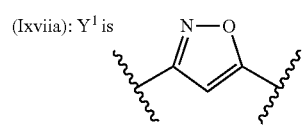
(lxviib): Y¹ is 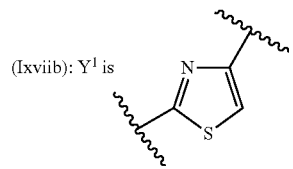
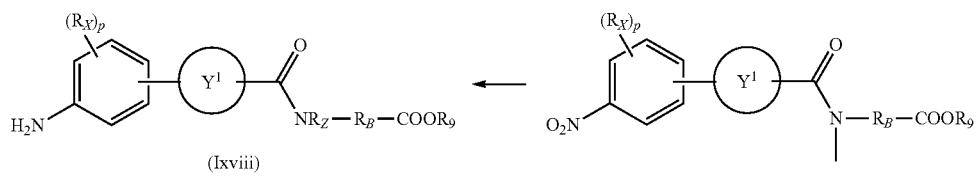
(lxviii)
(lxviiia): Y¹ is 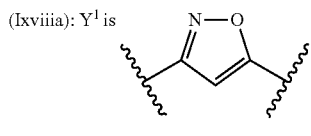
(lxviiib): Y¹ is 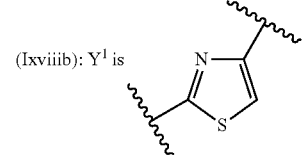
(lxxi)
(lxxia): Y¹ is 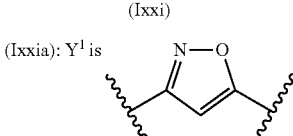
(lxxib): Y¹ is 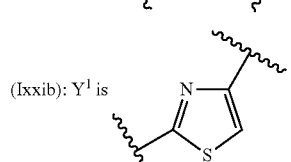
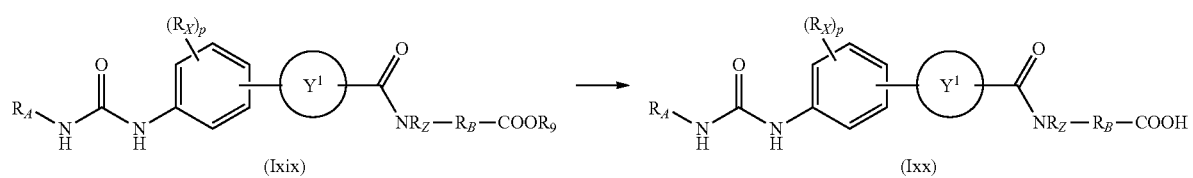
(lxix)
(lxixa): Y¹ is 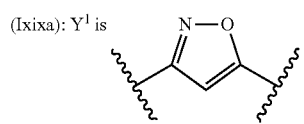
(lxixb): Y¹ is 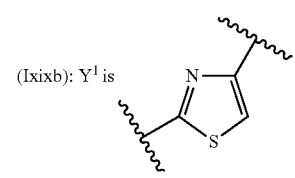
(lxx)
(lxxa): Y¹ is 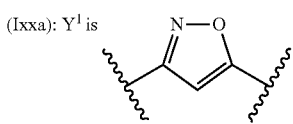
(lxxb): Y¹ is 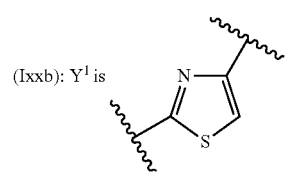

In a further sequence of steps as shown in Scheme-16, a compound of formula (lxviiia) (wherein $R_Z$ is H or methyl and $R_9$ is the same as defined for formula I) may be reacted with a

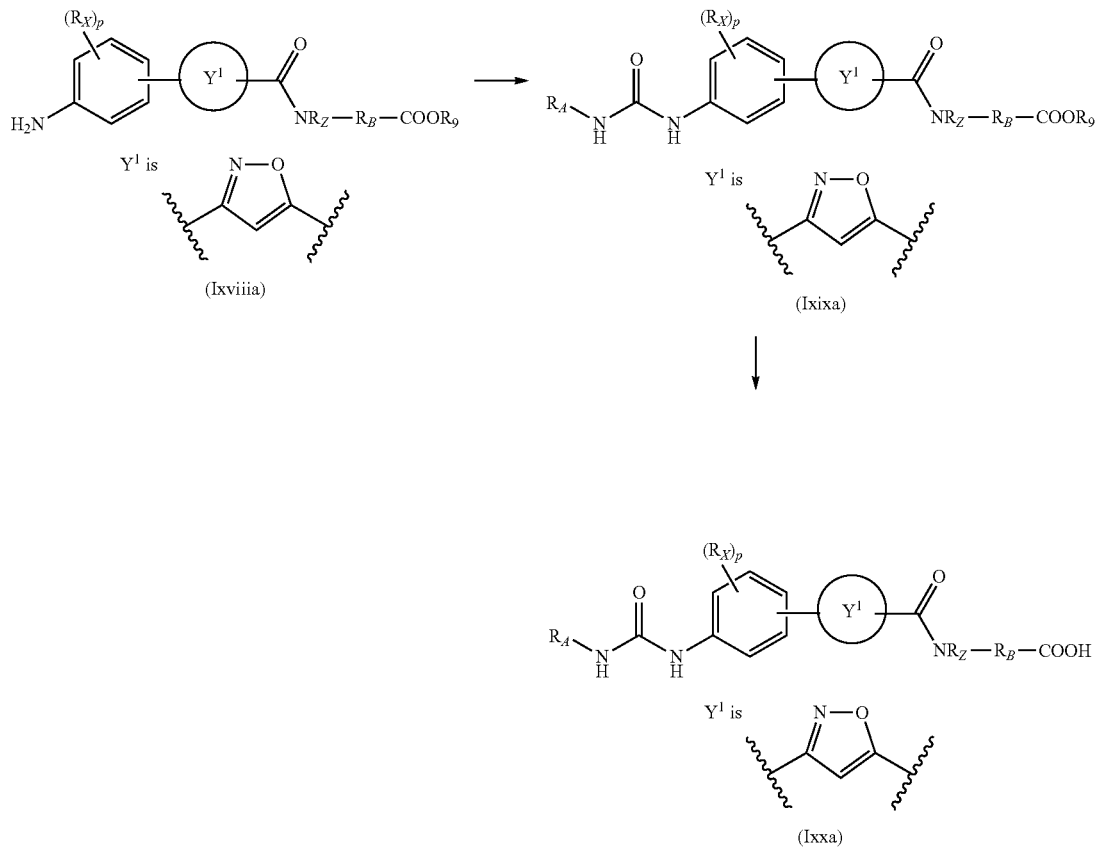

compound of formula $R_A$—$NH_2$ in presence of a coupling agent such as carbonyl diimidazole to form a compound of formula (lxixa), which may be further hydrolyzed in presence of a base such as lithium hydroxide to form a compound of formula (lxxa), wherein $R_A$, $R_X$, $R_B$ and p are the same as defined for formula I.

In a further sequence of steps as shown in Scheme-17, a compound of formula (lxxii) may be reacted with a compound of formula $R_A$—Br, wherein $R_A$ is substituted or unsubstituted alkylaryl to form a compound of formula (lxxiii). The compound of formula (lxxiii) may be refluxed with hydroxylamine hydrochloride in a solvent such as methanol to form an oxime of formula (lxxiv). The oxime of formula (lxxiv) may be reacted with a chlorinating agent such as N-chlorosuccinimide to form a compound of formula (lxxv). The compound of formula (lxxv) may be reacted with compound of formula HC≡C—$COOR_p$ in a solvent such as toluene in presence a base such as triethylamine to form a compound of formula (lxxvi), wherein $R_p$ is the same as defined for formula 1c. The compound of formula (lxxvi) may be Scheme-17

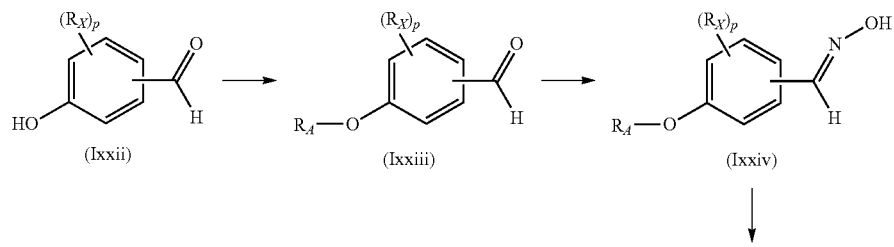

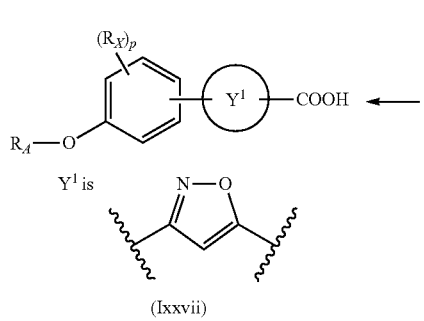
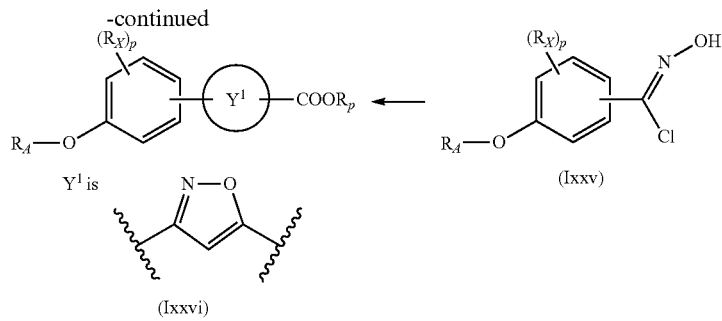

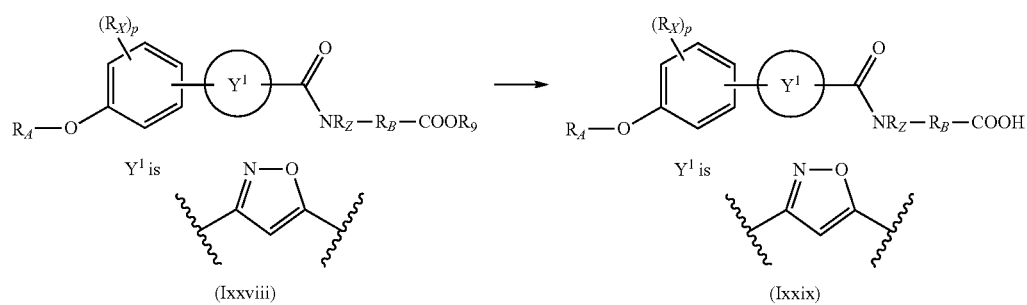

hydrolyzed in presence of a base such as sodium hydroxide to form a compound of formula (lxxvii). The compound of formula (lxxvii) may be reacted with compound of formula $NHR_ZR_BCOOR_9$ in a solvent such as tetrahydrofuran and in presence of a coupling agent such as isobutyl chloroformate and a base such as N-methylmorpholine or triethylamine to form a compound of formula (lxxviii), wherein $R_9$ is the same as defined for formula I. The compound of formula (lxxviii) may be hydrolyzed in presence of a base such as lithium hydroxide to form a compound of formula (lxxix), wherein $R_X$, $R_Z$, $R_B$, $R_p$ and p are the same as defined for formula I.

In a further sequence of steps as shown in Scheme-18, a compound of formula (lxxviii), (wherein $R_A$ is unsubstituted alkylaryl and $R_9$ is as defined for formula I) may be converted to a compound of formula (lxxx) by reacting with hydrogen on palladium carbon in a solvent such as tetrahydrofuran. The compound of formula (lxxx) may be reacted with a compound of formula $R_A$—Cl, to form a compound of formula (lxxviii), wherein $R_A$ is heteroaryl or substituted alkylaryl. The compound of formula (lxxviii) may be hydrolyzed in presence of a base such as lithium hydroxide to form a compound of formula (lxxix), wherein $R_X$, $R_Z$, $R_B$ and p are the same as defined for formula I.

Scheme-18

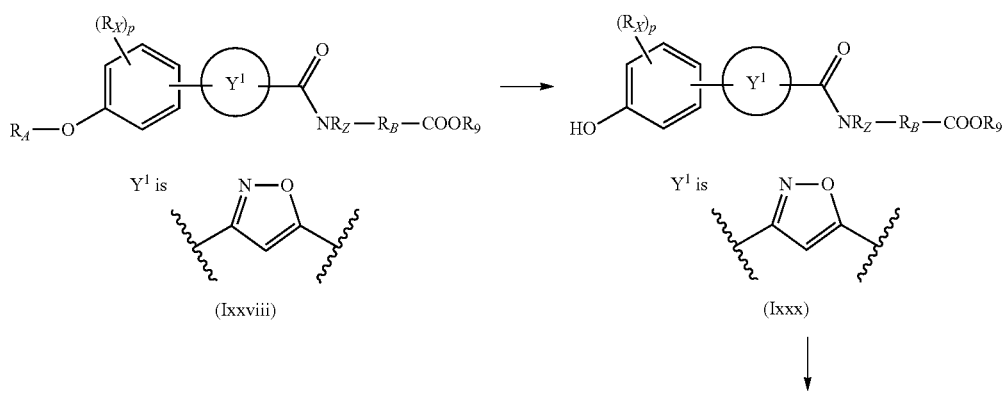

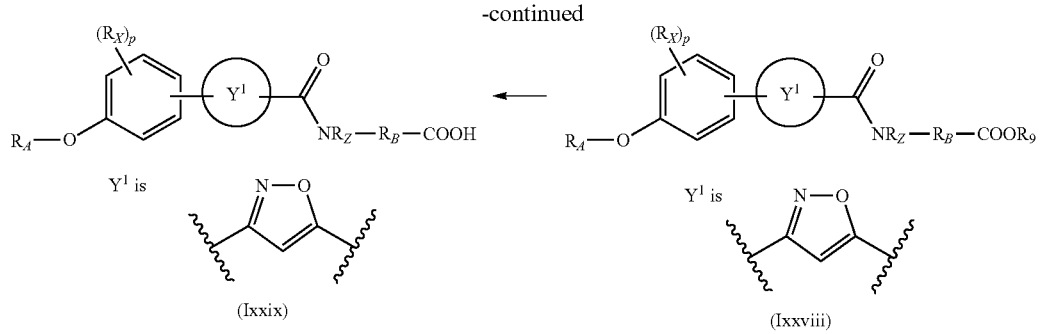

(Ixxix) ← (Ixxviii)

In a further sequence of steps as shown in Scheme-19, a compound of formula $R_A$—$NH_2$ may be reacted with a compound of formula (Ixviiia), wherein $R_9$ is as defined for formula I in presence of oxalyl chloride in a solvent such as ethyl acetate to form a compound of formula (Ixxxi), which may be further hydrolyzed in presence of a base such as lithium hydroxide to form a compound of formula (Ixxxii), wherein $R_A$, $R_X$, $R_Z$, $R_B$ and p are the same as defined for formula I.

Scheme-19

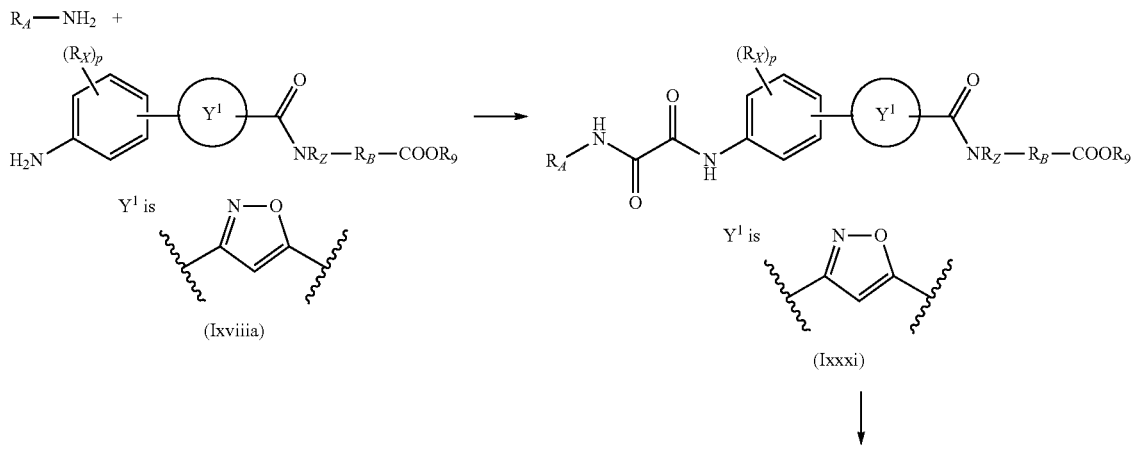

(Ixviiia) → (Ixxxi)

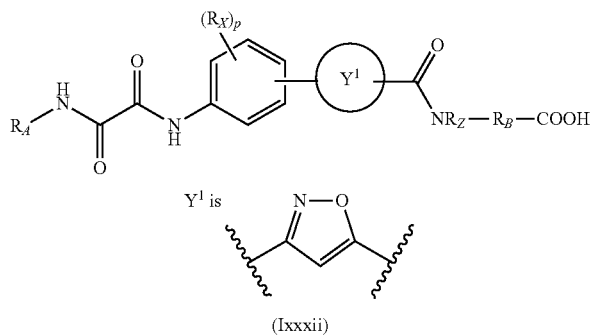

(Ixxxii)

In a further sequence of steps as shown in Scheme-20, a compound of formula (Iv) may be reacted with a compound of formula NHR$_Z$CH(CH$_2$OH)COOR$_9$ in presence of a coupling agent such as hydroxybenzotriazole and a base such as triethylamine to form a compound of formula (lxxxiii). The compound of formula (lxxxiii) may be further hydrolyzed in presence of a base such as lithium hydroxide to form a compound of formula (lxxxiv). The compound of formula (lxxxiii) can also be reacted with mesyl chloride in presence of a base such as In a further sequence of steps as shown in Scheme-21, a compound of formula (lxvic) may be reacted with a compound of formula NHR$_Z$—CH(CH$_2$OH)COOR$_9$ in presence of a coupling agent such as N-hydroxybenzotriazole and dicyclohexylcarbodiimide to form a compound of formula (lxxxvii). The compound of formula (lxxxvii) may be reacted with mesyl chloride in presence of base such as triethylamine in a solvent such as dichloromethane to form a compound of formula (lxxxviii). The compound of formula (lxxxviii) may be reduced to form a compound of formula (lxxxix), in pres-

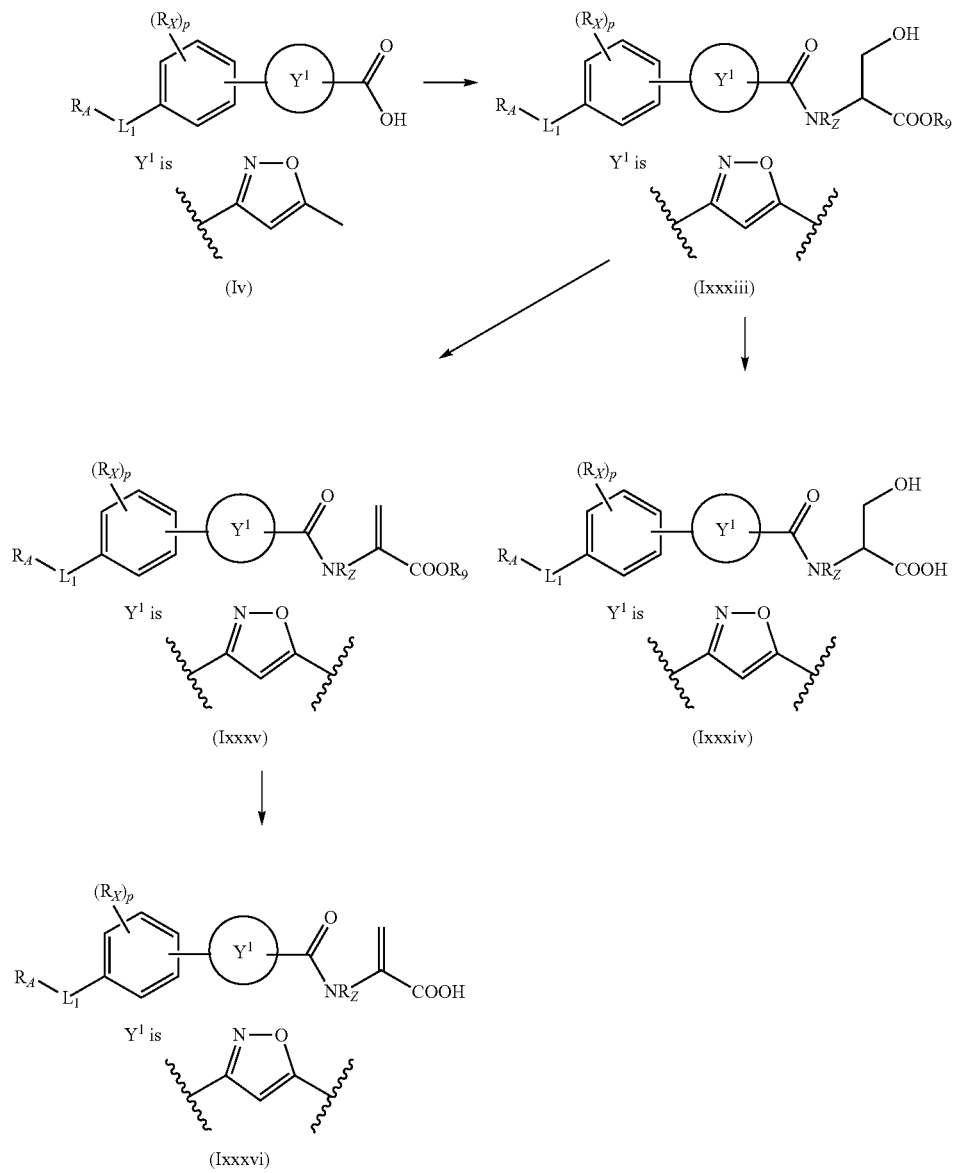

triethylamine in a solvent such as dichloromethane to form a compound of formula (lxxxv), wherein R$_9$ is the same as defined for formula I. The compound of formula (lxxxv) may be hydrolyzed in presence of a base such as lithium hydroxide, in a solvent such as tetrahydrofuran to form a compound of formula (lxxxvi), wherein L$_1$ is NH(CO)NH, R$_A$, R$_X$, R$_Z$ and p are the same as defined for formula I.

ence of reducing agent such as Fe in presence of ammonium chloride, ethanol and water. The compound of formula (lxxxix) may be reacted with an isocyanate of formula R$_A$—N=C=O to form a compound of formula (lxxxv), which may be further hydrolyzed to form a compound of formula (lxxxvi), wherein L$_1$ is NH(CO)NH, R$_A$, R$_X$, R$_Z$ and p are the same as defined for formula I.

Scheme-21

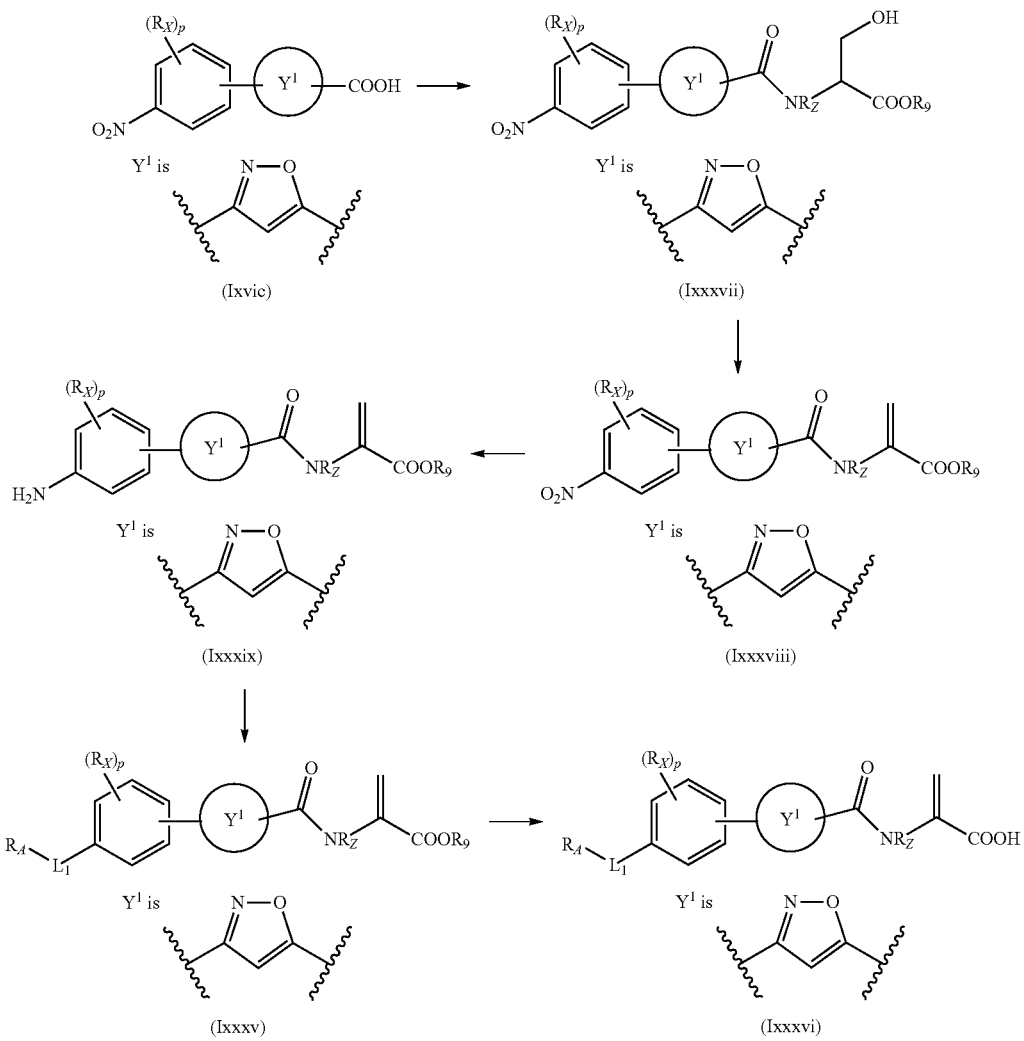

In a further sequence of steps as shown in Scheme-22, a compound of formula (lvii) may be reacted with ethyl iodide in a solvent such as acetone in presence of a base such as potassium carbonate to form a compound of formula (lxxxvii). The compound of formula (lxxxvii) may be reacted with hydroxylamine hydrochloride in a solvent such as methanol in presence of a base such as sodium carbonate to form a compound of formula (lxxxviii).

Scheme-22

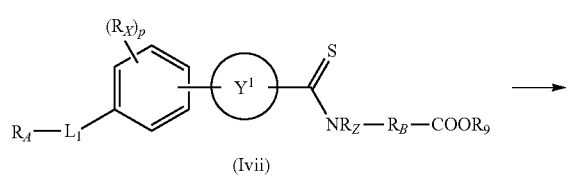

-continued

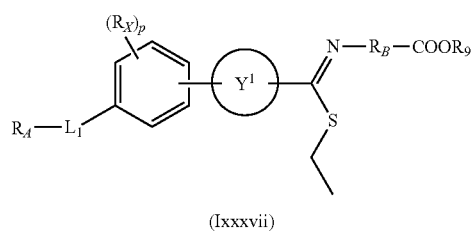

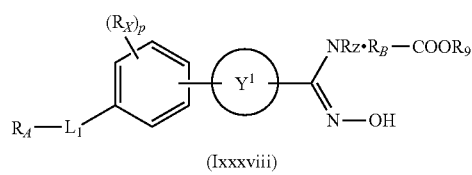

Compounds described in Schemes 1-22 may optionally be converted to their salts.

It will be appreciated by those skilled in the art that the compounds of the present invention may also be utilized in the form of their pharmaceutically acceptable salts or solvates. The pharmaceutically acceptable salts of the compounds of the present invention are in particular salts which are non-toxic or which can be used physiologically.

Thus, when the compounds of the present invention represented by the general formula (I) contain one or more basic groups, i.e. groups which can be protonated, they can form an addition salt with an inorganic or organic acid. Examples of suitable inorganic: acids include: boric acid, perchloric acid, hydrochloric acid, hydrobromic acid, hydrofluoric acid, sulfuric acid, sulfamic acid, phosphoric acid, nitric acid and other inorganic acids known to the person skilled in the art. Examples of suitable organic acids include: acetic acid, propionic acid, succinic acid, glycolic acid, stearic acid, lactic acid, malic acid, tartaric acid, citric acid, ascorbic acid, pamoic acid, maleic acid, hydroxymaleic acid, fumaric acid, phenylacetic acid, glutamic acid, benzoic acid, salicylic acid, sulfanilic acid, 2-acetoxybenzoic acid, toluenesulfonic acid, methanesulfonic acid, benzenesulfonic acid, ethane disulfonic acid, oxalic acid, isethionic acid, ketoglutaric acid, glycerophosphoric acid, aspartic acid, picric acid, lauric acid, palmitic acid, cholic acid, pantothenic acid, alginic acid, naphthoic acid, mandelic acid, tannic acid, camphoric acid and other organic acids known to the person skilled in the art.

Thus, when the compounds of the present invention represented by the general formula (I) contain an acidic group they can form an addition salt with a suitable base. For example, such salts of the compounds of the present invention may include their alkali metal salts such as Li, Na, and K salts, or alkaline earth metal salts like Ca, Mg salts, or aluminium salts, or salts with ammonia or salts of organic bases such as lysine, arginine, guanidine, diethanolamine, choline, tromethamine [TRIS(HYDROXYMETHYL)AMINOMETHANE].

The pharmaceutically acceptable salts of the present invention can be synthesized from the subject compound, which contains a basic or an acidic moiety, by conventional chemical methods. Generally the salts are prepared by contacting the free base or acid with stoichiometric amounts or with an excess of the desired salt-forming inorganic or organic acid or base in a suitable solvent or dispersant or from another salt by cation or anion exchange. Suitable solvents are, for example, ethyl acetate, ether, alcohols, acetone, tetrahydrofuran (THF), dioxane or mixtures of these solvents.

The present invention furthermore includes all solvates of the compounds of the formula (I), for example hydrates, and the solvates formed with other solvents of crystallization, such as alcohols, ethers, ethyl acetate, dioxane, dimethylformamide (DMF), or a lower alkyl ketone, such as acetone, or mixtures thereof.

The present invention also includes prodrugs and other physiologically acceptable derivatives of compounds of formula (I).

The process of the present invention described herein therefore comprises the optional step of forming a salt and/or a solvate and/or a prodrug of the compound of formula (I), (Iaa), (Iab), (Iac), (Iad), (Iae), (Iaf), (Iag), (Iah), (Iai), (Iaj), (Ib) or (Ic).

An optically active from of a compound of the present invention may be obtained by using an optically active starting material or by resolution of a racemic form of the compound using standard procedures.

Methods of Treatment

The present compounds are DGAT1 inhibitors and find use in the treatment of clinical conditions associated with obesity and obesity related disorders in a warm-blooded animal. The compounds of the present invention are particularly useful for the prevention, delay or treatment of a range of disease states associated with obesity, including diabetes mellitus, more specifically type 2 diabetes mellitus (T2DM), and complications arising therefrom (for example retinopathy, neuropathy and nephropathy), insulin resistance, impaired glucose tolerance (IGT), conditions of impaired fasting glucose, metabolic acidosis, ketosis, steatosis, dysmetabolic syndrome, arthritis, osteoporosis, and other obesity related disorders, which include peripheral vascular disease, (including intermittent claudication), cardiac failure and certain cardiac myopathies, hypertension, myocardial ischaemia, myocardial infarction, arteriosclerosis, atherosclerosis, hypercholesterolemia, hypertriglyceridemia, hyperlipidaemia, cerebral ischaemia and reperfusion, infertility and polycystic ovary syndrome, muscle weakness, diseases of the skin such as acne, various immunomodulatory diseases such as psoriasis, inflammatory bowel syndrome and inflammatory bowel disease such as Crohn's disease and ulcerative colitis.

According to another aspect of the present invention, there is provided a method for the treatment of diseases mediated by DGAT1, comprising administering to a mammal in need thereof a therapeutically effective amount of a compound of formula I or a pharmaceutically acceptable salt or a pharmaceutically acceptable solvate thereof.

According to another aspect of the present invention, there is provided a method for the treatment of diseases mediated by DGAT1 selected from obesity and obesity related disorders comprising administering to a mammal in need thereof a therapeutically effective amount of a compound of formula I or a pharmaceutically acceptable salt or a pharmaceutically acceptable solvate thereof.

According to another aspect of the present invention, there is provided the use of a compound of formula (I) in the treatment of diseases mediated by DGAT1.

According to another aspect of the present invention, there is provided the use of a compound of formula (I) in the treatment of diseases mediated by DGAT1 selected from obesity and obesity related disorders.

According to another aspect of the present invention, there is provided the use of a compound of formula (I) or a pharmaceutically acceptable salt or a pharmaceutically acceptable solvate thereof, for the manufacture of a medicament for the treatment of diseases mediated by DGAT1.

According to another aspect of the present invention, there is provided the use of a compound of formula (I) or a pharmaceutically acceptable salt or a pharmaceutically acceptable solvate thereof, for the manufacture of a medicament for the treatment of diseases mediated by DGAT1 selected from obesity and obesity related disorders.

According to another aspect of the present invention, the obesity related disorders are selected from peripheral vascular disease, diabetes mellitus, insulin resistance, impaired glucose tolerance, diabetic neuropathy, diabetic nephropathy, diabetic retinopathy, hypercholesterolemia, hypertriglyceridemia, hyperlipidemia, metabolic acidosis, ketosis, steatosis, dysmetabolic syndrome, arthritis, osteoporosis, cardiovascular diseases such as hypertension, cardiac failure, cardiomyopathy, myocardial ischaemia, myocardial infarction, arteriosclerosis and atherosclerosis, cerebral ischaemia and reperfusion, infertility, polycystic ovary syndrome, muscle weakness, diseases of the skin such as acne, various immunomodulatory diseases such as psoriasis, inflammatory bowel syndrome and inflammatory bowel disease such as Crohn's disease and ulcerative colitis comprising administering to a mammal in need thereof a therapeutically effective amount of a compound of formula I or a pharmaceutically acceptable salt or a pharmaceutically acceptable solvate thereof.

According to another aspect of the present invention, the obesity related disorders are selected from diabetes mellitus, insulin resistance, impaired glucose tolerance, diabetic neuropathy, diabetic nephropathy, diabetic retinopathy, metabolic acidosis, ketosis and steatosis, comprising administering to a mammal in need thereof a therapeutically effective amount of a compound of formula I or a pharmaceutically acceptable salt or a pharmaceutically acceptable solvate thereof.

According to another aspect of the present invention, the obesity, related disorders are selected from peripheral vascular disease, hypercholesterolemia, hypertriglyceridemia, hyperlipidemia, dysmetabolic syndrome, cardiovascular diseases such as hypertension, cardiac failure, cardiomyopathy, myocardial ischaemia, myocardial infarction, arteriosclerosis and atherosclerosis, comprising administering to a mammal in need thereof a therapeutically effective amount of a compound of formula I or a pharmaceutically acceptable salt or a pharmaceutically acceptable solvate thereof.

According to another aspect of the present invention, the obesity related disorders are selected from, arthritis, osteoporosis, cerebral ischaemia and reperfusion, infertility, polycystic ovary syndrome, muscle weakness, diseases of the skin such as acne, various immunomodulatory diseases such as psoriasis, inflammatory bowel syndrome and inflammatory bowel disease such as Crohn's disease and ulcerative colitis comprising administering to a mammal in need thereof a therapeutically effective amount of a compound of formula I or a pharmaceutically acceptable salt or a pharmaceutically acceptable solvate thereof.

In particular, the compounds of the present invention are of interest for the prevention, delay or treatment of diabetes mellitus and/or obesity and/or obesity related disorders. The inhibition of DGAT1 activity may be applied as a sole therapy or in combination with one or more pharmaceutically active compound for the indication being treated. Conjoint treatment may be beneficial in the treatment of metabolic syndrome (as defined by International Diabetes Federation). Such conjoint treatments may include the following main categories:

1) Anti-obesity therapies, such as those that cause weight loss by effects on food intake, nutrient absorption or energy expenditure, such as orlistat, sibutramine and the like;
2) CB1 receptor blocker such as rimonabant;
3) Insulin secretagogues, including sulphonylureas (for example glibenclamide, glipizide), prandial glucose regulators (for example repaglinide, nateglinide);
4) Agents that improve incretin action (for example dipeptidyl peptidase IV (DPPIV) inhibitors, and GLP-I agonists) or incretin mimetics such as exenatide;
5) Insulin sensitising agents, including PPARgamma agonists (for example pioglitazone and rosiglitazone), and agents with combined PPARalpha and gamma activity;
6) Agents that modulate hepatic glucose balance (for example metformin, fructose 1,6 bisphosphatase inhibitors, glycogen phopsphorylase inhibitors, glycogen synthase kinase inhibitors, glucokinase activators);
7) Agents designed to reduce the absorption of glucose from the intestine (for example acarbose);
8) Agents that prevent the reabsorption of glucose by the kidney (SGLT inhibitors);
9) Agents designed to treat the complications of prolonged hyperglycaemia (for example, aldose reductase inhibitors);
10) Anti-dyslipidaemia agents such as, HMG-CoA reductase inhibitors (e.g. statins), PPARα-agonists (fibrates, eg gemfibrozil); bile acid sequestrants (cholestyramine); cholesterol absorption inhibitors (plant stanols, synthetic inhibitors); bile acid absorption inhibitors (IBATi) and nicotinic acid and analogues (niacin and slow release formulations);
11) Antihypertensive agents such as, β-blockers (e.g., atenolol, inderal); ACE inhibitors (e.g., lisinopril); Calcium antagonists (e.g., nifedipine); Angiotensin receptor antagonists (e.g., candesartan), α antagonists and diuretic agents (e.g., furosemide, benzthiazide);
12) Haemostasis modulators, such as antithrombotics, activators of fibrinolysis and antiplatelet agents; thrombin antagonists; factor Xa inhibitors; factor VIIa inhibitors); antiplatelet agents (eg. aspirin, clopidogrel); anticoagulants (heparin and low molecular weight analogues, hirudin) and warfarin;
13) Agents which antagonise the actions of glucagon;
14) Anti-inflammatory agents, such as non-steroidal anti-inflammatory drugs (eg. aspirin) and steroidal anti-inflammatory agents (eg. cortisone);

In addition to their use in therapeutic medicine the compounds are also useful as pharmacological tools in the development and standardisation of in vitro and in vivo test systems for the evaluation of the effects of inhibitors of DGAT1 activity in laboratory animals, such as cats, dogs, rabbits, monkeys, rats and mice, as part of the search for new therapeutic agents.

Pharmaceutical Compositions and Methods

According to another aspect of the present invention, there is provided a pharmaceutical composition comprising a compound of formula (I) described hereinabove as active ingredient, or a pharmaceutical salt thereof or pharmaceutically acceptable solvent thereof, in association with a pharmaceutically acceptable carrier or excipient. The pharmaceutical composition is for use in the treatment of diseases mediated by DGAT1 such as obesity, diabetes, insulin resistance, impaired glucose tolerance and conditions associated therewith.

The pharmaceutical preparations according to the invention are prepared in a manner known per se and familiar to one skilled in the art. Pharmaceutically acceptable inert inorganic and/or organic carriers and/or additives can be used in addition to the compounds of formula (I), and/or their physiologically tolerable salts. For the production of pills, tablets, coated tablets and hard gelatin capsules, it is possible to use, for example, lactose, corn starch or derivatives thereof, gum arabica, magnesia or glucose, etc. Carriers for soft gelatin capsules and suppositories are, for example, fats, waxes, natural or hardened oils, etc. Suitable carriers for the production of solutions, for example injection solutions, or of emulsions or syrups are, for example, water, physiological sodium chloride solution or alcohols, for example, ethanol, propanol or glycerol, sugar solutions, such as glucose solutions or mannitol solutions, or a mixture of the various solvents which have been mentioned.

According to another aspect of the present invention, there is provided a method for the manufacture of a medicament comprising bringing a compound of formula (I) into association with a pharmaceutically acceptable carrier or excipient, the medicaments being useful for the treatment of obesity, diabetes, insulin resistance, impaired glucose tolerance and conditions associated therewith.

The pharmaceutical preparations normally contain about 1 to 99%, for example, about 5 to 70%, or from about 5 to about 30% or from by weight of the compound of the formula (I) and/or its physiologically tolerable salt. The amount of the active ingredient of the compound of formula (I) and/or its physiologically tolerable salt in the pharmaceutical preparations normally is from about 5 to 500 mg.

The dose of the compounds of this invention, which is to be administered, can cover a wide range. The dose to be administered daily is to be selected to suit the desired effect. A suitable dosage is about 0.001 to 100 mg/kg/day of the compound of formula (I), and/or its physiologically tolerable salt, for example, about 0.01 to 50 mg/kg/day of a compound of formula (I), or a pharmaceutically acceptable salt of the compound. If required, higher or lower daily doses can also be administered. Actual dosage levels of the active ingredients in the pharmaceutical compositions of this invention may be varied so as to obtain an amount of the active ingredient, which is effective to achieve the desired therapeutic response for a particular patient, composition, and mode of administration without being toxic to the patient.

The pharmaceuticals can be administered orally, for example in the form of pills, tablets, coated tablets, capsules, granules or elixirs. Administration, however, can also be carried out rectally, for example in the form of suppositories, or parenterally, for example intravenously, intramuscularly or subcutaneously, in the form of injectable sterile solutions or suspensions, or topically, for example in the form of solutions or transdermal patches, or in other ways, for example in the form of aerosols or nasal sprays.

The selected dosage level will depend upon a variety of factors, including the activity of the particular compound of the present invention employed, the route of administration, the time of administration, the rate of excretion of the particular compound being employed, the duration of the treatment, other drugs, compounds and/or materials used in combination with the particular compounds employed, the age, sex, weight, condition, general health and prior medical history of the patient being treated, and like factors well known in the medical arts.

In addition to the active ingredient of the compound of general formula (I) and/or its physiologically acceptable salt and carrier substances, the pharmaceutical preparations can contain additives such as, for example, fillers, antioxidants, dispersants, emulsifiers, defoamers, flavors, preservatives, solubilizers or colorants. They can also contain two or more compounds of the general formula (I), and/or their physiologically tolerable salts. Furthermore, in addition to at least one compound of the general formula (I), and/or its physiologically tolerable salt, the pharmaceutical preparations can also contain one or more other therapeutically or prophylactically active ingredients:

By "pharmaceutically acceptable" is meant that the carrier, diluent, excipients, and/or salt must be compatible with the other ingredients of the formulation, and not deleterious to the recipient thereof.

It is understood that modifications that do not substantially affect the activity of the various embodiments of this invention are included within the invention disclosed herein. Accordingly, the following Examples are intended to illustrate but not to limit the present invention.

EXAMPLES

The invention is further understood by reference to the following Examples, which are intended to be purely exemplary of the invention. The present invention is not limited in scope by the exemplified embodiments, which are intended as illustrations of single aspects of the invention only. Any methods that are functionally equivalent to those described in the Examples are within the scope of the invention. Various modifications of the invention in addition to those described herein will become apparent to those skilled in the art from the foregoing description. Such modifications fall within the scope of the appended claims.

Unless otherwise stated, all temperatures are in degree Celsius. Also, in these Examples and elsewhere, abbreviations have the following meanings:

| g | Gram | EtOH | Ethanol |
|---|---|---|---|
| mmol | Millimolar | ml | Milliliter |
| Ala | L-Alanine | matom | Milliatom |
| Cys | L-cysteine | $CHCl_3$ | Chloroform |
| Gly | Glycine | $Na_2SO_4$ | Sodium sulfate |
| MeOH | Methanol | $Et_3N$ | Triethylamine |
| EtOAc | Ethyl acetate | NaOH | Sodium hydroxide |
| DCU | 1,3-dicyclohexyl urea | HCl | Hydrogen chloride |
| HOBt | 1-hydroxybenzotriazole | KBr | Potassium bromide |
| LiOH | Lithium hydroxide | DMSO | Dimethyl sulfoxide |
| DMF | Dimethyl formamide | $NaHCO_3$ | Sodium bicarbonate |
| $NH_4Cl$ | Ammonium chloride | DCC | 1,3-dicyclohexyl-carbodiimide |
| THF | Tetrahydrofuran | | |
| DCM | Dichloromethane | RT | Room temperature |

Experimental

Example 1

3-[4-(6-Fluoro-benzothiazol-2-ylamino)-phenyl]-isoxazole-5-carboxylic acid ethyl ester Step 1: 3-(4-Nitro-phenyl)-isoxazol-5-carboxylic acid ethyl ester To a solution of N-hydroxy-4-nitro-benzimidoyl chloride (2.0 g; 10 mmol) and ethyl propiolate (2.02 ml; 20 mmol) in toluene (25 ml) was added $Et_3N$ (1.46 ml; 10.5 mmol) drop wise for 10 minutes. The resulting reaction mixture was heated at 80° C. for 2.5 hours, and then diluted with EtOAc (50 ml) and transferred in a separating funnel. The EtOAc layer was washed with 0.1N HCl (10 ml) followed by water (3×10 ml) and brine (10 ml). The EtOAc layer was dried over anhydrous $Na_2SO_4$, solvent was evaporated and the residue was crystallized from $CHCl_3$ and light petroleum to afford the title compound of step 1 (1.35 g; 51.7%). Mass ($ES^+$), 263 ($M^++1$); $^1H$ NMR ($CDCl_3$) δ: 1.45 (t, 3H), 4.48 (q, 2H), 7.26 (s, 1H), 8.02 (d, 2H), 8.35 (d, 2H).

Step 2: 3-(4-Amino-phenyl)-isoxazol-5-carboxylic acid ethyl ester

To a solution of the compound of step 1 (1.0 g; 3.8 mmol) and $NH_4Cl$ (0.61 g; 11.4 mmol) in EtOH (30 ml), THF (20 ml) and water (5.0 ml), was added iron powder (0.5 g, 8.9 mmol) under vigorous stirring. The resulting reaction mixture was heated at 80° C. under stirring for 3 hours. The reaction mixture was cooled to 25° C. and filtered through celite and washed with EtOH. The filtrate was concentrated and basified with $NaHCO_3$. The oil separated was extracted with dichloromethane (3×20 ml). The dichloromethane layer was washed with water (2×10 ml) and dried over anhydrous $Na_2SO_4$. The solvent was evaporated, and the residue was purified by flash chromatography with EtOAc: light petroleum (1:1) to give the title compound of step 2 (0.67 g; 75%).

Mass (ES⁻), 231 (M−1); ¹H NMR (DMSO-d$_6$) δ: 1.31 (t, 3H), 4.36 (q, 2H), 5.64 (s, 2H), 6.61 (d, 2H), 7.60 (d, 2H), 7.66 (s, 1H).

Step 3: 3-[4-(6-Fluoro-benzothiazol-2-ylamino)-phenyl]-isoxazole-5-carboxylic acid ethyl ester A mixture of the compound of step 2 (3.0 g; 12.9 mmol) and 2-chloro-6-fluoro benzothiazole (2.67 g; 14.2 mmol) in EtOH (60 ml) was heated at 60° C. to get a clear solution. To the hot solution 4N HCl in dioxane (1.6 ml; 6.45 mmol) was added and the resulting reaction mixture was refluxed for 20 hours. The reaction mixture was cooled to room temperature and the solid was filtered, and washed with EtOH (2×10 ml). The solid was dried under vacuum to yield 2.83 g (57.2%) of the title compound. Mass (ES⁻) 382 (M−1); IR (KBr): 3410 (br), 2710 (br), 1729, 1719, 1630, 1598; ¹H NMR (DMSO-d$_6$): δ 1.36 (t, 3H), 4.41 (q, 2H), 7.20 (m, 1H), 7.67 (m, 1H), 7.78 (m, 1H), 7.81 (s, 1H), 7.87-7.99 (m, 4H), 10.92 (br, 1H).

Example 2

3-[4-(6-Fluoro-benzothiazol-2-ylamino)-phenyl]-isoxazole-5-carboxylic acid

3-[4-(6-Fluoro-benzothiazol-2-ylamino)-phenyl]-isoxazole-5-carboxylic acid ethyl ester was dissolved in 2-propanol (500 ml) by heating at 55-60° C. The solution was cooled. A solution of 1N NaOH was added to it. On completion of reaction, the reaction mixture was acidified with conc. HCl to a pH 2, and extracted with EtOAc (3×50 ml). The EtOAc extract was washed with water (3×20 ml) followed by brine (10 ml), and the EtOAc layer was dried over anhydrous Na$_2$SO$_4$ to obtain 6.4 g (86.3.7%) of the title compound. Mass (ES⁺), 356 (M⁺+1); IR (KBr): 3447 (br), 1647 (br), 1611, 1478, 1466; ¹H NMR (DMSO-d$_6$) δ: 7.18 (m, 1H), 7.64 (m, 1H), 7.73 (s, 1H), 7.76 (m, 1H), 7.89-7.96 (m, 4H), 10.86 (br, 1H).

Example 3

3-[4-(6-Fluoro-benzothiazol-2-ylamino)-phenyl]-isoxazole-5-carboxylic acid amide A mixture of 3-[4-(6-fluoro-benzothiazol-2-ylamino)-phenyl]-isoxazole-5-carboxylic acid ethyl ester (4.0 g; 10.44 mmol) and saturated methanolic ammonia (250 ml) was stirred to obtain a white solid. The solvent was evaporated, and the residue was stirred with light petroleum and filtered. The residue was washed with light petroleum and dried to obtain 3.6 g (97.4%) of the title compound. Mass (ES⁺), 355 (M⁺+1); IR (KBr): 3463, 3123 (br), 1700, 1607, 1553 (br); 1447 (br); ¹H NMR (DMSO-d$_6$) δ: 7.18 (m, 1H), 7.54 (s, 1H), 7.64 (m, 1H), 7.76 (m, 1H), 7.87-7.90 (br, 4H), 7.98, 8.37(2× br, 2H, NH$_2$).

Example 4

3-[4-(6-Fluoro-benzothiazol-2-ylamino)-phenyl]-isoxazole-5-carbothioic acid amide To a solution of 3-[4-(6-fluoro-benzothiazol-2-ylamino)-phenyl]-isoxazole-5-carboxylic acid amide (3.54 g; 10 mmol) in dioxane (25 ml), was added Lawesson's reagent (4.11 g; 10 mmol) and the resulting reaction mixture was refluxed for 45 min. The pH of the reaction mixture was adjusted to near neutral, the solvent was removed and the residue was diluted with water (20 ml) and extracted with EtOAc (3×30 ml). The EtOAc layer was washed with water (3×10 ml) followed by brine (10 ml), and dried over anhydrous Na$_2$SO$_4$. The solvent was removed, and the residue was triturated with dichloromethane, filtered and dried to afford 3.0 g (80%) of the title compound. Mass (ES⁻), 369 (M−1); IR (KBr): 3282 (br), 3142 (br), 1651, 1608, 1588, 1555, 1441 (br); ¹H NMR (DMSO-d$_6$) δ: 7.18 (m, 1H), 7.58 (s, 1H), 7.65 (m, 1H), 7.77 (m, 1H), 7.88-7.94 (br, 4H), 7.97, 10.33 (2×br, 2H), 10.79 (s, 1H).

Example 5

(S)-2-({3-[4-(6-Fluoro-benzothiazol-2-ylamino)-phenyl]-isoxazole-5-carbonyl}-amino)-3-methyl-butyric acid methyl ester To a chilled solution of 3-[4-(6-fluoro-benzothiazol-2-ylamino)-phenyl]-isoxazole-5-carboxylic acid (3.0 g, 8.45 mmol) and (S)-Val-OMe. HCl (1.67 g; 10.14 mmol) in DMF (75 ml) was added Et$_3$N (1.41 ml; 10.14 mmol) under stirring followed by DCC (2.09 g; 10.14 mmol). After 5 minutes HOBt (1.42 g; 8.45 mmol) was added, and the reaction mixture was stirred at 0° C. for 1 hour and then at room temperature for 18 hours. The precipitated DCU was filtered off, and dried under vacuum pump. The residue was purified by flash chromatography over silica gel with 30% EtOAc in light petroleum. The pure solid was triturated with dichloromethane and filtered. The solid was dried to obtain 2.9 g (73.4%) of the title compound. Mass (ES⁻): 467 (M−1); IR (KBr): 3326 (br), 2966, 2931, 1722, 1679, 1609, 1560 (br), 1458, 1443; ¹H NMR (DMSO-d$_6$) δ: 0.95, 0.99 (2×d, 6H), 2.22 (m, 1H), 3.69 (s, 3H), 4.32 (m; 1H), 7.20 (m, 1H), 7.66 (m, 1H), 7.70 (s, 1H), 7.78 (m, 1H), 7.93 (s, 4H), 9.23 (d, 1H), 1039 (s, 1H).

Example 6

(S)-2-({3-[4-(6-Fluoro-benzothiazol-2-ylamino)-phenyl]-isoxazole-5-carbothioyl}-amino)-3-methyl-butyric acid methyl ester This title compound was prepared according to the procedure as set forth in Example 4, except that (S)-2-({3-[4-(6-Fluoro-benzothiazol-2-ylamino)-phenyl]-isoxazole-5-carbonyl}-amino)-3-methyl-butyric acid methyl ester was used as the starting material. The crude product was purified by flash chromatography with 25% EtOAc in chloroform and finally crystallized from dichloromethane and light petroleum to yield the title compound in 82% yield. Mass (ES⁻): 483 (M−1); IR (KBr): 3373, 2963, 2931, 1724, 1609, 1547 (br), 1455, 1436; ¹H NMR (CDCl$_3$) δ: 1.06, 1.13 (2×d, 6H), 2.49 (m, 1H), 3.85 (s, 3H), 5.24 (m, 1H), 7.13 (m, 1H), 7.41 (m, 2H), 7.59 (br, 1H), 7.64 (m, 1H), 7.70 (d, 2H), 7.88 (d, 2H), 8.63 (d, 1H), 10.79 (s, 1H).

Example 7

(S)-2-({3-[4-(6-Fluoro-benzothiazol-2-ylamino)-phenyl]-N-hydroxy-isoxazole-5-carboximidoyl}-amino)-3-methyl-butyric acid methyl ester To a solution of freshly cleaned sodium pieces (0.043 g; 1.86 matom) in dry MeOH (30 ml) was added (S)-2-({3-[4-(6-fluoro-benzothiazol-2-ylamino)-phenyl]-isoxazole-5-carbothioyl}-amino)3-methyl-butyric acid methyl ester (0.9 g; 1.86 mmol) under stirring followed by iodomethane (0.23 ml; 3.72 mmol). The stirring was continued for 2 hours at room temperature. Hydroxylamine hydrochloride (0.284 g; 4.09 mmol) was added to this solution followed by NaHCO$_3$ (0.343 g; 4.09 mmol) and the resulting reaction mixture was refluxed for 3 hours. The solid thus obtained was filtered, dried and purified by flash chromatography over silica gel with 5% MeOH in chloroform to obtain 0.61 g (68%) of the title compound. Mass (ES$^-$): 482 (M−1); IR (KBr): 3384, 3196, 2963, 1737, 1642, 1611, 1546 (br), 1462 (br); $^1$H NMR (DMSO-d$_6$) δ: 0.89, 0.94 (2×d, 6H), 2.08 (m, 1H), 3.65 (s, 3H), 3.99 (m, 1H), 5.85 (d, 1H), 7.20 (m, 1H), 7.29 (s, 1H), 7.66 (m, 1H), 7.79 (m, 1H), 7.93 (s, 4H), 10.78 (s, 1H); 10.85 (s, 1H).

Example 8

(S)-2-({3-[4-(6-Fluoro-benzothiazol-2-ylamino)-phenyl]-N-hydroxy-isoxazole-5-carboximidoyl}-amino)-3-methyl-butyric acid To a solution of (S)-2-({3-[4-(6-Fluoro-benzothiazol-2-ylamino)-phenyl]-N-hydroxy-isoxazole-5-carboximidoyl}-amino)-3-methyl-butyric acid methyl ester (0.3 g; 0.62 mmol) in THF (3 ml) was added 1N LiOH (0.81 ml; 0.81 mmol) under stirring for 48 hours, followed by heating at 40-45° C. for 2 hours. Solvent was removed from the reaction mixture and the residue was diluted with water (5 ml) and acidified to pH 2 with 2N HCl. The semisolid material obtained was extracted with EtOAc, washed with water (2×5 ml), and dried over anhydrous Na$_2$SO$_4$. The residue was purified by flash chromatography with 10-50% MeOH in chloroform. The pure material obtained was triturated with acetone and light petroleum, filtered and dried under vacuum pump to yield 0.16 g (55%) of the title compound. Mass (ES$^-$): 468 (M−1); IR (KBr): 3356 (br), 33265 (br), 2965 (br), 1721, 1610 (br), 1547 (br), 1463 (br); $^1$H NMR (DMSO-d$_6$) δ: 0.91, 0.98 (2×d, 6H), 2.04 (m, 1H), 3.82 (m, 1H), 5.76 (d, 1H), 7.19 (m, 1H), 7.28 (s, 1H), 7.66 (m, 1H), 7.77 (m, 1H), 7.93 (s, 4H).

Example 9

(S)-2-({3-[4-(6-Fluoro-benzothiazol-2-ylamino)-phenyl]-isoxazole-5-carbonyl}-amino)-3-hydroxy-propionic acid methyl ester The title compound was prepared according to the procedure as set forth in Example 5, except that (S)-serine methyl ester hydrochloride was used in place of (S)-Val-OMe.HCl to yield 67.5% of the title compound. Mass (ES$^-$): 455 (M−1); IR (KBr): 3326 (br), 2954, 2930, 1742, 1685, 1609, 1551 (br), 1458, 1443; $^1$H NMR (DMSO-d$_6$) δ: 3.68 (s, 3H), 3.84 (s, 2H), 4.58 (m, 1H), 5.16 (br, 1H), 7.20 (m, 1H), 7.67 (m, 1H), 7.71 (s, 1H), 7.78 (m, 1H), 7.94 (s, 4H), 9.12 (d, 1H), 10.79 (s, 1H, NH).

Example 10

(S)-2-({3-[4-(6-Fluoro-benzothiazol-2-ylamino)-phenyl]-isoxazole-5-carbonyl}-amino)-3-hydroxy-propionic acid (S)-2-({3-[4-(6-Fluoro-benzothiazol-2-ylamino)-phenyl]-isoxazole-5-carbonyl}-amino)-3-hydroxyl-propionic acid methyl ester was hydrolyzed by lN NaOH in MeOH to obtain the title compound in 53% yield. Mass (ES$^-$): 443 (M$^+$+1); IR (KBr): 3435 (br), 3306, 171718, 1683, 1609, 1590, 1571 (br), 1439; $^1$H NMR (DMSO-d$_6$) δ: 3.83 (m, 2H), 4.47 (m, 1H), 7.20 (m, 1H), 7.66 (m, 1H), 7.73 (s, 1H), 7.78 (m, 1H), 7.94 (br, 4H), 8.95 (d, 1H), 10.89 (br, COOH).

Example 11

(S)-2-{3-[4-(6-Fluoro-benzothiazol-2-ylamino)-phenyl]-isoxazol-5-yl}-4,5-dihydro-thiazole-4-carboxylic acid methyl ester A mixture of the compound of Example 9 (1.0 g; 2.19 mmol) and Lawesson's reagent (1.064 g; 2.63 mmol) in dioxane (25 ml) was refluxed for 2 hours. The reaction mixture was neutralized with aqueous Na$_2$CO$_3$ and solvent was removed. The residue was extracted with EtOAc (3×20 ml). The EtOAc extract was washed with water (2×10 ml), dried over anhydrous Na$_2$SO$_4$, and the residue was purified by flash chromatography over silica gel with 5-10% acetone in dichloromethane. The pure material obtained was triturated with chloroform, filtered and dried to obtain. 0.413 g (41.5%) of the title compound. Mass (ES$^-$): 453 (M−1); IR (KBr): 3452 (br), 3351, 2908, 1745, 1605, 1551 (br), 1459, 1436; $^1$H NMR (DMSO-d$_6$) δ: 3.74 (s, 3H), 3.77 (m, 2H), 5.51 (t, 1H), 7.20 (m, 1H), 7.66 (dd, 1H), 7.76 (s, 1H), 7.77 (dd, 1H), 7.93 (2×d, 4H), 10.77 (s, 1H).

Example 12

(S)-2-({3-[4-(6-Fluoro-benzothiazol-2-ylamino)-phenyl]-isoxazole-5-carbonyl}-amino)-3-methoxy-propionic acid methyl ester The title compound was prepared according to the procedure as set forth in Example 5, except that (S)-2-amino-3-methoxy-propionic acid methyl ester hydrochloride was used in place of (S)-Val-OMe.HCl to yield 94% of the title compound. Mass (ES$^+$): 471 (M$^+$+1); IR (KBr): 3314 (br), 2929, 1734, 1683, 1610, 1551 (br), 1458, 1443; $^1$H NMR (DMSO-d$_6$) δ: 3.33 (s, 3H), 3.69 (s, 3H), 3.77 (m, 2H), 4.76 (m, 1H), 7.21 (m, 1H), 7.67 (dd, 1H), 7.71 (s, 1H), 7.79 (dd, 1H), 7.94 (s, 4H), 9.35 (d, 1H), 10.79 (s, 1H, NH).

Example 13

(S)-2-({3-[4-(6-Fluoro-benzothiazol-2-ylamino)-phenyl]-isoxazole-5-carbonyl}-amino)-3-methoxy-propionic acid The title compound was prepared according to the procedure as set forth in Example 8, except that (S)-2-({3-[4-(6-Fluoro-benzothiazol-2-ylamino)-phenyl]-isoxazole-5-carbonyl}-amino)-3-methoxy-propionic acid methyl ester was used as starting material to yield 84% of the title compound. Mass (ES$^-$): 455 (M−1); IR (KBr): 3432, 3326, 3120, 2929, 1671, 1611 (br), 1560 (br), 1458, 1437; $^1$H NMR (DMSO-d$_6$) δ: 3.25 (s, 3H), 3.71 (m, 2H), 4.62 (m, 1H), 7.15 (m, 1H), 7.62 (m, 1H), 7.67 (s, 1H), 7.74 (m, 1H), 7.89 (s, 4H), 9.10 (d; 1H), 10.76 (s, 1H), 12.09 (br 1H).

Example 14

(S)-2-({3-[4-(6-Fluoro-benzothiazol-2-ylamino)-phenyl]-isoxazole-5-carbothioyl}-amino)-3-methoxy-propionic acid methyl ester This title compound was prepared according to the procedure as set forth in Example 4, except that (S)-2-({3-[4-(6-

Fluoro-benzothiazol-2-ylamino)-phenyl]-isoxazole-5-carbonyl}-amino)-3-methoxy-propionic acid methyl ester was used as starting material. The crude product was purified by flash chromatography with 50% EtOAc in chloroform and finally crystallized from dichloromethane and light petroleum to yield the title compound in 82% yield. Mass (ES$^+$): 487 (M$^+$+1); IR (KBr): 3389, 2950, 1741, 1610, 1557 (br), 1506, 1456, 1437; $^1$H NMR (DMSO-d$_6$) δ: 3.32 (s, 3H), 3.70 (s, 3H), 3.82 (dd, 1H), 3.97 (dd, 1H), 5.33 (m, 1H), 7.20 (m, 1H), 7.67 (m, 2H), 7.79 (m, 1H), 7.95 (2×d, 4H), 10.79 (s, 1H), 11.07 (d, 1H).

Example 15

(S)-2-({3-[4-(6-Fluoro-benzothiazol-2-ylamino)-phenyl]-isoxazole-5-carbothioyl}-amino)-3-methoxy-propionic acid The title compound was prepared according to the procedure as set forth in Example 4, except that (S)-2-({3-[4-(6-fluoro-benzothiazol-2-ylamino)-phenyl]-isoxazole-5-carbothioyl}-amino)-3-methoxy-propionic acid methyl ester was used as starting material to yield 85.2% of the title compound. Mass (ES$^-$): 471 (M−1); IR (KBr): 3350 (br), 2927 (br), 1718 (br), 1611 (br), 1545 (br), 1499, 1458; $^1$H NMR (DMSO-d$_6$) δ: 3.29 (s, 3H), 3.80 (dd, 1H), 3.96 (m, 1H), 5.28 (m, 1H), 7.19 (m, 1H), 7.64 (s, 1H), 7.67 (m, 1H), 7.76 (m, 1H), 7.93 (2×d, 4H), 10.78 (s, 1H), 10.90 (d, 1H), 13.20 (br 1H).

Example 16

(S)-2-({3-[4-(6-Fluoro-benzothiazol-2-ylamino)-phenyl]-N-hydroxy-isoxazole-5-carboximidoyl}-amino)-3-methoxy-propionic acid methyl ester The title compound was prepared according to the procedure as set forth in Example 7, except that (S)-2-({3-[4-(6-fluoro-benzothiazol-2-ylamino)-phenyl]-isoxazole-5-carbothioyl}-amino)-3-methoxy-propionic acid methyl ester was used as the starting material to yield 33.2% of the title compound. Mass (ES$^+$): 486 (M$^+$+1), 508 (M$^+$+Na); IR (KBr): 3386, 3259, 3110, 1745, 1640, 1618 (br), 1541 (br), 1458 (br); $^1$H NMR (DMSO-d$_6$) δ: 3.27 (s, 3H), 3.62 (m, 1H), 3.64 (s, 3H), 3.75 (dd, 1H), 4.47 (m, 1H), 6.03 (d, 1H), 7.18 (m, 1H), 726 (s, 1H), 7.64 (m, 1H), 7.76 (m, 1H), 7.92 (s, 4H), 10.75, 10.77 (2×s, 2H).

Example 17

(S)-2-({3-[4-(6-Fluoro-benzothiazol-2-ylamino)-phenyl]-N-hydroxy-isoxazole-5-carboximidoyl}-amino)-3-methoxy-propionic acid The title compound was prepared according to the procedure as set forth in Example 8, except that S)-2-({3-[4-(6-fluoro-benzothiazol-2-ylamino)-phenyl]-N-hydroxy-isoxazole-5-carboximidoyl}-amino)-3-methoxy-propionic acid methyl ester was used as the starting material to yield 63.2% of the title compound. Mass (ES$^-$): 470 (M−1); IR (KBr): 3396 (br), 1711, 1638, 1617 (br), 1567, 1541 (br), 1459 (br); $^1$H NMR (DMSO-d$_6$) δ: 3.27 (s, 3H), 3.58 (m, 1H), 3.75 (m, 1H), 4.36 (m, 1H), 5.95 (d, 1H), 7.18 (m, 1H), 7.26 (s, 1H), 7.63 (m, 1H), 7.76 (m, 1H), 7.91 (s, 4H), 10.72, 10.83 (2×s, 2H), 12.89 (br, 1H).

Example 18

(S)-1-{3-[4-(6-Fluoro-benzothiazol-2-ylamino)-phenyl]-isoxazole-5-carbonyl}-pyrrolidine-2-carboxylic acid methyl ester The title compound was prepared according to the procedure as set forth in Example 5, except that (S)-pyrrolidine-2-carboxylic acid methyl ester hydrochloride was used as the starting material to yield 72% of the title compound. Mass (ES$^+$): 467 (M$^+$+1); IR (KBr): 3317, 3269, 3062, 1749, 1735, 1721, 1605, 1559, 1543, 1459; $^1$H NMR (CDCl$_3$) δ: 1.95-2.4 (2×m, 4H), 3.79 (s, 3H), 4.08-4.17 (m, 2H), 4.70 (m, 1H), 7.10 (m, 1H), 7.23 (m, 1H), 7.37 (dd, 1H), 7.63 (dd, 1H), 7.66-7.69 (m, 3H), 7.83 (dd, 2H).

Example 19

(S)-1-{3-[4-(6-Fluoro-benzothiazol-2-ylamino)-phenyl]-isoxazole-5-carbonyl}-pyrrolidine-2-carboxylic acid (S)-1-{3-[4-(6-Fluoro-benzothiazole-2-ylamino)-phenyl-isoxazole-5-carbonyl}pyrrolidine-2-carboxylic acid methyl ester was hydrolyzed by IN NaOH in MeOH to obtain the title compound in 54% yield. Mass (ES$^+$), 453 (M$^+$+1); IR (KBr): 3280 (br), 3067, 2979, 2930, 1719, 1610 (br), 1542, 1458, 1431; $^1$H NMR (DMSO-d$_6$) δ: 1.8-2.3 (4×m, 4H), 3.63, 3.90 (2×m, 2H), 4.47 (m, 1H), 7.20 (m, 1H), 7.66 (s, 1H), 7.67 (dd, 1H), 7.79 (dd, 1H), 7.91-8.0 (m, 4H), 10.79 (s, 1H), 12.81 (br, <1H).

Example 20

3-[3-(6-Fluoro-benzothiazol-2-ylamino)-phenyl]-isoxazole-5-carboxylic acid ethyl ester Step 1: 3-(3-Amino-phenyl)-isoxazole-5-carboxylic acid ethyl ester The title compound was prepared according to the procedure as set forth in Example 1 for the preparation of 3-(4-amino-phenyl)-isoxazol-5-carboxylic acid ethyl ester, except that 3-(3-nitro-phenyl)-isoxazole-5-carboxylic acid ethyl ester was used in place of 3-(4-nitro-phenyl)-isoxazole-5-carboxylic acid ethyl ester. The crude product was purified by flash chromatography with 15% EtOAc in light petroleum. Mass (ES$^+$), 233 (M$^+$+1), 255 (M$^+$+Na); IR (KBr): 3460, 3369, 1727, 1615, 1431; $^1$H NMR (CDCl$_3$) δ: 1.43 (t, 3H), 3.83 (s, 2H), 4.45 (q, 2H), 6.78 (m, 1H), 7.13-7.19 (m, 4H).

Step 2: 3-[3-(6-Fluoro-benzothiazol-2-ylamino)-phenyl]-isoxazole-5-carboxylic acid ethyl ester The title compound was prepared by reacting 3-(3-amino-phenyl)-isoxazole-5-carboxylic acid ethyl ester with 2-chloro-6-fluoro-benzothiazole as described in Example 1, step 3. The solid was separated, filtered, washed with EtOH and dried to give the title compound in 90% yield. Mass (ES$^+$), 384 (M$^+$+1); IR (KBr): 3423 (br), 2666 (br), 1723, 1629, 1598; $^1$H NMR (DMSO-d$_6$) δ: 1.33 (t, 3H), 4.39 (q, 2H), 7.15 (m, 1H), 7.52 (m, 1H), 7.61 (m, 2H), 7.82 (s, 1H), 7.74 (m, 1H), 7.97 (m, 1H), 8.34 (m, 1H), 10.97 (br, 1H).

Example 21

3-[3-(6-Fluoro-benzothiazol-2-ylamino)-phenyl]-isoxazole-5-carboxylic acid

The title compound was prepared according to the procedure as set forth in Example 2, except that 3-[3-(6-fluoro-benzothiazol-2-ylamino)-phenyl]-isoxazole-5-carboxylic acid ethyl ester was used instead of the compound of Example 1. The crude product was triturated with acetone and filtered, washed with acetone and light petroleum to give the title compound in a yield of 78.2%. Mass (ES$^+$): 356 (M$^+$+1), 378 (M$^+$+Na); IR (KBr): 3451 (br), 1716, 1628, 1583; $^1$H NMR (DMSO-d$_6$) δ: 7.15 (m, 1H), 7.31-7.63 (m, 3H), 7.71 (s, 1H), 7.76 (m, 1H), 7.98 (m, 1H), 8.34 (s, 1H), 10.93 (br, 1H).

Example 22

(S)-2-({3-[3-(6-Fluoro-benzothiazol-2-ylamino)-phenyl]-isoxazole-5-carbonyl}-amino)-3-methyl-butyric acid methyl ester The title compound was prepared according to the procedure as set forth in Example 5, except that 3-[3-(6-fluoro-benzothiazol-2-ylamino)-phenyl]-isoxazole-5-carboxylic acid was used instead of the compound of Example 2. The crude product was purified by flash chromatography over silica gel with 25% EtOAc in light petroleum to obtain the title compound in a yield of 66%. Mass (ES$^+$): 469 (M$^+$+1); IR (KBr): 3327 (br), 2923, 2851, 1742, 1655, 1627, 1571 (br), 1459; $^1$H NMR (DMSO-d$_6$) δ: 0.99, 1.07 (2×d, 6H), 2.20 (m, 1H), 3.67 (s, 3H), 4.31 (m, 1H), 7.18 (m, 1H), 7.53 (m, 2H), 7.62 (m, 1H), 7.59 (s, 1H), 7.78 (m, 1H), 7.96 (s, 1H), 8.32 (s, 1H), 9.24 (d, 1H), 10.70 (s, 1H, NH).

Example 23

(S)-2-({3-[3-(6-Fluoro-benzothiazol-2-ylamino)-phenyl]-isoxazole-5-carbonyl}-amino)-3-methyl-butyric acid The title compound was prepared according to the procedure as set forth in Example 8, except that (S)-2-({3-[3-(6-Fluoro-benzothiazol-2-ylamino)-phenyl]-isoxazole-5-carbonyl}-amino)-3-methyl-butyric acid methyl ester was used instead of the compound of Example 7 to yield 43% of the title compound. Mass (ES$^-$): 453 (M$^-$−1); IR (KBr): 3379 (br), 2967, 2935, 1737, 1675, 1629, 1582 (br), 1446; $^1$H NMR (DMSO-d$_6$) δ: 0.95, 0.98 (2×d, 6H), 2.21 (m, 1H), 3.67 (s, 3H), 4.29 (m, 1H), 7.17 (m, 1H), 7.53 (m, 2H), 7.61 (m, 1H), 7.73 (s, 1H), 7.75 (m, 1H), 7.96 (m, 1H), 8.32 (s, 1H), 9.01 (d, 1H), 10.70 (s, 1H), 12.87 (br, 1H).

Example 24

(S)-2-({3-[3-(6-Fluoro-benzothiazol-2-ylamino)-phenyl]-isoxazole-5-carbothioyl}-amino)-3-methyl-butyric acid methyl ester The title compound was prepared according to the procedure as set forth in Example 4, except that (S)-2-({3-[3-(6-Fluoro-benzothiazol-2-ylamino)-phenyl]-isoxazole-5-carbonyl}-amino)-3-methyl-butyric acid methyl ester was used instead of the compound of Example 3. The crude product was purified by flash chromatography with 5-20% EtOAc in chloroform and finally crystallized from dichloromethane and light petroleum to provide the title compound in a yield of 61%. Mass (ES$^+$): 485 (M$^+$+1); IR (KBr): 3354 (br), 2964, 2931, 1736, 1606, 1549 (br), 1460; $^1$H NMR (CDCl$_3$) δ: 1.04, 1.13 (2×d, 6H), 2.47 (m, 1H), 3.83 (s, 3H), 5.20 (m, 1H), 7.09 (m, 1H), 7.32 (m, 1H), 7.36 (s, 1H), 7.44-7.61 (m, 4H), 7.69 (m, 1H), 8.01 (s, 1H), 8.67 (d, 1H), 10.70 (s, 1H, NH).

Example 25

(S)-2-({3-[3-(6-Fluoro-benzothiazol-2-ylamino)-phenyl]-isoxazole-5-carbothioyl}-amino)-3-methyl-butyric acid The title compound was prepared according to the procedure as set forth in Example 8, except that (S)-2-({3-[3-(6-Fluoro-benzothiazol-2-ylamino)-phenyl]-isoxazole-5-carbothioyl}-amino)-3-methyl-butyric acid methyl ester was used instead of the compound of Example 7 to yield 63% of the title compound. Mass (ES$^+$): 471 (M$^+$+1); IR (KBr): 3324, 2962, 2929, 1626 (br), 1583, 1468; $^1$H NMR (DMSO-d$_6$): δ 1.0 (m, 6H), 2.37 (m, 1H), 4.83 (m, 1H), 7.19 (m, 1H), 7.49-7.62 (m, 3H), 7.59 (s, 1H), 7.41 (m, 1H), 7.97 (m, 1H), 8.32 (s, 1H), 10.71 (s, 1H), 8.80 (d, 1H), 12.93 (br, 1H).

Example 26

(S)-2-({3-[3-(6-Fluoro-benzothiazol-2-ylamino)-phenyl]-N-hydroxy-isoxazole-5-carboximidoyl}-amino)-3-methyl-butyric acid methyl ester The title compound was prepared according to the procedure as set forth in Example 7, except that (S)-2-({3-[3-(6-Fluoro-benzothiazol-2-ylamino)-phenyl]-isoxazole-5-carbothioyl}-amino)-3-methyl-butyric acid methyl ester was used instead of the compound of Example 6. The crude product was purified by flash chromatography over silica gel with 3-5% MeOH in chloroform to afford title compound in a yield of 73.5%. Mass (ES$^+$): 484 (M$^+$+1); IR (KBr): 3283 (br), 2964, 1775, 1743, 1604 (br), 1560, 1462; $^1$H NMR (DMSO-d$_6$) δ: 0.95 (m, 6H), 2.13 (m, 1H), 3.63 (s, 3H), 4.01 (m, 1H), 5.89 (d, 1H), 7.17 (m, 1H), 7.51-7.64 (m, 3H), 7.75 (m, 1H), 7.97 (m, 1H), 8.32 (m, 1H), 8.69 (s, 1H), 10.69 (s, 1H), 10.87 (s, 1H).

Example 27

(S)-2-({3-[3-(6-Fluoro-benzothiazol-2-ylamino)-phenyl]-N-hydroxy-isoxazole-5-carboximidoyl}-amino)-3-methyl-butyric acid The title compound was prepared according to the procedure as set forth in Example 8, except that 2-({3-[3-(6-Fluoro-benzothiazol-2-ylamino)-phenyl]-N-hydroxy-isoxazole-5-carboximidoyl}-amino)-3-methyl-butyric acid methyl ester was used as starting material to yield 51% of the title compound. Mass (ES$^+$): 470 (M$^+$+1); IR (KBr): 3342 (br), 2964, 1656, 1644, 1620 (br), 1578, 1460; $^1$H NMR (DMSO-d$_6$) δ: 0.96 (m, 6H), 2.04 (m, 1H), 3.94 (dd, 1H), 5.75 (d, 1H), 7.16 (m, 1H), 7.27 (s, 1H), 7.48-7.64 (m, 4H), 7.75 (m, 1H), 7.93 (m, 1H), 8.31 (m, 1H, OH), 10.71 (s, 1H), 10.83 (s, 1H).

Example 28

(S)-2-({3-[3-(6-Fluoro-benzothiazol-2-ylamino)-phenyl]-isoxazole-5-carbonyl}-amino)-3-methoxy-propionic acid methyl ester The title compound was prepared according to the procedure as set forth in Example 5, except that 3-[3-(6-fluorobenzothiazol-2-ylamino)-phenyl]-isoxazole-5-carboxylic acid was used instead of the compound of Example 2 and (S)-2-amino-3-methoxy-propionic acid methyl ester hydrochloride was used instead of (S)-Val-OMe.HCl to yield 68% of the title compound. Mass (ES$^+$): 471 (M$^+$+1), 493 (M$^+$+Na); IR (KBr): 3319, 2929, 1740, 1670, 1571, 1474; $^1$H NMR (DMSO-d$_6$) δ: 3.29 (s, 3H), 3.67 (s, 3H), 3.74 (m, 2H), 4.74 (m, 1H), 7.18 (m, 1H), 7.53 (m, 2H), 7.62 (dd, 1H), 7.72 (s, 1H), 7.76 (dd, 1H), 7.95 (m, 1H), 8.32 (s, 1H), 9.39 (d, 1H), 10.70 (s, 1H).

Example 29

(S)-2-({3-[3-(6-Fluoro-benzothiazol-2-ylamino)-phenyl]-isoxazole-5-carbonyl}-amino)-3-methoxy-propionic acid The title compound was prepared according to the procedure as set forth in Example 8, except that 2-({3-[3-(6-Fluoro-benzothiazol-2-ylamino)-phenyl]-isoxazole-5-carbonyl}-amino)-3-methoxy-propionic acid methyl ester was used instead of the compound of Example 7 to yield 68.7% of the title compound. Mass (ES$^+$): 457 (M$^+$+1); IR (KBr): 3376 (br), 2926, 1671, 1654, 1586, 1474 (br); $^1$H NMR (DMSO-d$_6$) δ: 3.29 (s, 3H), 3.74 (m, 2H), 4.66 (m, 1H), 7.17 (m, 1H), 7.52 (br, 1H), 7.54 (br, 1H), 7.61 (dd, 1H), 7.71 (s, 1H), 7.75 (dd, 1H), 7.96 (m, 1H), 8.32 (s, 1H), 9.19 (d, 1H), 10.70 (s, 1H), 12.97 (br, 1H).

Example 30

(S)-2-({3-[3-(6-Fluoro-benzothiazol-2-ylamino)-phenyl]-isoxazole-5-carbothioyl}-amino)-3-methoxy-propionic acid methyl ester The title compound was prepared according to the procedure as set forth in Example 4, except that 2-({3-[3-(6-Fluoro-benzothiazol-2-ylamino)-phenyl]-isoxazole-5-carbonyl}-amino)-3-methoxy-propionic acid methyl ester was used instead of the compound of Example 3 to yield 80.4% of the title compound. Mass (ES$^+$): 487 (M$^+$+1), 509 (M$^+$+Na); IR (KBr): 3363, 2926, 1742, 1606, 1547, 1500; $^1$H NMR (CDCl$_3$) δ: 3.39 (s, 3H), 3.85 (s, 3H), 3.88, 4.01 (2×dd, 2H), 5.41 (br, 1H), 7.07 (m, 1H), 7.35 (dd, 1H), 7.38 (s, 1H), 7.48 (dd, 1H), 7.52 (br, 1H), 7.55 (br, 1H), 7.57 (dd, 1H), 7.68 (m, 1H), 8.02 (s, 1H), 8.93 (br, 1H).

Example 31

(S)-2-({3-[3-(6-Fluoro-benzothiazol-2-ylamino)-phenyl]-isoxazole-5-carbothioyl}-amino)-3-methoxy-propionic acid The title compound was prepared according to the procedure as set forth in Example 8, except that (S)-2-({3-[3-(6-fluoro-benzothiazol-2-ylamino)-phenyl]-isoxazole-5-carbothioyl}-amino)-3-methoxy-propionic acid methyl ester was used in place of the compound of Example 7 to yield 45% of the title compound. Mass (ES$^+$): 473 (M$^+$+1); IR (KBr): 3307, 2925, 1642, 1629 (br), 1574; $^1$H NMR (DMSO-d$_6$) δ: 3.29 (s, 3H), 3.81, 3.98 (2×dd, 2H), 5.27 (br, 1H), 7.18 (m, 1H), 7.49-7.61 (m, 3H), 7.63 (s, 1H), 7.75 (m, 1H), 7.98 (m, 1H), 8.32 (s, 1H), 10.72 (br, 1H), 10.96 (d, 1H), 13.15 (br, 1H).

Example 32

(S)-2-({3-[3-(6-Fluoro-benzothiazol-2-ylamino)-phenyl]-N-hydroxy-isoxazole-5-carboximidoyl}-amino)-3-methoxy-propionic acid methyl ester The title compound was prepared according to the procedure as set forth in Example 7, except that (S)-2-({3-[3-(6-Fluoro-benzothiazol-2-ylamino)-phenyl]-isoxazole-5-carbothioyl}-amino)-3-methoxy-propionic acid methyl ester was used instead, of the compound of Example 6. The crude product was purified by flash chromatography over silica gel with 15-30% EtOAc in chloroform to obtain the title compound in a yield of 47%. Mass (ES$^-$): 484 (M$^-$−1); IR (KBr): 3340, 2917 (br), 1719, 1648, 1611, 1552 (br), 1506, 1458; $^1$H NMR (DMSO-d$_6$) δ: 3.08 (s, 3H), 3.53 (s, 3H), 3.54 (br, 1H), 3.66 (dd, 1H), 4.41 (m, 1H), 5.96 (d, 1H), 7.08 (m, 1H), 7.17 (s, 1H), 7.43 (m, 2H), 7.52 (dd, 1H), 7.6 (dd, 1H), 7.83 (m, 1H), 8.19 (s, 1H), 10.57 (s, 1H), 10.71 (br, 1H).

Example 33

(S)-2-({3-[3-(6-Fluoro-benzothiazol-2-ylamino)-phenyl]-N-hydroxy-isoxazole-5-carboximidoyl}-amino)-3-methoxy-propionic acid The title compound was prepared according to the procedure as set forth in Example 8, except that (S)-2-({3-[3-(6-Fluoro-benzothiazol-2-ylamino)-phenyl]-N-hydroxy-isoxazole-5-carboximidoyl}-amino)-3-methoxy-propionic acid methyl ester was used instead of Example 7 to yield 40% of the title compound. Mass (ES$^+$): 472 (M$^+$+1); IR (KBr): 3386 (br), 2364, 1668, 1656, 1629, 1459; $^1$H NMR (DMSO-d$_6$) δ: 3.27 (s, 3H), 3.69, 3.76 (2×dd, 2H), 4.39 (m, 1H), 5.97 (d, 1H), 7.16 (m, 1H), 7.26 (s, 1H), 7.53 (m, 2H), 7.61 (dd, 1H), 7.75 (dd, 1H), 7.93 (m, 1H), 8.29 (s, 1H), 10.69 (s, 1H), 10.76 (br, 1H), 12.88 (br, 1H).

Example 34

(S)-1-{3-[3-(6-Fluoro-benzothiazol-2-ylamino)-phenyl]-isoxazole-5-carbonyl}-pyrrolidine-2-carboxylic acid methyl ester The title compound was prepared according to the procedure as set forth in Example 5, except that 3-[3-(6-fluoro-benzothiazol-2-ylamino)-phenyl]-isoxazole-5-carboxylic acid was used instead of the compound of Example 2 and (S)-pyrrolidine-2-carboxylic acid methyl ester hydrochloride was used in place of (S)-Val-OMe.HCl to yield 41% of the title compound. Mass (ES$^+$): 467 (M$^+$+1), 489 (M$^+$+Na); IR (KBr): 3295, 3110, 2951, 1742, 1626, 1613, 1568 (br), 1454, 1411; $^1$H NMR (DMSO-d$_6$) δ: 1.70-2.39 (4×m, 4H), 3.65 (s, 3H), 3.64, 3.92 (2×m, 2H), 4.55, 5.10 (2×m, 1H), 7.17 (m, 1H), 7.52-7.64 (m, 3H), 7.65 (s, 1H), 7.75 (dd, 1H), 7.95 (m, 1H), 8.32 (m, 1H), 10.68 (s, 1H).

Example 35

(S)-1-{3-[3-(6-Fluoro-benzothiazol-2-ylamino)-phenyl]-isoxazole-5-carbonyl}-pyrrolidine-2-carboxylic acid The title compound was prepared according to the procedure as set forth in Example 8, except that (S)-1-{3-[3-(6-Fluoro-benzothiazol-2-ylamino)-phenyl]-isoxazole-5-carbonyl}-pyrrolidine-2-carboxylic acid methyl ester was used instead of the compound of Example 7 to yield 68.7% of the title compound. Mass (ES⁻): 451 (M⁻−1); IR (KBr): 3286 (br), 3096 (br), 2958, 1734 (br), 1629 (br), 1546 (br), 1459; ¹H NMR (DMSO-d₆) δ: 1.70-2.40 (4×m, 4H), 3.62, 3.89 (2×m, 2H), 4.46, 4.98 (2×m, 1H), 7.16 (m, 1H), 7.51-7.67 (m, 4H), 7.74 (dd, 1H), 7.94 (m, 1H), 8.31 (m, 1H), 10.68 (s, 1H), 12.86 (br, 1H).

Example 36

(S)-1-{3-[3-(6-Fluoro-benzothiazol-2-ylamino)-phenyl]-isoxazole-5-carbothioyl}-pyrrolidine-2-carboxylic acid methyl ester The title compound was prepared according to the procedure as set forth in Example 4, except that (S)-1-{3-[3-(6-Fluoro-benzothiazol-2-ylamino)-phenyl]-isoxazole-5-carbonyl}-pyrrolidine-2-carboxylic acid methyl ester was used instead of the compound of Example 3 to yield 93.2% of the title compound. Mass (ES⁺): 483 (M⁺+1); IR (KBr): 3336 (br), 2951, 1743, 1731, 1605, 1546 (br), 1458; ¹H NMR (CDCl₃) δ: 2.08-2.50 (2×m, 4H), 3.79 (s, 3H), 4.17 (m, 2H), 5.07, 5.16 (2×m, 1H), 7.05 (m, 1H), 7.26 (s, 1H), 7.33 (dd, 1H), 7.41-7.52 (m, 2H), 7.56 (dd, 1H), 7.65 (m, 1H), 7.96 (m, 1H), 8.55 (s, 1H).

Example 37

(S)-1-{3-[3-(6-Fluoro-benzothiazol-2-ylamino)-phenyl]-isoxazole-5-carbothioyl}-pyrrolidine-2-carboxylic acid The title compound was prepared according to the procedure as set forth in Example 8, except that (S)-1-{3-[3-(6-fluoro-benzothiazol-2-ylamino)-phenyl]-isoxazole-5-carbothioyl}-pyrrolidine-2-carboxylic acid methyl ester was used instead of the compound of Example 7 to yield 82.4% of the title compound. Mass (ES⁻): 467 (M⁻−1); IR (KBr): 3437 (br), 3283 (br), 3094 (br), 2957, 1719 (br), 1606 (br), 1547 (br), 1460; ¹H NMR (DMSO-d₆) δ: 1.90-2.50 (3×m, 4H), 3.97 (m, 2H), 4.89, 5.08 (2×m, 1H), 7.16 (m, 1H), 7.41-7.63 (m, 4H), 7.75 (dd, 1H), 7.94 (m, 1H), 8.30 (m, 1H), 10.69 (s, 1H), 13.00 (br, 1H).

Example 38

(R)-2-({3-[4-(6-Fluoro-benzothiazol-2-ylamino)-phenyl]-isoxazole-5-carbonyl}-amino)-3-methyl-butyric acid methyl ester The title compound was prepared according to the procedure as set forth in Example 5, except that (R)-Val-OMe.HCl was used instead of (S)-Val-OMe.HCl. The crude product was purified by flash chromatography with 25% EtOAc in chloroform. The pure solid was triturated with dichloromethane and filtered. The solid was dried to obtain the title compound in a yield of 69.5%. Mass (ES⁺): 469 (M⁺+1); IR (KBr): 3324 (br), 2967, 1722, 1680, 1610, 1560 (br), 1458, 1442; ¹H NMR (DMSO-d₆) δ: 0.95, 0.99 (2×d, 6H), 2.22 (m, 1H), 3.69 (s, 3H), 4.33 (m, 1H), 7.20 (m, 1H), 7.67 (m, 1H), 7.71 (s, 1H), 7.78 (m, 1H), 7.93 (s, 4H), 9.22 (d, 1H), 10.79 (s, 1H).

Example 39

(R)-2-({3-[4-(6-Fluoro-benzothiazol-2-ylamino)-phenyl]-isoxazole-5-carbothioyl}-amino)-3-methyl-butyric acid methyl ester The title compound was prepared according to the procedure as set forth in Example 4, except that (R)-2-({3-[4-(6-Fluoro-benzothiazol-2-ylamino)-phenyl]-isoxazole-5-carbonyl}-amino)-3-methyl-butyric acid methyl ester was used instead of the compound of Example 3. The crude product was purified by flash chromatography with 25% EtOAc in chloroform and finally crystallized from dichloromethane and light petroleum to give the title compound in a yield of 80%. Mass (ES⁺): 485 (M⁺+1); IR (KBr): 3373, 2963, 1736, 1724, 1608, 1546 (br), 1455, 1436; ¹H NMR (CDCl₃+DMSO-d₆) δ: 0.88, 0.91 (2×d, 6H), 2.28 (m, 1H), 3.61 (s, 3H), 4.93 (m, 1H), 6.86 (m, 1H), 7.16 (m, 1H), 7.19 (s, 1H), 7.42 (m, 1H), 7.61 (d, 2H), 7.71 (d, 2H), 9.08 (d, 1H), 9.92 (s, 1H, NH).

Example 40

(R)-2-({3-[4-(6-Fluoro-benzothiazol-2-ylamino)-phenyl]-N-hydroxy-isoxazole-5-carboximidoyl}-amino)-3-methyl-butyric acid methyl ester The title compound was prepared according to the procedure as set forth in Example 7, except that (R)-2-({3-[4-(6-Fluoro-benzothiazol-2-ylamino)-phenyl]-isoxazole-5-carbothioyl}-amino)-3-methyl-butyric acid methyl ester was used instead of the compound of Example 6 to yield 60% of the title compound. Mass (ES⁺), 484 (M⁺+1); IR (KBr): 3282, 2925, 1737, 1654, 1642, 1492 (br); ¹H NMR (DMSO-d₆) δ: 0.89, 0.94 (2×d, 6H); 2.08 (m, 1H), 3.66 (s, 3H), 3.99 (m, 1H), 5.85 (d, 1H), 7.20 (m, 1H), 7.29 (s, 1H), 7.66 (m, 1H), 739 (m, 1H), 7.93 (s, 4H), 10.78 (s, 1H); 10.85 (s, 1H).

Example 41

(R)-2-({3-[4-(6-Fluoro-benzothiazol-2-ylamino)-phenyl]-N-hydroxy-isoxazole-5-carboximidoyl}-amino)-3-methyl-butyric acid The title compound was prepared according to the procedure as set forth in Example 8, except that (R)-2-({3-[4-(6-Fluoro-benzothiazol-2-ylamino)-phenyl]-N-hydroxy-isoxazole-5-carboximidoyl}-amino)-3-methyl-butyric acid methyl ester was used instead of the compound of Example 7 to yield 60% of the title compound. Mass (ES⁺): 470 (M⁺+1); IR (KBr): 3358, 3269, 2968, 1725, 1638, 1615 (br), 1567 (br), 1464 (br); ¹H NMR (DMSO-d₆) δ: 0.91, 0.97 (2×d, 6H), 2.04 (m, 1H), 3.90 (m, 1H), 5.71 (d, 1H), 7.17 (m, 1H), 7.27 (s, 1H), 7.63 (m, 1H), 7.76 (m, 1H), 7.91 (s, 4H), 10.77 (m, >1H), 12.85 (br, <1H).

Example 42

(R)-2-({3-[4-(6-Fluoro-benzothiazol-2-ylamino)-phenyl]-isoxazole-5-carbonyl}-amino)-3-methyl-butyric acid The title compound was prepared according to the procedure as set forth in Example 8, except that (R)-2-({3-[4-(6-Fluoro-benzothiazol-2-ylamino)-phenyl]-isoxazole-5-carbonyl}-amino)-3-methyl-butyric acid methyl ester was used instead of the compound of Example 7 to yield 86% of the title compound. Mass (ES⁺): 454 (M⁺+1); IR (KBr): 3320 (br), 2967, 1720, 1664 (br), 1610 (br), 1458, 1437; ¹H NMR (DMSO-d₆) δ: 0.94, 0.97 (2×d, 6H), 2.22 (m, 1H), 4.25 (m, 1H), 7.19 (m, 1H), 7.65 (m, 1H), 7.70 (s, 1H), 7.78 (m, 1H), 7.92 (s, 4H), 8.95 (d, 1H), 10.78 (s, 1H).

Example 43

(R)-2-({3-[4-(6-Fluoro-benzothiazol-2-ylamino)-phenyl]-isoxazole-5-carbothioyl}-amino)-3-methyl-butyric acid The title compound was prepared according to the procedure as set forth in Example 8, except that (R)-2-({3-[4-(6-Fluoro-benzothiazol-2-ylamino)-phenyl]-isoxazole-5-carbothioyl}-amino)-3-methyl-butyric acid methyl ester was used instead of the compound of Example 7 to yield 57% of the title compound. Mass (ES$^+$): 471 (M$^+$+1); IR (KBr): 3281 (br), 2963, 2526 (br), 1642, 1598 (br), 1584, 1458; $^1$H NMR (DMSO-d$_6$) δ: 1.02 (m, 6H), 2.38 (m, 1H), 4.85 (m, 1H), 7.18 (m, 1H), 7.59 (s, 1H), 7.65 (dd, 1H), 7.76 (dd, 1H), 7.91, 7.95 (2×d, 4H), 10.77 (m, 2H), 12.99 (s, 1H).

Example 44

(S)-2-({3-[4-(6-Fluoro-benzothiazol-2-ylamino)-phenyl]-isoxazole-5-carbonyl}-amino)-3-methyl-butyric acid The title compound was prepared according to the procedure as set forth in Example 8, except that the compound of Example 5 was used instead of the compound of Example 7 to yield 85% of the title compound. Mass (ES$^+$): 454 (M$^+$+1); IR (KBr): 3322 (br), 2968, 1720, 1664 (br), 1610 (br), 1596 (br), 1458, 1437; $^1$H NMR (DMSO-d$_6$) δ: 0.94, 0.97 (2×d, 6H), 2.22 (m, 1H), 4.27 (m, 1H), 7.19 (m, 1H), 7.66 (m, 1H), 7.70 (s, 1H), 7.77 (m, 1H), 7.91 (s, 4H), 8.97 (d, 1H), 10.78 (s, 1H), 12.90 (br, 1H).

Example 45

(S)-2-({3-[4-(6-Fluoro-benzothiazol-2-ylamino)-phenyl]-isoxazole-5-carbothioyl}-amino)-3-methyl-butyric acid The title compound was prepared according to the procedure as set forth in Example 8, except that the compound of Example 6 was used instead of the compound of Example 7 to yield 48% of the title compound. Mass (ES$^+$): 471 (M$^+$+1); IR (KBr): 3283 (br), 2964, 2548 (br), 1642, 1599 (br), 1584, 1458; $^1$H NMR (DMSO-d$_6$) δ: 1.02 (m, 6H), 2.39 (m, 1H), 4.85 (m, 1H), 7.20 (m, 1H), 7.62 (s, 1H), 7.67 (dd, 1H), 7.78 (dd, 1H), 7.91, 7.95 (2×d, 4H), 10.79 (m, 2H), 13.02 (s, 1H).

Example 46

(S)-2-({3-[4-(6-Fluoro-benzothiazol-2-ylamino)-phenyl]-isoxazole-5-carbonyl}-amino)-4-methyl-pentanoic acid methyl ester The title compound was prepared according to the procedure as set forth in Example 5, except that (s)-Leu-OMe.HCl was used instead of (s)-Val-OMe.HCl. The crude product was purified by flash chromatography with 25% EtOAc in chloroform. The pure solid was triturated with dichloromethane, filtered and dried to obtain the title compound in a yield of 85.3%. Mass (ES$^+$): 483 (m$^+$+1); IR (KBr): 3432, 3264, 2959, 1682 (br), 1611 (br), 1560 (br), 1511, 1458, 1439; $^1$H NMR (DMSO-d$_6$) δ: 0.89 (m, 6H), 1.62 (m, 2H), 1.81 (m, 1H), 3.66 (s, 3H), 4.50 (m, 1H), 7.19 (m, 1H), 7.63 (s, 1H), 7.66 (m, 1H), 7.77 (dd, 1H), 7.92 (s, 4H), 9.35 (d, 1H), 10.77 (s, 1H).

Example 47

(S)-2-({3-[4-(6-fluoro-benzothiazol-2-ylamino)-phenyl]-isoxazole-5-carbonyl}-amino)-4-methyl-pentanoic acid The title compound was prepared according to the procedure as set forth in Example 8, except that compound of Example 49 was used instead of the compound of Example 7 to yield 93.2% of the title compound. Mass (ES$^+$): 469 (M$^+$+1); IR (KBr): 3432, 2959, 1680 (br), 1611 (br), 1560, 1509, 1458, 1439; $^1$HNMR (DMSO-d$_6$) δ: 0.91, (m, 6H), 1.63 (m, 2H), 1.79 (m, 1H), 4.42 (m, 1H), 7.20(m, 1H), 7.63 (s, 1H), 7.66 (m, 1H), 7.70 (s, 1H), 7.77 (m, 1H), 7.92 (s, 4H), 9.20 (d, 1H), 10.77 (s, 1H), 12.80 (s, 1H).

Example 48

(S)-2-({3-[4-(6-Fluoro-benzothiazol-2-ylamino)-phenyl]-isoxazole-5-carbothioyl}-amino)-4-methyl-pentanoic acid methyl ester The title compound was prepared according to the procedure as set forth in Example 4, except that the compound of Example 49 was used instead of the compound of Example 3 to yield 93.7% of the title compound. Mass (ES$^+$): 499 (M$^+$+1); IR (KBr): 3302 (br), 2956, 1744 (br), 1609 (br), 1542 (br), 1458, 1437; $^1$H NMR (DMSO-d$_6$) δ: 0.88, 0.93 (2×d, 6H), 1.68 (m, 2H), 2.05 (m, 1H), 3.67 (s, 3H), 5.13 (m, 1H), 7.18 (m, 1H), 7.62 (s, 1H), 7.66 (m, 1H), 7.76 (dd, 1H), 7.93 (dd, 4H), 10.77 (s, 1H), 11.07 (d, 1H).

Example 49

(S)-2-({3-[4-(6-Fluoro-benzothiazol-2-ylamino)-phenyl]-isoxazole-5-carbothioyl}-amino)-4-methyl-pentanoic acid The title compound was prepared according to the procedure as set forth in Example 8, except that the compound of Example 51 was used instead of the compound of Example 7 to yield 65.9% of the title compound. Mass (ES$^+$): 485 (M$^+$+1); IR (KBr): 3285 (br), 2958, 1734, 1818, 1701, 1607, 1543, 1458; $^1$H NMR (DMSO-d$_6$) δ: 0.88, 0.92 (2×d, 6H), 1.69 (m, 2H), 2.04 (m, 1H), 5.09 (m, 1H), 7.19 (m, 1H), 7.60 (s, 1H), 7.65 (m, 1H), 7.78 (dd, 1H), 7.93 (m, 4H), 10.78 (s, 1H), 10.96 (d, 1H), 12.96 (br, 1H).

Example 50

(S)-2-({3-[4-(6-Fluoro-benzothiazol-2-ylamino)-phenyl]-N-hydroxy-isoxazole-5-carboximidoyl}-amino)-4-methyl-pentanoic acid methyl ester The title compound was prepared according to the procedure as set forth in Example 7, except that (S)-2-({3-[4-(6-fluoro-benzothiazol-2-ylamino)-phenyl]-isoxazole-5-carbothioyl}-amino)-4-methyl-pentanoic acid methyl ester was used instead of the compound of Example 6 to yield 64.6% of the title compound. Mass (ES$^+$), 498 (M$^+$+1); IR (KBr): 3375, 3198, 2957, 1742, 1638, 1612, 1560, 1550, 1458, 1434; $^1$H NMR (DMSO-d6) δ: 0.89 (m, 6H), 1.48 (m, 1H), 1.75 (m, 2H), 3.67 (s, 3H), 4.16 (m, 1H), 6.10 (d, 1H), 7.18 (m, 1H), 7.24 (s, 1H), 7.65 (dd, 1H), 7.76 (dd, 1H), 7.91 (s, 4H), 10.76 (s, 1H), 10.83 (s, 1H).

Example 51

(S)-2-({3-[4-(6-Fluoro-benzothiazol-2-ylamino)-phenyl]-N-hydroxy-isoxazole-5-carboximidoyl}-amino)-4-methyl-pentanoic acid The title compound was prepared according to the procedure as set forth in Example 8, except that (S)-2-({3-[4-(6-fluoro-benzothiazol-2-ylamino)-phenyl]-N-hydroxy-isoxazole-5-carboximidoyl}-amino)-4-methyl-pentanoic acid methyl ester was used instead of the compound of Example 7 to yield 56.6% of the title compound. Mass (ES$_{3^0}$): 484 (M$^+$+1); IR (KBr): 3349 (br), 3265 (br), 2958, 1709, 1636, 1610, 1550 (br), 1459; $^1$H NMR (DMSO-d$_6$) δ: 0.89 (m, 6H), 1.49 (m, 1H), 1.72 (m, 2H), 4.07 (m, 1H), 5.91 (d, 1H), 7.18 (m, 1H), 7.24 (s, 1H), 7.64 (m, 1H), 7.76 (m, 1H), 7.90 (s, 4H), 10.61 (s, 1H), 10.77 (s, 1H), 12.66 (br, 1H).

Example 52

(S)-({3-[4-(6-Fluoro-benzothiazol-2-ylamino)-phenyl]-isoxazole-5-carbonyl}-amino)-phenyl-acetic acid methyl ester The title compound was prepared according to the procedure as set forth in Example 5, except that (S)-Phg-OMe.HCl was used instead of (S)-Val-OMe.HCl. The crude product was purified by flash chromatography with 25% EtOAc in chloroform. The pure solid was triturated with dichloromethane, filtered and dried to obtain the title compound in 78% yield. Mass (ES$^+$): 503 (M$^+$+1); IR (KBr): 3398, 3341, 1733, 1682, 1667, 1605, 1550 (br), 1458, 1433; $^1$H NMR (DMSO-d$_6$) δ: 3.67 (s, 3H), 5.68 (d, 1H), 7.19 (m, 1H), 7.36-7.49 (2×m, 5H), 7.65 (dd, 1H), 7.71 (s, 1H), 7.77 (dd, 1H), 7.90 (s, 4H), 9.76 (d, 1H), 10.77 (s, 1H).

Example 53

(S)-({3-[4-(6-Fluoro-benzothiazol-2-ylamino)-phenyl]-isoxazole-5-carbonyl}-amino)-phenyl-acetic acid The title compound was prepared according to the procedure as set forth in Example 8, except that (S)-({3-[4-(6-fluoro-benzothiazol-2-ylamino)-phenyl]-isoxazole-5-carbonyl}-amino)-phenyl-acetic acid methyl ester was used instead of the compound of Example 7 to yield 65.6% of the title compound. Mass (ES$^+$), 489 (M$^+$+1); IR (KBr): 3423, 1677, 1612 (br), 1560, 1552, 1499, 1458, 1438; $^1$H NMR (DMSO-d$_6$) δ: 5.53 (d, 1H), 7.18 (m, 1H), 7.34-7.49 (2×m, 5H), 7.65 (dd, 1H), 7.71 (s, 1H), 7.76 (dd, 1H), 7.90 (2×d, 4H), 9.52 (d, 1H), 10.77 (s, 1H), 13.14 (br, 1H).

Example 54

(S)-({3-[4-(6-Fluoro-benzothiazol-2-ylamino)-phenyl]-isoxazole-5-carbothioyl}-amino)-phenyl-acetic acid methyl ester The title compound was prepared according to the procedure as set forth in Example 8, except that (S)-({3-[4-(6-fluoro-benzothiazol-2-ylamino)-phenyl]-isoxazole-5-carbonyl}-amino)-phenyl-acetic acid methyl ester was used instead of the compound of Example 7 to yield 93.3% of the title compound. Mass (ES$^+$): 519 (M$^+$+1); IR (KBr): 3361, 1724, 1604, 1543 (br), 1495, 1458, 1435; $^1$H NMR (DMSO-d$_6$) δ: 3.69 (s, 3H), 6.23 (br, 1H), 7.17 (m, 1H), 7.38-7.49 (2×m, 5H), 7.62 (s, 1H), 7.64 (m, 1H), 7.75 (m, 1H), 7.90 (2×d, 4H), 10.75 (s, 1H), 11.44 (br, 1H).

Example 55

(S)-({3-[4-(6-Fluoro-benzothiazol-2-ylamino)-phenyl]-isoxazole-5-carbothioyl}-amino)-phenyl-acetic acid The title compound was prepared according to the procedure as set forth in Example 8, except that (S)-({3-[4-(6-fluoro-benzothiazol-2-ylamino)-phenyl]-isoxazole-5-carbothioyl}-amino)-phenyl-acetic acid methyl ester was used instead of the compound of Example 7 to yield 65.6% of the title compound. Mass (ES$^+$): 489 (M$^+$+1); IR (KBr): 3424, 1702, 1677; 1612, 1560; 1552, 1499, 1458, 1438; $^1$H NMR (DMSO-d$_6$) δ: 5.53 (m, 1H), 7.18 (m, 1H), 734-7.49 (3×m, 5H), 7.65 (m, 1H), 7.61 (s, 1H), 7.76 (dd, 1H), 7.90 (2×d, 4H), 9.52 (d, 1H), 10.77 (s, 1H), 13.14 (br, 1H).

Example 56

(S)-({3-[4-(6-Fluoro-benzothiazol-2-ylamino)-phenyl]-N-hydroxy-isoxazole-5-carboximidoyl}-amino)-phenyl-acetic acid methyl ester The title compound was prepared according to the procedure as set forth in Example 7, except that (S)-({3-[4-(6-fluoro-benzothiazol-2-ylamino)-phenyl]-isoxazole-5-carbothioyl}-amino)-phenyl-acetic acid methyl ester was used instead of the compound of Example 6 to yield 53.4% of the title compound. Mass (ES$^+$): 518 (M$^+$+1); IR (KBr): 3388, 3259, 3112, 2956, 1737, 1638, 1618, 1560, 1546 (br), 1459, 1434; $^1$H NMR (DMSO-d$_6$) δ: 3.62 (s, 3H), 5.50 (d, 1H), 6.41 (d, 1H), 7.16-7.18 (m, 2H), 7.27-7.38 (2×m, 5H), 7.63 (dd, 1H), 7.76 (m, 1H), 7.88 (2×d, 4H), 10.75 (s, 1H), 11.03 (s, 1H).

Example 57

(S)-({3-[4-(6-Fluoro-benzothiazol-2-ylamino)-phenyl]-N-hydroxy-isoxazole-5-carboximidoyl}-amino)-phenyl-acetic acid The title compound was prepared according to the procedure as set forth in Example 8, except that (S)-({3-[4-(6-fluoro-benzothiazol-2-ylamino)-phenyl]-N-hydroxy-isoxazole-5-carboximidoyl}-amino)-phenyl-acetic acid methyl ester was used instead of the compound of Example 7 to yield 55.7% of the title compound. Mass (ES$^+$): 504 (M$^+$+1); IR (KBr): 3362, 3110 (br), 2846, 1709 (br), 1638, 1613, 1560, 1546 (br), 1458; $^1$H NMR (DMSO-d$_6$) δ: 5.35 (d, 1H), 6.42 (d, 1H), 7.14 (s, 1H), 7.18 (m, 1H), 7.22-7.31 (2×m, 5H), 7.64 (dd, 1H), 7.76 (m, 1H), 7.86 (2×d, 4H), 10.74 (s, 1H), 10.98 (s, 1H), 13.37 (br, 1H).

Example 58

({3-[4-(6-Fluoro-benzothiazol-2-ylamino)-phenyl]-isoxazole-5-carbonyl}-amino)-acetic acid methyl ester The title compound was prepared according to the procedure as set forth in Example 5, except that Gly-OMe.HCl was used instead of (S)-Val-OMe.HCl. The crude product was purified by flash chromatography with 10-40% EtOAc in chloroform. The pure solid was triturated with dichloromethane, filtered and dried to afford the title compound in 85% yield. Mass (ES⁺): 427 (M⁺+1); IR (KBr): 3414, 3366, 1736, 1677, 1606, 1546 (br), 1514, 1459, 1451, 1432; ¹H NMR (DMSO-d₆) δ: 3.65 (s, 3H), 4.03 (d, 1H), 7.18 (m, 1H), 7.64 (m, 2H), 7.76 (dd, 1H), 7.91 (s, 4H), 9.44 (t, 1H), 10.85 (s, 1H).

Example 59

({3-[4-(6-Fluoro-benzothiazol-2-ylamino)-phenyl]-isoxazole-5-carbonyl}-amino)-acetic acid The title compound was prepared according to the procedure as set forth in Example 8, except that ({3-[4-(6-fluoro-benzothiazol-2-ylamino)-phenyl]-isoxazole-5-carbonyl}-amino)-acetic acid methyl ester was used instead of the compound, of Example 7 to yield 65.3% of the title compound. Mass (ES⁺): 413 (M⁺+1); IR (KBr): 3422, 3287, 3107, 1679 (br), 1607, 1482 (br); ¹H NMR (DMSO-d₆) δ: 3.93 (d, 1H), 7.18 (m, 1H), 7.63 (s, 1H), 7.66 (m, 1H), 7.77 (dd, 1H), 7.92 (s, 4H), 9.32 (t, 1H), 10.87 (s, 1H).

Example 60

({3-[4-(6-fluoro-benzothiazol-2-ylamino)-phenyl]-isoxazole-5-carbothioyl}-amino)-acetic acid methyl ester The title compound was prepared according to the procedure as set forth in Example 4, except that ({3-[4-(6-fluoro-benzothiazol-2-ylamino)-phenyl]-isoxazole-5-carbonyl}-amino)-acetic acid methyl ester was used instead of compound of Example 3 to yield 81.4% of the title compound. Mass (ES⁻): 441 (M⁻−1); IR (KBr): 3366, 1733, 1602, 1542 (br), 1457; ¹H NMR (DMSO-d₆) δ: 3.69 (s, 3H), 4.49 (s, 2H), 7.21 (br, 1H), 7.56 (m, 2H)., 7.79 (m, 2H), 7.94-7.97 (m, 4H), 10.79 (s, 1H), 11.17 (br, 1H).

Example 61

({3-[4-(6-fluoro-benzothiazol-2-ylamino)-phenyl]-isoxazole-5-carbothioyl}-amino)-acetic acid The title compound was prepared according to the procedure as set forth in Example 8, except that ({3-[4-(6-fluoro-benzothiazol-2-ylamino)-phenyl]isoxazole-5-carbothioyl}-amino)-acetic acid methyl ester was used instead of the compound of Example 7 to yield 65.2% of the title compound. Mass (ES⁻): 427 (M⁻−1); IR (KBr): 3344, 1636, 1608, 1543 (br); ¹H NMR (DMSO-d₆) δ: 4.38 (d, 2H), 7.18 (m, 1H), 7.63 (s, 1H), 7.66 (m, 1H), 7.76 (dd, 1H), 7.93 (2×d, 4H), 10.77 (s, 1H), 11.03 (br, 1H), 12.84 (br, 0.64H).

Example 62

1-({3-[4-(6-fluoro-benzothiazol-2-ylamino)-phenyl]-isoxazole-5-carbonyl}-amino)-cyclopentanecarboxylic acid methyl ester The title compound was prepared according to the procedure as set forth in Example 5, except that 1-amino-cyclopentanecarboxylic acid methyl ester hydrochloride was used instead of (S)-Val-OMe.HCl. The crude product was purified by flash chromatography with 10-40% EtOAc in chloroform. The pure solid was triturated with dichloromethane, filtered and dried to afford the title compound in 67.46% yield. Mass (ES⁺): 481 (M⁺+1); IR (KBr): 3374, 2955, 1742, 1672, 1610, 1543 (br), 1509; ¹H NMR (DMSO-d₆) δ: 1.70 (m, 4H), 2.10 (m, 4H), 3.59 (s, 3H), 7.19 (m, 1H), 7.61 (s, 1H), 7.65 (m, 1H), 7.77 (m, 1H), 7.91 (s, 4H), 9.29 (s, 1H), 10.77 (s, 1H).

Example 63

1-({3-[4-(6-Fluoro-benzothiazol-2-ylamino)-phenyl]-isoxazole-5-carbonyl}-amino)-cyclopentanecarboxylic acid The title compound was prepared according to the procedure as set forth in Example 8, except that 1-({3-[4-(6-fluoro-benzothiazol-2-ylamino)-phenyl]-isoxazole-5-carbonyl}-amino)-cyclopentanecarboxylic acid methyl ester was used instead of the compound of Example 7 to yield 84.9% of the title compound. Mass (ES⁻): 465 (M⁻−1); IR (KBr): 3430, 3033, 1679, 1648, 1613, 1560 (br); ¹H NMR (DMSO-d₆) δ: 1.69 (m, 4H), 2.10 (m, 4H), 7.18 (m, 1H), 7.59 (s, 1H), 7.65 (m, 1H), 7.77 (m, 1H), 7.91 (s, 4H), 9.09 (s, 1H), 10.77 (s, 1H), 12.42 (br, 1H).

Example 64

1-({3-[4-(6-Fluoro-benzothiazol-2-ylamino)-phenyl]-isoxazole-5-carbothioyl}-amino)cyclopentanecarboxylic acid methyl ester The title compound was prepared according to the procedure as set forth in Example 4, except that 1-({3-[4-(6-fluoro-benzothiazol-2-ylamino)-phenyl]-isoxazole-5-carbonyl}-amino)-cyclopentanecarboxylic acid methyl ester was used instead of the compound of Example 3. The crude product was purified by flash chromatography with 25% EtOAc in chloroform. The pure solid was triturated with dichloromethane-light petroleum, filtered and dried to obtain the title compound in 79% yield. Mass (ES⁻): 495 (M⁻−1); IR (KBr): 3372, 2952, 1740 (br), 1609, 1542 (br); ¹H NMR (DMSO-d₆) δ: 1.70 (m, 4H), 2.28 (m, 4H), 3.57 (s, 3H), 7.19 (m, 1H), 7.56 (s, 1H), 7.65 (m, 1H), 7.77 (dd, 1H), 7.92 (2×d, 4H), 10.76 (s, 2H).

Example 65

1-({3-[4-(6-Fluoro-benzothiazol-2-ylamino)-phenyl]-isoxazole-5-carbothioyl}-amino)-cyclopentanecarboxylic acid The title compound was prepared according to the procedure as set forth in Example 8, except that 1-({3-[4-(6-fluoro-benzothiazol-2-ylamino)-phenyl]-isoxazole-5-carbothioyl}-amino)-cyclopentanecarboxylic acid methyl ester was used instead of the compound of Example 7. The crude product was purified by crystallization from refluxing alcohol, and dried to afford the title compound in 66% yield. Mass (ES⁺): 483 (M⁺+1); IR (KBr): 3388, 3256, 2958, 1686 (br), 1610, 1552 (br); ¹H NMR (DMSO-d₆) δ: 1.70 (m, 4H), 2.29 (m, 4H), 7.19 (m, 1H), 7.53 (s, 1H), 7.65 (m, 1H), 7.77 (dd, 1H), 7.91 (2×d, 4H), 10.61 (s, 1H), 10.77 (s, 1H), 12.47 (br, 1H).

Example 66

1-({3-[4-(6-Fluoro-benzothiazol-2-ylamino)-phenyl]-N-hydroxy-isoxazole-5-carboximidoyl}-amino)-cyclopentanecarboxylic acid The title compounds were prepared from 1-({3-[4-(6-fluoro-benzothiazol-2-ylamino)-phenyl]-isoxazole-5-carbothioyl}-amino)-cyclopentanecarboxylic acid methyl ester by the same procedure as described for the synthesis of the compound in Example 7. The reaction mixture was evaporated to dryness. Ethyl acetate was added and the solid was filtered. The solid was suspended in water and sonicated for 10 min and filtered. The solid was dried to give the title compound in 26.5% yield. Mass (ES+), 482 (M++1); IR (KBr): 3385, 3285, 2952, 1770, 1606, 1542 (br), 1458; $^1$H NMR (DMSO-$d_6$) δ: 1.72 (m, 2H), 1.84 (m, 4H), 2.19 (m, 2H), 7.19 (m, 1H), 7.62 (s, 1H), 7.65 (m, 1H), 7.77 (dd, 1H), 7.92 (br, 4H), 8.71 (s, 1H), 10.74 (s, 1H).

Example 67

7-{3-[4-(6-Fluoro-benzothiazol-2-ylamino)-phenyl]-isoxazole-5-yl}-9-oxa-6,8-diaza-spiro[4,5]dec-7-en-10-one The EtOAc layer of Example 66 was dried over anhydrous $Na_2SO_4$ and evaporated. The residue was purified by flash chromatography with 5-10% EtOAc in chloroform. The compound obtained after evaporation of solvent was triturated with dichloromethane and light petroleum, filtered and dried to provide the title compound in 26.6% yield. Mass (ES+), 468 (M++1); IR (KBr): 1699, 1610, 1560 (br), 1458, 1448; $^1$H NMR (DMSO-$d_6$): δ 1.75-1.97 (m, 8H), 7.19 (m, 1H), 7.65 (m, 1H), 7.76 (s, 1H), 7.77 (m, 1H), 7.94 (2×d, 4H), 10.79 (s, 1H), 11.38 (s, 1H).

Example 68

(S)-2-({3-[4-(6-Fluoro-benzothiazol-2-ylamino)-phenyl]-5-phenyl-isoxazole-4-carbonyl}-amino)-3-methyl-butyric acid methyl ester Step 1:
3-(4-Nitro-phenyl)-5-phenyl-isoxazole-4-carboxylic acid ethyl ester The title compound was prepared from N-hydroxy-4-nitro-benzimidoyl chloride and phenyl propionic acid ethyl ester by the same procedure as described for the synthesis of 3-(4-nitro-phenyl)-isoxazol-5-carboxylic acid ethyl ester in Example 1. The reaction mixture was refluxed for 16 hours instead of heating at 80° C. for 2.5 hours. The crude product was purified by flash chromatography over silica gel with 10-30% EtOAc in light petroleum to give the title compound in 40% yield. $^1$H NMR (DMSO-$d_6$) δ: 0.98 (t, 3H), 4.11 (q, 2H), 7.53-7.61 (m, 3H), 7.87-7.93 (m, 4H), 8.32 (d, 2H); Mass (ES+), 339 (M++1).

Step 2:
3-(4-Amino-phenyl)-5-phenyl-isoxazole-4-carboxylic acid ethyl ester

The title compound was prepared using 3-(4-nitro-phenyl)-5-phenyl-isoxazole-4-carboxylic acid ethyl ester by the same procedure as described for the preparation of 3-(4-amino-phenyl)-isoxazol-5-carboxylic acid ethyl ester in Example 1. The reaction mixture was refluxed for 16 hours instead of heating at 80° C. for 3 hours. The crude product was purified by flash chromatography over silica gel with 10% EtOAc in chloroform to give the title compound in 74% yield. IR (KBr): 3374, 1712 (br), 1628, 1610, 1439; $^1$H NMR (DMSO-$d_6$) δ: 1.15 (t, 3H), 4.20 (q, 2H), 5.57 (s, 2H), 6.63 (d, 2H), 7.34 (d, 2H), 7.53-7.62 (m, 3H), 7.75-7.89 (m, 2H); Mass (ES+), 309 (M++1).

Step 3: 3-[4-(6-Fluoro-benzothiazol-2-ylamino)-phenyl]-5-phenyl-isoxazole-4-carboxylic acid ethyl ester The title compound was prepared using 3-(4-amino-phenyl)-5-phenyl-isoxazole-4-carboxylic acid ethyl ester by following the procedure as described in Example 1. The crude product was purified by triturating with alcohol and filtered. It was dried to give the title compound in 71.6% yield. IR (KBr): 3192 (br), 1729 (br), 1622, 1610, 1572, 1459; $^1$H NMR (DMSO-$d_6$) δ: 1.06 (t, 3H), 4.19 (q, 2H), 7.18 (m, 1H), 7.55-7.67 (m, 6H), 7.77 (dd, 1H), 7.84-7.7.92 (m, 4H), 10.76 (s, 1H); Mass (ES−), 458 (M−−1).

Step 4: 3-[4-(6-Fluoro-benzothiazol-2-ylamino)-phenyl]-5-phenyl-isoxazole-4-carboxylic acid The compound 3-[4-(6-fluoro-benzothiazol-2-ylamino)-phenyl]-5-phenyl-isoxazole-4-carboxylic acid ethyl ester (10.9 g; 23.7 mmol) was dissolved in 100 ml THF by heating at reflux to get a clear solution. To the solution, 1N NaOH (47.4 ml; 44.7 mmol) was added and the reaction mixture was stirred for 2 h. The solvent was removed. The residue was taken up in water and acidified with 2N HCl to pH 2. The solid was filtered and dried to provide 8 g of the title compound in 78.2% yield. $^1$H NMR (DMSO-$d_6$) δ: 7.18 (m, 1H), 7.54-7.59 (m, 3H), 7.62-7.69 (m 3H), 7.76 (2×d, 1H), 7.84-7.92 (m, 4H), 10.76 (s, 1H); Mass (ES+), 432 (M++1).

Step 5: (S)-2-({3-[4-(6-Fluoro-benzothiazol-2-ylamino)-phenyl]-5-phenyl-isoxazole-4-carbonyl}-amino)-3-methyl-butyric acid methyl ester The title compound was prepared using 3-[4-(6-fluoro-benzothiazol-2-ylamino)-phenyl]-5-phenyl-isoxazole-4-carboxylic acid and (S)-Val-OMe.HCl by the same procedure adopted for the preparation of the compound in Example 5 and was obtained in 64% yield. $^1$H NMR (DMSO-$d_6$) δ: 0.79 (m, 6H), 2.0 (m, 1H), 3.65 (s, 3H), 4.29 (m, 1H), 7.18 (m, 1H), 7.52 (m, 3H), 7.59 (m, 1H), 7.71-7.76 (m, 3H), 7.78-7.81 (m, 2H), 7.86 (d, 2H), 9.24 (d, 1H), 10.72 (s, 1H, NH); mass (ES−), 543 (M−−1).

Example 69

(S)-2-({3-[4-(6-Fluoro-benzothiazol-2-ylamino)-phenyl]-5-phenyl-isoxazole-4-carbonyl}-amino)-3-methyl-butyric acid The title compound was prepared according to the procedure as set forth in Example 8, except that (S)-2-({3-[4-(6-fluoro-benzothiazol-2-ylamino)-phenyl]-5-phenyl-isoxazole-4-carbonyl}-amino)-3-methyl-butyric acid methyl ester was used instead of the compound of Example 7. The crude product was purified by crystallization from $CHCl_3$-MeOH-light petroleum to afford the title compound in 79% yield. $^1$H NMR (DMSO-$d_6$) δ: 0.80 (m, 6H), 2.05 (m, 1H), 4.25 (m, 1H), 7.18 (m, 1H), 7.51-7.53 (m, 3H), 7.62 (m, 1H), 7.74-7.87 (4×m, 7H), 9.14 (d, 1H), 10.72 (s, 1H, NH), 12.81 (br, 1H).

Example 70

(S)-2-({3-[4-(6-Fluoro-benzothiazol-2-ylamino)-phenyl]-5-phenyl-isoxazole-4-carbonyl}-amino)-3-methoxy-propionic acid methyl ester The title compound was prepared from 3-[4-(6-fluoro-benzothiazol-2-ylamino)-phenyl]-5-phenyl-isoxazole-4-carboxylic acid and (S)-2-amino-3-methoxy-propionic acid methyl ester hydrochloride as set forth in Example 5 and was obtained in 69% yield. Mass (ES$^+$): 547 (M$^+$+1); IR (KBr): 3342, 3270, 1718, 1648, 1605, 1542; $^1$H NMR (DMSO-d$_6$) δ: 3.23 (s, 3H), 3.61-3.68 (br, 5H), 4.79 (m, 1H), 7.16 (m, 1H), 7.53-7.58 (m, 4H), 7.80-7.87 (m, 7H), 9.53 (d, 1H), 10.73 (s, 1H, NH).

Example 71

(S)-2-({3-[4-(6-Fluoro-benzothiazol-2-ylamino)-phenyl]-5-phenyl-isoxazole-4-carbonyl}-amino)-3-methoxy-propionic acid The title compound was prepared from (S)-2-({3-[4-(6-fluoro-benzothiazol-2-ylamino)-phenyl]-5-phenyl-isoxazole-4-carbonyl}-amino)-3-methoxy-propionic acid methyl ester as set forth in Example 8. The crude product was purified by crystallization from CHCl$_3$-MeOH-light petroleum. The solid was dried to give the title compound in 66% yield. IR (KBr): 3398, 3266, 2926, 1638 (br), 1608, 1577; $^1$H NMR (DMSO-d$_6$) δ: 3.25 (s, 3H), 3.61-3.71 (m, 2H), 4.60 (m, 1H), 7.14 (m, 1H), 7.49 (m, 3H), 7.59 (m, 1H), 7.7 (dd, 1H), 7.85 (br, 4H), 7.93 (m, 2H), 9.17 (d, 1H), 10.79 (s, 1H); Mass (ES$^-$), 531 (M$^-$–1).

Example 72

(S)-2-({3-[4-(6-Fluoro-benzothiazol-2-ylamino)-phenyl]-5-phenyl-isoxazole-4-carbothioyl}-amino)-3-methyl-butyric acid methyl ester The title compound was prepared from (S)-2-({3-[4-(6-fluoro-benzothiazol-2-ylamino)-phenyl]-5-phenyl-isoxazole-4-carbonyl}-amino)-3-methyl-butyric acid methyl ester as set forth in Example 4. The crude product was purified by flash chromatography with 2% MeOH in chloroform. The pure solid was triturated with dichloromethane-light petroleum and filtered. The solid was dried to give the title compound in 76% yield. Mass (ES$^+$), 560 (M$^+$+1); IR (KBr): 3299, 2964, 1735, 1607, 1550; $^1$H NMR (DMSO-d$_6$) δ: 0.80 (m, 6H), 2.15 (m, 1H), 3.69 (s, 3H), 4.76 (m, 1H), 7.15 (m, 1H), 7.50 (m, 3H), 7.59 (m, 1H), 7.71-7.74 (m, 3H), 7.79-7.88 (m, 4H), 10.70 (s, 1H), 11.22 (d, 1H).

Example 73

(S)-2-({3-[4-(6-Fluoro-benzothiazol-2-ylamino)-phenyl]-5-phenyl-isoxazole-4-carbothioyl}-amino)-3-methyl-butyric acid The title compound was prepared from (S)-2-({3-[4-(6-fluoro-benzothiazol-2-ylamino)-phenyl]-5-phenyl-isoxazole-4-carbothioyl}-amino)-3-methyl-butyric acid methyl ester as set forth in Example 8. The crude product was purified by crystallization from refluxing alcohol. The solid was dried to give the title compound in 22% yield. Mass (ES$^+$): 546 (M$^+$+1); IR (KBr): 3213, 2964, 1686, 1616, 1561; $^1$H NMR (DMSO-d$_6$) δ: 0.86 (m, 6H), 2.18 (m, 1H), 4.77 (m, 1H), 7.18 (m, 1H), 7.48-7.50 (m, 3H), 7.62 (m, 1H), 733-7.87 (m, 7H), 10.70 (s, 1H), 11.16 (d, 1H), 13.08 (s, 1H).

Example 74

(S)-2-({3-[4-(6-Fluoro-benzothiazol-2-ylamino)-phenyl]-5-phenyl-isoxazole-4-carbothioyl}-amino)-3-methoxy-propionic acid methyl ester The title compound was prepared from (S)-2-({3-[4-(6-fluoro-benzothiazol-2-ylamino)-phenyl]-5-phenyl-isoxazole-4-carbonyl}-amino)-3-methoxy-propionic acid methyl ester as set forth in Example 4. The crude product was purified by flash chromatography with 20% EtOAc in chloroform. The pure solid was triturated with dichloromethane-light petroleum and filtered. The solid was dried to give the title compound in 80.5% yield. Mass (ES$^+$): 562 (M$^+$+1); IR (KBr): 3216, 2944, 1752, 1604, 1546 (br); $^1$H NMR (DMSO-d$_6$) δ: 3.27 (s, 3H), 3.69-3.74 (br, 4H), 3.86 (dd, 1H), 5.41 (m, 1H), 7.16 (m, 1H), 7.50-7.52 (m, 3H), 7.59 (m, 1H), 7.72-7.76 (dd, 1H), 7.79 (d, 2H), 7.84-7.88 (m, 4H), 10.71 (s, 1H), 11.59 (d, 1H).

Example 75

(S)-2-({3-[4-(6-Fluoro-benzothiazol-2-ylamino)-phenyl]-5-phenyl-isoxazole-4-carbothioyl}-amino)-3-methoxy-propionic acid The title compound was prepared from (S)-2-({3-[4-(6-fluoro-benzothiazol-2-ylamino)-phenyl]-5-phenyl-isoxazole-4-carbothioyl}-amino)-3-methoxy-propionic acid methyl ester as set forth in Example 8. The crude product was purified by crystallization from refluxing alcohol. The solid was dried to give the title compound in 38% yield.
Mass (ES$^+$): 548 (M$^+$+1); IR (KBr): 3423 (br), 3199, 2972, 1690 (br), 1611, 1560; $^1$H NMR (DMSO-d$_6$) δ: 3.27 (s, 3H), 3.77 (2×dd, 2H), 5.35 (m, 1H), 7.15 (m, 1H), 7.44-7.49 (m, 3H), 7.58 (m, 1H), 7.73 (dd, 1H), 7.81 (br, 4H), 7.87-7.91 (m, 2H), 10.68 (s, 1H), 11.53 (d, 1H), 13.11 (br 1H).

Example 76

(S)-3-Methyl-2-({3-[4-(3-phenyl-ureido)-phenyl]-isoxazole-5-carbonyl}-amino)-butyric acid methyl ester Step 1: 3-[4-(3-phenyl-ureido)-phenyl]-isoxazole-5-carboxylic acid ethyl ester 3-(4-Amino-phenyl)-isoxazol-5-carboxylic acid ethyl ester (5.0 g; 21.55 mmol) was dissolved in THF (100 ml) and phenyl isocyanate (2.82 g; 23.72 mmol) was added at room temperature under stirring. The resulting reaction mixture was stirred for 16 h. The solvent was removed and the residue was purified by flash chromatography over silica gel with 10% EtOAc in chloroform. After removing the solvent, the solid was triturated with dichloromethane and light petroleum to get a solid 6.9 g (91.3%). Mass (ES$^+$): 352 (M$^+$+1); IR (KBr): 3294, 1727, 1640, 1610, 1596, 1582; $^1$H NMR (DMSO-d$_6$) δ: 1.34 (t, 3H), 4.38 (q, 2H), 6.98 (t, 1H), 7.28 (t, 2H), 7.45 (d, 2H), 7.60 (d, 2H), 7.83 (s, 1H), 7.88 (d, 2H), 8.76 (s, 1H), 8.96 (s, 1H).

Step 2: 3-[4-(3-phenyl-ureido)-phenyl]-isoxazole-5-carboxylic acid

The title compound was prepared from 3-[4-(3-phenyl-ureido)-phenyl]-isoxazole-5-carboxylic acid ethyl ester as set forth in example 8 and was obtained in 95.6% yield. Mass (ES$^+$): 324 (M$^+$+1); IR (KBr): 3312, 1711, 1645, 1599, 1461; $^1$H NMR (DMSO-d$_6$) δ: 6.97 (t, 1H), 7.28 (t, 2H), 7.45 (d, 2H), 7.59 (d, 2H), 7.71 (s, 1H), 7.87 (d, 2H), 8.76 (s, 1H), 8.96 (s, 1H).

Step 3: (S)-3-Methyl-2-({3-[4-(3-phenyl-ureido)-phenyl]-isoxazole-5-carbonyl}-amino)-butyric acid methyl ester The title compound was prepared from 3-[4-(3-phenyl-ureido)-phenyl]-isoxazole-5-carboxylic acid and (S)-2- amino-3-methyl-butyric acid methyl ester hydrochloride as set forth in Example 5 and was obtained in 65% yield. Mass (ES+): 437 (M++1); IR (KBr): 3342, 3262, 1743; 1665, 1598, 1550; $^1$H NMR (DMSO-d$_6$) δ: 0.92 (2×d, 6H), 2.18 (m, 1H), 3.63 (s, 3H), 4.27 (t, 1H), 6.94 (t, 1H), 7.25 (t, 2H), 7.42 (d, 2H), 7.58 (d, 2H), 7.64 (s, 1H), 7.80 (d, 2H), 8.72 (s, 1H), 8.92 (s, 1H), 9.14 (d, 1H).

Example 77

(S)-3-Methyl-2-({3-[4-(3-phenyl-ureido)-phenyl]-isoxazole-5-carbonyl}-amino)-butyric acid The title compound was prepared from (S)-3-methyl-2-({3-[4-(3-phenyl-ureido)-phenyl]-isoxazole-5-carbonyl}-amino)-butyric acid methyl ester as set forth in Example 8 and was obtained in 83% yield. Mass (ES+): 423 (M++1); IR (KBr): 3347, 3317, 1708, 1671 (br), 1599, 1547 (br); $^1$H NMR (DMSO-d$_6$) δ: 0.95 (2×d, 6H), 2.20 (m, 1H), 4.27 (q, 2H), 6.97 (t, 1H), 7.28 (t, 2H), 7.45 (d, 2H), 7.60 (d, 2H), 7.68 (s, 1H), 7.82 (d, 2H), 8.75 (s, 1H), 8.94 (d, 1H), 8.96 (d, 1H).

Example 78

(S)-3-Methyl-2-({3-[4-(3-phenyl-ureido)-phenyl]-isoxazole-5-carbonyl}-amino)-pentanoic acid methyl ester The title compound was prepared from 3-[4-(3-phenyl-ureido)-phenyl]-isoxazole-5-carboxylic acid and (S)-2-amino-4-methyl-pentanoic acid methyl ester hydrochloride as set forth in Example 5 and was obtained in 67.7% yield. Mass (ES+): 451 (M++1); IR (KBr): 3340 (br), 2958, 1745, 1666, 1599, 1540 (br); $^1$H NMR (DMSO-d$_6$) δ: 0.87, 0.91 (2×d, 6H), 1.54-1.70 (m, 2H), 1.76-1.84 (m, 1H), 3.65 (s, 3H), 4.49 (m, 1H), 6.97 (t, 1H), 7.28 (t, 2H), 7.45 (d, 2H), 7.60 (d, 2H), 7.62 (s, 1H), 7.83 (d, 2H), 8.75 (br, 1H), 8.96 (br, 1H), 9.33 (d, 1H).

Example 79

(S)-3-Methyl-2-({3-[4-(3-phenyl-ureido)-phenyl]-isoxazole-5-carbonyl}-amino)-pentanoic acid The title compound was prepared from (S)-3-methyl-2-({3-[4-(3-phenyl-ureido)-phenyl]-isoxazole-5-carbonyl}-amino)-pentanoic acid methyl ester as set forth in Example 8 and was obtained in 66.5% yield. Mass (ES+): 437 (M++1); IR (KBr): 3336, 3280, 1717, 1667 (br), 1599, 1542 (br); $^1$H NMR (DMSO-d$_6$) δ: 0.84, 0.88 (2×d, 6H), 1.51-1.68 (m, 2H), 1.71-1.79 (m, 1H), 4.36 (m, 1H), 6.94 (t, 1H), 7.25 (t, 2H), 7.42 (d, 2H), 7.57 (d, 2H), 7.58 (s, 1H), 7.80 (d, 2H), 8.77 (br, 1H), 8.97 (br, 1H), 9.13 (d, 1H).

Example 80

(S)-2-(S)-2-({3-[4-(3-cyclohexyl-ureido)-phenyl]-isoxazole-5-carbonyl}-amino)-3-methyl-butyric acid methyl ester Step 1: 3-[4-(3-cyclohexyl-ureido)-phenyl]-isoxazole-5-carboxylic acid ethyl ester The title compound was prepared from 3-(4-amino-phenyl)-isoxazol-5-carboxylic acid ethyl ester and cyclohexyl isocyanate by same procedure as set forth for the preparation of 3-[4-(3-phenyl-ureido)-phenyl]-isoxazole-5-carboxylic acid ethyl ester and was obtained in 75% yield. Mass (ES+), 358 (M++1); IR (KBr): 3304, 2928, 2852, 1731, 1634, 1570 (br); $^1$H NMR (DMSO-d$_6$) δ: 1.33 (t, 3H), 1.14-1.81 (4×m, 10H), 3.45 (br, 1H), 4.37 (q, 2H), 6.18 (d, 1H), 7.50 (d, 2H), 7.60 (s, 1H), 7.79 (s, 1H), 7.8.1 (d, 2H), 8.59 (s, 1H).

Step 2: 3-[4-(3-cyclohexyl-ureido)-phenyl]-isoxazole-5-carboxylic acid

The title compound was prepared from 3-[4-(3-cyclohexyl-ureido)-phenyl]-isoxazole-5-carboxylic acid ethyl ester as set forth in Example 8 and was obtained in 92% yield. Mass (ES+): 330 (M++1); IR (KBr): 3318, 2927, 2853, 1711, 1637, 1563; $^1$H NMR (DMSO-d$_6$) δ: 1.05-1.80 (4×m, 10H), 3.45 (br, 1H), 6.17 (d, 1H), 7.49 (d, 2H), 7.66 (s, 1H), 7.79 (d, 2H), 8.58 (s, 1H), 14.5 (br, ~0.5H).

Step 3: (S)-2-({3-[4-(3-cyclohexyl-ureido)-phenyl]-isoxazole-5-carbonyl}-amino)-3-methyl-butyric acid methyl ester The title compound was prepared from 3-[4-(3-cyclohexyl-ureido)-phenyl]-isoxazole-5-carboxylic acid and (S)-2-amino-3-methyl-butyric acid methyl ester hydrochloride as set forth in Example 5 and was obtained in 68% yield. Mass (ES+): 443 (M++1); IR (KBr): 3382, 3345, 3290, 2932, 1746, 1665, 1652, 1543; $^1$H NMR (DMSO-d$_6$) δ: 0.91 (2×d, 6H), 1.08-1.78 (4×m, 10H), 2.16 (m, 1H), 3.42 (br, 1H), 3.53 (s, 3H), 4.26 (t, 1H), 6.14 (d, 1H), 7.48 (d, 2H), 7.60 (s, 1H), 7.72 (d, 2H), 8.56 (s, 1H), 9.12 (d, 1H).

Example 81

(S)-2-({3-[4-(3-cyclohexyl-ureido)-phenyl]-isoxazole-5-carbonyl}-amino)-3-methyl-butyric acid The title compound was prepared from (S)-2-({3-[4-(3-cyclohexyl-ureido)-phenyl]-isoxazole-5-carbonyl}-amino)-3-methyl-butyric acid methyl ester as set forth in Example 8 and was obtained in 62% yield. Mass (ES+): 429 (M++1); IR (KBr): 3339, 2933, 1744; 1651 (br), 1594, 1527 (br); $^1$H NMR (DMSO-d$_6$) δ: 0.92-0.96 (2×d, 6H), 1.09-1.79 (4×m, 10H), 2.18 (m, 1H), 3.45 (br, 1H), 4.25 (dd, 1H), 6.18 (d, 1H), 7.50 (d, 2H), 7.63 (s, 1H), 7.74 (d, 2H), 8.59 (s, 1H), 8.89 (d, 1H), 12.84 (br, 1H).

Example 82

(S)-2-({3-[4-(3-cyclohexyl-ureido)-phenyl]-isoxazole-5-carbonyl}-amino)-4-methyl-pentanoic acid methyl ester The title compound was prepared from 3-[4-(3-cyclohexyl-ureido)-phenyl]-isoxazole-5-carboxylic acid and (S)-2-amino-4-methyl-pentanoic acid methyl ester hydrochloride as set forth in Example 5 and was obtained in 67.9% yield. Mass (ES+): 457 (M++1); IR (KBr): 3328, 2931, 1752 (br), 1655 (br), 1542 (br); $^1$H NMR (DMSO-d$_6$) δ: 0.87, 0.91 (2×d, 6H), 1.14-1.81 (5×m, 13H), 3.47 (br, 1H), 3.65 (s, 3H), 4.49 (m, 1H), 6.17 (d, 1H), 7.52 (d, 2H), 7.59 (s, 1H), 7.77 (d, 2H), 8.59 (s, 1H), 8.96 (br, 1H), 9.32 (d, 1H).

Example 83

(S)-2-({3-[4-(3-cyclohexyl-ureido)-phenyl]-isoxazole-5-carbonyl}-amino)-4-methyl-pentanoic acid The title compound was prepared from (S)-2-({3-[4-(3-cyclohexyl-ureido)-phenyl]-isoxazole-5-carbonyl}-amino)-

4-methyl-pentanoic acid methyl ester as set forth in Example 8 and was obtained in 70.7% yield. Mass (ES$^+$): 443 (M$^+$+1); IR (KBr): 3326, 3305, 2935, 1748, 1635 (br), 1544, 1529; $^1$H NMR (DMSO-d$_6$) δ: 0.87, 0.91 (2×d, 6H), 1.09-1.81 (5×m, 13H), 3.45 (br, 1H), 4.38 (m, 1H), 6.16 (d, 1H), 7.50 (d, 2H), 7.56 (s, 1H), 7.75 (d, 2H), 8.58 (s, 1H), 9.14 (d, 1H), 12.76 (br, 1H).

Example 84

(S)-2-[(3-{4-[3-(4-Fluoro-phenyl}-ureido]-phenyl)-isoxazole-5-carbonyl)-amino]-3-methyl-butyric acid methyl ester Step 1: 3-{4-[3-(4-Fluoro-phenyl)-ureido]-phenyl}-isoxazole-5-carboxylic acid ethyl ester The title compound was prepared from 3-(4-amino-phenyl)-isoxazol-5-carboxylic acid ethyl ester and 4-phenyl isocyanate as set forth in Example 76 to obtain 3-[4-(3-phenyl-ureido)-phenyl]-isoxazole-5-carboxylic acid ethyl ester in 79.2% yield. Mass (ES$^+$): 370 (M$^+$+1); IR (KBr): 3315, 1725, 1651, 1558; $^1$H NMR (DMSO-d$_6$) δ: 1.30 (t, 3H), 4.36 (q, 2H), 7.09 (t, 1H), 7.43 (m, 2H), 7.56 (d, 2H), 7.79 (s, 1H), 7.85 (d, 2H), 8.76 (s, 1H), 8.93 (s, 1H).

Step 2: 3-{-4-[3-(4-Fluoro-phenyl)-ureido]-phenyl}-isoxazole-5-carboxylic acid

The title compound was prepared from 3-{4-[3-(4-fluoro-phenyl)-ureido]-phenyl}-isoxazole-5-carboxylic acid ethyl ester using the procedure as set forth in Example 8 and was obtained in 95.2% yield. Mass (ES$^+$): 342 (M$^+$+1); IR (KBr): 3307, 3004 (br), 2871 (br), 1711, 1640, 1601, 1546; $^1$H NMR (DMSO-d$_6$) δ: 7.08 (t, 2H), 7.43 (m, 2H), 7.49 (d, 2H), 7.67 (s, 1H), 7.84 (d, 2H), 8.77 (s, 1H), 8.93 (s, 1H).

Step 3: (S)-2-[(3-{4-[3-(4-Fluoro-phenyl)-ureido]-phenyl}-isoxazole-5-carbonyl)-amino]-3-methyl-butyric acid methyl ester The title compound was prepared from 3-{4-[3-(4-fluoro-phenyl)-ureido]-phenyl}-isoxazole-5-carboxylic acid and (S)-2-amino-3-methyl-butyric acid methyl ester hydrochloride using the procedure as set forth in Example 5 and was obtained in 84.2% yield. Mass (ES$^+$): 455 (M$^+$+1); IR (KBr): 3310, 1742, 1672, 1553 (br), 1506, 1434; $^1$H NMR (DMSO-d$_6$) δ: 0.92 (2×d, 6H), 2.18 (m, 1H), 3.65 (s, 3H), 4.29 (t, 1H), 7.11 (t, 2H), 7.59 (d, 2H), 7.66 (s, 1H), 7.82 (d, 2H), 8.77 (s, 1H), 8.94 (s, 1H), 9.16 (d, 1H).

Example 85

(S)-2-[(3-{4-[3-(4-Fluoro-phenyl)-ureido]-phenyl}-isoxazole-5-carbonyl)-amino]-3-methyl-butyric acid The title compound was prepared from (S)-2-[(3-{4-[3-(4-Fluoro-phenyl)-ureido]-phenyl}-isoxazole-5-carbonyl)-amino]-3-methyl-butyric acid methyl ester using the procedure as set forth in Example 8 and was obtained in 42% yield. Mass (ES$^+$): 441 (M$^+$+1); IR (KBr): 3316 (br), 1718, 1668 (br), 1612, 1600, 1552, 1510; $^1$H NMR (DMSO-d$_6$) δ: 0.95 (2×d, 6H), 2.20 (m, 1H), 4.27 (q, 2H), 7.12 (t, 2H), 7.46 (m, 2H), 7.60 (d, 2H), 7.68 (s, 1H), 7.82 (d, 2H), 8.79 (s, 1H), 8.93 (s, 1H), 8.95 (d, 1H).

Example 86

(S)-2-[(3-{4-[3-(4-Fluoro-phenyl)-ureido]-phenyl}-isoxazole-5-carbonyl)-amino]-4-methyl-pentanoic acid methyl ester The title compound was prepared from 3-{4-[3-(4-fluoro-phenyl)-ureido]-phenyl}-isoxazole-5-carboxylic acid and (S)-2-amino-4-methyl-pentanoic acid methyl ester hydrochloride using the procedure as set forth in Example 5 and was obtained in 69.5% yield. Mass (ES$^+$): 469 (M$^+$+1); IR (KBr): 3312 (br), 2960, 1743, 1665 (br), 1612, 1597, 1542 (br), 1508; $^1$H NMR (DMSO-d$_6$) δ: 0.85, 0.90 (2×d, 6H), 1.59 (m, 2H), 1.79 (m, 1H), 3.64 (s, 3H), 4.47 (m, 1H), 7.11 (t, 1H), 7.45 (m, 2H), 7.58 (d, 2H), 7.60 (s, 1H), 7.82 (d, 2H), 8.78 (sr, 1H), 8.95 (s, 1H), 9.32 (d, 1H).

Example 87

(S)-2-[(3-{4-[3-(4-Fluoro-phenyl)-ureido]-phenyl}-isoxazole-5-carbonyl)-amino]-4-methyl-pentanoic acid The title compound was prepared from (S)-2-[(3-{4-[3-(4-Fluoro-phenyl)-ureido]-phenyl}-isoxazole-5-carbonyl)-amino]-4-methyl-pentanoic acid methyl ester using the procedure as set forth in Example 8 and was obtained in 58% yield. Mass (ES$^+$): 455 (M$^+$+1); IR (KBr): 3336 (br), 2962, 1724, 1664 (br), 1600, 1543 (br), 1510 (br); $^1$H NMR (DMSO-d$_6$) δ: 0.87, 0.91 (2×d, 6H), 1.57-1.68 (m, 2H), 1.74-1.82 (m, 1H), 4.41 (m, 1H), 7.12 (t, 2H), 7.46 (m, 2H), 7.59 (d, 2H), 7.61 (s, 1H), 7.82 (d, 2H), 8.80 (s, 1H), 8.97 (s, 1H), 9.17 (d, 1H).

Example 88

(S)-3-Methyl-2-({4-phenyl-3-[4-(3-phenyl-ureido)-phenyl]-isoxazole-5-carbonyl}-amino)-butyric acid methyl ester Step 1: 4-Phenyl-3-[4-(3-phenyl-ureido)-phenyl]-isoxazole-5-carboxylic acid ethyl ester The title compound was prepared from 3-(4-amino-phenyl)-5-phenyl-isoxazole-4-carboxylic acid ethyl ester and 4-phenyl isocyanate as set forth in the preparation of 3-[4-(3-phenyl-ureido)-phenyl]-isoxazole-5-carboxylic acid ethyl ester in Example 76 and was obtained in 82% yield. Mass (ES$^+$): 428 (M$^+$+1); IR (KBr): 3280, 1725, 1638, 1590, 1573, 1557; $^1$H NMR (DMSO-d$_6$) δ: 1.05 (t, 3H), 4.16 (q, 2H), 6.96 (t, 1H), 7.27 (t, 2H), 7.45 (d, 2H), 7.53-7.62 (m, 7H), 7.82-7.85 (m, 2H), 8.80 (br 1H), 8.99 (br, 1H).

Step 2: 4-Phenyl-3-[4-(3-phenyl-ureido)-phenyl]-isoxazole-5-carboxylic acid

The title compound was prepared from 4-phenyl-3-[4-(3-phenyl-ureido)-phenyl]-isoxazole-5-carboxylic acid ethyl ester using the procedure as set forth in Example 8 and was obtained in 72.5% yield. Mass (ES$^+$): 400 (M$^+$+1); $^1$H NMR (DMSO-d$_6$) δ: 6.96 (m, 1H), 7.27 (t, 2H), 7.45 (d, 2H), 7.54-7.62 (m, 7H), 7.84-7.87 (m, 2H), 8.74 (br 1H), 8.92 (br, 1H), 13.45 (br, 1H).

Step 3: (S)-3-Methyl-2-({4-phenyl-3-[4-(3-phenyl-ureido)-phenyl]-isoxazole-5-carbonyl}-amino)-butyric acid methyl ester The title compound was prepared from 4-phenyl-3-[4-(3-phenyl-ureido)-phenyl]-isoxazole-5-carboxylic acid and (S)-

2-amino-3-methyl-butyric acid methyl ester hydrochloride using the procedure as set forth in Example 5 and was obtained in 76.5% yield. $^1$H NMR (DMSO-d$_6$) δ: 0.79 (m, 6H), 2.01 (m, 1H), 4.30 (m, 1H), 6.96 (t, 1H), 7.27 (t, 2H), 7.44 (d, 2H), 7.53 (m, 3H), 7.56 (d, 2H), 7.67 (d, 2H), 7:81 (m, 2H), 8.72 (s, 1H), 8.93 (s, 1H), 9.25 (d, 1H); Mass (ES$^+$), 513 (M$^+$+1).

Example 89

(S)-3-Methyl-2-({4-phenyl-3-[4-(3-phenyl-ureido)-phenyl]-isoxazole-5-carbonyl}-amino)-butyric acid The title compound was prepared from (S)-3-methyl-2-({4-phenyl-3-[4-(3-phenyl-ureido)-phenyl]-isoxazole-5-carbonyl}-amino)-butyric acid methyl ester using the procedure as set forth in Example 8 and was obtained in 82.3% yield. Mass (ES$^+$): 499 (M$^+$+1); $^1$H NMR (DMSO-d$_6$) δ: 0.80 (2×d, 6H), 2.06 (m, 1H), 4.24 (m, 1H), 6.96 (t, 1H), 7.27 (t, 2H), 7.44 (d, 2H), 7.48-7.52 (m, 3H), 7.55 (d, 2H), 7.70 (d, 2H), 7.84 (m, 2H), 8.73 (s, 1H), 8.93 (s, 1H), 9.14 (d, 1H), 12.81 (s, 1H).

Example 90

(S)-4-Methyl-2-({4-phenyl-3-[4-(3-phenyl-ureido)-phenyl]-isoxazole-5-carbonyl}-amino)-pentanoic acid methyl ester The title compound was prepared from 4-phenyl-3-[4-(3-phenyl-ureido)-phenyl]-isoxazole-5-carboxylic acid and (S)-2-amino-4-methyl-pentanoic acid methyl ester hydrochloride using the procedure as set forth in Example 5 and was obtained in 83% yield. Mass (ES$^-$): 525 (M$^-$−1); $^1$H NMR (DMSO-d$_6$) δ: 0.75, 0.81 (2×d, 6H), 1.35-1.58 (m, 3H), 3.66 (s, 3H), 4.49 (m, 1H), 6.96 (t, 1H), 7.27 (t, 2H), 7.44 (d, 2H), 7.54 (m, 3H), 7.56 (d, 2H), 7.66 (d, 2H), 7.82 (m, 2H), 8.72 (br, 1H), 8.95 (br, 1H), 9.31 (d, 1H).

Example 91

(S)-4-Methyl-2-({4-phenyl-3-[4-(3-phenyl-ureido)-phenyl]-isoxazole-5-carbonyl}-amino)-pentanoic acid The title compound was prepared from (S)-4-methyl-2-({4-phenyl-3-[4-(3-phenyl-ureido)-phenyl]-isoxazole-5-carbonyl}-amino)-pentanoic acid methyl ester using the procedure as set forth in Example 8 and was obtained in 82.5% yield. Mass (ES$^+$): 513 (M$^+$+1); $^1$H NMR (DMSO-d$_6$) δ: 0.76, 0.83 (2×d, 6H), 1.38-1.59 (m, 3H), 4.34 (m, 1H), 6.96 (t, 1H), 7.27 (t, 2H), 7.46 (d, 2H), 7.48-7.69 (m, 5H), 7.73 (d, 2H), 7.86 (m, 2H), 8.73 (s, 1H), 8.94 (s, 1H), 9.22 (d, 1H), 12.83 (s, 1H).

Example 92

(S)-2-[(3-{4-[3-(4-Fluoro-phenyl)-ureido]-phenyl}-4-phenyl-isoxazole-5-carbonyl)-amino]-3-methyl-butyric acid methyl ester Step 1: 3-{4-[3-(4-Fluoro-phenyl)-ureido]-phenyl}-4-phenyl-isoxazole-5-carboxylic acid ethyl ester The title compound was prepared from 3-(4-amino-phenyl)-5-phenyl-isoxazole-4-carboxylic acid ethyl ester and 4-phenyl isocyanate as set forth in the preparation of 3-[4-(3-phenyl-ureido)-phenyl]-isoxazole-5-carboxylic acid ethyl ester in Example 76 and was obtained in 70% yield. Mass (ES$^+$): 445 (M$^+$+1); IR (KBr): 3286, 1726, 1640, 1590, 1564, 1508; $^1$H NMR (DMSO-d$_6$) δ: 1.05 (t, 3H), 4.17 (q, 2H), 7.11 (t, 2H), 7.46 (m, 2H), 7.57-7.58 (m, 7H), 7.83 (m, 2H), 8.77 (s 1H), 8.93 (s, 1H).

Step 2: 3-{4-[3-(4-Fluoro-phenyl)-ureido]-phenyl}-4-phenyl-isoxazole-5-carboxylic acid ethyl ester The title compound was prepared from 3-{4-[3-(4-fluoro-phenyl)-ureido]-phenyl}-4-phenyl-isoxazole-5-carboxylic acid ethyl ester using the procedure as set forth in Example 8 and was obtained in 71.5% yield. Mass (ES$^+$): 445 (M$^+$+1); IR (KBr): 3356, 3302, 3057 (br), 1727, 1657, 1576, 1552, 1509; $^1$H NMR (DMSO-d$_6$) δ: 7.12 (t, 2H), 7.47 (m, 2H), 7.54-7.59 (m, 7H), 7.87 (m, 2H), 8.79 (s 1H), 8.93 (s, 1H).

Step 3: (S)-2-[(3-{4-[3-(4-Fluoro-phenyl)-ureido]-phenyl}-4-phenyl-isoxazole-5-carbonyl)-amino]-3-methyl-butyric acid methyl ester The title compound was prepared from 3-{4-[3-(4-fluoro-phenyl)-ureido]-phenyl}-4-phenyl-isoxazole-5-carboxylic acid ethyl ester and (S)-2-amino-3-methyl-butyric acid methyl ester hydrochloride using the procedure as set forth in Example 5 and was obtained in 88.7% yield. Mass (ES$^+$): 531 (M$^+$+1); $^1$H NMR (DMSO-d$_6$) δ: 0.79 (m, 6H), 2.02 (m, 1H), 3.65 (s, 3H), 4.29 (m, 1H), 7.11 (t, 1H), 7.43-7.47 (m, 2H), 7.52 (m, 3H), 7.55 (d, 2H), 7.67 (d, 2H), 7.81 (m, 2H), 8.74 (s, 1H), 8.93 (s, 1H), 9.25 (d, 1H).

Example 93

(S)-2-[(3-{4-[3-(4-Fluoro-phenyl)-ureido]-phenyl}-4-phenyl-isoxazole-5-carbonyl)-amino]-3-methyl-butyric acid The title compound was prepared from (S)-2-[(3-{4-[3-(4-fluoro-phenyl)-ureido]-phenyl}-4-phenyl-isoxazole-5-carbonyl)-amino]-3-methyl-butyric acid methyl ester using the procedure as set forth in Example 8 and was obtained in 86.7% yield. Mass (ES$^+$): 517 (M$^+$+1); $^1$H NMR (DMSO-d$_6$) δ: 0.82, 0.90 (2×d, 6H), 2.06 (m, 1H), 4.24 (m, 1H), 7.11 (t, 1H), 7.45 (m, 2H); 7.49 (m, 3H), 7.55 (d, 2H), 7.70 (d, 2H), 7.84 (m, 2H), 8.78 (s, 1H), 8.94 (s, 1H), 9.14 (d, 1H), 12.82 ((s, 1H).

Example 94

(S)-2-({3-[4-(6-Fluoro-benzothiazol-2-ylamino)-phenyl]-4-phenyl-isoxazole-5-carbonyl}-amino)-4-methyl-pentanoic acid methyl ester The title compound was prepared from 3-[4-(6-fluoro-benzothiazol-2-ylamino)-phenyl]-5-phenyl-isoxazole-4-carboxylic acid and (S)-2-amino-4-methyl-pentanoic acid methyl ester hydrochloride using the procedure as set forth in Example 5 and was obtained in 83% yield. Mass (ES$^+$): 559 (M$^+$+1); IR (KBr): 3357, 3265, 2953, 1709, 1638, 1607, 1546, 1458; $^1$H NMR (DMSO-d$_6$) δ: 0.76, 0.84 (2×d, 6H), 1.41-1.57 (m, 3H), 3.69 (s, 3H), 4.45 (m, 1H), 7.19 (m, 1H), 7.55-7.57 (m, 3H), 7.61 (m, 1H), 7.75 (d, 2H), 7.77 (m, 1H), 7.85 (m, 2H), 7.90 (d, 2H), 9.34 (d, 1H), 10.76 (s, 1H, NH).

Example 95

(S)-2-({3-[4-(6-Fluoro-benzothiazol-2-ylamino)-phenyl]-4-phenyl-isoxazole-5-carbonyl}-amino)-4-methyl-pentanoic acid The title compound was prepared from (S)-2-({3-[4-(6-fluoro-benzothiazol-2-ylamino)-phenyl]-4-phenyl-isoxazole-5-carbonyl}-amino)-4-methyl-pentanoic acid methyl ester using the procedure as set forth in Example 8. The crude product was purified by crystallization from refluxing alcohol. The solid was dried to give title compound in 86.2% yield. Mass (ES$^+$): 544 (M$^+$+1); $^1$H NMR (DMSO-d$_6$) δ: 0.75, 0.83 (2×d, 6H), 1.37-1.58 (m, 3H), 4.34 (m, 1H), 7.18 (m, 1H), 7.48-7.53 (m, 3H), 7.60 (m, 1H), 7.74-7.78 (m, 3H), 7.85 (br, 2H), 7.88 (br, 2H), 9.23 (d, 1H), 10.73 (s, 1H), 12.82 (s, 1H).

Example 96

(S)-2-[3-{3-Fluoro-4-[3-(4-fluoro-phenyl)-ureido]-phenyl}-isoxazole-5-carbonyl)-amino]-3-methyl-butyric acid methyl ester Step 1: 3-Fluoro-4-nitro-benzaldehyde: To a solution of 3-fluoro-4-nitro-benzyl bromide 23.4 g (100 mmol) dissolved in chloroform (250 ml), hexamine 15.4 g (110 mmol) was added under stirring. The stirring was continued for 6 hours. The precipitated white solid was filtered and washed with chloroform. The solid was dried to give hexamine salt 34.4 g (92%). The hexamine salt obtained above (30 g; 80.2 mmol) was taken up in TFA (160 mL) and heated at 70-75° C. for 20 hours. To the reaction mixture 2N HCl (100 mL) was added and heating continued for 30 minutes. The TFA was distilled off. The residue was further diluted with water (100 mL). The oil was extracted with ethyl acetate. The organic layer was washed with water and brine. It was dried over anhydrous Na$_2$SO$_4$. The solvent was removed and the residue was purified by flash chromatography over silica gel with 15-20% ethyl acetate in light petroleum to give 11.65 g of the title compound (86%); IR (KBr): 3108, 3091, 2888, 1700, 1615, 1601 cm$^{-1}$; MS (m/z): 169; $^1$H NMR (CDCl$_3$) δ: 7.79-7.85 (m, 2H), 8.18 (m, 1H), 10.08 (s, 1H, CHO).

Step 2: 3-Fluoro-4-nitro-benzaldehyde oxime: A mixture of 3-fluoro-4-nitro-benzaldehyde (9.5; 56.21 mmol) and hydroxylamine hydrochloride (4.29 g; 61.83 mmol) in ethanol (50 mL) was heated at 60-65° C. for 2 hours. The solvent was distilled off. The residue was purified by flash chromatography over silica gel with 10-15% ethyl acetate in light petroleum to give 8 g of the title compound (77.4%); IR (KBr): 3091, 3056, 2501, 2431, 1597, 1513, 1488, 1400 cm$^{-1}$; MS (m/z): 185 (M$^+$+1); $^1$H NMR (CDCl$_3$) δ: 7.62-7.70 (m, 2H), 8.14-8.19 (m, 1H), 8.24 (s, 1H NH), 11.99 (s, 1H, NHOH).

Step 3: 3-(3-Fluoro-4-nitro-phenyl)-isoxazole-5-carboxylic acid ethyl ester: To a solution of 3-fluoro-4-nitro-benzaldehyde oxime (6 g; 32.6 mmol) in acetonitrile (120 mL) was added hydroxy tosyloxy iodobenzene (16.58 g; 42.3 mmol) and ethyl propiolate (6.38 g; 65.2 mmol) under stirring. The resulting reaction mixture was stirred at 80° C. for 2-3 h. After the completion of the reaction, it was evaporated to dryness. The solid thus obtained was dissolved in ethyl acetate and washed with brine and dried over anhydrous Na$_2$SO$_4$. The solvent was removed and the residue was purified by flash chromatography over silica gel with 20% ethyl acetate in light petroleum to give 6.4 g (74%) of the title compound. IR (KBr): 3134, 3060, 2975, 1717, 1610, 1593, 1522, 1458, 1446 cm$^{-1}$; MS (m/z): 279 (M$^-$−1); $^1$H NMR (DMSO-d$_6$) δ: 1.31-136 (t, 3H, CH$_2$CH$_3$), 4.36-4.43 (q, 2H, CH$_2$CH$_3$), 8.04 (d, 1H, J=9.0, 6'-H), 8.09 (s, 1H, 4-H), 8.16 (d, 1H), 8.30 (t, 1H).

Step 4: 3-(4-Amino-3-Fluoro-phenyl)-isoxazole-5-carboxylic acid ethyl ester: The title compound was prepared from 3-(3-fluoro-4-nitro-phenyl)-isoxazole-5-carboxylic acid ethyl ester by following the procedure as described for the preparation of 3-(4-Amino-phenyl)-isoxazol-5-carboxylic acid ethyl ester (Example 1, Step 2) in 55% yield; MS (m/z): 250; $^1$H NMR (DMSO-d$_6$) δ: 1.31 (t, 3H, CH$_2$CH$_3$), 4.36 (q, 2H, CH$_2$CH$_3$), 5.7 (s, 2H, NH$_2$), 6.81 (t, 1H), 7.48 (d, 1H, J=9.0), 7.56 (d, 1H), 7.74 (s, 1H, 4-H).

Step 5: 3-{3-Fluoro-4-[3-(4-fluoro-phenyl)-ureido]-phenyl}-isoxazole-5-carboxylic acid ethyl ester: The title compound was prepared from 3-(4-amino-3-fluoro-phenyl)-isoxazole-5-carboxylic acid ethyl ester by using the procedure as described for the preparation of 3-[4-(3-phenyl-ureido)-phenyl]-isoxazole-5-carboxylic acid ethyl ester (Example 76, step 1) and was obtained in 74% yield; MS (m/z): 388 (M$^+$+1); $^1$H NMR (DMSO-d$_6$) δ: 1.33 (t, 3H, CH$_2$CH$_3$), 4.37 (q, 2H, CH$_2$CH$_3$), 7.13 (t, 2H), 7.46 (m, 2H), 7.77 (d, 1H), 7.85 (m, 1H), 7.88 (s, 1H, 4-H), 8.32 (t, 1H), 8.78, 9.17 (2×s, 2H, 2×NH).

Step 6: 3-{3-Fluoro-4-[3-(4-fluoro-phenyl)-ureido]-phenyl}-isoxazole-5-carboxylic acid: The title compound was prepared from 3-{3-fluoro-4-[3-(4-fluoro-phenyl)-ureido]-phenyl}-isoxazole-5-carboxylic acid ethyl ester by using the procedure as described for the preparation of 3-[4-(3-phenyl-ureido)-phenyl]-isoxazole-5-carboxylic acid (Example 76, step 2) and was obtained in 89% yield; MS (m/z): 360 (M$^+$+1); $^1$H NMR (DMSO-d$_6$) δ: 7.13 (t, 2H), 7.46 (m, 2H), 7.76 (m, 2H), 7.84 (m, 1H), 8.32 (t, 1H), 8.78, 9.18 (2×s, 2H, 2×NH).

Step 7: S)-2-[3-{3-Fluoro-4-[3-(4-fluoro-phenyl)-ureido]-phenyl}-isoxazole-5-carbonyl)-amino]-3-methyl-butyric acid methyl ester: The title compound was prepared from 3-{3-fluoro-4-[3-(4-fluoro-phenyl)-ureido]-phenyl}-isoxazole-5-carboxylic acid and valine methylester hydrochloride by using the procedure as described for the preparation of (S)-3-methyl-2-({3-[4-(3-phenyl-ureido)-phenyl]-isoxazole-5-carbonyl}-amino)-butyric acid methyl ester (Example 76) and was obtained in 40% yield; MS (m/z): 473 (M$^+$+1); $^1$H NMR (DMSO-d$_6$) δ: 0.94 (m, 6H, 2×CH$_3$), 2.20 (m, 1H, CHMe$_2$), 4.29 (m, 1H), 3.66 (s, 3H, OCH$_3$), 7.12 (t, 2H), 7.45 (m, 2H), 7.76 (m, 2H), 7.79 (m, 1H), 8.35 (t, 1H), 8.79, 9.20 (2×s, 2H, 2×NH).

Example 97

(S)-2-[3-{3-Fluoro-4-[3-(4-fluoro-phenyl)-ureido]-phenyl}-isoxazole-5-carbonyl)-amino]-3-methyl-butyric acid The title compound was prepared from (S)-2-[3-{3-fluoro-4-[3-(4-fluoro-phenyl)-ureido]-phenyl}-isoxazole-5-carbonyl)-amino]-3-methyl-butyric acid methyl ester by using the procedure as described for the preparation of (S)-3-methyl-2-({3-[4-(3-phenyl-ureido)-phenyl]-isoxazole-5-carbonyl}-amino)-butyric acid (Example 77) and was obtained in 86% yield; ms (m/z): 459 (M$^+$+1); $^1$H NMR (DMSO-d$_6$) δ: 1.0 (m, 6H, 2×CH$_3$), 2.20 (m, 1H, CHMe$_2$), 4.30 (m, 1H), 7.15 (m, 2H), 7.46 (m, 2H), 7.72 (m, 2H), 7.79 (m, 1H), 8.34 (t, 1H), 8.81, 9.21 (2×s, 2H, 2×NH); 12.80-13.0 (br, 1H, COOH).

Example 98

2-(3-(4-(3-(2,6-Difluorophenyl)ureido)-3-methylphenyl)isoxazole-5-carboxamido)-3-methylbutanoic acid Step 1: 3-methyl-4-nitrobenzaldehyde: To a solution of (3-methyl-4-nitrophenyl)methanol (1.0 equiv.) in dichloromethane, pyridinium chlorochromate (1.1 equiv.) was added and the reaction mixture was stirred at room temperature for 3 hours. The reaction mixture was filtered through celite and the filtrate was evaporated. The residue was adsorbed on silica (100-200 mesh) and purified by flash chromatography on silica gel, eluting with 5% ethyl acetate in petroleum ether (60-80), to provide the title compound in the form of creamish crystals (93%); $^1$H NMR (300 MHz, CDCl$_3$) δ: 2.66 (s, 3H), 7.84-7.87 (m, 2H), 8.04-8.07 (d, J=8.7 Hz, 1H), 10.12 (s, 1H); IR (KBr) 3104, 3079, 2981, 2857, 2743, 1702, 1607, 1518, 1383, 1361, 1308, 1226, 1153, 1008, 832, 735 cm$^{-1}$.

Step 2: (E)-3-methyl-4-nitrobenzaldehyde oxime: To a warm solution of 3-methyl-4-nitrobenzaldehyde (1.0 equiv.) in methanol was added hydroxylamine hydrochloride (2.0 equiv.) and the mixture was stirred at 65° C. for 2 hours. Methanol was evaporated and the residue was diluted with ethyl acetate. The organic layer was washed with water, brine, dried over Na$_2$SO$_4$, filtered and concentrated in vacuo. The residue was then recrystallized from ethyl acetate and petroleum ether 60-80, to provide the title compound as a creamish solid (81%); $^1$H NMR (300 MHz, CDCl$_3$) δ: 2.62 (s, 3H), 7.54-7.56 (m, 2H), 7.89 (s, 1H), 7.98-8.01 (d, J=9.0 Hz, 1H), 8.14 (s, 1H); IR (KBr) 3375, 3207, 3087, 2994, 1607, 1585, 1506, 1384, 1319, 1161, 986, 841, 755 cm$^{-1}$.

Step 3: (Z)—N-hydroxy-3-methyl-4-nitrobenzimidoyl chloride: To a solution of (E)-3-methyl-4-nitrobenzaldehyde oxime (1.0 equiv.) in dimethylformamide, N-chlorosuccinimide (1.2 equiv.) was added in 3 portions over the period of 1 hr and the reaction mixture was stirred at r.t. for 5 hours. DMF was evaporated and the residue was diluted with EtOAc. The organic layer was washed with water, brine, dried over Na$_2$SO$_4$, filtered and concentrated in vacuo. The residue was purified by flash chromatography on silica gel, eluting with 5% ethyl acetate in petroleum ether (60-80), to provide the title compound as a creamish solid (78%); $^1$H NMR (300 MHz, DMSO-d$_6$) δ: 2.55 (s, 3H), 7.81-7.84 (d, J=8.7 Hz, 2H), 7.86 (s, 1H), 8.04-8.07 (d, J=8.4 Hz, 1H), 12.86 (s, 1H); IR (KBr) 3320, 3105, 2925, 1607, 1583, 1521, 1440, 1387, 1358, 1310, 1259, 1183, 1010, 860 cm$^{-1}$.

Step 4: Ethyl 3-(3-methyl-4-nitrophenyl)isoxazole-5-carboxylate: To a solution of (Z)—N-hydroxy-3-methyl-4-nitrobenzimidoyl chloride (1.0 equiv.), ethyl propiolate (2.0 equiv.) in toluene was dropwise added Et$_3$N over a period of 30 min. at RT and continued stirring at RT for 15 min. The reaction mixture was then heated at 80° C. for 16 hours. Reaction mass was diluted with EtOAc and neutralized with dilute HCl. The organic layer was washed with water, brine, dried over Na$_2$SO$_4$, filtered and concentrated in vacuo. The residue was purified by flash chromatography on silica gel, eluting with 100% CHCl$_3$, to provide the title compound as creamish crystals (65%); $^1$H NMR (300 MHz, DMSO-d$_6$) δ: 1.31-1.36 (t, J=7.0 Hz, 3H), 2.56 (s, 3H), 4.35-4.42 (q, 2H), 7.99-8.02 (m, 2H), 8.08 (s, 1H), 8.11 (m, 1H); IR (KBr) 3124, 3091, 2995, 2908, 1727, 1612, 1588, 1520, 1443, 1344, 1285, 1140, 1015, 950, 873, 771 cm$^{-1}$.

Step 5: Ethyl 3-(4-amino-3-methylphenyl)isoxazole-5-carboxylate: Ethyl 3-(3-methyl-4-nitrophenyl)isoxazole-5-carboxylate (1.0 equiv.), iron powder (2.0 equiv.), and ammonium chloride (3.0 equiv.) in a mixture of ethanol, tetrahydrofuran and water (4:2:1) were heated to 80° C. for 9 hours. Reaction mixture was cooled and filtered through celite. The filtrate was evaporated to dryness under vacuum and the residue was diluted with EtOAc. The organic layer was washed with water, brine, dried over Na$_2$SO$_4$, filtered and concentrated in vacuo. The residue was purified by flash chromatography on silica gel, eluting with 0-2% acetone in chloroform, to provide the title compound as a pale green solid (81%); $^1$H NMR (300 MHz, DMSO-d$_6$) δ: 1.28-1.33 (t, J=7.2 Hz, 3H), 2.07 (s, 3H), 4.31-4.38 (q, 2H), 5.38 (s, 2H), 6.62-6.65 (d, J=8.4 Hz, 1H), 7.45-7.48 (dd, J=8.1 Hz, 1.8 Hz, 1H), 7.52 (s, 1H), 7.63 (s, 1H); IR (KBr) 3490, 3381, 3135, 2975, 2905, 1725, 1628, 1606, 1471, 1417, 1381, 1279, 1134, 1027, 924, 828, 769 cm$^{-1}$.

Step 6: Ethyl 3-(4-(3-(2,6-difluorophenyl)ureido)-3-methylphenyl)isoxazole-5-carboxylate Ethyl 3-(4-amino-3-methylphenyl)isoxazole-5-carboxylate (1.0 equiv.), 2,6-difluoro phenyl isocyanate (1.2 equiv.) and tetrahydrofuran was taken in a round bottom flask and was stirred at room temperature for 48 hours. The solid precipitate was filtered and washed with minimum quantity of THF and dried in vacuo to afford the title compound as a white solid (91%); $^1$H NMR (300 MHz, DMSO-d$_6$) δ: 1.29-1.34 (t, J=7.0 Hz, 3H), 2.31 (s, 3H), 4.33-4.40 (q, 2H), 7.11-7.17 (m, 2H), 7.24-7.31 (m, 1H), 7.71-7.74 (dd, J=8.7 Hz, 1.8 Hz, 1H), 7.81 (s, 2H), 8.04-8.07 (d, J=8.7 Hz, 1H), 8.31 (s, 1H), 8.65 (s, 1H); IR (KBr) 3292, 3132, 2984, 1723, 1644, 1621, 1588, 1560 1471, 1449, 1288, 1235, 1125, 1006, 849, 768 cm$^{-1}$.

Step 7: 3-(4-(3-(2,6-Difluorophenyl)ureido)-3-methylphenyl)isoxazole-5-carboxylic acid Into a 100 ml round bottom flask was added ethyl 3-(4-(3-(2,6-difluorophenyl)ureido)-3-methylphenyl)isoxazole-5-carboxylate (1.0 equiv.), NaOH (5.0 equiv.) and 150 ml of 2:1 THF/Water. The mixture was stirred at room temperature for 15 minutes. The reaction mixture was slightly acidified to pH <7 by adding 2N HCl and then the solvent was evaporated. The solid was suspended in water and filtered, given water washings and air-dried. The resulting solid was triturated with minimum quantity of acetone and collected by filtration. This yielded the title compound as a white solid (91%) after it was dried in vacuo; mp 254-258° C. (dec.); $^1$H NMR (300 MHz; DMSO-d$_6$) δ: 2.31 (s, 3H), 7.10-7.18 (m, 2H), 7.24-7.34 (m, 1H), 7.68-7.72 (m, 2H), 7.78 (s, 1H), 8.03-8.06 (d, J=8.4 Hz, 1H), 8.31 (s, 1H), 8.65 (s, 1H); IR (KBr) 3323, 3189, 3074, 3006, 1743, 1649, 1641, 1569, 1492, 1469, 1243, 1218, 1181, 1003, 833, 733 cm$^{-1}$.

Step 8: Methyl 2-(3-(4-(3-(2,6-difluorophenyl)ureido)-3-methylphenyl) isoxazole-5-carboxamido)-3-methylbutanoate 3-(4-(3-(2,6-difluorophenyl)ureido)-3-methylphenyl) isoxazole-5-carboxylic acid (1.0 equiv.) was dissolved in 25 ml of DMF, N,N'-dicyclocarbodiimide (1.2 equiv.) and 1-hydroxybenzotriazole (1.0 equiv.) was added and stirred at room temperature for 10 min. L-valine methyl ester hydrochloride (1.5 equiv.) was neutralized with triethylamine (1.5 equiv.) in 10 ml of DMF and was added to the above mixture and the resulting reaction mixture was stirred at room temperature for 48 hours. DMF was evaporated and then diluted with EtOAc. The organic layer was washed with water, brine, dried over Na$_2$SO$_4$, filtered and concentrated in vacuo. The residue was dissolved in a chloroform and methanol mixture, adsorbed on silica (100-200 mesh) and purified by flash chromatography on silica gel, and then eluted with 0-2% methanol in chloroform to obtain a crude product.

Step 9: 2-(3-(4-(3-(2,6-Difluorophenyl)ureido)-3-methylphenyl)isoxazole-5-carboxamido)-3-methylbutanoic acid A mixture of the crude compound of step 8, LiOH (3.0 equiv.) and 50 ml of 5:1 THF/water was stirred at room temperature for 15 minutes. The reaction mixture was slightly acidified to pH <7 by adding 2N HCl and then evaporated to dryness under vacuum. The residue was dissolved in a chloroform and methanol mixture, adsorbed on silica (100-200 mesh) and purified by flash chromatography on silica gel, and then eluted with 2-15% methanol in chloroform to provide the title compound as a pale green solid after drying in vacuo; $^1$H NMR (300 MHz, DMSO-d$_6$) δ: 0.85-0.88 (d, J=6.6 Hz, 6H), 2.14-2.19 (m, 1H), 2.34 (s, 3H), 3.92-3.96 (m, 1H), 7.11-7.16 (m, 2H), 7.24-7.31 (m, 1H), 7.60 (S, 1H), 7.67-7.70 (d, J=8.7 Hz, 1H), 7.76 (s, 1H), 8.01-8.04 (m, 2H), 8.86 (s, 1H), 9.24 (s, 1H); ms (ESI) m/z 473.2 [M+H]$^+$.

Example 99

Methyl 2-(3-(4-(3-(2,6-difluorophenyl)ureido)-3-methylphenyl) isoxazole-5-carboxamido)-4-methylpentanoate The title compound was prepared using the same procedure as described for the preparation of methyl 2-(3-(4-(3-(2,6-difluorophenyl)ureido)-3-methylphenyl)isoxazole-5-carboxamido)-3-methylbutanoate (Example 98, step 8) substituting L-leucine methyl ester hydrochloride for L-valine methyl ester hydrochloride.

Example 100

2-(3-(4-(3-(2,6-Difluorophenyl)ureido)-3-methylphenyl)isoxazole-5-carboxamido)-4-methylpentanoic acid The title compound was prepared from the compound of Example 99 using the same procedure as described in step 9 of Example 98 to obtain an off-white solid after drying in vacuo; $^1$H NMR (300 MHz, DMSO-d$_6$) δ: 0.87 (s, 6H), 1.57-1.65 (m, 3H), 2.36 (s, 3H), 4.16-4.21 (m, 1H), 7.10-7.15 (m, 2H), 7.25-7.28 (m, 1H), 7.58 (s, 1H), 7.63-7.66 (d, J=8.7 Hz, 1H), 7.72 (s, 1H), 8.01-8.04 (d, J=8.4 Hz, 1H), 8.30-8.32 (d, J=6.9 Hz, 1H), 9.07 (s, 1H), 9.53 (s, 1H); ms (ESI) m/z 487.2 [M+H]$^+$.

Example 101

Methyl 2-(3-(4-(3-(2,6-difluorophenyl)ureido)-3-methylphenyl) isoxazole-5-carboxamido)propanoate To a solution of 3-(4-(3-(2,6-difluorophenyl)ureido)-3-methylphenyl)isoxazole-5-carboxylic acid (1.0 equiv.) in 50 ml of THF was added N-methylmorpholine (1.0 equiv.) at RT. The reaction mixture was then cooled to −20° C. and isobutylchloroformate (1.0 equiv.) was added and stirred at −20° C. for 5 min. L-alanine methyl ester hydrochloride (1.1 equiv.) was neutralized with Et$_3$N (1.1 equiv.) in 25 ml of THF and added to the above mixture. The mixture was stirred at −20° C. for 5 min and then gradually warmed to RT over a period of 1 hr. THF was evaporated under vacuum and the residue was triturated with EtOAc with minimum quantity of MeOH and collected by filtration. This yielded the title compound as a white solid (92%) after drying in vacuo. $^1$H NMR (300 MHz, DMSO-d$_6$) δ: 1.38-1.41 (d, J=7.2 Hz, 3H), 2.32 (s, 3H), 3.64 (s, 3H), 4.47-4.51 (t, J=7.2 Hz, 1H), 7.12-7.17 (m, 2H), 7.25-7.32 (m, 1H), 7.61 (S, 1H), 7.67-7.70 (d, J=8.4 Hz, 1H), 7.76 (s, 1H), 8.05-8.08 (d, J=8.7 Hz, 1H), 8.34 (s, 1H), 8.67 (s, 1H), 9.35-9.37 (d, J=6.9 Hz, 1H); ms (ESI) m/z 459.1 [M+H]$^+$.

Example 102

2-(3-(4-(3-(2,6-Difluorophenyl)ureido)-3-methylphenyl)isoxazole-5-carboxamido)propanoic acid A mixture of Methyl 2-(3-(4-(3-(2,6-difluorophenyl)ureido)-3-methylphenyl)isoxazole-5-carboxamido)propanoate (Example 101) (1.0 equiv.) and LiOH (3.0 equiv.) in 25 ml of 4:1 THF/water was stirred at room temperature for 15 min. The mixture was slightly acidified to pH <7 by adding 2N HCl and then the solvent was evaporated. The solid was suspended in water and filtered, given water washings and air-dried. The resulting solid was triturated with acetone and methanol and collected by filtration. This yielded the title compound as a white solid (43%) after drying in vacuo; $^1$H NMR (300 MHz, DMSO-d$_6$) δ: 1.38-1.40 (d, J=7.2 Hz, 3H), 2.32 (s, 3H), 4.38-4.43 (m, 1H), 7.12-7.18 (m, 2H), 7.27-7.32 (m, 1H), 7.60 (S, 1H), 7.67-7.70 (d, J=8.4 Hz, 1H), 7.76 (s, 1H), 8.05-8.08 (d, J=8.7 Hz, 1H), 832 (s, 1H), 8.65 (s, 1H), 9.18-9.21 (d, J=7.2 Hz, 1H), 12.76 (brs, 1H); ms (ESI) m/z 445.1 [M+H]$^+$.

Example 103

2-(3-(4-(3-(2,4-Difluorophenyl)ureido)-3-methylphenyl)isoxazole-5-carboxamido)-3-methylbutanoic acid Step 1: Ethyl 3-(4-(3-(2,4-difluorophenyl)ureido)-3-methylphenyl)isoxazole-5-carboxylate Ethyl 3-(4-amino-3-methylphenyl)isoxazole-5-carboxylate (1.0 equiv.), 2,4-difluoro phenyl isocyanate (1.2 equiv.) and tetrahydrofuran in a round-bottom flask was stirred at room temperature for 48 hours. The solid precipitate was filtered and washed with a minimum quantity of THF and dried in vacuo to afford the title compound as a white solid (75%); $^1$H NMR (300 MHz, DMSO-d$_6$) δ: 1.29-1.34 (t, J=7.0 Hz, 3H), 2.29 (s, 3H), 4.32-4.39 (q, 2H), 7.00-7.05 (m, 1H), 7.26-7.33 (m, 1H), 7.72-7.75 (d, J=8.4 Hz, 1H), 7.80 (s, 2H), 8.09-8.16 (m, 2H), 8.45 (s, 1H), 9.09 (s, 1H); IR (KBr) 3297, 3134, 2991, 1727, 1654, 1590, 1558, 1500, 1460, 1424, 1287, 1250, 1139, 1029, 841 cm$^1$.

Step 2: 3-(4-(3-(2,4-Difluorophenyl)ureido)-3-methylphenyl)isoxazole-5-carboxylic acid The title compound was prepared using ethyl 3-(4-(3-(2,4-difluorophenyl)ureido)-3-methylphenyl)isoxazole-5-carboxylate following the same procedure as described for preparation of the compound of step 7 of Example 98. The title compound was obtained as a white solid (91%) after drying in vacuo; $^1$H NMR (300 MHz, DMSO-d$_6$) δ: 2.30 (s, 3H), 7.01-7.06 (m, 1H), 7.27-7.34 (m, 1H), 7.66 (S, 1H), 7.71-7.74 (d, J=8.7 Hz, 1H), 7.78 (s, 1H), 8.08-8.17 (m, 2H), 8.48 (s, 1H), 9.11 (s, 1H); IR (KBr) 3289, 3076, 2926, 1709, 1651, 1594, 1557, 1502, 1426, 1285, 1230, 1142, 1100, 964, 851 cm$^{-1}$.

Step 3: Methyl 2-(3-(4-(3-(2,4-difluorophenyl)ureido)-3-methylphenyl) isoxazole-5-carboxamido)-3-methylbutanoate The title compound was prepared from 3-(4-(3-(2,4-difluorophenyl)ureido)-3-methylphenyl)isoxazole-5-carboxylic acid using the same procedure as described for preparation of the compound of step 8 of Example 98. The title compound was obtained in crude form.

Step 4: 2-(3-(4-(3-(2,4-Difluorophenyl)ureido)-3-methylphenyl)isoxazole-5-carboxamido)-3-methylbutanoic acid The title compound was prepared from methyl 2-(3-(4-(3-(2,4-difluorophenyl)ureido)-3-methylphenyl)isoxazole-5-carboxamido)-3-methylbutanoate using the same procedure as described for preparation of the compound of step 9 of Example 98. The compound was obtained as an off-white solid after drying in vacuo. $^1$H NMR (300 MHz, DMSO-d$_6$) δ: 0.86-0.88 (d, J=6.6 Hz, 6H), 2.12-2.18 (m, 1H), 2.33 (s, 3H), 3.95-3.99 (m, 1H), 7.00-7.05 (m, 1H), 7.25-7.33 (m, 1H), 7.62 (S, 1H), 7.68-7.71 (d, J=8.4 Hz, 1H), 7.76 (s, 1H), 7.99-8.11 (m, 3H), 8.89 (s, 1H), 9.45 (s, 1H); ms (ESI) m/z 473.2 [M+H]$^+$.

Example 104

2-(3-(4-(3-(2,4-difluorophenyl)ureido)phenyl)-1,2,4-oxadiazole-5-carboxamido)-3-methylbutanoic acid Step 1: N'-hydroxy-4-nitrobenzimidamide Potassium carbonate and hydroxylamine hydrochloride were added to an ethanolic solution of 4-nitrobenzonitrile. The solution was refluxed at 80° C. for 5 hours. After completion of the reaction the solvent was evaporated and the crude so obtained was dissolved in EtOAc and washed with water, brine, then dried by sodium sulfate and concentrated to give a solid. It was the purified by column chromatography and further recrystallized from EtOAc: petroleum ether to obtain the title product in 86.88% yield. $^1$H NMR (DMSO-d$_6$) δ: 6.071 (s, 2H, NH$_2$) 8.24 (d, 2H, CH), 8.317 (d, 2H, CH), 10.138 (S, 1H, OH), ms (m/z) 180 (M$^-$–H).

Step 2: Ethyl 3-(4-nitrophenyl)-1,2,4-oxadiazole-5-carboxylate

Ethyl oxalyl chloride in dry chloroform was added at 0° C. over a period of 45 minutes to a stirred solution of N'-hydroxy-4-nitrobenzimidamide in chloroform containing pyridine. The mixture was stirred at RT for 1 hr. and refluxed at 61° C. for 14 hours. After completion of the reaction, chloroform was added and the resulting product was successively washed with 2N HCl, water, bicarbonate solution and water. The product organic layer was then dried over sodium sulphate and evaporated to obtain a pale green colored solid. The solid was recrystallized from CHCl$_3$ petroleum ether to obtain the title product in 52.72% yield. $^1$H NMR (CDCl$_3$) δ: 1.531 (t, 3H CH$_3$), 4.633 (q, 2H, CH$_2$), 8.403 (s, 4H, CH).

Step 3: Methyl 3-methyl-2-(3-(4-nitrophenyl)-1,2,4-oxadiazole-5-carboxamido) butanoate Ethyl 3-(4-nitrophenyl)-1,2,4-oxadiazole-5-carboxylate was added to ethanol and stirred at reflux temperature to become a clear solution. To this was added a neutralized solution of L-valine methyl ester hydrochloride and triethylamine in ethanol and the resultant mixture was stirred at reflux temperature overnight. After completion of the reaction, the reaction mass was concentrated to dryness and the crude product obtained was dissolved in ethyl acetate and washed with water, brine, dried using sodium sulphate and then concentrated to give a solid. The solid was the purified by column chromatography and further re-crystallized from chloroform: Petroleum ether to obtain the title compound in 78.60% yield; $^1$H NMR (DMSO-d$_6$) δ: 1.062 (t, 6H C(CH$_3$)$_2$), 2.39 (m, 1H, CHMe$_2$), 3.82 (s, 3H, OCH$_3$), 4.79 (m, 1H, NHCH), 7.61 (d, NH), 8.4 (m, 4H), ms (m/z) 371 (M$^+$+Na).

Step 4: Methyl 2-(3-(4-aminophenyl)-1,2,4-oxadiazole-5-carboxamido)-3methylbutanoate The title compound was obtained by reduction of methyl 3-methyl-2-(3-(4-nitrophenyl)-1,2,4-oxadiazole-5-carboxamido) butanoate with iron, ammonium chloride in ethanol: THF:water in 4:2:1 ratio at 80° C. The reaction mass was refluxed for 4 hours. After completion of the reaction, the reaction mass was filtered through celite, the filtrate was concentrated and the solid material obtained was dissolved in ethyl acetate, washed with water, brine, dried by sodium sulphate and then concentrated to give a solid. The solid was then purified by column chromatography. Finally, the compound was re-crystallized from Chloroform: Pet ether and was obtained in a yield of 79.5%; $^1$H NMR (DMSO-d$_6$) δ: 0.978 (dd, 6H, C(CH$_3$)$_2$), 2.25 (m, 1H, CHMe$_2$), 3.69 (s, 3H, OCH$_3$), 4.33 (m, 1H, NHCH), 5.87 (s, NH$_2$), 6.67 (d, 2H, CH), 7.74 (d, 2H, CH) 9.60 (d, 2H, NH); ms (m/z) 319 (M$^+$+H).

Step 5: Methyl 2-(3-(4-(3-(2,4-difluorophenyl) ureido)phenyl)-1,2,4-oxadiazole-5-carboxamido)-3-methylbutanoate Methyl 2-(3-(4-aminophenyl)-1,2,4-oxadiazole-5-carboxamido)-3 methylbutanoate and 2,4-difluoro-1-isocyanatobenzene was added to THF and stirred at room temperature overnight. After completion of the reaction, the solvent was evaporated and the crude product so obtained was dissolved in ethyl acetate and washed with water, brine, dried by sodium sulfate and concentrated to give a solid. The solid was re-crystallized from Ethyl acetate: Pet ether and was obtained in a yield of 98.65%; $^1$H NMR (DMSO-d$_6$) δ: 0.970 (t, 6H C(CH$_3$)$_2$), 2.488 (m, 1H, CHMe$_2$), 3.68 (s, 3H, OCH$_3$), 4.35 (m, 1H, NHCH), 7.082 (m, 1H CH), 7.35 (m, 1H, CH), 7.67 (d, 2H, CH) 8.011 (d, 2H CH), 8.099 (m, 1H, CH), 8.96 (s, 1H, NH), 9.384 (s, 1H, NH), 9.677 (d, 1H, NH); ms (m/z) 474 (M$^+$+H).

Step 6: 2-(3-(4-(3-(2,4-difluorophenyl)ureido)phenyl)-1,2,4-oxadiazole-5-carboxamido)-3-methylbutanoic acid Methyl 2-(3-(4-(3-(2,4-difluorophenyl) ureido)phenyl)-1,2,4-oxadiazole-5-carboxamido)-3-methylbutanoate was added to THF and to this 1N lithium hydroxide was added and stirred at room temperature. After completion of the reaction the solvent was evaporated and the crude product so obtained was dissolved in ethyl acetate and washed with water, brine, dried by sodium sulphate and concentrated to give a solid. The solid was then purified by column chromatography. Yield 81.89%; $^1$H NMR (DMSO-d$_6$) δ: 0.96 (d, 6H, C(CH$_3$)$_2$), 2.20 (m, 1H, CHMe$_2$), 4.231 (m, 1H, NHCH), 7.07 (m, 1H), 7.35

(m, 1H), 7.67 (d, 2H), 8.011 (d, 2H), 8.10 (m, 1H), 8.61 (s, 1H, NH), 9.372 (s, 1H, NH), 9.39 (s, 1H, NH), 13.025 (s, 1H, COOH); MS (m/z) 458 (M⁺−1).

Example 105

2-[(3-{4-[3-(2-Fluoro-phenyl)ureido]-phenyl}-isoxazole-5-carbonyl)-amino]-3-methyl-butyric acid methyl ester Step 1: 3-{4-[3-(2-Fluoro-phenyl)ureido]-phenyl}-isoxazole-5-carboxylic acid ethyl ester Ethyl 3-(4-aminophenyl)isoxazole-5-carboxylate (4 g) was dissolved in THF (80 ml). 2-Fluorophenyl isocyanate (2.83 g) was added and stirred at RT overnight. Reaction mixture was concentrated under reduced pressure and purified by silica gel column chromatography in 1:9 EtOAc:CHCl₃ to get off white solid which was crystallized from CH₂Cl₂/Pet ether to yield 5 gm (78%) white solid. MS (ES+): m/z 370 (M+1); ¹HNMR (DMSO-d₆, 300 MHz) δ: 9.32 (s, 1H), 8.62 (s, 1H), 8.12 (m, 1H), 7.89 (d, 2H), 7.81 (s, 1H), 7.59 (d, 2H), 7.24 (m, 1H), 7.12 (m, 1H), 7.05 (m, 1H), 4.38 (q, 2H), 1.31 (t, 3H).

Step 2: 3-(4-(3-(2-fluorophenyl)ureido)phenyl)isoxazole-5-carboxylic acid

3-{4-[3-(2-Fluoro-phenyl)ureido]-phenyl}-isoxazole-5-carboxylic acid ethyl ester (4.6 g) was dissolved in THF (92 ml). 1M aqueous NaOH solution (65 ml) was added and stirred at RT for 15-20 minutes. The reaction mixture was acidified with dilute HCl and extracted with EtOAc. Organic layer was separated, dried over Na₂SO₄ and concentrated under reduced pressure to get off white solid, which was crystallized from CH₂Cl₂ to yield 3.68 g (86%) white solid. MS (ES+): m/z 342 (M+1); ¹HNMR (DMSO-d₆, 300 MHz): δ 9.33 (s, 1H), 8.63 (s, 1H), 8.13 (m, 1H), 7.89 (d, 2H), 7.7 (s, 1H), 7.6 (d, 2H), 7.23 (m, 1H), 7.13 (m, 1H), 7.02 (m, 1H).

Step 3: 2-[(3-{4-[3-(2-Fluoro-phenyl)ureido]-phenyl}-isoxazole-5-carbonyl)-amino]-3-methyl-butyric acid methyl ester 3-(4-(3-(2-fluorophenyl)ureido)phenyl)isoxazole-5-carboxylic acid (1 g) was dissolved in DMF (20 ml). N,N'-Dicyclohexyl carbodiimide (906 mg) and 1-Hydroxy benzotriazole (396 mg) were added and the reaction mixture was stirred at RT for 15 minutes. L-Valine methyl ester hydrochloride (640 mg) was dissolved in DMF (5 ml), neutralized with TEA (0.53 ml) and added into the above reaction mixture, which was then stirred at RT for 16 h. DMF was removed under reduced pressure to get a pale brown solid which was taken in water and extracted with EtOAc. Organic layer was dried over Na₂SO₄ and concentrated to get a pale yellow solid which was purified by silica gel column chromatography in 2:8 EtOAc:CHCl₃ to get off white solid which was crystallized from DCM/Pet ether to yield 1.1 gm (82%) white solid. ¹HNMR (DMSO-d₆, 300 MHz): δ 9.33 (s, 1H), 9.18 (d, 1H), 8.62 (s, 1H), 8.13 (m, 1H), 7.85 (d, 2H), 7.67 (s, 1H), 7.59 (d, 2H), 7.24 (m, 1H), 7.16 (m, 1H), 7.02 (m, 1H), 4.29 (m, 2H), 3.66 (s, 3H), 2.2 (m, 1H), 0.95 (d, 6H); MS (ES+): m/z 455 (M+1).

Example 106

2-(3-(4-(3-(2-Fluorophenyl)ureido)phenyl)isoxazole-5-carboxamido)-3-methylbutanoic acid 2-[(3-{4-[3-(2-Fluoro-phenyl)ureido]-phenyl}-isoxazole-5-carbonyl)-amino]-3-methyl-butyric acid methyl ester (800 mg) was dissolved in THF (20 ml). 1M aqueous LiOH solution (3.52 ml) was added and stirred at RT for 14 h. The reaction mixture was acidified with dilute HCl and extracted with EtOAc. Organic layer was separated, dried over Na₂SO₄ and concentrated under reduced pressure to get off white solid which was crystallized from EtOAc to yield 490 mg (63%) white solid. MS (ES+): m/z 441 (M+1); ¹HNMR (DMSO-d₆, 300 MHz): δ 12.83 (bs, 1H), 9.34 (s, 1H), 8.95 (d, 1H), 8.63 (s, 1H), 8.13 (m, 1H), 7.85 (d, 2H), 7.68 (s, 1H), 7.62 (d, 2H), 7.24 (m, 1H), 7.14 (m, 1H), 7.02 (m, 1H), 4.26 (m, 1H), 2.21 (m, 1H), 0.95 (dd, 6H).

Example 107

Methyl 2-(3-(4-(3-benzylureido)phenyl)isoxazole-5-carboxamido)-3-methylbutanoate The title compound was prepared according to the procedure as set forth in example 76, except that benzyl isocyanate was used in place of phenyl isocyanate to yield 67% of title compound. MS (ES+): m/z 451 (M+1); ¹HNMR (DMSO-d₆, 300 MHz) δ 9.16 (d, 1H), 8.85 (s, 1H), 7.77 (d, 2H), 7.63 (s, 1H), 7.55 (d, 2H), 7.19-7.34 (m, 5H), 6.73 (t, 1H), 4.29 (d, 2H), 4.25 (m, 1H), 3.64 (s, 3H), 2.19 (m, 1H), 0.92 (d, 6H).

Example 108

2-(3-(4-(3-Benzylureido)phenyl)isoxazole-5-carboxamido)-3-methylbutanoic acid

The title compound was prepared from methyl 2-(3-(4-(3-benzylureido)phenyl)isoxazole-5-carboxamido)-3-methylbutanoate as set forth in example 8 and was obtained in 44% yield. MS (ES+): m/z 437 (M+1); ¹HNMR (DMSO-d₆, 300 MHz): δ 12.82 (bs, 1H), 8.93 (d, 1H), 8.86 (s, 1H), 7.77 (d, 2H), 7.64 (s, 1H), 7.56 (d, 2H), 7.19-7.34 (m, 5H), 6.72 (t, 1H), 4.29 (d, 2H), 4.25 (m, 1H), 2.19 (m, 1H), 0.93 (d, 6H).

Example 109

Methyl 2-(3-(4-(3-benzylureido)phenyl)isoxazole-5-carboxamido)-4-methylpentanoate The title compound was prepared according to the procedure as set forth in example 76, except that benzyl isocyanate was used in place of phenyl isocyanate to yield 76% of title compound. MS (ES+): m/z 465 (M+1); ¹HNMR (DMSO-d₆, 300 MHz): δ 9.31 (d, 1H), 8.85 (s, 1H), 7.78 (d, 2H), 7.57 (s, 1H), 7.55 (d, 2H), 7.2-7.34 (m, 5H), 6.71 (t, 1H), 4.48 (m, 1H), 4.29 (d, 2H), 3.63 (s, 3H), 1.78 (m, 1H), 1.63 (m, 2H), 0.88 (d, 6H).

Example 110

2-(3-(4-(3-Benzylureido)phenyl)isoxazole-5-carboxamido)-4-methyl pentanoic acid

The title compound was prepared from Methyl 2-(3-(4-(3-benzylureido)phenyl)isoxazole-5-carboxamido)-4-methylpentanoate as set forth in example 8 and was obtained in 59% yield. MS (ES+): m/z 451 (M+1); ¹HNMR (DMSO-d₆, 300 MHz): δ 12.76 (bs, 1H), 9.16 (d, 1H), 8.86 (s, 1H), 7.77 (d, 2H), 7.57 (s, 1H), 7.55 (d, 2H), 7.19-7.34 (m. 5H), 6.71 (t, 1H), 4.38 (m, 1H), 4.29 (d, 2H), 1.76 (m, 1H), 1.63 (m, 2H), 0.88 (d, 6H).

Example 111

Methyl 2-(3-(4-(3-(2,4-difluorophenyl)ureido)phenyl)isoxazole-5-carboxamido)-3-methylbutanoate The title compound was prepared according to the procedure as set forth in example 76, except that 2,4 difluorophenyl isocyanate was used in place of phenyl isocyanate to yield 62% of title compound. MS (ES+): m/z 473 (M+1); $^1$HNMR (DMSO-$d_6$, 300 MHz): δ 9.27 (s, 1H), 9.17 (d, 1H), 8.56 (s, 8.04 (m, 1H), 7.84 (d, 2H), 7.66 (s, 1H), 7.6 (d, 2H), 7.30 (m, 1H), 7.03 (m, 1H), 4.28 (m, 1H), 3.65 (s, 3H), 2.19 (m, 1H), 0.94 (d, 6H).

Example 112

2-(3-(4-(3-(2,4-Difluorophenyl)ureido)phenyl)isoxazole-5-carboxamido)-3-methylbutanoic acid The title compound was prepared from methyl 2-(3-(4-(3-(2,4-difluorophenyl)ureido) phenyl)isoxazole-5-carboxamido)-3-methylbutanoate as set forth in example 8 and was obtained in 44% yield. MS (ES+): m/z 459 (M+1); $^1$HNMR (DMSO-$d_6$, 300 MHz): δ 12.8 (bs, 1H), 9.27 (s, 1H), 8.94 (d, 1H), 8.57 (s, 1H), 8.04 (m, 1H), 7.83 (d, 2H), 7.67 (s, 1H), 7.57 (d, 2H), 7.13 (m, 1H), 7.04 (m, 1H), 4.25 (m, 1H), 2.17 (m, 1H), 0.93 (dd, 6H).

Example 113

Methyl 2-(3-(4-(3-(2,4-difluorophenyl)ureido)phenyl)isoxazole-5-carboxamido)-4-methylpentanoate The title compound was prepared according to the procedure as set forth in example 76, except that 2,4 difluorophenyl isocyanate was used in place of phenyl isocyanate to yield 63% of title compound. MS (ES+): m/z 487 (M+1); $^1$HNMR (DMSO-$d_6$, 300 MHz): δ 9.33 (d, 1H), 9.27 (s, 1H), 8.57 (s, 1H), 8.06 (m, 1H), 7.84 (d, 2H), 7.65 (s, 1H), 7.6 (d, 2H), 7.29 (m, 1H), 7.03 (m, 1H), 4.47 (m, 1H), 3.63 (s, 3H), 1.79 (m, 1H), 1.6 (m, 2H), 0.88 (d, 6H).

Example 114

2-(3-(4-(3-(2,4-Difluorophenyl)ureido)phenyl)isoxazole-5-carboxamido)-4-methylpentanoic acid The title compound was prepared from methyl 2-(3-(4-(3-(2,4-difluorophenyl)ureido) phenyl)isoxazole-5-carboxamido)-4-methylpentanoate as set forth in example 8 and was obtained in 74% yield. MS (ES+): m/z 473 (M+1); $^1$HNMR (DMSO-$d_6$, 300 MHz): 12.78 (bs, 1H), 9.29 (s, 1H), 9.19 (d, 1H), 8.58 (s, 1H), 8.05 (m, 1H), 7.85 (d, 2H), 7.61 (s, 1H), 7.58 (d, 2H), 7.31 (m, 1H), 7.05 (m, 1H), 4.4 (m, 1H), 1.78 (m, 1H), 1.6 (m, 2H), 0.87 (d, 6H).

Example 115

Methyl 2-(3-(4-(3-(4-fluorophenyl)ureido)phenyl)isoxazole-5-carboxamido)propanoate The title compound was prepared according to the procedure as set forth in example 76, except that 4-fluoro phenylisocyanate was used in place of phenyl isocyanate to yield 94% of title compound. MS (ES+): m/z–427 (M+1); $^1$HNMR (DMSO-$d_6$, 300 MHz): δ 9.37 (d, 1H), 8.97 (s, 1H), 8.8 (s, 1H), 7.84 (d, 2H), 7.61 (s, 1H), 7.6 (d, 2H), 7.46 (m, 2H), 7.11 (m, 2H), 4.49 (m, 1H), 3.64 (s, 3H), 1.41 (d, 3H).

Example 116

2-(3-(4-(3-(4-fluorophenyl)ureido)phenyl)isoxazole-5-carboxamido) propanoic acid The title compound was prepared from methyl 2-(3-(4-(3-(4-fluorophenyl)ureido) phenyl)isoxazole-5-carboxamido) propanoate as set forth in Example 8 and was obtained in 57% yield. MS (ES+): m/z 413 (M+1); $^1$HNMR (DMSO-$d_6$, 300 MHz): δ 12.74 (bs, 1H), 9.22 (d, 1H), 8.96 (s, 1H), 8.8 (s, 1H), 7.84 (d, 2H), 7.6 (s, 1H), 7.58 (d, 2H), 7.47 (m, 2H), 7.12 (m, 2H), 4.4 (m, 1H), 1.4 (d, 3H).

Example 117

Methyl 2-(3-(4-(3-(4-fluorophenyl)ureido)phenyl)isoxazole-5-carboxamido)-2-methylpropanoate The title compound was prepared according to the procedure as set forth in example 76, except that 4-fluoro phenyl isocynate was used in place of phenyl isocyanate to yield 76% of title compound. MS (ES+): m/z 441 (M+1); $^1$HNMR (DMSO-$d_6$, 300 MHz): δ 9.21 (s, 1H), 8.95 (s, 1H), 8.79 (s, 1H), 7.83 (d, 2H), 7.6 (d, 2H), 7.58 (s, 1H), 7.46 (m, 2H), 7.11 (m, 2H), 3.59 (s, 3H), 1.46 (s, 6H).

Example 118

2-(3-(4-(3-(4-fluorophenyl)ureido)phenyl)isoxazole-5-carboxamido)-2-methylpropanoic acid The title compound was prepared from methyl 2-(3-(4-(3-(4-fluorophenyl)ureido)phenyl)isoxazole-5-carboxamido)-2-methylpropanoate as set forth in example 8 and was obtained in 80% yield. MS (ES+): m/z 427 (M+1); $^1$HNMR (DMSO-$d_6$, 300 MHz): δ 12.47 (bs, 1H), 8.97 (s, 1H), 8.96 (s, 1H), 8.79 (s, 1H), 7.82 (d, 2H), 7.6 (d, 2H), 7.56 (s, 1H), 7.45 (m, 2H), 7.1 (m, 2H), 1.45 (s, 6H).

Example 119

Methyl 1-(3-(4-(3-(4-fluorophenyl)ureido)phenyl)isoxazole-5-carboxamido)cyclopentanecarboxylate The title compound was prepared according to the procedure as set forth in example 76, except that 4-fluoro phenyl isocynate was used in place of phenyl isocyanate to yield 55% of title compound. MS (ES+): m/z 465 (M−1); $^1$HNMR (DMSO-$d_6$, 300 MHz): δ 9.26 (s, 1H), 8.96 (s, 1H), 8.79 (s, 1H), 7.83 (d, 2H), 7.6 (d, 2H), 7.58 (s, 1H), 7.47 (m, 2H), 7.12 (m, 2H), 3.59 (s, 3H), 2.11 (m, 4H), 1.7 (m, 4H).

Example 120

1-(3-(4-(3-(4-fluorophenyl)ureido)phenyl)isoxazole-5-carboxamido) cyclopentanecarboxylic acid The title compound was prepared from methyl 1-(3-(4-(3-(4-fluorophenyl)ureido) phenyl)isoxazole-5-carboxamido) cyclopentanecarboxylate as set forth in example 8 and was obtained in 53% yield. MS (ES+): m/z 453 (M+1); $^1$HNMR (DMSO-$d_6$, 300 MHz): δ 12.41 (bs, 1H), 9.05 (s, 1H), 8.95 (s, 1H), 8.79 (s, 1H), 7.83 (d, 2H), 7.6 (s, 1H), 7.58 (d, 2H), 7.46 (m, 2H), 7.11 (m, 2H), 2.11 (m, 4H), 1.69 (m, 4H).

Example 121

Methyl 2-methyl-2-(3-(4-(3-phenylureido)phenyl) isoxazole-5-carboxamido)propanoate The title compound was prepared according to the procedure as set forth in example 76, except that methy 2-amino-2-methylpropanoate was used in place of (S)-methyl 2-amino-3-methylbutanoate to yield 60% of the title compound. MS (ES+): m/z 423 (M+1); $^1$HNMR (DMSO-d$_6$, 300 MHz): δ 9.22 (s, 1H), 8.98 (s, 1H), 8.78 (s, 1H), 7.83 (d, 2H), 7.61 (d, 2H), 7.59 (s, 1H), 7.46 (m, 2H), 7.27 (m, 2H), 6.97 (m, 1H), 3.59 (s, 3H), 1.46 (s, 6H).

Example 122

2-methyl-2-(3-(4-(3-phenylureido)phenyl)isoxazole-5-carboxamido) propanoic acid

The title compound was prepared from methyl 2-methyl-2-(3-(4-(3-phenylureido) phenyl)isoxazole-5-carboxamido) propanoate as set forth in example 8 and was obtained in 63% yield. MS (ES+): m/z 408 (M+1); $^1$HNMR (DMSO-d$_6$, 300 MHz): δ 12.49 (bs, 1H), 8.99 (s, 1H), 8.98 (s, 1H), 8.78 (s, 1H), 7.85 (d, 2H), 7.63 (d, 2H), 7.59 (s, 1H), 7.48 (m, 2H), 7.29 (m, 2H), 6.99 (m, 1H), 1.48 (s, 6H).

Example 123

Methyl 2-(3-(4-(3-(2,6-difluorophenyl)ureido)phenyl)isoxazole-5-carboxamido)-3-methylbutanoate The title compound was prepared according to the procedure as set forth in example 76, except that 2,6 difluorophenyl isocyanate was used in place of phenyl isocyanate to yield 80% of title compound. MS (ES+): m/z 473 (M+1); $^1$HNMR (DMSO-d$_6$, 300 MHz): δ 9.24 (s, 1H), 9.18 (d, 1H), 8.21 (s, 1H), 7.83 (d, 2H), 7.66 (s, 1H), 7.61 (d, 2H), 7.31 (m, 1H), 7.15 (m, 2H), 4.29 (m, 1H), 3.66 (s, 3H), 2.2 (m, 1H), 0.95 (d, 6H).

Example 124

2-(3-(4-(3-(2,6-difluorophenyl)ureido)phenyl)isoxazole-5-carboxamido)-3-methylbutanoic acid The title compound was prepared from methyl 2-(3-(4-(3-(2,6-difluorophenyl)ureido) phenyl)isoxazole-5-carboxamido)-3-methylbutanoate as set forth in example 8 and was obtained in 80% yield. MS (ES+): m/z 459 (M+1); $^1$HNMR (DMSO-d$_6$, 300 MHz): δ 12.83 (bs, 1H), 9.24 (s, 1H), 8.94 (d, 1H), 8.22 (s, 1H), 7.83 (d, 2H), 7.67 (s, 1H), 7.61 (d, 2H), 7.31 (m, 1H), 7.15 (m, 2H), 4.26 (m, 1H), 2.2 (m, 1H), 0.94 (d, 6H).

Example 125

Methyl 3-methyl-2-(3-(4-(3-p-tolylureido)phenyl) isoxazole-5-carboxamido)butanoate The title compound was prepared according to the procedure as set forth in example 76, except that 4-methylphenyl isocyanate was used in place of phenyl isocyanate to yield 63% of title compound. MS (ES+): m/z 451 (M+1); $^1$HNMR (DMSO-d$_6$, 300 MHz): δ 9.18 (d, 1H), 8.9 (s, 1H), 8.63 (s, 1H), 7.83 (d, 2H), 7.66 (s, 1H), 7.61 (d, 2H), 7.35 (d, 2H), 7.09 (d, 2H), 4.29 (m, 1H), 3.66 (s, 3H), 2.2 (s, 3H), 2.16 (m, 1H), 0.93 (d, 6H).

Example 126

3-Methyl-2-(3-(4-(3-p-tolylureido)phenyl)isoxazole-5-carboxamido) butanoic acid

The title compound was prepared from 3-methyl-2-(3-(4-(3-p-tolylureido)phenyl) isoxazole-5-carboxamido) butanoic acid as set forth in example 8 and was obtained in 66% yield. MS (ES+): m/z 437 (M+1); $^1$HNMR (DMSO-d$_6$, 300 MHz): δ 12.8 (bs, 1H), 8.95 (d, 1H), 8.9 (s, 1H), 8.64 (s, 1H), 7.83 (d, 2H), 7.68 (s, 1H), 7.61 (d, 2H), 7.35 (d, 2H), 7.09 (d, 2H), 4.27 (m, 1H), 2.23 (s, 3H), 2.16 (m, 1H), 0.93 (dd, 6H).

Example 127

Methyl 2-(3-(4-(3-(4-methoxyphenyl)ureido)phenyl) isoxazole-5-carboxamido)-3-methylbutanoate The title compound was prepared according to the procedure as set forth in example 76, except that 4-methoxyphenyl isocyanate was used in place of phenyl isocyanate to yield 59% of title compound. MS (ES+): m/z 467 (M+1); $^1$HNMR (DMSO-d$_6$, 300 MHz): δ 9.17 (d, 1H), 8.87 (s, 1H), 8.55 (s, 1H), 7.82 (d, 2H), 7.68 (s, 1H), 7.6 (d, 2H), 7.36 (d, 2H), 6.87 (d, 2H), 4.29 (m, 1H), 3.7 (s, 3H), 3.66 (s, 3H), 2.18 (m, 1H), 0.91 (d, 6H).

Example 128

2-(3-(4-(3-(4-Methoxyphenyl)ureido)phenyl)isoxazole-5-carboxamido)-3-methylbutanoic acid The title compound was prepared from methyl 2-(3-(4-(3-(4-methoxyphenyl)ureido) phenyl)isoxazole-5-carboxamido)-3-methylbutanoate as set forth in example 8 and was obtained in 52% yield. MS (ES+): m/z 453 (M+1); $^1$HNMR (DMSO-d$_6$, 300 MHz): δ 12.61 (bs, 1H), 9.0 (s, 1H), 8.92 (d, 1H), 8.68 (s, 1H), 7.82 (d, 2H), 7.67 (s, 1H), 7.61 (d, 2H), 7.37 (d, 2H), 6.87 (d, 2H), 4.26 (m, 1H), 3.7 (s, 3H), 2.18 (m, 1H), 0.95 (dd, 6H).

Example 129

(S)-methyl 2-(3-(4-(3-(3,4-difluorophenyl)ureido) phenyl)isoxazole-5-carboxamido)-3-methylbutanoate The title compound was prepared according to the procedure as set forth in example 76, except that 1,2-difluoro-4-isocyanatobenzene was used in place of phenyl isocyanate to yield 66% of the title compound. MS: ES (−): m/z 471 (M−1); ES (+): m/z 473 (M+1); $^1$HNMR (DMSO-d$_6$, 300 MHz) δ: 9.208 (d, 1H), 9.055 (s, 1H), 8.993 (s, 1H), 7.864 (d, 2H), 7.720 (m, 2H), 7.638 (d, 2H), 7.410 (m, 1H), 7.164 (m, 1H), 4.340 (m, 1H), 3.681 (s, 3H), 2.248 (m, 1H), 0.993 (d, 3H), 0.955 (d, 3H).

Example 130

(S)-2-(3-(4-(3-(3,4-difluorophenyl)ureido)phenyl) isoxazole-5-carboxamido)-3-methylbutanoic acid The title compound was prepared from (S)-methyl 2-(3-(4-(3-(3,4-difluorophenyl)ureido)phenyl)isoxazole-5-carboxamido)-3-methylbutanoate as set forth in example 8 and was obtained in 38% yield. MS: ES (−): m/z 457 (M−1); ES (+): m/z 459 (M+1); $^1$HNMR (DMSO-d$_6$, 300 MHz) δ: 12.861 (s, 1H), 9.087 (s, 1H), 9.027 (s, 1H), 8.964 (d, 1H), 7.864 (d, 2H), 7.723 (m, 2H), 7.638 (d, 2H), 7.412 (m, 1H), 7.167 (m, 1H), 4.309 (m, 1H), 2.274 (m, 1H), 2.229 (d, 3H), 2.184 (d, 3H).

Example 131

Methyl 2-(3-(5-(3-(4-fluorophenyl)ureido)-2-methylphenyl)isoxazole-5-carboxamido)-4-methylpentanoate The title compound was prepared according to the procedure as set forth in example 76, except that 1-fluoro-4-isocyanatobenzene was used in place of phenyl isocyanate and L-leucine methyl ester was used in place of L-valine methyl ester to yield 79% of the title compound. MS (ESI) m/z 483.2 [M+H]$^+$; $^1$H NMR (DMSO-d$_6$, 300 MHz): δ 9.37 (d, 1H), 8.75 (d, 2H), 7.76 (d, 1H), 7.46 (m, 4H), 7.39 (d, 1H), 7.28 (d, 1H), 7.31 (t, 2H), 4.51 (m, 1H), 3.65 (S, 3H), 2.35 (s, 3H), 1.82 (m, 1H), 1.66 (m, 2H), 0.92 (dd, 6H).

Example 132

2-(3-(5-(3-(4-fluorophenyl)ureido)-2-methylphenyl) isoxazole-5-carboxamido)-4-methylpentanoic acid The title compound was prepared from methyl 2-(3-(5-(3-(4-fluorophenyl)ureido)-2-methylphenyl)isoxazole-5-carboxamido)-4-methylpentanoate as set forth in example 8 and was obtained in 84% yield. MS (ESI) m/z 469.2 [M+H]$^+$; $^1$H NMR (DMSO-d$_6$, 300 MHz): δ 12.80 (bs, 1H), 9.22 (d, 1H), 8.76 (d, 2H), 7.77 (d, 1H), 7.47 (m, 4H), 7.39 (d, 1H), 7.28 (d, 1H), 7.12 (t, 2H), 4.46 (m, 1H), 2.36 (s, 3H), 1.81 (m, 1H), 1.69 (m, 2H), 0.92 (dd, 6H).

Example 133

Methyl 2-(3-(4-(3-(4-fluorophenyl)ureido)-2-methylphenyl)isoxazole-5-carboxamido)-3-methylbutanoate The title compound was prepared according to the procedure as set forth in example 76, except that 1-fluoro-4-isocyanatobenzene was used in place of phenyl isocyanate to yield 81% of the title compound. MS (ESI) m/z 467.2. [M−H]$^+$; $^1$H NMR (DMSO-d$_6$, 300 MHz): δ 9.16 (d, 1H), 8.83 (s, 1H), 8.75 (s, 1H), 7.53 (d, 2H), 7.47 (m, 4H), 7.13 (t, 2H), 4.32 (t, 1H), 3.65 (S, 3H), 2.42 (s, 3H), 2.19 (m, 1H), 0.96 (dd, 6H).

Example 134

2-(3-(4-(3-(4-fluorophenyl)ureido)-2-methylphenyl) isoxazole-5-carboxamido)-3-methylbutanoic acid The title compound was prepared from methyl 2-(3-(4-(3-(4-fluorophenyl)ureido)-2-methylphenyl)isoxazole-5-carboxamido)-3-methylbutanoate as set forth in example 8 and was obtained in 91% yield. MS (ESI) m/z 455.2 [M+H]$^+$; $^1$HNMR (DMSO-d$_6$, 300 MHz): δ 9.16 (s, 1H), 9.07 (s, 1H), 8.85 (d, 1H), 7.53 (s, 2H), 7.50 (m, 5H), 7.12 (t, 2H), 4.28 (t, 1H), 2.42 (s, 3H), 2.20 (m, 1H), 0.96 (dd, 6H).

Example 135

Methyl 2-(3-(4-(3-(2-fluorophenyl)ureido)-2-methylphenyl)isoxazole-5-carboxamido)-3-methylbutanoate The title compound was prepared according to the procedure as set forth in example 76, except that 1-fluoro-2-isocyanatobenzene was used in place of phenyl isocyanate and ethyl 3-(4-amino-2-methylphenyl)isoxazole-5-carboxylate was used in place of ethyl 3-(4-aminophenyl)isoxazole-5-carboxylate to yield 63% of the title compound. MS (ESI): m/z 469.2 (M+H)$^+$; $^1$HNMR (DMSO-d$_6$, 300 MHz): δ 9.24 (s, 1H), 9.18 (d, 1H), 8.62 (d, 1H), 8.16 (dt, 1H), 7.56 (d, 2H), 7.47 (d, 2H), 7.27 (m, 1H), 7.16 (t, 1H), 7.02 (m, 1H), 4.33 (t, 1H), 3.66 (s, 3H), 2.45 (s, 3H), 2.20 (m, 1H), 0.97 (dd, 6H).

Example 136

2-(3-(4-(3-(2-Fluorophenyl)ureido)-2-methylphenyl) isoxazole-5-carboxamido)-3-methylbutanoic acid The title compound was prepared from methyl 2-(3-(4-(3-(2-fluorophenyl)ureido)-2-methylphenyl)isoxazole-5-carboxamido)-3-methylbutanoate as set forth in example 8 and was obtained in 68% yield. MS (ESI): m/z 453.2 (M−H)$^+$; $^1$HNMR (DMSO-d$_6$, 300 MHz): δ 12.8 (bs, 1H), 9.27 (s, 1H), 8.95 (d, 1H), 8.64 (d, 1H), 8.16 (dt, 1H), 7.56 (t, 2H), 7.47 (d, 2H), 7.26 (m, 1H), 7.15 (t, 1H), 7.04 (m, 1H), 4.30 (t, 1H), 2.45 (s, 3H), 2.25 (m, 1H), 0.97 (dd, 6H).

Example 137

Methyl 2-(3-(4-(3-(2,4-difluorophenyl)ureido)-2-methylphenyl) isoxazole-5-carboxamido)-3-methylbutanoate The title compound was prepared according to the procedure as set forth in example 135, except that 2,4-difluoro-1-isocyanatobenzene was used in place of phenyl isocyanate to yield 65% of the title compound. MS (ESI) m/z 487.1 [M+H]$^+$; $^1$H NMR (DMSO-d$_6$, 300 MHz): δ 9.19 (d, 1H), 9.15 (s, 1H), 8.57 (s, 1H), 8.10 (m, 1H), 7.55 (d, 1H), 7.53 (s, 1H), 7.46 (d, 2H), 7.35 (m, 1H), 7.07 (t, 1H), 4.33 (t, 1H), 3.65 (s, 3H), 2.44 (s, 3H), 2.24 (m, 1H), 0.97 (dd, 6H).

Example 138

2-(3-(4-(3-(2,4-difluorophenyl)ureido)-2-methylphenyl)isoxazole-5-carboxamido)-3-methylbutanoic acid The title compound was prepared from methyl 2-(3-(4-(3-(2,4-difluorophenyl)ureido)-2-methylphenyl)isoxazole-5-carboxamido)-3-methylbutanoate as set forth in example 8 and was obtained in 90% yield. MS (ESI) m/z 473.1 [M+H]$^+$; $^1$H NMR (DMSO-d$_6$, 300 MHz): δ 9.25 (s, 1H), 8.90 (d, 1H), 8.63 (s, 1H), 8.07 (m, 1H), 7.55 (t, 2H), 7.46 (d, 2H), 7.34 (m, 1H), 7.04 (m, 1H), 4.28(t, 1H), 2.44 (s, 3H), 2.20 (m, 1H), 0.96 (dd, 6H).

Example 139

Methyl 2-(3-(4-(3-(2,4-difluorophenyl)ureido)-2-methylphenyl) isoxazole-5-carboxamido)-4-methylpentanoate The title compound was prepared according to the procedure as set forth in example 135, except that 2,4-difluoro-1- isocyanatobenzene was used in place of phenyl isocyanate and L-leucine methyl ester was used in place of L-valine methyl ester to yield 85% of the title compound. MS (ESI) m/z 501.2 [M+H]$^+$; $^1$H NMR (DMSO-d$_6$, 300 MHz): δ 9.33 (d, 1H), 9.20 (s, 1H), 8.58 (s, 1H), 8.11 (m, 1H), 7.57 (d, 1H), 7.48 (s, 1H), 7.45 (d, 2H), 7.34 (t, 1H), 7.07 (t, 1H), 4.52 (s, 1H), 3.67 (s, 3H), 2.46 (s, 3H), 1.84 (m, 1H), 1.68 (m, 2H), 0.94 (dd, 6H).

Example 140

2-(3-(4-(3-(2,4-difluorophenyl)ureido)-2-methylphenyl)isoxazole-5-carboxamido)-4-methylpentanoic acid The title compound was prepared from methyl 2-(3-(4-(3-(2,4-difluorophenyl)ureido)-2-methylphenyl)isoxazole-5-carboxamido)-4-methylpentanoate as set forth in example 8 and was obtained in 87% yield. MS (ESI) m/z 487.2 [M+H]$^+$; $^1$HNMR (DMSO-d$_6$, 300 MHz): δ 12.79 (bs, 1H), 9.27 (s, 1H), 9.14 (d, 1H), 8.64 (s, 1H), 8.08 (m, 1H), 7.56 (d, 1H), 7.47 (d, 3H), 7.33 (t, 1H), 7.05 (t, 1H), 4.43 (s, 1H), 2.50 (s, 3H), 1.79 (m, 1H), 1.69 (m, 2H), 0.93 (dd, 6H).

Example 141

(S)-Methyl 2-(3-(4-(3-(2,4-difluorophenyl)ureido)-2-fluorophenyl) isoxazole-5-carboxamido)-3-methylbutanoate The title compound was prepared according to the procedure as set forth in example 76, except that 2,4-difluoro-1-isocyanatobenzene was used in place of phenyl isocyanate and ethyl 3-(4-amino-2-fluorophenyl)isoxazole-5-carboxylate was used in place of ethyl 3-(4-aminophenyl)isoxazole-5-carboxylate to yield 77% of the title compound. MS (ESI) m/z: 491(M+H)$^+$; $^1$HNMR (DMSO-d$_6$, 300 MHz): δ 9.496 (s, 1H), 9.250 (d, 1H), 8.655 (s, 1H), 8.071 (dd, 1H), 7.892 (t, 1H), 7.733 (d, 1H), 7.627 (d, 1H), 7.357 (m, 1H), 7.255 (d, 1H), 7.087 (t, 1H), 4.340 (t, 1H), 3.667 (s, 3H), 2.243 (m, 1H), 1.037 (dd, 6H).

Example 142

(S)-2-(3-(4-(3-(2,4-difluorophenyl)ureido)-2-fluorophenyl)isoxazole-5-carboxamido)-3-methylbutanoic acid The title compound was prepared from (S)-methyl 2-(3-(4-(3-(2,4-difluorophenyl)ureido)-2-fluorophenyl)isoxazole-5-carboxamido)-3-methylbutanoate as set forth in example 8 and was obtained in 58% yield. MS (ESI) m/z: 475(M−H)$^−$; $^1$HNMR (DMSO-d$_6$; 300 MHz): δ 12.855 (s, 1H), 9.527 (s, 1H), 9.046 (d, 1H), 8.669 (s, 1H), 8.065 (m, 1H), 7.891 (t, 1H), 7.734 (dd, 1H), 7.644 (d, 1H), 7.357 (m, 1H), 7.290 (d, 1H), 7.226 (t, 1H), 4.307 (t, 1H), 2.246 (m, 1H), 0.969 (dd, 6H).

Example 143

(S)-methyl 2-(3-(2-fluoro-4-(3-(2-fluorophenyl)ureido)phenyl) isoxazole-5-carboxamido)-3-methylbutanoate The title compound was prepared according to the procedure as set forth in example 141, except that 1-fluoro-2-isocyanatobenzene was used in place of phenyl isocyanate to yield 69% of the title compound. MS (ESI) m/z: 473(M+H)$^+$; $^1$HNMR (DMSO-d$_6$, 300 MHz): δ 9.542 (s, 1H), 9.247 (d, 1H), 8.698 (s, 1H), 8.135 (t, 1H), 7.896 (t, 1H), 7.751 (d, 1H), 7.630 (d, 1H), 7.273 (m, 2H), 7.174 (d, 1H), 7.069 (t, 1H), 4.340 (t, 1H), 3.666 (s, 3H), 2.220 (m, 1H), 0.972 (dd, 6H).

Example 144

(S)-2-(3-(2-Fluoro-4-(3-(2-fluorophenyl)ureido)phenyl)isoxazole-5-carboxamido)-3-methylbutanoic acid The title compound was prepared from (S)-methyl 2-(3-(2-fluoro-4-(3-(2-fluorophenyl)ureido)phenyl)isoxazole-5-carboxamido)-3-methylbutanoate as set forth in example 8 and was obtained in 61% yield. MS (ESI) m/z: 459(M+H)$^+$; $^1$HNMR (DMSO-d$_6$, 300 MHz): δ 12.849 (s, 1H), 9.542 (s, 1H), 9.047 (d, 1H), 8.700 (s, 1H), 8.131 (t, 1H), 7.896 (t, 1H), 7.750 (d, 1H), 7.648 (d, 1H), 7.273 (m, 2H), 7.174 (t, 1H), 7.068 (m, 1H), 4.312 (t, 1H), 2.248 (m, 1H), 0.972 (dd, 6H).

Example 145

(S)-Methyl 2-(3-(2-fluoro-4-(3-(4-fluorophenyl)ureido)phenyl) isoxazole-5-carboxamido)-3-methylbutanoate The title compound was prepared according to the procedure as set forth in example 141, except that 1-fluoro-4-isocyanatobenzene was used in place of phenyl isocyanate to yield 59% of the title compound. MS (ESI) m/z: 473(M+H)$^+$; $^1$HNMR (DMSO-d$_6$, 300 MHz): δ 9.239 (d, 1H), 9.192 (s, 1H), 8.874 (s, 1H), 7.878 (t, 1H), 7.725 (t, 1H), 7.621 (d, 1H), 7.490 (dd, 2H), 7.280 (d, 1H), 7.157 (d, 2H), 4.339 (t, 1H), 3.665 (s, 3H), 2.242 (m, 1H), 0.934 (dd, 6H).

Example 146

(S)-2-(3-(2-fluoro-4-(3-(4-fluorophenyl)ureido)phenyl)isoxazole-5-carboxamido)-3-methylbutanoic acid The title compound was prepared from (S)-methyl 2-(3-(2-fluoro-4-(3-(4-fluorophenyl)ureido)phenyl)isoxazole-5-carboxamido)-3-methylbutanoate as set forth in example 8 and was obtained in 75% yield. MS (ESI) m/z: 459(M+H)$^+$; $^1$HNMR (DMSO-d$_6$, 300 MHz): δ 9.743 (s, 1H), 9.387 (s, 1H), 8.885 (s, 1H), 7.859 (t, 1H), 7.715 (d, 1H), 7.618 (d, 1H), 7.510 (dd, 2H), 7.337 (d, 1H), 7.142 (d, 2H), 4.266 (t, 1H), 2.243 (m, 1H), 0.967 (dd, 6H).

Example 147

Methyl 2-(3-(3-fluoro-4-(3-(2-fluorophenyl)ureido) phenyl)isoxazole-5-carboxamido)-3-methylbutanoate The title compound was prepared according to the procedure as set forth in example 76, except that 1-fluoro-2-isocyanatobenzene was used in place of phenyl isocyanate and ethyl 3-(4-amino-3-fluorophenyl)isoxazole-5-carboxylate was used in place of ethyl 3-(4-aminophenyl)isoxazole-5-carboxylate to yield 57% of the title compound. MS (ESI): m/z 471.1 (M−H); $^1$HNMR (DMSO-d$_6$, 300 MHz): δ 9.30 (d, 1H), 9.23 (d, 1H), 9.15 (d 1H), 8.41 (t, 1H), 8.19 (t, 1H), 7.82

(dd, 1H), 7.74 (m 1H), 7.72 (s, 1H), 7.28 (m, 1H), 7.21 (t, 1H), 7.06 (m, 1H), 4.29 (t, 1H), 3.66 (s, 3H), 2.25 m, 1H), 0.97 (dd, 6H).

Example 148

2-(3-(3-fluoro-4-(3-(2-fluorophenyl)ureido)phenyl) isoxazole-5-carboxamide)-3-methylbutanoic acid The title compound was prepared from methyl 2-(3-(3-fluoro-4-(3-(2-fluorophenyl)ureido)phenyl)isoxazole-5-carboxamido)-3-methylbutanoate as set forth in example 8 and was obtained in 79% yield. MS (ESI): m/z 459.1 (M+H)$^+$; $^1$HNMR (DMSO-d$_6$, 300 MHz): δ 9.32 (s, 1H), 9.17 (s, 1H), 8.93 (d 1H), 8.41 (t, 1H), 8.20 (t, 1H), 7.83 (d, 1H), 7.75 (s 2H), 7.28 (t, 1H), 7.18 (t, 1H), 7.05 (s, 1H), 4.28 (t, 1H), 2.24 (m, 1H), 0.98 (dd, 6H).

Example 149

Methyl 2-(3-(4-(3-(2,4-difluorophenyl)ureido)-3-fluorophenyl) isoxazole-5-carboxamido)-3-methylbutanoate The title compound was prepared according to the procedure as set forth in example 147, except that 2,4-difluoro-1-isocyanatobenzene was used in place of phenyl isocyanate to yield 54% of the title compound. MS (ESI): m/z 491.1 (M+H)$^+$; $^1$HNMR (DMSO-d$_6$, 300 MHz): δ 9.24 (d, 1H), 9.22 (d, 1H), 9.09 (d 1H), 8.40 (t, 1H), 8.13 (m, 1H), 7.82 (dd, 1H), 7.73 (m 1H), 7.71 (s, 1H), 7.35 (dt, 1H), 7.08 (m, 1H), 4.31 (t, 1H), 3.66 (s, 3H), 2.23 m, 1H), 0.97 (dd, 6H).

Example 150

2-(3-(4-(3-(2,4-Difluorophenyl)ureido)-3-fluorophenyl)isoxazole-5-carboxamido)-3-methylbutanoic acid The title compound was prepared from methyl 2-(3-(4-(3-(2,4-difluorophenyl)ureido)-3-fluorophenyl)isoxazole-5-carboxamido)-3-methylbutanoate as set forth in example 8 and was obtained in 73% yield. MS (ESI): m/z 477.1 (M+H)$^+$; $^1$HNMR (DMSO-d$_6$, 300 MHz): δ 9.27 (d, 1H), 9.13 (d, 1H), 8.92 (d, 1H), 8.38 (t, 1H), 8.15 (m, 1H), 7.81 (dd, 1H), 7.73 (s, 1H), 7.70 (m, 1H), 7.35 (m, 1H), 7.08 (m, 1H), 4.27 (t, 1H), 2.23 (m, 1H), 0.96 (dd, 6H).

Example 151

Methyl 2-(3-(4-(3-(3-fluorophenyl)ureido)phenyl) isoxazole-5-carboxamido)-3-methylbutanoate Step 1: 3-(4-nitrophenyl)isoxazole-5-carboxylic acid Ethyl 3-(4-nitrophenyl)isoxazole-5-carboxylate (11 g) was dissolved in THF (220 ml). 1 Molar aqueous NaOH (210 ml) was added and stirred at RT for 15-20 minutes. The reaction mass was acidified with 1 molar HCl. The reaction mixture was extracted with ethyl acetate, organic layer washed with brine, dried over Na$_2$SO$_4$ and concentrated under reduced pressure to get off white solid. Solid was crystallized from acetone/Pet ether to yield 8 g (81%) white solid. MS (ES+): m/z 235 (M+1); $^1$H NMR (DMSO-d$_6$, 300 MHz) δ: 8.39 (d, 2H), 8.27 (d, 2H), 7.97 (s, 1H).

Step 2: Methyl 3-methyl-2-(3-(4-nitrophenyl)isoxazole-5-carboxamido) butanoate 3-(4-nitrophenyl)isoxazole-5-carboxylic acid (2 g) was dissolved in THF (80 ml). To this N-methyl morpholine (0.94 ml) was added and stirred for 10 minutes at RT. The reaction mixture was cooled to −20° C., isobutyl chloroformate (1.1 ml) was added and stirred for 15-20 minutes at −20 to −30° C. L-valine methyl ester hydrochloride (2 g) neutralized with Et$_3$N (1.66 ml) in THF (20 ml) was added to the above reaction mass, stirred at −20 to −30° C. for 5 minutes, then the reaction mixture gradually allowed to warm to RT over a period of 1 h. The solvent was removed under reduced pressure and the crude material was chromatographed on silica gel in 15:85 EtOAc:CHCl$_3$ to get off white solid which was crystallized from methylene chloride/Pet ether to yield 2.2 g (74%) white solid. MS (ES+): m/z 346 (M−1); $^1$H NMR (DMSO-d$_6$, 300 MHz): δ 9.3 (d, 1H), 8.39 (d, 2H), 8.21 (d, 2H), 7.89 (s, 1H), 4.31 (m, 1H), 3.66 (s, 3H), 2.21 (m, 1H), 0.95 (t, 6H).

Step 3: Methyl 2-(3-(4-aminophenyl)isoxazole-5-carboxamido)-3-methylbutanoate

Methyl 3-methyl-2-(3-(4-nitrophenyl)isoxazole-5-carboxamido)butanoate (2 g) was dissolved in EtOH (20 ml), THF (8 ml), and water (8 ml). Then ammonium chloride (925 mg) and Iron (756 mg) was added and refluxed at 80° C. for 3 h. The reaction mixture was cooled, filtered through celite and solvent removed under reduced pressure to get dark brown residue. Residue was taken in water and extracted with ethyl acetate, organic layer separated, dried over Na$_2$SO$_4$ and concentrated to get dark brown residue which was purified by silica gel column chromatography in 1:1 EtOAc:Pet ether to get yellow solid which was crystallized from methylene chloride/Pet ether to yield 1.2 g (65%) pale yellow solid. MS (ES+): m/z 318 (M+1); $^1$HNMR (DMSO-d$_6$, 300 MHz): δ 9.1 (d, 1H), 7.55 (d, 2H), 7.51 (s, 1H), 6.63 (d, 2H), 5.63 (bs, 1H), 4.27 (m, 1H), 3.65 (s, 3H), 2.19 (m, 1H), 0.94 (d, 6H).

Step 4: Methyl 2-(3-(4-(3-(3-fluorophenyl)ureido) phenyl)isoxazole-5-carboxamido)-3-methylbutanoate To methyl 2-(3-(4-aminophenyl)isoxazole-5-carboxamido)-3-methylbutanoate (500 mg) dissolved in THF (10 ml) was added 1-fluoro-3-isocyanatobenzene (260 mg) and stirred at RT overnight. The solid was filtered and washed with THF to yield 460 mg (64%) white solid. MS (ES+): m/z 455 (M+1); $^1$H NMR (DMSO-d$_6$, 300 MHz): δ 9.19 (d, 1H), 9.16 (s, 1H), 9.13 (s, 1H), 7.84 (d, 2H), 7.67 (s, 1H), 7.62 (d, 2H), 7.5 (dd, 1H), 7.31 (m, 1H), 7.13 (dd, 1H), 6.78 (m, 1H), 4.29 (m, 1H), 3.66 (s, 3H), 2.2 (m, 1H), 0.95 (d, 6H).

Example 152

2-(3-(4-(3-(3-fluorophenyl)ureido)phenyl)isoxazole-5-carboxamido)-3-methylbutanoic acid To methyl 2-(3-(4-(3-(3-fluorophenyl)ureido)phenyl) isoxazole-5-carboxamido)-3-methyl butanoate (310 mg) dissolved in THF (8 ml) was added 1 M aqueous solution of LiOH monohydrate (1.025 ml) and stirred at RT for 14 hours. The reaction mixture was acidified with dilute HCl and extracted with EtOAc. The organic layer was separated, dried over Na$_2$SO$_4$ and concentrated under reduced pressure to get off white solid, which was crystallized from EtOAc to yield 140 mg (46%) white solid. MS (ES+): m/z 441 (M+1); $^1$H NMR (DMSO-d$_6$, 300 MHz): δ 12.84 (bs, 1H), 9.11 (s, 1H), 9.08 (s, 1H), 8.93 (d, 1H), 7.84 (d, 2H), 7.68 (s, 1H), 7.62 (d, 2H), 7.51 (dd, 1H), 7.31 (m, 1H), 7.14 (dd, 1H), 6.79 (m, 1H), 4.28 (m, 1H), 2.21 (m, 1H), 0.95 (dd, 6H).

Example 153

Methyl 3-methyl-2-(3-(4-(3-o-tolylureido)phenyl) isoxazole-5-carboxamido) butanoate The title compound was prepared according to the procedure as set forth in example 151, except that 1-isocyanato-2-methylbenzene was used in place of 1-fluoro-3-isocyanatobenzene to yield 80% of the title compound. MS (ES+): m/z 451 (M+1); $^1$H NMR (DMSO-d$_6$, 300 MHz): δ 9.29 (s, 1H), 9.18 (d, 1H), 8.0 (s, 1H), 7.84 (dd, 1H), 7.82 (d, 2H), 7.66 (s, 1H), 7.63 (d, 2H), 7.16 (m, 2H), 6.95 (m, 1H), 4.29, (m, 1H), 3.66 (s, 3H), 2.23 (s, 3H), 2.16 (m, 1H), 0.95 (d, 6H).

Example 154

3-methyl-2-(3-(4-(3-o-tolylureido)phenyl)isoxazole-5-carboxamido) butanoic acid

The title compound was prepared from methyl 3-methyl-2-(3-(4-(3-o-tolylureido)phenyl)isoxazole-5-carboxamido) butanoate as set forth in example 152 and was obtained in 59% yield. MS (ES+): m/z 437 (M+1); $^1$H NMR (DMSO-d$_6$, 300 MHz): δ 12.84 (bs, 1H), 9.33 (s, 1H), 8.93 (d, 1H), 8.03 (s, 1H), 7.84 (dd, 1H), 7.81 (d, 2H), 7.68 (s, 1H), 7.63 (d, 2H), 7.16 (m, 2H), 6.95 (m, 1H), 4.26, (m, 1H), 2.24 (s, 3H), 2.18 (m, 1H), 0.95 (dd, 6H).

Example 155

Methyl 2-(3-(4-(3-(2-fluoro-5-methylphenyl)ureido) phenyl)isoxazole-5-carboxamido)-3-methylbutanoate The title compound was prepared according to the procedure as set forth in example 151, except that 1-fluoro-2-isocyanato-4-methylbenzene was used in place of 1-fluoro-3-isocyanatobenzene to yield 92% of the title compound. MS (ES+): m/z 469 (M+1); $^1$H NMR (DMSO-d$_6$, 300 MHz): δ 9.33 (s, 1H), 9.19 (d, 1H), 8.57 (s, 1H), 8.0 (dd, 1H), 7.87 (d, 2H), 7.69 (s, 1H), 7.63 (d, 2H), 7.12 (m, 1H), 6.82 (m, 1H), 4.31, (m, 1H), 3.68 (s, 3H), 2.28 (s, 3H), 2.22 (m, 1H), 0.95 (d, 6H).

Example 156

2-(3-(4-(3-(2-fluoro-5-methylphenyl)ureido)phenyl) isoxazole-5-carboxamido)-3-methylbutanoic acid The title compound was prepared from Methyl 2-(3-(4-(3-(2-fluoro-5-methylphenyl)ureido) phenyl)isoxazole-5-carboxamido)-3-methylbutanoate as set forth in example 152 and was obtained in 81% yield. MS (ES+): m/z 455 (M+1); $^1$H NMR (DMSO-d$_6$, 300 MHz): δ 12.82 (bs, 1H), 9.35 (s, 1H), 8.95 (d, 1H), 8.59 (s, 1H), 8.0 (dd, 1H), 7.87 (d, 2H), 7.7 (s, 1H), 7.64 (d, 2H), 7.12 (m, 1H), 6.84 (m, 1H), 4.28, (m, 1H), 2.28 (s, 3H), 2.23 (m, 1H), 0.97 (d, 6H).

Example 157

Methyl 2-(3-(4-(3-(4-butylphenyl)ureido)phenyl) isoxazole-5-carboxamido)-3-methylbutanoate The title compound was prepared according to the procedure as set forth in example 151, except that 1-butyl-4-isocyanatobenzene was used in place of 1-fluoro-3-isocyanatobenzene to yield 92% of the title compound. $^1$H NMR (DMSO-d$_6$, 300 MHz): δ 9.19 (d, 1H), 8.92 (s, 1H), 8.65 (s, 1H), 7.85 (d, 2H), 7.68 (s, 1H), 7.6 (d, 2H), 7.34 (d, 2H), 7.09 (d, 2H), 4.31 (m, 1H), 3.68 (s, 3H), 2.5 (m, 2H), 2.22 (m, 1H), 1.5 (m, 2H), 1.3 (m, 2H), 0.95 (d, 6H), 0.93 (t, 3H); MS (ES+): m/z 493 (M+1).

Example 158

2-(3-(4-(3-(4-butylphenyl)ureido)phenyl)isoxazole-5-carboxamido)-3-methylbutanoic acid The title compound was prepared from methyl 2-(3-(4-(3-(4-butylphenyl)ureido)phenyl) isoxazole-5-carboxamido)-3-methylbutanoate as set forth in example 152 and was obtained in 54% yield. MS (ES+): m/z 479 (M+1); $^1$H NMR (DMSO-d$_6$, 300 MHz): δ 8.96 (d, 1H), 8.93 (s, 1H), 8.66 (s, 1H), 7.84 (d, 2H), 7.69 (s, 1H), 7.62 (d, 2H), 7.37 (d, 2H), 7.12 (d, 2H), 4.28 (m, 1H), 2.54 (m, 2H), 2.22 (m, 1H), 1.52 (m, 2H), 1.28 (m, 2H), 0.97 (dd, 6H), 0.89 (t, 3H).

Example 159

Methyl 2-(3-(4-(3-(3,5-difluorophenyl)ureido)phenyl)isoxazole-5-carboxamido)-3-methylbutanoate The title compound was prepared according to the procedure as set forth in example 151, except that 1,3-difluoro-5-isocyanatobenzene was used in place of 1-fluoro-3-isocyanatobenzene to yield 76% of the title compound. MS (ES+): m/z 473 (M+1); $^1$H NMR (DMSO-d$_6$, 300 MHz): δ 9.2 (d, 1H), 9.19 (s, 1H), 9.16 (s, 1H), 7.87 (d, 2H), 7.69 (s, 1H), 7.64 (d, 2H), 7.22 (d, 2H), 6.82 (m, 1H), 4.31 (m, 1H), 3.68 (s, 3H), 2.22 (m, 1H), 0.97 (d, 6H).

Example 160

2-(3-(4-(3-(3,5-difluorophenyl)ureido)phenyl)isoxazole-5-carboxamido)-3-methylbutanoic acid The title compound was prepared from methyl 2-(3-(4-(3-(3,5-difluorophenyl)ureido) phenyl)isoxazole-5-carboxamido)-3-methylbutanoate as set forth in example 152 and was obtained in 76% yield. MS (ES+): m/z 459 (M+1); $^1$H NMR (DMSO-d$_6$, 300 MHz): δ 12.82 (bs, 1H), 9.2 (s, 1H), 9.17 (s, 1H), 8.96 (d, 1H), 7.87 (d, 2H), 7.7 (s, 1H), 7.64 (d, 2H), 7.22 (d, 2H), 6.81 (m, 1H), 4.28 (m, 1H), 2.23 (m, 1H), 0.98 (d, 6H).

Example 161

Methyl 2-(3-(4-(3-(3-chloro-4-fluorophenyl)ureido) phenyl)isoxazole-5-carboxamido)-3-methylbutanoate The title compound was prepared according to the procedure as set forth in example 151, except that 2-chloro-1-fluoro-4-isocyanatobenzene was used in place of 1-fluoro-3-isocyanatobenzene to yield 69% of the title compound. MS (ES+): m/z 489 (M+1); $^1$H NMR (DMSO-d$_6$, 300 MHz): δ 9.2 (d, 1H), 9.0 (s, 1H), 8.97 (s, 1H), 7.86 (d, 2H), 7.8 (d, 1H), 7.68 (s, 1H), 7.64 (d, 2H), 7.35 (m, 1H), 7.33 (m, 1H), 4.31 (m, 1H), 3.68 (s, 3H), 2.22 (m, 1H), 0.97 (d, 6H).

Example 162

2-(3-(4-(3-(3-chloro-4-fluorophenyl)ureido)phenyl) isoxazole-5-carboxamido)-3-methylbutanoic acid The title compound was prepared from methyl 2-(3-(4-(3-(3-chloro-4-fluorophenyl)ureido)phenyl)isoxazole-5-carboxamido)-3-methylbutanoate as set forth in example 152 and was obtained in 51% yield. MS (ES+): m/z 475 (M+1); $^1$H NMR (DMSO-d$_6$, 300 MHz): δ 12.82 (bs, 1H), 9.0 (s, 1H), 8.99 (s, 1H), 8.95 (d, 1H), 7.86 (d, 2H), 7.81 (d, 1H), 7.7 (s, 1H), 7.64 (d, 2H), 7.35 (m, 1H), 7.33 (m, 1H), 4.28 (m, 1H), 2.23 (m, 1H), 0.97 (d, 6H).

Example 163

(S)-methyl 3-methyl-2-(3-(4-(3-(2-(trifluoromethyl) phenyl)ureido) phenyl)isoxazole-5-carboxamido) butanoate The title compound was prepared according to the procedure as set forth in example 151, except that 1-isocyanato-2-(trifluoromethyl)benzene was used in place of 1-fluoro-3-isocyanatobenzene to yield 84% of the title compound. MS (ESI) m/z: 505(M+H)$^+$; $^1$HNMR (DMSO-d$_6$): δ 9.648 (s, 1H), 9.216 (d, 1H), 8.184 (s, 1H), 7.956 (d, 1H), 7.881 (d, 2H), 7.716 (d, 3H), 7.657 (d, 2H), 7.338 (t, 1H), 4.339 (t, 1H), 3.681 (s, 3H), 2.248 (m, 1H), 0.993 (dd, 6H).

Example 164

(S)-3-methyl-2-(3-(4-(3-(2-(trifluoromethyl)phenyl) ureido)phenyl) isoxazole-5-carboxamido)butanoic acid The title compound was prepared from (S)-methyl 3-methyl-2-(3-(4-(3-(2-(trifluoromethyl)phenyl)ureido)phenyl) isoxazole-5-carboxamido)butanoate as set forth in example 152 and was obtained in 76% yield. MS (ESI) m/z: 491(M+H)$^+$; $^1$HNMR (DMSO-d$_6$): δ 12.893 (s, 1H), 9.688 (s, 1H), 8.955 (d, 1H), 8.227 (s, 1H), 7.952 (d, 1H), 7.878 (d, 2H), 7.714 (t, 2H); 7.652 (d, 3H), 7.338 (t, 1H), 4.308 (t, 1H), 2.253 (m, 1H), 0.991 (dd, 6H).

Example 165

(S)-Methyl 2-(3-(4-(3-(2,5-dimethoxyphenyl)ureido) phenyl)isoxazole-5-carboxamido)-3-methylbutanoate The title compound was prepared according to the procedure as set forth in example 151, except that 2-isocyanato-1,4-dimethoxybenzene was used in place of 1-fluoro-3-isocyanatobenzene to yield 89% of the title compound. MS (ESI) m/z: 497(M+H)$^+$; $^1$HNMR (DMSO-d$_6$): δ 9.653 (s, 1H), 9.217 (d, 1H), 8.352 (s, 1H), 7.865 (d, 3H), 7.881 (s, 1H), 7.636 (d, 2H), 6.956 (d, 1H), 6.535 (dd, 1H), 4.339 (t, 1H), 3.837 (s, 3H), 3.699 (s, 3H), 3.682 (s, 3H), 2.248 (m, 1H), 0.994 (dd, 6H).

Example 166

(S)-2-(3-(4-(3-(2,5-Dimethoxyphenyl)ureido)phenyl) isoxazole-5-carboxamido)-3-methylbutanoic acid The title compound was prepared from (S)-methyl 2-(3-(4-(3-(2,5-dimethoxyphenyl)ureido)phenyl)isoxazole-5-carboxamido)-3-methylbutanoate as set forth in example 152 and was obtained in 51% yield. MS (ESI) m/z: 483(M+H)$^+$; $^1$HNMR (DMSO-d$_6$, 300 MHz): δ 12.954 (s, 1H), 9.650 (s, 1H), 8.972 (d, 1H), 8.349 (s, 1H), 7.901 (d, 3H), 7.700 (s, 1H), 7.636 (d, 2H), 6.956 (d, 1H), 6.535 (dd, 1H), 4.312 (t, 1H), 3.837 (s, 3H), 3.682 (s, 3H), 2.252 (m, 1H), 0.993 (dd, 6H).

Example 167

(S)-2-(3-(4-(3-(3,5-difluorophenyl)ureido)phenyl) isoxazole-5-carboxamido)-3-methylbutanoic acid The title compound was prepared from methyl 2-(3-(4-(3-(3,5-difluorophenyl) ureido) phenyl)isoxazole-5-carboxamido)-3-methylbutanoate as set forth in example 152 and was obtained in 75% yield. MS (ESI) m/z: 459(M+H)$^+$; $^1$HNMR (DMSO-d$_6$, 300 MHz): δ 12.934 (s, 1H), 9.222 (s, 1H), 9.184 (s, 1H), 8.973 (d, 1H), 7.908 (d, 2H), 7.705 (s, 1H), 7.664 (d, 2H), 7.250 (m, 2H), 6.856 (m, 1H), 4.311 (m, 1H), 2.273 (m, 1H), 0.992 (dd, 6H).

Example 168

(S)-methyl 2-(3-(4-(3-(2,4-dimethoxyphenyl)ureido) phenyl)isoxazole-5-carboxamido)-3-methylbutanoate The title compound was prepared according to the procedure as set forth in example 151, except that 1-isocyanato-2,4-dimethoxybenzene was used in place of 1-fluoro-3-isocyanatobenzene to yield 94% of the title compound. MS (ESI) m/z: 497(M+H)$^+$;
$^1$HNMR (DMSO-d$_6$, 300 MHz): δ 9.452 (s, 1H), 9.211 (d, 1H), 8.091 (s, 1H), 8.091 (s, 1H), 7.952 (d, 2H), 7.847 (d, 2H), 7.680 (s, 1H), 7.618 (d, 2H), 6.638 (d, 1H), 6.515 (dd, 1H), 4.337 (t, 1H), 3.870 (s, 3H), 3.740 (s, 3H), 3.680 (s, 3H), 2.247 (m, 1H), 0.993 (dd, 6H).

Example 169

(S)-2-(3-(4-(3-(2,4-dimethoxyphenyl)ureido)phenyl) isoxazole-5-carboxamido)-3-methylbutanoic acid The title compound was prepared from (S)-methyl 2-(3-(4-(3-(2,4-dimethoxyphenyl)ureido)phenyl)isoxazole-5-carboxamido)-3-methylbutanoate as set forth in example 152 and was obtained in 82% yield. MS (ESI) m/z: 483(M+H)$^+$; $^1$HNMR (DMSO-d$_6$): δ 12.913 (s, 1H), 9.448 (s, 1H), 8.965 (d, 1H), 8.087 (s, 1H), 7.952 (d, 1H), 7.845 (s, 2H), 7.690 (s, 1H), 7.690(d, 2H), 6.638 (d, 1H), 6.516 (dd, 1H), 4.310 (t, 1H), 3.871 (s, 3H), 3.741 (s, 3H), 2.229 (m, 1H), 0.992 (dd, 6H).

Example 170

(S)-methyl 2-(3-(4-(3-(2,4-dimethylphenyl)ureido) phenyl)isoxazole-5-carboxamido)-3-methylbutanoate The title compound was prepared according to the procedure as set forth in example 151, except that 1-isocyanato-2, 4-dimethylbenzene was used in place of 1-fluoro-3-isocyanatobenzene to yield 82%. MS (ESI) m/z: 465(M+H)+; $^1$HNMR (DMSO-d$_6$): δ 9.233 (s, 1H), 9.210 (d, 1H), 7.948 (s, 1H), 7.853 (d, 2H), 7.682 (s, 1H), 7.660 (t, 3H), 7.004 (m, 2H), 4.338 (t, 1H), 3.681 (s, 3H), 2.234 (m, 7H), 0.993 (dd, 6H).

Example 171

(S)-2-(3-(4-(3-(2,4-dimethylphenyl)ureido)phenyl) isoxazole-5-carboxamido)-3-methylbutanoic acid The title compound was prepared from (S)-methyl 2-(3-(4-(3-(2,4-dimethylphenyl)ureido)phenyl)isoxazole-5-carboxamido)-3-methylbutanoate as set forth in example 152 and was obtained in 53% yield. MS (ESI) m/z: 451(M+H)+; $^1$HNMR (DMSO-d$_6$): δ 12.912 (bs, 1H), 9.247 (s, 1H), 8.964 (d, 1H), 7.957 (s, 1H), 7.851 (d, 2H), 7.692 (s, 1H), 7.659 (t, 3H), 7.004 (d, 2H), 4.310 (t, 1H), 2.235 (m, 7H), 0.992 (dd, 6H).

Example 172

(S)-methyl 2-(3-(4-(3-(3,4-dimethylphenyl)ureido) phenyl)isoxazole-5-carboxamido)-3-methylbutanoate The title compound was prepared according to the procedure as set forth in example 151, except that 4-isocyanato-1,2-dimethylbenzene was used in place of 1-fluoro-3-isocyanatobenzene to yield 83% of the title compound. MS (ESI) m/z: 465(M+H)+;

$^1$H NMR (DMSO-d$_6$, 300 MHz): δ 9.211 (d, 1H), 8.917 (s, 1H), 8.585 (s, 1H), 8.397 (d, 1H), 7.849 (d, 2H), 7.688 (s, 1H), 7.627 (d, 2H), 7.249 (d, 1H), 7.197 (m, 1H), 7.052 (t, 1H), 4.339 (t, 1H), 3.681 (s, 3H), 2.270 (m, 7H), 0.992 (dd, 6H).

Example 173

(S)-2-(3-(4-(3-(3,4-dimethylphenyl)ureido)phenyl) isoxazole-5-carboxamido)-3-methylbutanoic acid The title compound was prepared from (S)-methyl 2-(3-(4-(3-(3,4-dimethylphenyl)ureido)phenyl)isoxazole-5-carboxamido)-3-methylbutanoate as set forth in example 152 and was obtained in 64% yield. MS (ESI) m/z: 451(M+H)+; $^1$HNMR (DMSO-d$_6$): δ 12.799 (bs, 1H), 8.955 (d, 1H), 8.620 (s, 1H), 7.846 (d, 2H), 7.697 (s, 1H), 7.631 (d, 2H), 7.252 (s, 1H), 7.221 (m, 2H), 7.051 (s, 1H), 4.311 (t, 1H), 2.252 (m, 7H), 0.993 (dd, 6H).

Example 174

(S)-Methyl 2-(3-(4-(3-(2-chloro-6-methylphenyl) ureido)phenyl) isoxazole-5-carboxamido)-3-methylbutanoate The title compound was prepared according to the procedure as set forth in example 151, except that 1-chloro-2-isocyanato-3-methylbenzene was used in place of 1-fluoro-3-isocyanatobenzene to yield 87% of the title compound. MS (ESI) m/z: 485(M+H)+; $^1$HNMR (DMSO-d$_6$): δ 9.216 (s, 1H), 9.203 (d, 1H), 8.082 (s, 1H), 7.844 (d, 2H), 7.677 (s, 1H), 7.637 (d, 2H), 7.376 (d, 1H), 7.269 (m, 2H), 4.338 (t, 1H), 3.679 (s, 3H), 2.273 (s, 3H), 2.223 (m, 1H), 0.991 (dd, 6H).

Example 175

(S)-2-(3-(4-(3-(2-Chloro-6-methylphenyl)ureido) phenyl)isoxazole-5-carboxamido)-3-methylbutanoic acid The title compound was prepared from (S)-methyl 2-(3-(4-(3-(2-chloro-6-methylphenyl)ureido)phenyl)isoxazole-5-carboxamido)-3-methylbutanoate as set forth in example 152 and was obtained in 70% yield. MS (ESI) m/z: 471(M+H)+; $^1$HNMR (DMSO-d$_6$): δ 12.843 (s, 1H), 9.239 (s, 1H), 8.952 (d, 1H), 8.098 (s, N1H), 7.882 (d, 2H), 7.689 (s, 1H), 7.639 (d, 2H), 7.375 (d, 1H), 7.268 (m, 2H), 4.312 (t, 1H), 2.276 (s, 3H), 2.251 (m, 1H), 0.991 (dd, 6H).

Example 176

(S)-Methyl 2-(3-(4-(3-benzo[d][1,3]dioxol-5-ylureido)phenyl)isoxazole-5-carboxamido)-3-methylbutanoate The title compound was prepared according to the procedure as set forth in example 151, except that 5-isocyanato-benzo[d][1,3]dioxole was used in place of 1-fluoro-3-isocyanatobenzene to yield 88% of the title compound. MS (ESI) m/z: 481(M+H)+; $^1$HNMR (DMSO-d$_6$): δ 9.206 (d, 1H), 8.913 (s, 1H), 8.658 (s, 1H), 7.846 (d, 2H), 7.680 (s, 1H), 7.618 (d, 2H), 7.212 (s, 1H), 6.861 (m, 2H), 5.979 (s, 2H), 4.339 (t, 1H), 3.680 (s, 3H), 2.271(m, 1H), 0.993 (dd, 6H).

Example 177

(S)-2-(3-(4-(3-benzo[d][1,3]dioxol-5-ylureido)phenyl)isoxazole-5-carboxamido)-3-methylbutanoic acid The title compound was prepared from (S)-methyl 2-(3-(4-(3-benzo[d][1,3]dioxol-5-ylureido)phenyl)isoxazole-5-carboxamido)-3-methylbutanoate as set forth in example 152 and was obtained in 82% yield. MS (ESI) m/z: 467(M+H)+; $^1$HNMR (DMSO-d$_6$): δ 12.798 (s, 1H), 8.979 (s, 1H), 8.941 (d, 1H), 8.725 (s, 1H), 7.845 (d, 2H), 7.691 (s, 1H), 7.623 (d, 2H), 7.221 (d, 1H), 6.860 (d, 1H), 6.805 (dd, 1H), 5.978 (s, 2H), 4.308 (t, 1H), 2.252 (m, 1H), 0.992 (dd, 6H).

Example 178

(S)-methyl 2-(3-(4-(3-(4-chlorophenyl)ureido)phenyl)isoxazole-5-carboxamido)-3-methylbutanoate The title compound was prepared according to the procedure as set forth in example 151, except that 1-chloro-4-isocyanatobenzene was used in place of 1-fluoro-3-isocyanatobenzene to yield 80% of the title compound. MS (ESI) m/z: 471(M+H)+; $^1$HNMR (DMSO-d$_6$): δ 9.210(d, 1H), 9.020 (s, 1H), 8.922 (s, 1H), 7.860 (d, 2H), 7.685 (s, 1H), 7.635 (d, 2H), 7.519 (d, 2H), 7.359 (d, 2H), 4.338 (t, 1H), 3.680 (s, 3H), 2.247 (m, 1H), 0.992 (dd, 6H).

Example 179

(S)-2-(3-(4-(3-(4-Chlorophenyl)ureido)phenyl)isoxazole-5-carboxamido)-3-methylbutanoic acid The title compound was prepared from (S)-methyl 2-(3-(4-(3-(4-chlorophenyl)ureido) phenyl)isoxazole-5-carboxamido)-3-methylbutanoate as set forth in example 152 and was obtained in 89% yield. MS (ESI) m/z: 457(M+H)⁺; ¹HNMR (DMSO-d$_6$): δ 12.911 (bs, 1H), 9.089 (s, 1H), 8.993 (s, 1H), 8.960 (d, 1H), 7.860 (d, 2H), 7.699 (s, 1H), 7.640 (d, 2H), 7.524 (d, 2H), 7.358 (d, 2H), 4.309 (t, 1H), 2.274 (m, 1H), 0.992 (dd, 6H).

Example 180

(S)-methyl 2-(3-(4-(3-(2,3-dihydro-1H-inden-5-yl)ureido)phenyl) isoxazole-5-carboxamido)-3-methylbutanoate The title compound was prepared according to the procedure as set forth in example 151, except that 5-isocyanato-2,3-dihydro-1H-indene was used in place of 1-fluoro-3-isocyanatobenzene to yield 93% of the title compound. MS (ESI) m/z: 477(M+H)⁺; ¹HNMR (DMSO-d$_6$): δ 9.205 (d, 1H), 8.922 (s, 1H), 8.630 (s, 1H), 7.848 (d, 2H), 7.683 (s, 1H), 7.627 (d, 2H), 7.394 (d, 1H), 7.173 (m, 2H), 4.338 (t, 1H), 3.681 (s, 3H), 2.860 (m, 4H), 2.270 (m, 1H), 2.051 (m, 2H), 0.993 (dd, 6H).

Example 181

(S)-2-(3-(4-(3-(2,3-dihydro-1H-inden-5-yl)ureido)phenyl)isoxazole-5-carboxamido)-3-methylbutanoic acid The title compound was prepared from (S)-methyl 2-(3-(4-(3-(2,3-dihydro-1H-inden-5-yl)ureido)phenyl)isoxazole-5-carboxamido)-3-methylbutanoate as set forth in example 152 and was obtained in 85% yield. MS (ESI) m/z: 463(M+H)⁺; ¹HNMR (DMSO-d$_6$): δ 12.838 (bs, 1H), 8.962 (d, 2H), 8.638 (s, 1H), 7.847 (d, 2H), 7.694 (s, 1H), 7.628 (d, 2H), 7.395 (d, 1H), 7.177 (d, 2H), 4.309 (t, 1H), 2.861 (m, 4H), 2.251 (m, 1H), 2.053 (m, 2H), 1.048 (dd, 6H).

Example 182

(S)-methyl 2-(3-(4-(3-(3-chloro-2-fluorophenyl)ureido)phenyl) isoxazole-5-carboxamido)-3-methylbutanoate The title compound was prepared according to the procedure as set forth in example 151, except that 1-chloro-2-fluoro-3-isocyanatobenzene was used in place of 1-fluoro-3-isocyanatobenzene to yield 97% of the title compound. MS (ESI) m/z: 487(M−H)⁻;
¹HNMR (DMSO-d$_6$): δ 9.445 (s, 1H), 9.208 (d, 1H), 8.809 (s, 1H), 8.143 (m, 1H), 7.881 (d, 2H), 7.693 (s, 1H), 7.644 (d, 2H), 7.201 (m, 2H), 4.340 (t, 1H), 3.681 (s, 3H), 2.273 (m, 1H), 0.993 (dd, 6H).

Example 183

(S)-2-(3-(4-(3-(3-chloro-2-fluorophenyl)ureido)phenyl)isoxazole-5-carboxamido)-3-methylbutanoic acid The title compound was prepared from (S)-methyl 2-(3-(4-(3-(3-chloro-2-fluorophenyl)ureido)phenyl) isoxazole-5-carboxamido)-3-methylbutanoate as set forth in example 152 and was obtained in 88% yield. MS (ESI) m/z: 475(M+H)⁺; ¹HNMR (DMSO-d$_6$): δ 12.826 (s, 1H), 9.413 (s, 1H), 9.236 (s, 1H), 8.968 (d, 1H), 7.818 (d, 1H), 8.158 (m, 2H), 7.879 (d, 2H), 7.704 (s, 1H), 7.645 (d, 2H), 4.309 (t, 1H), 2.273 (m, 1H), 0.992 (dd, 6H).

Example 184

(S)-methyl 2-(3-(4-(3-(2-methoxyphenyl)ureido)phenyl)isoxazole-5-carboxamido)-3-methylbutanoate The title compound was prepared according to the procedure as set forth in example 151, except that 1-isocyanato-2-methoxybenzene was used in place of 1-fluoro-3-isocyanatobenzene to yield 95% yield of the title compound. MS (ESI) m/z: 467(M+H)⁺; ¹HNMR (DMSO-d$_6$): δ 9.605 (s, 1H), 9.197 (d, 1H), 8.318 (s, 1H), 8.154 (dd, 1H), 7.862 (d, 2H), 7.682 (s, 1H), 7.637 (d, 2H), 7.053 (m, 2H), 6.942 (m, 1H), 4.343 (t, 1H), 3.892 (s, 3H), 3.683 (s, 3H), 2.273 (m, 1H), 0.995 (dd, 6H).

Example 185

(S)-2-(3-(4-(3-(2-methoxyphenyl)ureido)phenyl)isoxazole-5-carboxamido)-3-methylbutanoic acid The title compound was prepared from (S)-methyl 2-(3-(4-(3-(2-methoxyphenyl)ureido)phenyl)isoxazole-5-carboxamido)-3-methylbutanoate as set forth in example 152 and was obtained in 84% yield. MS (ESI) m/z: 453(M+H)⁺; ¹HNMR (DMSO-d$_6$): δ 12.840 (s, 1H), 9.627 (s, 1H), 8.960 (d, 1H), 8.327 (s, 1H), 8.150 (d, 1H), 7.680 (d, 2H), 7.697 (s, 1H), 7.638 (d, 2H), 7.048 (dd, 2H), 6.935 (m, 1H), 4.310 (t, 1H), 2.253 (m, 1H), 0.993 (dd, 6H).

Example 186

(S)-methyl 3-methyl-2-(3-(4-(3-(4-(trifluoromethoxy)phenyl)ureido) phenyl)isoxazole-5-carboxamido)butanoate The title compound was prepared according to the procedure as set forth in example 151, except that 1-isocyanato-4-(trifluoromethoxy)benzene was used in place of 1-fluoro-3-isocyanatobenzene to yield 97% of the title compound. MS (ESI) m/z: 521(M+H)⁺; ¹HNMR (DMSO-d$_6$): δ 9.204 (d, 1H), 9.035 (s, 1H), 8.986 (s, 1H), 7.866 (d, 2H), 7.688 (d, 1H), 7.644-7.543 (m, 4H), 7.319 (m, 2H), 4.342 (t, 1H), 3.682 (s, 3H), 2.250 (m, 1H), 0.994 (dd, 6H).

Example 187

(S)-3-methyl-2-(3-(4-(3-(4-(trifluoromethoxy)phenyl)ureido)phenyl) isoxazole-5-carboxamido)butanoic acid The title compound was prepared from (S)-methyl 3-methyl-2-(3-(4-(3-(4-(trifluoromethoxy)phenyl)ureido)phenyl) isoxazole-5-carboxamido)butanoate as set forth in example 152 and was obtained in 64% yield. MS (ESI) m/z: 505(M−H)⁻; ¹HNMR (DMSO-d$_6$): δ 12.950 (s, 1H), 9.053 (s, 1H), 9.005 (s, 1H), 8.970 (d, 1H), 7.864 (d, 2H), 7.700 (s, 1H), 7.645 (d, 2H), 7.595 (m, 2H), 7.320 (d, 2H), 4.311(t, 1H), 2.252 (m, 1H), 0.992 (dd, 6H).

Example 188

(S)-methyl 2-(3-(4-(3-(2-chloro-5-methylphenyl) ureido)phenyl) isoxazole-5-carboxamido)-3-methylbutanoate The title compound was prepared according to the procedure as set forth in example 151, except that 1-chloro-2-isocyanato-4-methylbenzene was used in place of 1-fluoro-3-isocyanatobenzene to yield 96% of the title compound. MS (ESI) m/z: 485(M+H)$^+$; $^1$HNMR (DMSO-d$_6$): δ 9.680 (s, 1H), 9.199 (d, 1H), 8.329 (s, 1H), 8.020 (d, 1H), 7.808 (d, 2H), 7.696 (s, 1H), 7.653 (d, 2H), 7.353 (d, 1H), 6.894 (dd, 1H), 4.344 (t, 1H), 3.684 (s, 3H), 2.298 (s, 3H), 2.252 (m, 1H), 0.997 (dd, 6H).

Example 189

(S)-2-(3-(4-(3-(2-chloro-5-methylphenyl)ureido) phenyl)isoxazole-5-carboxamido)-3-methylbutanoic acid The title compound was prepared from (S)-methyl 2-(3-(4-(3-(2-chloro-5-methylphenyl)ureido)phenyl) isoxazole-5-carboxamido)-3-methylbutanoate as set forth in example 152 and was obtained in 56% yield. MS (ESI) m/z: 472(M–H)$^-$; $^1$HNMR (DMSO-d$_6$): δ 13.095 (s, 1H), 9.743 (s, 1H), 8.971 (d, 1H), 8.356 (s, 1H), 8.015 (d, 1H), 7.877 (d, 2H), 7.734 (s, 1H), 7.656 (d, 2H), 7.352 (d, 1H), 6.893 (dd, 1H), 4.312 (t, 1H), 2.297 (s, 2.253 (m, 1H), 0.994 (dd, 6H).

Example 190

(S)-Methyl 3-methyl-2-(3-(4-(3-(2,3,4-trifluorophenyl)ureido)phenyl)isoxazole-5-carboxamido)butanoate The title compound was prepared according to the procedure as set forth in example 151, except that 1,2,3-trifluoro-4-isocyanatobenzene was used in place of 1-fluoro-3-isocyanatobenzene to yield 99% of the title compound. MS (ESI) m/z: 491(M+H)$^+$; $^1$HNMR (DMSO-d$_6$): δ 9.333 (s, 1H), 9.202 (d, 1H), 8.775 (s, 1H), 7.9.13 (d, 3H), 7.691 (s, 1H), 7.637 (d, 2H), 7.336 (m, 1H), 4.341 (t, 1H), 3.682 (s, 3H), 2.272 (m, 1H), 0.994 (dd, 6H).

Example 191

(S)-3-Methyl-2-(3-(4-(3-(2,3,4-trifluorophenyl)ureido)phenyl) isoxazole-5-carboxamido)butanoic acid The title compound was prepared from (S)-methyl 3-methyl-2-(3-(4-(3-(2,3,4-trifluorophenyl)ureido)phenyl)isoxazole-5-carboxamido)butanoate as set forth in example 152 and was obtained in 67% yield. MS (ESI) m/z: 475(M–H)$^-$; $^1$H NMR (DMSO-d$_6$): δ 12.869 (s, 1H), 9.345 (s, 1H), 8.970 (d, 1H), 8.784 (s, 1H), 7.912 (m, 3H), 7.703 (s, 1H), 7.637 (d, 2H), 7.343 (m, 1H), 4.311 (t, 1H), 2.273 (m, 1H), 0.992 (dd, 6H).

Example 192

(S)-methyl 2-(3-(4-(3-(4-chloro-2-fluorophenyl)ureido)phenyl) isoxazole-5-carboxamido)-3-methylbutanoate The title compound was prepared according to the procedure as set forth in example 151, except that 4-chloro-2-fluoro-1-isocyanatobenzene was used in place of 1-fluoro-3-isocyanatobenzene to yield 97% of the title compound. MS (ESI) m/z: 489(M+H)$^+$; $^1$HNMR (DMSO-d$_6$): δ 9.363 (s, 1H), 9.203 (d, 1H), 8.739 (s, 1H), 8.207 (t, 1H), 7.877 (d, 2H), 7.692 (s, 1H), 7.636 (d, 2H), 7.509 (dd, 1H), 7.269 (d, 1H), 4.342 (t, 1H), 3.682 (s, 3H), 2.273 (m, 1H), 0.994 (dd, 6H).

Example 193

(S)-2-(3-(4-(3-(4-chloro-2-fluorophenyl)ureido)phenyl)isoxazole-5-carboxamido)-3-methylbutanoic acid The title compound was prepared from (S)-methyl 2-(3-(4-(3-(4-chloro-2-fluorophenyl)ureido)phenyl)isoxazole-5-carboxamido)-3-methylbutanoate as set forth in example 152 and was obtained in 68% yield. MS (ESI) m/z: 475(M+H)$^+$; $^1$HNMR (DMSO-d$_6$): δ 12.854 (s, 1H), 9.381 (s, 1H), 8.971 (d, 1H), 8.749 (s, 1H), 8.206 (t, 1H), 7.875 (d, 2H), 7.704 (s, 1H), 7.636 (d, 2H), 7.502 (dd, 1H), 7.267 (d, 1H), 4.310 (t, 1H), 2.273 (m, 1H), 0.991 (dd, 6H).

Example 194

(S)-methyl 2-(3-(4-(3-(5-chloro-2-methylphenyl) ureido)phenyl) isoxazole-5-carboxamido)-3-methylbutanoate The title compound was prepared according to the procedure as set forth in example 151, except that 4-chloro-2-isocyanato-1-methylbenzene was used in place of 1-fluoro-3-isocyanatobenzene to yield 96% of the title compound. MS (ESI) m/z: 485(M+H)$^+$. $^1$HNMR (DMSO-d$_6$, 300 MHz): δ 9.438 (s, 1H), 9.201 (d, 1H), 8.140 (s, 1H), 8.058 (d, 1H), 7.879 (d, 2H), 7.694 (s, 1H), 7.651 (d, 2H), 7.228 (d, 1H), 7.022 (dd, 1H), 4.343 (t, 1H), 3.684 (s, 3H), 2.273 (s, 3H), 2.243 (m, 1H), 0.996 (dd, 6H).

Example 195

(S)-2-(3-(4-(3-(5-chloro-2-methylphenyl)ureido) phenyl)isoxazole-5-carboxamido)-3-methylbutanoic acid The title compound was prepared from (S)-methyl 2-(3-(4-(3-(5-chloro-2-methylphenyl)ureido)phenyl) isoxazole-5-carboxamido)-3-methylbutanoate as set forth in example 152 and was obtained in 56% yield. MS (ESI) m/z: 471(M+H)$^+$; $^1$HNMR (DMSO-d$_6$, 300 MHz): δ 12.852 (s, 1H), 9.483 (s, 1H), 8.969 (d, 1H), 8.174 (s, 1H), 8.056 (d, 1H), 7.877 (d, 2H), 7.708 (s, 1H), 7.653 (d, 2H), 7.228 (d, 1H), 7.021 (dd, 1H), 4.311 (t, 1H), 2.244 (s, 3H), 2.208 (m, 1H), 0.994 (dd, 6H).

Example 196

(S)-Methyl 3-methyl-2-(3-(4-(3-(4-(methylthio)phenyl)ureido)phenyl) isoxazole-5-carboxamido)butanoate The title compound was prepared according to the procedure as set forth in example 151, except that (4-isocyanatophenyl)(methyl)sulfane was used in place of 1-fluoro-3-isocyanatobenzene to yield 98% of the title compound. MS (ESI) m/z: 483(M+H)$^+$; $^1$HNMR (DMSO-d$_6$, 300 MHz): δ 9.199 (d, 1H), 8.963 (s, 1H), 8.782 (s, 1H), 7.856 (d, 1H), 7.864 (s, 1H), 7.633 (d, 2H), 7.457(d, 2H), 7.250 (d, 2H), 4.342 (t, 1H), 3.682 (s, 3H), 2.445 (s, 3H), 2.250 (m, 1H), 0.995 (dd, 6H).

Example 197

(S)-3-methyl-2-(3-(4-(3-(4-(methylthio)phenyl)ureido)phenyl) isoxazole-5-carboxamido)butanoic acid The title compound was prepared from (S)-methyl 3-methyl-2-(3-(4-(3-(4-(methylthio) phenyl)ureido)phenyl)isoxazole-5-carboxamido)butanoate as set forth in example 152 and was obtained in 61% yield. MS (ESI) m/z: 469(M+H)$^+$; $^1$HNMR (DMSO-d$_6$, 300 MHz): δ 12.893 (s, 1H), 8.970 (d, 2H), 8.791 (s, 1H), 7.854 (d, 2H), 7.698 (s, 1H), 7.633 (d, 2H), 7.458 (d, 2H), 7.250 (d, 2H), 4.312 (t, 1H), 2.444 (s, 3H), 2.273 (m, 1H). 0.993 (dd, 6H).

Example 198

(S)-methyl 2-(3-(4-(3-(2,5-difluorophenyl)ureido)phenyl)isoxazole-5-carboxamido)-3-methylbutanoate The title compound was prepared according to the procedure as set forth in example 151, except that 1,4-difluoro-2-isocyanatobenzene was used in place of 1-fluoro-3-isocyanatobenzene to yield 98% of the title compound. MS (ESI) m/z: 473(M+H)$^+$; $^1$HNMR (DMSO-d$_6$, 300 MHz): δ 9.422 (s, 1H), 9.205 (d, 1H), 8.856 (s, 1H), 8.083 (m, 1H), 7.886 (d, 2H), 7.698 (s, 1H), 7.642 (d, 2H), 7.356 (d, 1H), 6.889 (m, 1H), 4.344 (t, 1H), 3.683 (s, 3H), 2.273 (m, 1H), 0.996 (dd, 6H).

Example 199

(S)-2-(3-(4-(3-(2,5-Difluorophenyl)ureido)phenyl) isoxazole-5-carboxamido)-3-methylbutanoic acid The title compound was prepared from (S)-methyl 2-(3-(4-(3-(2,5-difluorophenyl)ureido)phenyl)isoxazole-5-carboxamido)-3-methylbutanoate as set forth in example 152 and was obtained in 82%. MS (ESI) m/z: 459(M+H)$^+$; $^1$HNMR (DMSO-d$_6$, 300 MHz): δ 13.123 (s, 1H), 9.482 (s, 1H), 9.970 (d, 1H), 8.995 (s, 1H), 8.079 (m, 1H), 7.883 (d, 2H), 7.710 (s, 1H), 7.644 (d, 2H), 7.352 (m, 1H), 6.886 (m, 1H), 4.312 (t, 1H), 2.252 (m, 1H), 0.992 (dd, 6H).

Example 200

(S)-Methyl 2-(3-(4-(3-(4-chloro-2-phenoxyphenyl)ureido)phenyl) isoxazole-5-carboxamido)-3-methylbutanoate The title compound was prepared according to the procedure as set forth in example 151, except that 4-chloro-1-isocyanato-2-phenoxybenzene was used in place of 1-fluoro-3-isocyanatobenzene to yield 79% of the title compound. MS (ESI) m/z: 563(M+H)$^+$;

$^1$HNMR (DMSO-d$_6$, 300 MHz): δ 9.636 (s, 1H), 9.197 (d, 1H), 8.754 (s, 1H), 8.406 (d, 1H), 7.873 (d, 2H), 7.689 (s, 1H), 7.624 (d, 2H), 7.473 (d, 2H), 7.229 (t, 1H), 7.115 (d, 2H), 7.035 (dd, 1H), 6.859 (d, 1H), 4.340 (t, 1H), 3.681 (s, 3H), 2.249 (m, 1H), 0.994 (dd, 6H).

Example 201

(S)-2-(3-(4-(3-(4-Chloro-2-phenoxyphenyl)ureido) phenyl)isoxazole-5-carboxamido)-3-methylbutanoic acid The title compound, was prepared from (S)-methyl 2-(3-(4-(3-(4-chloro-2-phenoxyphenyl)ureido)phenyl)isoxazole-5-carboxamido)-3-methylbutanoate as set forth in example 152 and was obtained in 82%. MS (ESI) m/z: 549(M+H)$^+$; $^1$HNMR (DMSO-d$_6$, 300 MHz): δ 9.786 (s, 1H), 8.867 (s, 1H), 8.387 (d, 1H), 8.200 (m, 1H), 7.876 (d, 2H), 7.667 (s, 1H), 7.621 (d, 2H), 7.459 (t, 2H), 7.214 (t, 1H), 7.105 (d, 2H), 7.021 (dd, 1H), 6.854 (d, 1H), 4.098 (t, 1H), 2.278 (m, 1H), 0.917 (dd, 6H).

Example 202

(S)-Methyl 3-methyl-2-(3-(4-(3-(2-(trifluoromethoxy)phenyl) ureido) phenyl)isoxazole-5-carboxamido)butanoate The title compound was prepared according to the procedure as set forth in example 151, except that 1-isocyanato-2-(trifluoromethoxy)benzene was used in place of 1-fluoro-3-isocyanatobenzene to yield 79% of the title compound. MS (ESI) m/z: 521(M+H)$^+$; $^1$HNMR (DMSO-d$_6$, 300 MHz): δ 9.561 (s, 1H), 9.204 (d, 1H), 8.564 (s, 1H), 8.277 (d, 1H), 7.887 (d, 2H), 7.694 (s, 1H), 7.654 (d, 2H), 7.410 (dd, 2H), 7.148 (t, 1H), 4.342 (t, 1H), 3.683 (s, 3H), 2.273 (m, 1H), 0.995 (dd, 6H).

Example 203

(S)-3-methyl-2-(3-(4-(3-(2-(trifluoromethoxy)phenyl)ureido)phenyl) isoxazole-5-carboxamido)butanoic acid The title compound was prepared from (S)-methyl 3-methyl-2-(3-(4-(3-(2-(trifluoromethoxy)phenyl)ureido)phenyl) isoxazole-5-carboxamido)butanoate as set forth in example 152 and was obtained in 82% yield. MS (ESI) m/z: 507(M+H)$^+$; $^1$HNMR (DMSO-d$_6$, 300 MHz): δ 12.872 (s, 1H), 9.572 (s, 1H), 8.965 (d, 1H), 8.569 (s, 1H), 8.278 (d, 1H), 7.884 (d, 2H), 7.706 (s, 1H), 7.654 (d, 2H), 7.407 (dd, 2H), 7.144 (t, 1H), 4.312 (t, 1H), 2.275 (m, 1H), 0.995 (dd, 6H).

Example 204

(S)-methyl 2-(3-(4-(3-(3,5-dimethylphenyl)ureido) phenyl)isoxazole-5-carboxamido)-3-methylbutanoate The title compound was prepared according to the procedure as set forth in example 151, except that 1-isocyanato-3,5-dimethylbenzene was used in place of 1-fluoro-3-isocyanatobenzene to yield 91% of the title compound. MS (ESI) m/z: 465(M+H)$^+$. $^1$HNMR (DMSO-d$_6$): δ 9.198 (d, 1H), 8.933 (s, 1H), 8.603 (s, 1H), 7.851 (d, 2H), 7.688 (s, 1H), 7.630 (d, 2H), 7.090 (s, 2H), 6.636 (s, 1H), 4.339 (t, 1H), 3.680 (s, 3H), 2.506 (s, 6H), 2.203 (m, 1H), 0.993 (dd, 6H).

Example 205

(S)-2-(3-(4-(3-(3,5-dimethylphenyl)ureido)phenyl) isoxazole-5-carboxamido)-3-methylbutanoic acid The title compound was prepared from (S)-methyl 2-(3-(4-(3-(3,5-dimethylphenyl)ureido)phenyl)isoxazole-5-carboxamido)-3-methylbutanoate as set forth in example 152 and was obtained in 86% yield. MS (ESI) m/z: 451(M+H)$^+$; $^1$HNMR (DMSO-d$_6$): δ 12.867 (s, 1H), 8.952 (d, 1H), 8.936 (s, 1H), 8.607 (s, 1H), 7.850 (d, 2H), 7.700 (s, 1H), 7.633 (d, 2H), 7.091 (s, 2H), 6.636 (s, 1H), 4.313 (t, 1H), 2.240 (s, 6H), 2.187 (m, 1H), 0.993 (dd, 6H).

Example 206

(S)-methyl 2-(3-(4-(3-(6-chloropyridin-3-yl)ureido) phenyl)isoxazole-5-carboxamido)-3-methylbutanoate The title compound was prepared according to the procedure as set forth in example 151, except that 2-chloro-5-isocyanatopyridine was used in place of 1-fluoro-3-isocyanatobenzene to yield 94% of the title compound. MS (ESI) m/z: 472(M+H)$^+$; $^1$HNMR (DMSO-d$_6$): δ 9.186 (s, 2H), 9.109 (s, 1H), 8.502 (d, 1H), 8.024 (dd, 1H), 7.873 (d, 2H), 7.690 (s, 1H), 7.650 (d, 2H), 7.466 (d, 1H), 4.341 (t, 1H), 3.682 (s, 3H), 2.249 (m, 1H), 0.994 (dd, 6H).

Example 207

(S)-2-(3-(4-(3-(6-chloropyridin-3-yl)ureido)phenyl) isoxazole-5-carboxamido)-3-methylbutanoic acid The title compound was prepared from (S)-methyl 2-(3-(4-(3-(6-chloropyridin-3-yl)ureido)phenyl)isoxazole-5-carboxamido)-3-methylbutanoate as set forth in example 152 and was obtained in 72% yield. MS (ESI) m/z: 458(M+H)$^+$; $^1$H NMR (DMSO-d$_6$): δ 13.050 (s, 1H), 9.211 (s, 1H), 9.139 (s, 1H), 8.969 (d, 1H), 8.502 (dd, 1H), 8.023 (dd, 1H), 7.871 (d, 2H), 7.703 (s, 1H), 7.650 (d, 2H), 7.466 (d, 1H), 4.311 (t, 1H), 2.273 (m, 1H), 0.992 (dd, 6H).

Example 208

(S)-methyl 2-(3-(4-(3-(3-chlorophenyl)ureido)phenyl)isoxazole-5-carboxamido)-3-methylbutanoate The title compound was prepared according to the procedure as set forth in example 151, except that 1-chloro-3-isocyanatobenzene was used in place of 1-fluoro-3-isocyanatobenzene to yield 94% of the title compound. MS (ESI) m/z: 471(M+H)$^+$; $^1$HNMR (DMSO-d$_6$): δ 9.203 (d, 1H), 9.064 (s, 1H), 8.990 (d, 1H), 7.868 (d, 2H), 7.734 (d, 2H), 7.643 (d, 2H), 7.350 (m, 2H), 7.061 (m, 1H), 4.342 (t, 1H), 3.683 (s, 3H), 2.273 (m, 1H), 0.995 (dd, 6H).

Example 209

(S)-2-(3-(4-(3-(3-chlorophenyl)ureido)phenyl)isoxazole-5-carboxamido)-3-methylbutanoic acid The title compound was prepared from (S)-methyl 2-(3-(4-(3-(3-chlorophenyl)ureido) phenyl)isoxazole-5-carboxamido)-3-methylbutanoate as set forth in example 152 and was obtained in 77% yield. MS (ESI) m/z: 457(M+H)$^+$; $^1$HNMR (DMSO-d$_6$): δ 12.962 (s, 1H), 9.484 (s, 1H), 9.421 (s, 1H), 8.890 (d, 1H), 7.886 (d, 2H), 7.749 (m, 4H), 7.327 (m, 2H), 7.050 (m, 1H), 4.302 (t, 1H), 2.281 (m, 1H), 0.994 (dd, 6H).

Example 210

(S)-methyl 2-(3-(4-(3-(2-chloro-5-(trifluoromethyl) phenyl) ureido) phenyl)isoxazole-5-carboxamido)-3-methylbutanoate The title compound was prepared according to the procedure as set forth in example 151, except that 1-chloro-2-isocyanato-4-(trifluoromethyl)benzene was used in place of 1-fluoro-3-isocyanatobenzene to yield 98% of the title compound. MS (ESI) m/z: 539(M+H)$^+$; $^1$HNMR (DMSO-d$_6$) δ 9.849 (s, 1H), 9.213 (d, 1H), 8.707 (s, 1H), 8.647 (s, 1H), 7.898 (d, 2H), 7.755 (d, 1H), 7.727 (d, 1H), 7.670 (d, 2H), 7.420 (dd, 1H), 4.343 (t, 1H), 3.683 (s, 3H), 2.251 (m, 1H), 0.996 (dd, 6H).

Example 211

(S)-2-(3-(4-(3-(2-chloro-5-(trifluoromethyl)phenyl) ureido)phenyl) isoxazole-5-carboxamido)-3-methylbutanoic acid The title compound was prepared from (S)-methyl 2-(3-(4-(3-(2-chloro-5-(trifluoromethyl)phenyl)ureido)phenyl)isoxazole-5-carboxamido)-3-methylbutanoate as set forth in example 152 and was obtained in 68% yield. MS (ESI) m/z: 525(M+H)$^+$; $^1$HNMR (DMSO-d$_6$): δ 12.915 (s, 1H), 9.860 (s, 1H), 8.961 (d, 1H), 8.707 (s, 1H), 8.646 (s, 1H), 7.896 (d, 2H), 7.752 (d, 2H), 7.672 (d, 2H), 7.418 (d, 1H), 4.317 (t, 1H), 2.277 (m, 1H), 0.996 (dd, 6H).

Example 212

(S)-Methyl 2-(3-(4-(3-(4-fluoro-2-(trifluoromethyl) phenyl)ureido) phenyl)isoxazole-5-carboxamido)-3-methylbutanoate The title compound was prepared according to the procedure as set forth in example 151, except that 4-fluoro-1-isocyanato-2-(trifluoromethyl)benzene was used in place of 1-fluoro-3-isocyanatobenzene to yield 99% yield of the title compound. MS (ESI) m/z: 523(M+H)$^+$; $^1$HNMR (DMSO-d$_6$): δ 9.554 (s, 1H), 9.206 (d, 1H), 8.200 (s, 1H), 7.915 (dd, 1H), 7.883 (d, 2H), 7.688 (s, 1H), 7.638 (m, 3H), 7.568 (dd, 1H), 4.338 (t, 1H), 3.680 (s, 3H), 2.272 (m, 1H), 0.992 (dd, 6H).

Example 213

(S)-2-(3-(4-(3-(4-fluoro-2-(trifluoromethyl)phenyl) ureido)phenyl) isoxazole-5-carboxamido)-3-methylbutanoic acid The title compound was prepared from (S)-methyl 2-(3-(4-(3-(4-fluoro-2-(trifluoromethyl)phenyl)ureido)phenyl)isoxazole-5-carboxamido)-3-methylbutanoate as set forth in example 152 and was obtained in 72% yield. MS (ESI) m/z: 509(M+H)$^+$; $^1$HNMR (DMSO-d$_6$): δ 12.776 (s, 1H), 9.549 (s, 1H), 8.952 (d, 1H), 8.194 (s, 1H), 7.918 (m, 3H), 7.697 (s, 1H), 7.640 (m, 4H), 4.313 (t, 1H), 2.274 (m, 1H), 0.993 (dd, 6H).

Example 214

(S)-methyl 2-(3-(4-(3-(4-chloro-2-(trifluoromethyl) phenyl)ureido) phenyl)isoxazole-5-carboxamido)-3-methylbutanoate The title compound was prepared according to the procedure as set forth in example 151, except that 4-chloro-1- isocyanato-2-(trifluoromethyl)benzene was used in place of 1-fluoro-3-isocyanatobenzene to yield 94% of the title compound. MS (ESI) m/z: 523(M+H)$^+$; $^1$HNMR (DMSO-d$_6$): δ 9.682 (s; 1H), 9.209 (d, 1H), 8.258 (s, 1H), 8.017 (dd, 1H), 7.883 (d, 2H), 7.760 (d, 2H), 7.692 (s, 1H), 7.643 (d, 1H), 4.339 (t, 1H), 3.681 (s, 3H), 2.248 (m, 1H), 0.993 (dd, 6H).

Example 215

(S)-2-(3-(4-(3-(4-chloro-2-(trifluoromethyl)phenyl)ureido)phenyl) isoxazole-5-carboxamido)-3-methylbutanoic acid The title compound was prepared from (S)-methyl 2-(3-(4-(3-(4-chloro-2-(trifluoromethyl)phenyl)ureido)phenyl)isoxazole-5-carboxamido)-3-methylbutanoate as set forth in example 152 and was obtained in 75% yield. MS (ESI) m/z: 525(M+H)$^+$; $^1$HNMR (DMSO-d$_6$, 300 MHz): δ 9.861 (s, 1H), 8.926 (d, 1H), 8.378 (s, 1H), 7.999 (m, 1H), 7.877 (d, 2H), 7.755 (m, 3H), 7.653 (d, 2H), 4.303 (t, 1H), 2.273 (m, 1H), 0.990 (dd, 6H).

Example 216

(R)-methyl 2-(3-(4-(3-(2-cyanophenyl)ureido)phenyl)isoxazole-5-carboxamido)-3-methylbutanoate The title compound was prepared according to the procedure as set forth in example 151, except that 3-isocyanatobenzonitrile was used in place of 1-fluoro-3-isocyanatobenzene to yield 74% yield of the title compound. MS (ESI): m/z 462(M+H)$^+$; $^1$H NMR (DMSO-d$_6$, 300 MHz): δ 9.212 (d, 1H), 9.126 (d, 1H), 7.995 (s, 1H), 7.877 (d, 2H), 7.313 (m, 4H), 7.541 (m, 2H), 4.341 (t, 1H), 3.682 (s, 3H), 2.273 (m, 1H), 0.995 (d, 6H).

Example 217

(R)-2-(3-(4-(3-(3-cyanophenyl)ureido)phenyl)isoxazole-5-carboxamido)-3-methylbutanoic acid The title compound was prepared from (R)-methyl 2-(3-(4-(3-(2-cyanophenyl)ureido)phenyl) isoxazole-5-carboxamido)-3-methylbutanoate as set forth in example 152 and was obtained in 54% yield. MS (ESI): m/z 448(M+H)$^+$; $^1$HNMR (DMSO-d$_6$, 300 MHz): δ 12.839 (bs, 1H), 9.202 (d, 1H), 8.983 (d, 1H), 7.996 (s, 1H), 7.915 (d, 2H), 7.711 (s, 1H), 7.686 (s, 1H), 7.654 (d, 2H), 7.540 (m, 2H), 4.311 (t, 1H), 2.274 (m, 1H), 0.992 (d, 6H).

Example 218

(R)-methyl 2-(3-(4-(3-(4-cyanophenyl)ureido)phenyl)isoxazole-5-carboxamido)-3-methylbutanoate The title compound was prepared according to the procedure as set forth in example 151, except that 4-isocyanatobenzonitrile, was used in place of 1-fluoro-3-isocyanatobenzene to yield 60% of the title compound. MS (ESI): m/z 462(M+H)$^+$; $^1$HNMR (DMSO-d$_6$, 300 MHz): δ 9.304 (s, 1H), 9.220 (d, 1H), 9.173 (s, 1H), 7.881 (d, 2H), 7.769 (d, 2H), 7.697 (s, 1H), 7.670 (m, 4H), 4.340 (t, 1H), 3.681 (s, 3H), 2.249 (m, 1H), 0.993 (d, 6H).

Example 219

(R)-2-(3-(4-(3-(4-Cyanophenyl)ureido)phenyl)isoxazole-5-carboxamido)-3-methylbutanoic acid The title compound was prepared from (R)-methyl 2-(3-(4-(3-(4-cyanophenyl)ureido) phenyl)isoxazole-5-carboxamido)-3-methylbutanoate as set forth in example 152 and was obtained in 58% yield. MS (ESI): m/z 448 (M+H)$^+$; $^1$HNMR (DMSO-d$_6$, 300 MHz): δ 12.842 (bs, 1H), 9.312 (s, 1H), 9.177 (s, 1H), 8.980 (d, 1H), 7.916 (d, 2H), 7.766 (d, 2H), 7.707 (d, 3H), 7.652 (m, 2H), 4.313 (t, 1H), 2.274 (m, 1H), 0.992 (d, 6H).

Example 220

(R)-Methyl 2-(3-(4-(3-(2-chlorophenyl)ureido)phenyl)isoxazole-5-carboxamido)-3-methylbutanoate The title compound was prepared according to the procedure as set forth in example 151, except that 1-chloro-2-isocyanatobenzene was used in place of 1-fluoro-3-isocyanatobenzene to yield 87% of the title compound. MS (ESI): m/z 471(M+H)$^+$; $^1$HNMR (DMSO-d$_6$, 300 MHz): δ 9.697 (s, 1H), 9.212 (d, 1H), 8.404 (s, 1H), 8.1847 (d, 1H), 7.884 (d, 2H), 7.694 (s, 1H), 7.653 (d, 2H), 7.490 (d, 1H), 7.349 (m, 1H), 7.087 (m, 1H), 4.342 (t, 1H), 3.683 (s, 3H), 2.273 (m, 1H), 1.054 (d, 6H).

Example 221

(R)-2-(3-(4-(3-(2-Chlorophenyl)ureido)phenyl)isoxazole-5-carboxamido)-3-methylbutanoic acid The title compound was prepared from (R)-methyl 2-(3-(4-(3-(2-chlorophenyl)ureido)phenyl) isoxazole-5-carboxamido)-3-methylbutanoate as set forth in example 152 and was obtained in 56% yield. MS (ESI): m/z 457(M+H)$^+$; $^1$HNMR (DMSO-d$_6$, 300 MHz): δ 12.847 (bs, 1H), 9.700 (s, 1H), 8.979 (d, 1H), 8.406 (s, 1H), 8.183 (d, 1H), 7.882 (d, 2H), 7.707 (s, 1H), 7.653 (d, 2H), 7.490 (d, 1H), 7.346 (t, 1H), 7.083 (t, 1H), 4.312 (t, 1H), 2.274 (m, 1H); 0.992 (dd, 6H).

Example 222

(R)-Methyl 2-(3-(4-(3-(2-fluorophenyl)ureido)phenyl)isoxazole-5-carbothioamido)-3-methylbutanoate The title compound was prepared according to the procedure as set forth in example 151, except that 1-fluoro-2-isocyanatobenzene was used in place of 1-fluoro-3-isocyanatobenzene and (R)-methyl 2-(3-(4-aminophenyl)isoxazole-5-carbothioamido)-3-methylbutanoate was used in place of methyl 2-(3-(4-aminophenyl)isoxazole-5-carboxamido)-3-methylbutanoate to yield 65% of the title compound. MS (ESI): m/z 471(M+H)$^+$; $^1$HNMR (DMSO-d$_6$, 300 MHz): δ 10.935 (s, 1H), 9.355 (s, 1H), 8.640 (s, 1H), 8.161 (s, 1H), 7.891 (s, 2H), 7.634 (d, 3H), 7.256 (s, 1H), 7.162 (s, 1H), 7.038 (s, 1H), 4.835 (s, 1H), 3.689 (s, 3H), 2.507 (s, 1H), 1.049 (d, 6H).

Example 223

(R)-Methyl 3-methyl-2-(3-(4-(3-p-tolylureido)phenyl)isoxazole-5-carbothioamido)butanoate The title compound was prepared according to the procedure as set, forth in example 151, except that 1-isocyanato- 4-methylbenzene was used in place of 1-fluoro-3-isocyanatobenzene and (R)-methyl 2-(3-(4-aminophenyl)isoxazole-5-carbothioamido)-3-methylbutanoate was used in place of methyl 2-(3-(4-aminophenyl)isoxazole-5-carboxamido)-3-methylbutanoate to yield 65% of the title compound. MS (ESI): m/z 467(M+H); $^1$HNMR (DMSO-d$_6$, 300 MHz): δ 10.924 (d, 1H), 8.902 (s, 1H), 8.630 (s, 1H), 7.865 (d, 2H), 7.607(d, 3H), 7.351(d, 2H), 7.094(d, 2H), 4.810 (s, 1H), 3.665(s, 3H), 2.489 (m, 1H), 2.367(s, 3H), 1.033(m, 6H).

Example 224

(R,Z)-Methyl 2-(ethylthio(3-(4-(3-(2-fluorophenyl) ureido)phenyl) isoxazol-5-yl)methyleneamino)-3-methylbutanoate The title compound was prepared according to the procedure as set forth in example 151, except that 1-fluoro-2-isocyanatobenzene was used in place of 1-fluoro-3-isocyanatobenzene and (R,Z)-methyl 2-((3-(4-aminophenyl)isoxazol-5-yl)(ethylthio) methyleneamino)-3-methylbutanoate was used in place of methyl 2-(3-(4-aminophenyl)isoxazole-5-carboxamido)-3-methylbutanoate to yield 76% of the title compound. MS (ESI): m/z 499 (M+H)$^+$; $^1$HNMR (DMSO-d$_6$, 300 MHz): δ 8.124 (s, 1H), 8.101 (d, 1H), 7.858 (s, 1H), 7.593 (m, 1H), 7.406 (m, 1H), 7.260 (s, 2H), 7.095 (m, 2H), 6.991 (m, 1H), 6.701(d, 1H), 4.583 (d, 1H), 3.843 (s, 3H), 3.075 (m, 2H), 2.450 (s, 1H), 1.331 (t, 3H), 1.076 (d, 6H).

Example 225

(R,Z)-Methyl 2-(ethylthio(3-(4-(3-p-tolylureido) phenyl)isoxazol-5-yl)methyleneamino)-3-methylbutanoate The title compound was prepared according to the procedure as set forth in example 151, except that 1-isocyanato-4-methylbenzene was used in place of 1-fluoro-3-isocyanatobenzene and (R)-methyl 2-(3-(4-aminophenyl)isoxazole-5-carbothioamido) -3-methylbutanoate was used in place of methyl 2-(3-(4-aminophenyl)isoxazole-5-carboxamido)-3-methylbutanoate to yield 73% of the title compound. MS (ESI): m/z 495(M+H); $^1$HNMR (DMSO-d$_6$, 300 MHz): δ 7.683 (s, 1H), 7.546(d, 3H), 7.321 (m, 2H), 7.169(t, 2H), 7.028(d, 2H), 6.785(s, 1H), 4.558(s, 1H), 3.798(s, 3H), 3.113 (m, 2H), 2.469(m, 1H), 2.234(s, 3H), 1.337(t, 3H), 1.051(s, 6H).

Example 226

(R,E)-2-(3-(4-(3-(2-Fluorophenyl)ureido)phenyl)-N'-hydroxyisoxazole-5-carboximidamido)-3-methylbutanoic acid The title compound was prepared from (R,Z)-Methyl 2-(ethylthio(3-(4-(3-p-tolylureido)phenyl)isoxazol-5-yl)methyleneamino)-3-methylbutanoate as set forth in example 7 and was obtained in 45% yield. MS (ESI): m/z 456(M+H)$^+$; $^1$HNMR (DMSO-d$_6$, 300 MHz): δ 10.753 (bs, 1H), 9.349 (s, 1H), 8.961 (s, 1H), 8.636 (s, 1H), 8.149 (t, 1H), 7.868 (d, 2H), 7.608 (d, 2H), 7.259 (m, 3H), 7.018 (s, 1H), 5.790 (d, 1H), 3.594 (t, 1H), 1.839 (d, 1H), 0.915 (d, 6H).

Example 227

(S)-Methyl 2-(3-(4-(3-(4-isopropylphenyl)ureido) phenyl)isoxazole-5-carboxamido)-3-methylbutanoate The title compound was prepared according to the procedure as set forth in example 151, except that 1-isocyanato-4-isopropylbenzene was used in place of 1-fluoro-3-isocyanatobenzene to yield 88% of the title compound. MS (ESI) m/z: 479(M+H)$^+$; $^1$HNMR (DMSO-d$_6$): δ 9.205 (d, 1H), 8.930 (s, 1H), 8.670 (s, 1H), 7.852 (d, 2H), 7.685 (s, 1H), 7.632 (d, 2H), 7.391 (d, 2H), 7.178 (d, 2H), 4.341 (t, 1H), 3.682 (s, 3H), 2.831 (m, 1H), 2.250 (m, 1H); 1.198 (d, 6H), 0.992 (dd, 6H).

Example 228

(S)-2-(3-(4-(3-(4-Isopropylphenyl)ureido)phenyl) isoxazole-5-carboxamido)-3-methylbutanoic acid The title compound was prepared from (S)-methyl 2-(3-(4-(3-(4-isopropylphenyl)ureido)phenyl)isoxazole-5-carboxamido)-3-methylbutanoate as set forth in example 152 and was obtained in 62% yield. MS (ESI) m/z: 465(M+H)$^+$; $^1$HNMR (DMSO-d$_6$): δ 12.855 (s, 1H), 8.964 (s, 1H), 8.953 (d, 1H), 8.703(s, 1H), 7.849 (d, 2H), 7.694 (s, 1H), 7.635 (d, 2H), 7.394 (dd, 2H), 7.178 (t, 2H), 4.314 (t, 1H), 2.861 (m, 1H), 2.273 (m, 1H), 1.200 (dd, 6H), 0.990 (dd, 6H).

Example 229

(S)-Methyl 2-(3-(4-(3-(2-fluoro-6-(trifluoromethyl) phenyl)ureido) phenyl)isoxazole-5-carboxamido)-3-methylbutanoate The title compound was prepared according to the procedure as set forth in example 151, except that 1-fluoro-2-isocyanato-3-(trifluoromethyl)benzene was used in place of 1-fluoro-3-isocyanatobenzene to yield 97% of the title compound. MS (ESI) m/z: 523 (M−H)$^-$; $^1$HNMR (DMSO-d$_6$): δ 9.330 (s, 1H), 9.200 (d, 1H), 8.173 (s, 1H), 7.858 (d, 2H), 7.681 (m, 2H), 7.665 (m, 5H), 4.339 (t, 1H), 3.680 (s, 3H), 2.247 (m, 1H), 0.992 (dd, 6H).

Example 230

(S)-2-(3-(4-(3-(2-Fluoro-6-(trifluoromethyl)phenyl) ureido)phenyl) isoxazole-5-carboxamido)-3-methylbutanoic acid The title compound was prepared from (S)-methyl 2-(3-(4-(3-(2-fluoro-6-(trifluoromethyl)phenyl)ureido)phenyl)isoxazole-5-carboxamido)-3-methylbutanoate as set forth in example 152 and was obtained in 85% yield. MS (ESI) m/z: 509(M−H)$^-$; $^1$HNMR (DMSO-d$_6$): δ 12.837 (s, 1H), 9.448 (s, 1H), 8.964 (d, 1H), 8.249 (s, 1H), 7.83 (m, 2H), 7.700 (s, 1H), 7.600 (m, 5H), 4.308 (t, 1H), 2.272 (m, 1H), 0.990 (dd, 6H).

Example 231

(S)-Methyl 2-(3-(4-(3-(2-chloro-4-(trifluoromethyl) phenyl)ureido) phenyl)isoxazole-5-carboxamido)-3-methylbutanoate The title compound was prepared according to the procedure as set forth in example 151, except that 2-chloro-1- isocyanato-4-(trifluoromethyl)benzene was used in place of 1-fluoro-3-isocyanatobenzene to yield 90% of the title compound. MS (ESI) m/z: 537(M−H)⁻; ¹HNMR (DMSO-d₆): δ 9.980 (s, 1H), 9.214 (d, 1H), 8.711 (s, 1H), 8.496 (d, 1H), 7.718 (m, 3H), 7.718 (m, 4H), 4.342 (t, 1H), 3.683 (s, 3H), 2.273 (m, 1H), 0.996 (dd, 6H).

Example 232

(S)-2-(3-(4-(3-(2-Chloro-4-(trifluoromethyl)phenyl) ureido)phenyl) isoxazole-5-carboxamido)-3-methylbutanoic acid The title compound was prepared from (S)-methyl 2-(3-(4-(3-(2-chloro-4-(trifluoromethyl)phenyl)ureido)phenyl)isoxazole-5-carboxamido)-3-methylbutanoate as set forth in example 152 and was obtained in 82% yield. MS (ESI) m/z: 525(M+H)⁺; ¹HNMR (DMSO-d₆, 300 MHz): δ 12.795 (s, 1H), 9.906 (s, 1H), 8.972 (d, 1H), 8.720 (s, 1H), 8.500 (d, 1H), 7.901 (d, 3H), 7.713 (d, 2H), 7.640 (d, 2H), 4.313 (t, 1H), 2.275 (m, 1H), 0.994 (dd, 6H).

Example 233

(S)-Methyl 2-(3-(4-(3-(2-chloro-6-(trifluoromethyl) phenyl)ureido) phenyl)isoxazole-5-carboxamido)-3-methylbutanoate The title compound was prepared according to the procedure as set forth in example 151, except that 1-chloro-2-isocyanato-3-(trifluoromethyl)benzene was used in place of 1-fluoro-3-isocyanatobenzene to yield 98% the title compound. MS (ESI) m/z: 539(M+H)⁺; ¹HNMR (DMSO-d₆): δ 9.273 (s, 1H), 9.198 (d, 1H), 8.295 (s, 1H), 7.925 (d, 1H), 7.849 (d, 2H), 7.787 (d, 1H), 7.682 (s, 1H), 7.635 (d, 2H), 7.590 (t, 1H), 4.340 (t, 1H), 3.680 (s, 3H), 2.246 (m, 1H), 0.992 (dd, 6H).

Example 234

(S)-2-(3-(4-(3-(2-Chloro-6-(trifluoromethyl)phenyl) ureido)phenyl) isoxazole-5-carboxamido)-3-methylbutanoic acid The title compound was prepared from ((S)-methyl 2-(3-(4-(3-(2-chloro-6-(trifluoromethyl)phenyl)ureido)phenyl) isoxazole-5-carboxamido)-3-methylbutanoate as set forth in example 152 and was obtained in 98% yield. MS (ESI) m/z: 526(M+H)⁺; ¹HNMR (DMSO-d₆): δ 12.881 (s, 1H), 9.370 (s, 1H), 8.960 (d, 1H), 8.357 (s, 1H), 7.922 (d, 1H), 7.846 (d, 2H), 7.784 (d, 1H), 7.6696 (s, 1H), 7.636 (d, 2H), 7.588 (t, 1H), 4.310 (t, 1H), 2.249 (m, 1H), 1.036 (dd, 6H).

Example 235

(S)-Methyl 2-(3-(4-(3-(5-chloro-2-phenoxyphenyl) ureido)phenyl) isoxazole-5-carboxamido)-3-methylbutanoate The title compound was prepared according to the procedure as set forth in example 151, except that 4-chloro-2-isocyanato-1-phenoxybenzene was used in place of 1-fluoro-3-isocyanatobenzene to yield 94% of the title compound. MS (ESI) m/z: 561(M−H); ¹HNMR (DMSO-d₆): δ 9.640 (s, 1H), 9.210 (d, 1H), 8.760 (s, 1H), 8.408 (d, 1H), 7.874 (d, 2H), 7.694 (s, 1H), 7.624 (d, 2H), 7.473 (d, 2H), 7.229 (t, 1H), 7.115 (d, 2H), 7.034 (dd, 1H), 6.858 (d, 1H), 4.338 (t, 1H), 3.680 (s, 3H), 2.248 (m, 1H), 0.993 (dd, 6H).

Example 236

(S)-2-(3-(4-(3-(5-Chloro-2-phenoxyphenyl)ureido) phenyl)isoxazole-5-carboxamido)-3-methylbutanoic acid The title compound was prepared from (S)-methyl 2-(3-(4-(3-(5-chloro-2-phenoxyphenyl)ureido)phenyl)isoxazole-5-carboxamido)-3-methylbutanoate as set forth in example 152 and was obtained in 82% yield. MS (ESI) m/z: 549(M+H)⁺; ¹HNMR (DMSO-d₆): δ 12.849 (s, 1H), 9.655 (s, 1H), 8.956 (d, 1H), 8.760 (s, 1H), 8.307 (d, 1H), 7.872 (d, 2H), 7.704 (s, 1H), 7.627 (d, 2H), 7.473 (t, 2H), 7.229 (t, 1H), 7.116 (d, 2H), 7.034 (dd, 1H), 6.860 (d, 1H), 4.313 (t, 1H), 2.275 (m, 1H), 0.994 (dd, 6H).

Example 237

(S)-Methyl 3-methyl-2-(3-(4-(3-(2-phenoxyphenyl) ureido)phenyl) isoxazole-5-carboxamido)butanoate The title compound was prepared according to the procedure as set forth in example 151, except that 1-isocyanato-2-phenoxybenzene was used in place of 1-fluoro-3-isocyanatobenzene to yield 80% of the title compound. MS (ESI) m/z: 529(M+H)⁺; ¹HNMR (DMSO-d₆): δ 9.559 (s, 1H), 9.201 (d, 1H), 8.560 (s, 1H), 8.305 (d, 1H), 7.860 (d, 2H), 7.682 (s, 1H), 7.620 (d, 2H), 7.455 (d, 2H), 7.197 (m, 4H), 7.050 (dt, 1H), 6.866 (dd, 1H), 4.339 (t, 1H), 3.681 (s, 3H), 2.249 (m, 1H), 0.993 (dd, 6H).

Example 238

(S)-3-Methyl-2-(3-(4-(3-(2-phenoxyphenyl)ureido) phenyl)isoxazole-5-carboxamido)butanoic acid The title compound was prepared from (S)-methyl 3-methyl-2-(3-(4-(3-(2-phenoxyphenyl)ureido)phenyl)isoxazole-5-carboxamido)butanoate as set forth in example 152 and was obtained in 68% yield. MS (ESI) m/z: 515(M+H)⁺; ¹HNMR (DMSO-d₆): δ 12.854 (s, 1H), 9.562 (s, 1H), 8.969 (d, 1H), 8.564 (s, 1H), 8.306 (dd, 1H), 7.859 (d, 2H), 7.696 (s, 1H), 7.621 (d, 2H), 7.449 (t, 2H), 7.197 (m, 4H), 7.009 (dt, 1H), 6.958 (dd, 1H), 4.309 (t, 1H), 2.274 (m, 1H), 0.991 (dd, 6H).

Example 239

(S)-Methyl 3-methyl-2-(3-(4-(3-(4-phenoxyphenyl) ureido)phenyl) isoxazole-5-carboxamido)butanoate The title compound was prepared according to the procedure as set forth in example 151, except that 1-isocyanato-4-phenoxybenzene was used in place of 1-fluoro-3-isocyanatobenzene to yield 80% of the title compound. MS (ESI) m/z: 529(M+H)⁺; ¹HNMR (DMSO-d₆): δ 9.206 (d, 1H), 8.969 (s, 1H), 8.792 (s, 1H), 7.859 (d, 2H), 7.688 (s, 1H), 7.642 (d, 2H), 7.510 (d, 2H), 7.397 (t, 2H), 7.120 (t, 1H), 7.015 (t, 4H), 4.342 (t, 1H), 2.251 (m, 1H), 0.996 (dd, 6H).

Example 240

(S)-3-Methyl-2-(3-(4-(3-(4-phenoxyphenyl)ureido) phenyl)isoxazole-5-carboxamido)butanoic acid The title compound was prepared from (S)-methyl 3-methyl-2-(3-(4-(3-(4-phenoxyphenyl)ureido)phenyl)isoxazole- 5-carboxamido)butanoate as set forth in example 152 and was obtained in 75% yield. MS (ESI) m/z: 515(M+H)$^+$; $^1$HNMR (DMSO-d$_6$): δ 12.890 (s, 1H), 9.001 (s, 1H), 8.964 (d, 1H), 8.826 (s, 1H), 7.857 (d, 21-H), 7.698 (s, 1H), 7.645 (d, 2H), 7.512 (d, 2H), 7.396 (t, 2H), 7.121 (t, 1H), 7.014 (t, 4H), 4.313 (t, 1H), 2.275 (m, 1H), 0.994 (dd, 6H).

Example 241

Methyl 2-(3-(4-(3-(2-fluorophenyl)ureido)phenyl) isoxazole-5-carboxamido)-3-phenylpropanoate The title compound was prepared according to the procedure as set forth in example 151, except that 1-fluoro-2-isocyanatobenzene was used in place of 1-fluoro-3-isocyanatobenzene and methyl 2-(3-(4-aminophenyl)isoxazole-5-carboxamido)-3-phenylpropanoate was used in place of methyl 2-(3-(4-aminophenyl)isoxazole-5-carboxamido)-3-methylbutanoate to yield 88% of the title compound. MS (ESI): m/z 503.2 (M+H)$^+$; $^1$HNMR (DMSO-d$_6$, 300 MHz): δ 9.43 (d, 1H), 9.33 (s, 1H), 8.63 (s, 1H), 8.16 (dt, 1H), 7.84 (d, 2H), 7.61 (d, 2H), 7.56 (s, 1H), 7.27 (d, 4H), 7.23 (m, 2H), 7.15 (t, 1H), 7.00 (m, 1H), 4.74 (m, 1H), 3.65 (s, 3H), 3.23 (m, 2H).

Example 242

2-(3-(4-(3-(2-Fluorophenyl)ureido)phenyl)isoxazole-5-carboxamido)-3-phenylpropanoic acid The title compound was prepared from methyl 2-(3-(4-(3-(2-fluorophenyl)ureido)phenyl)isoxazole-5-carboxamido)-3-phenylpropanoate as set forth in example 152 and was obtained in 68% yield. MS (ESI): m/z 489.2 (M+H)$^+$; $^1$HNMR (DMSO-d$_6$, 300 MHz): δ 13.0 (bs, 1H), 9.38 (s, 1H), 9.22 (d, 1H), 8.67 (s, 1H), 8.15 (t, 1H), 7.84 (d, 2H), 7.61 (d, 2H), 7.55 (s, 1H), 7.27 (m, 7H), 7.04 (m, 1H), 4.74 (m. 1H), 3.10 (m, 3H).

Example 243

Methyl 3-phenyl-2-(3-(4-(3-p-tolylureido)phenyl) isoxazole-5-carboxamido) propanoate The title compound was prepared according to the procedure as set forth in example 151, except that 1-isocyanato-4-methylbenzene was used in place of 1-fluoro-3-isocyanatobenzene and methyl 2-(3-(4-aminophenyl)isoxazole-5-carboxamido)-3-phenylpropanoate was used in place of methyl 2-(3-(4-aminophenyl)isoxazole-5-carboxamido)-3-methylbutanoate to yield 75% of the compound. MS (ESI): m/z 499.2 (M+H)$^+$; $^1$HNMR (DMSO-d$_6$, 300 MHz): δ 9.43 (d, 1H), 8.91 (s, 1H), 8.64 (s, 1H), 7.82 (d, 2H), 7.60 (d, 2H), 7.55 (s, 1H), 7.35 (d, 2H), 7.27 (m, 4H), 7.20 (m, 1H), 7.09 (d, 2H), 4.74 (m. 1H), 3.65 (s, 3H), 3.23 (m, 2H), 2.22 (s, 3H).

Example 244

3-Phenyl-2-(3-(4-(3-p-tolylureido)phenyl)isoxazole-5-carboxamido) propanoic acid The title compound was prepared from methyl 3-phenyl-2-(3-(4-(3-p-tolylureido)phenyl)isoxazole-5-carboxamido) propanoate as set forth in example 152 and was obtained in 80%. MS (ESI): m/z 485.2 (M+H)$^+$; $^1$HNMR (DMSO-d$_6$, 300 MHz): δ 13.0 (bs, 1H), 9.23(d, 1H), 8.98(s, 1H), 8.71 (s, 1H), 7.82 (d, 2H), 7.60 (d, 2H), 7.54 (s, 1H), 7.35 (d, 2H), 7.27 (m, 4H), 7.19 (m, 1H), 7.09 (d, 2H), 4.66 (m, 1H), 3.24 (m, 1H), 3.11 (m, 1H), 2.22(s, 3H).

Example 245

Methyl 2-(3-(4-(3-(2,4-difluorophenyl)ureido)phenyl)isoxazole-5-carboxamido)-3-phenylpropanoate The title compound was prepared according to the procedure as set forth in example 151, except that 2,4-difluoro-1-isocyanatobenzene was used in place of 1-fluoro-3-isocyanatobenzene and methyl 2-(3-(4-aminophenyl)isoxazole-5-carboxamido)-3-phenylpropanoate was used in place of methyl 2-(3-(4-aminophenyl)isoxazole-5-carboxamido)-3-methylbutanoate to yield 62% of title compound. MS (ESI): m/z 521.2 (M+H)$^+$; $^1$HNMR (DMSO-d$_6$, 300 MHz) δ: 9.43 (d, 1H), 9.28 (s, 1H), 8.58(s, 1H), 8.10 (m, 1H), 7.84 (d, 2H), 7.60 (d, 2H), 7.55 (s, 1H), 7.34 (m, 5H), 7.20 (m, 1H), 7.07 (m, 1H), 4.74 (m. 1H), 3.64 (s, 3H), 3.23 (m, 2H).

Example 246

2-(3-(4-(3-(2,4-Difluorophenyl)ureido)phenyl)isoxazole-5-carboxamido)-3-phenylpropanoic acid The title compound was prepared from methyl 2-(3-(4-(3-(2,4-difluorophenyl)ureido) phenyl)isoxazole-5-carboxamido)-3-phenylpropanoate as set forth in example 152 and was obtained in 88% yield. MS (ESI): m/z 507.1 (M+H)$^+$; $^1$HNMR (DMSO-d$_6$, 300 MHz): δ 13.0 (bs, 1H), 9.38 (s, 1H), 9.19 (d, 1H), 8.67 (s, 1H), 8.06 (m, 1H), 7.83 (d, 2H), 7.60 (d, 2H), 7.55 (s, 1H), 7.27 (m, 5H), 7.18 (m, 1H), 7.06 (m, 1H), 4.61 (m, 1H), 3.64 (s, 3H), 3.23 (m, 2H).

Example 247

Methyl 2-(3-(4-(3-(3-chloro-4-methylphenyl)ureido) phenyl)isoxazole-5-carboxamido)-3-methylbutanoate The title compound was prepared according to the procedure as set forth in example 151, except that 2-chloro-4-isocyanato-1-methylbenzene was used in place of 1-fluoro-3-isocyanatobenzene to yield 57% of the title compound. MS (ESI): m/z 485.2 (M+H)$^+$; $^1$HNMR (DMSO-d$_6$, 300 MHz): δ 9.19 (d, 1H), 9.01 (s, 1H), 8.86 (s, 1H), 7.86 (d, 2H), 7.70 (d, 1H), 7.68 (s, 1H), 7.63 (d, 2H), 7.27 (d, 1H), 7.22 (dd, 1H), 4.34 (t, 1H), 3.68 (s, 3H), 2.22 (s, 3H), 2.20 (m, 1H), 0.99 (dd, 6H).

Example 248

2-(3-(4-(3-(3-Chloro-4-methylphenyl)ureido)phenyl) isoxazole-5-carboxamido)-3-methylbutanoic acid The title compound was prepared from methyl 2-(3-(4-(3-(3-chloro-4-methylphenyl)ureido)phenyl)isoxazole-5-carboxamido)-3-methylbutanoate as set forth in example 152 and was obtained in 66% yield. MS (ESI): m/z 471.2 (M+H)$^+$; $^1$HNMR (DMSO-d$_6$, 300 MHz): δ 10.00 (s, 1H), 9.82 (s, 1H), 8.58 (s, 1H), 7.85 (d, 2H), 7.75 (d, 1H), 7.75 (d, 2H), 7.67 (s, 1H), 7.31 (dd, 1H), 7.25 (d, 1H), 4.24(t, 1H), 2.26 (s, 3H), 2.12 (m, 1H), 1.15 (s, 1H), 0.98 (dd, 6H).

Example 249

Ethyl 2-(3-(4-(3-(3-fluoro-4-methylphenyl)ureido) phenyl)isoxazole-5-carboxamido)-3-methylbutanoate The title compound was prepared according to the procedure as set forth in example 151, except that 2-fluoro-4-isocyanato-1-methylbenzene was used in place of 1-fluoro-3-isocyanatobenzene to yield 81% of the title compound. MS (ESI): m/z 469.2 (M+H)$^+$; $^1$HNMR (DMSO-d$_6$, 300 MHz): δ 9.20 (d, 1H), 9.00 (s, 1H), 8.88 (s, 1H), 7.85 (d, 2H), 7.68 (s, 1H), 7.63 (d, 2H), 7.46 (dd, 1H), 7.20 (m, 1H), 7.06 (dd, 1H), 4.34 (t, 1H), 3.68 (s, 3H), 2.24 (m, 1H), 2.16 (s, 3H), 0.99 (dd, 6H).

Example 250

2-(3-(4-(3-(3-Fluoro-4-methylphenyl)ureido)phenyl) isoxazole-5-carboxamido)-3-methylbutanoic acid The title compound was prepared from ethyl 2-(3-(4-(3-(3-fluoro-4-methylphenyl) ureido)phenyl)isoxazole-5-carboxamido)-3-methylbutanoate as set forth in example 152 and was obtained in 72% yield. MS (ESI): m/z 455.2 (M+H)$^+$; $^1$HNMR (DMSO-d$_6$, 300 MHz): δ 12.78 (bs, 1H), 9.03 (s, 1H), 8.95 (s, 1H), 8.91 (s, 1H), 7.85 (d, 2H), 7.69 (s, 1H), 7.63 (d, 2H), 7.46 (dd, 1H), 7.20 (t, 1H), 7.06 (dd, 1H), 4.31 (t, 1H), 2.27 (m, 1H), 2.17 (s, 3H), 0.99 (dd, 6H).

Example 251

Methyl 2-(3-(4-(3-(5-fluoro-2-methylphenyl)ureido) phenyl)isoxazole-5-carboxamido)-3-methylbutanoate The title compound was prepared according to the procedure as set forth in example 151, except that 4-fluoro-2-isocyanato-1-methylbenzene was used in place of 1-fluoro-3-isocyanatobenzene to yield 72% of the title compound. MS (ESI): m/z 469.2 (M+H)$^+$; $^1$HNMR (DMSO-d$_6$, 300 MHz): δ 9.46 (s, 1H), 9.20 (d, 1H), 8.14 (s, 1H), 7.88 (d, 2H), 7.87 (m, 1H), 7.69 (s, 1H), 7.65 (d, 2H), 7.22 (t, 1H), 6.80 (td, 1H), 4.34 (t, 1H), 3.68 (s, 3H), 2.27 (m, 1H), 2.20 (s, 3H), 0.99(dd, 6H).

Example 252

2-(3-(4-(3-(5-Fluoro-2-methylphenyl)ureido)phenyl) isoxazole-5-carboxamido)-3-methylbutanoic acid The title compound was prepared from methyl 2-(3-(4-(3-(5-fluoro-2-methylphenyl)ureido)phenyl)isoxazole-5-carboxamido)-3-methylbutanoate as set forth in example 152 and was obtained in 80% yield. MS (ESI): m/z 453.2 (M−H)$^+$; $^1$HNMR (DMSO-d$_6$, 300 MHz): δ 12.90 (bs, 1H), 9.46 (s, 1H), 8.95 (d, 1H), 8.14 (s, 1H), 7.87 (m, 3H), 7.70 (s, 1H), 7.65 (d, 2H), 7.22 (t, 1H), 6.79 (dt, 1H), 4.31 (t, 1H), 2.23 (bs, 4H), 0.99 (dd, 6H).

Example 253

Methyl 4-(3-(4-(3-(2-fluorophenyl)ureido)phenyl) isoxazole-5-carboxamido)butanoate The title compound was prepared according to the procedure as set forth in example 151, except that 1-fluoro-2-isocyanatobenzene was used in place of 1-fluoro-3-isocyanatobenzene and methyl 4-(3-(4-aminophenyl)isoxazole-5-carboxamido)butanoate was used in place of methyl 2-(3-(4-aminophenyl)isoxazole-5-carboxamido)-3-methylbutanoate to yield 73% of the title compound. MS (ES+): m/z 441 (M+1); $^1$HNMR (DMSO-d$_6$, 300 MHz): δ 9.3 (s, 1H), 9.0 (t, 1H), 8.62 (s, 1H), 8.12 (m, 1H), 7.85 (d, 2H), 7.61 (d, 2H), 7.53 (s, 1H), 7.24 (m, 1H), 7.1 (m, 1H), 7.02 (m, 1H), 3.57 (s, 3H), 3.26 (q, 2H), 2.36 (t, 2H), 1.77 (m, 2H).

Example 254

4-(3-(4-(3-(2-Fluorophenyl)ureido)phenyl)isoxazole-5-carboxamido) butanoic acid

The title compound was prepared from methyl 4-(3-(4-(3-(2-fluorophenyl)ureido) phenyl)isoxazole-5-carboxamido) butanoate as set forth in example 152 and was obtained in 47% yield. MS (ES+): m/z 427 (M+1); $^1$H NMR (DMSO-d$_6$, 300 MHz): δ 12.07 (bs, 1H), 9.33 (s, 1H), 8.99 (t, 1H), 8.62 (s, 1H), 8.13 (m, 1H), 7.85 (d, 2H), 7.61 (d, 2H), 7.53 (s, 1H), 7.24 (m, 1H), 7.16 (m, 1H), 7.04 (m, 1H), 3.26 (q, 2H), 2.37 (t, 2H), 1.74 (m, 2H).

Example 255

Methyl 4-(3-(4-(3-p-tolylureido)phenyl)isoxazole-5-carboxamido) butanoate

The title compound was prepared according to the procedure as set forth in example 151, except that 1-isocyanato-4-methylbenzene was used in place of 1-fluoro-3-isocyanatobenzene and methyl 4-(3-(4-aminophenyl)isoxazole-5-carboxamido) butanoate was used in place of methyl 2-(3-(4-aminophenyl)isoxazole-5-carboxamido)-3-methylbutanoate to yield 83% of the title compound. MS (ES+): m/z 437 (M+1); $^1$HNMR (DMSO-d$_6$, 300 MHz): δ 9.01 (t, 1H), 8.91 (s, 1H), 8.65 (s, 1H), 7.84 (d, 2H), 7.61 (d, 2H), 7.53 (s, 1H), 7.36 (d, 2H), 7.1 (d, 2H), 3.59 (s, 3H), 3.29 (q, 2H), 2.38 (t, 2H), 2.25 (s, 3H), 1.8 (m, 2H).

Example 256

4-(3-(4-(3-p-Tolylureido)phenyl)isoxazole-5-carboxamido)butanoic acid

The title compound was prepared from methyl 4-(3-(4-(3-p-tolylureido)phenyl) isoxazole-5-carboxamido)butanoate as set forth in example 152 and was obtained in 15% yield. MS (ES+): m/z 423 (M+1); $^1$HNMR (DMSO-d$_6$, 300 MHz): δ 12.07 (bs, 1H), 8.98 (t, 1H), 8.91 (s, 1H), 8.64 (s, 1H), 7.82 (d, 2H), 7.59 (d, 2H), 7.52 (s, 1H), 7.34 (d, 2H), 7.09 (d, 2H), 3.28 (q, 2H), 2.26 (t, 2H), 2.23 (s, 3H), 1.74 (m, 2H).

Example 257

(R)-Methyl 2-(3-(4-(3-(2-fluorophenyl)ureido)phenyl)isoxazole-5-carboxamido)-3-methylbutanoate The title compound was prepared according to the procedure as set forth in example 151, except that 1-fluoro-2-isocyanatobenzene was used in place of 1-fluoro-3-isocyanatobenzene to yield 84% of the title compound. MS (ES+): m/z 455 (M+1); $^1$H NMR (DMSO-d$_6$, 300 MHz): δ 9.41 (s, 1H), 9.21 (d, 1H), 8.69 (s, 1H), 8.15 (m, 1H), 7.87 (d, 2H), 7.69 (s, 1H), 7.65 (d, 2H), 7.29 (m, 1H), 7.23 (m, 1H), 7.06 (m, 1H), 4.32 (m, 1H), 3.68 (s, 3H), 2.23 (m, 1H), 0.95 (d, 6H).

Example 258

(R)-2-(3-(4-(3-(2-Fluorophenyl)ureido)phenyl)isoxazole-5-carboxamido)-3-methylbutanoic acid The title compound was prepared from (R)-methyl 2-(3-(4-(3-(2-fluorophenyl)ureido) phenyl)isoxazole-5-carboxamido)-3-methylbutanoate as set forth in example 152 and was obtained in 78% yield. MS (ES+): m/z 441 (M+1); $^1$HNMR (DMSO-$d_6$, 300 MHz): δ 12.84 (bs, 1H), 9.36 (s, 1H), 8.98 (d, 1H), 8.65 (s, 1H), 8.16 (m, 1H), 7.88 (d, 2H), 7.71 (s, 1H), 7.65 (d, 2H), 7.26 (m, 1H), 7.16 (m, 1H), 7.04 (m, 1H), 4.29 (m, 1H), 2.23 (m, 1H), 0.98 (d, 6H).

Example 259

(R)-Methyl 1-(3-(4-(3-(2-fluorophenyl)ureido)phenyl)isoxazole-5-carbonyl)pyrrolidine-2-carboxylate The title compound was prepared according to the procedure as set forth in example 151, except that 1-fluoro-2-isocyanatobenzene was used in place of 1-fluoro-3-isocyanatobenzene and (R)-methyl 1-(3-(4-aminophenyl)isoxazole-5-carbonyl)pyrrolidine-2-carboxylate was used in place of methyl 2-(3-(4-aminophenyl) isoxazole-5-carboxamido)-3-methylbutanoate to yield 58% of the title compound. MS (ES+): m/z 453 (M+1); $^1$HNMR (DMSO-$d_6$, 300 MHz): δ 9.35 (s, 1H), 8.64 (s, 1H), 8.15 (m, 1H), 7.89 (d, 2H), 7.66 (s, 1H), 7.6 (d, 2H), 7.26 (m, 1H), 7.16 (m, 1H), 7.06 (m, 1H), 3.92 (t, 1H), 3.67 (s, 3H), 3.65 (m, 1H), 2.29 (m, 1H), 1.97 (m, 2H), 1.24 (m, 2H).

Example 260

(R)-1-(3-(4-(3-(2-Fluorophenyl)ureido)phenyl)isoxazole-5-carbonyl) pyrrolidine-2-carboxylic acid The title compound was prepared from (R)-methyl 1-(3-(4-(3-(2-fluorophenyl)ureido) phenyl)isoxazole-5-carbonyl)pyrrolidine-2-carboxylate as set forth in example 152 and was obtained in 56%. MS (ES+): m/z 439 (M+1); $^1$HNMR (DMSO-$d_6$, 300 MHz): δ 12.72 (bs, 1H), 9.35 (s, 1H), 8.64 (s, 1H), 8.15 (m, 1H), 7.9 (d, 2H), 7.64 (s, 1H), 7.62 (d, 2H), 7.26 (m, 1H), 7.16 (m, 1H), 7.04 (m, 1H), 4.47 (m, 1H), 3.89 (t, 1H), 3.61 (m, 1H), 2.24 (m, 1H), 2.1 (m, 1H), 2.0 (m, 2H).

Example 261

(S)-Methyl 1-(3-(4-(3-(2-fluorophenyl)ureido)phenyl)isoxazole-5-carbonyl)pyrrolidine-2-carboxylate The title compound was prepared according to the procedure as set forth in example 151, except that 1-fluoro-2-isocyanatobenzene was used in place of 1-fluoro-3-isocyanatobenzene and (S)-methyl 1-(3-(4-aminophenyl)isoxazole-5-carbonyl)pyrrolidine-2-carboxylate was used in place of methyl 2-(3-(4-aminophenyl)isoxazole-5-carboxamido)-3-methylbutanoate to yield 53% of the title compound. MS (ES+): m/z 453 (M+1); $^1$H NMR (DMSO-$d_6$, 300 MHz) δ: 9.35 (s, 1H), 8.65 (s, 1H), 8.15 (m, 1H), 7.92 (d, 2H), 7.66 (s, 1H), 7.6 (d, 2H), 7.26 (m, 1H), 7.16 (m, 1H), 7.04 (m, 1H), 3.92 (t, 1H), 3.67 (s, 3H), 3.65 (m, 1H), 2.29 (m, 1H), 1.97 (m, 2H), 1.24 (m, 2H).

Example 262

(S)-1-(3-(4-(3-(2-Fluorophenyl)ureido)phenyl)isoxazole-5-carbonyl) pyrrolidine-2-carboxylic acid The title compound was prepared from (S)-methyl 1-(3-(4-(3-(2-fluorophenyl)ureido) phenyl)isoxazole-5-carbonyl) pyrrolidine-2-carboxylate as set forth in example 152 and was obtained in 55% yield. MS (ES+): m/z 439 (M+1); $^1$HNMR (DMSO-$d_6$, 300 MHz): δ 12.77 (bs, 1H), 9.35 (s, 1H), 8.64 (s, 1H), 8.15 (m, 1H), 7.9 (d, 2H), 7.64 (s, 1H), 7.62 (d, 2H), 7.26 (m, 1H), 7.16 (m, 1H), 7.04 (m, 1H), 4.47 (m, 1H), 3.89 (t, 1H), 3.61 (m, 1H), 2.24 (m, 1H), 2.1 (m, 1H), 1.99 (m, 2H).

Example 263

Methyl 3-methyl-2-(3-(4-(3-(o-tolylsulfonyl)ureido)phenyl)isoxazole-5-carboxamido)butanoate The title compound was prepared according to the procedure as set forth in example 151, except that 2-methylbenzenesulfonyl isocyanate was used in place of 1-fluoro-3-isocyanatobenzene to yield 86% of the title compound. MS (ES+): m/z 515 (M+1); $^1$H NMR (CDCl$_3$, 300 MHz): δ 8.6 (s, 1H), 8.05 (m, 1H), 7.73 (d, 2H), 7.53 (s, 1H), 7.5 (d, 2H), 7.47 (m, 1H), 7.36 (m, 1H), 7.32 (m, 1H), 7.19 (s, 1H), 7.15 (d, 1H), 4.73 (m, 1H), 3.79 (s, 3H), 2.69 (s, 3H), 2.3 (m, 1H), 1.0 (d, 6H).

Example 264

3-Methyl-2-(3-(4-(3-(o-tolylsulfonyl)ureido)phenyl) isoxazole-5-carboxamido)butanoic acid The title compound was prepared from methyl 3-methyl-2-(3-(4-(3-(o-tolylsulfonyl)ureido)phenyl)isoxazole-5-carboxamido)butanoate as set forth in example 152 and was obtained in 61% yield. MS (ES+): m/z 501 (M+1); $^1$HNMR (DMSO-$d_6$, 300 MHz): δ 12.82 (bs, 1H), 11.02 (s, 1H), 8.95 (s, 1H), 8.92 (d, 1H), 7.98 (m, 1H), 7.83 (d, 2H), 7.67 (s, 1H), 7.46 (m, 1H), 7.44 (d, 2H), 7.42 (m, 1H), 7.35 (s, 1H), 4.73 (m, 1H), 2.69 (s, 3H), 2.3 (m, 1H), 1.0 (d, 6H).

Example 265

(S)-methyl 3-methyl-2-(3-(4-(3-m-tolylureido)phenyl)isoxazole-5-carboxamido)butanoate The title compound was prepared according to the procedure as set forth in example 151, except that 1-isocyanato-3-methylbenzene was used in place of 1-fluoro-3-isocyanatobenzene to yield 78% of the title compound. MS: ES (+) m/z 450 (M+1), $^1$HNMR (DMSO-$d_6$, 300 MHz) δ: 9.188 (d, 1H), 8.942 (s, 1H), 8.674 (s, 1H), 7.840 (d, 2H), 7.674 (s, 1H), 7.620 (d, 2H), 7.303 (s, 1H), 7.243 (d, 1H), 7.176 (t, 1H), 6.803 (d, 1H), 4.325 (m, 1H), 3.663 (s, 3H), 2.484 (s, 3H), 2.209 (m, 1H), 0.976 (s, 3H), 0.937 (s, 3H).

Example 266

(S)-3-methyl-2-(3-(4-(3-m-tolylureido)phenyl)isoxazole-5-carboxamido)butanoic acid The title compound was prepared from (S)-methyl 3-methyl-2-(3-(4-(3-m-tolylureido) phenyl)isoxazole-5-carboxamido)butanoate as set forth in example 152 and was obtained in 67% yield. MS: ES (+) m/z 437(M+1), $^1$HNMR (DMSO-d₆, 300 MHz): δ 12.828 (bs, 1H), 8.949 (s, 1H), 8.918 (s, 1H), 8.684 (d, 1H), 7.837 (d, 2H), 7.684 (s, 1H), 7.621 (s, 2H), 7.304 (s, 1H), 7.244 (m, 2H), 6.803 (d, 1H), 4.298 (m, 1H), 2.483 (s, 3H), 2.191 (m, 1H), 0.961 (dd, 6H).

Example 267

(S)-methyl 2-(3-(4-(3-(3-fluorophenyl)thioureido) phenyl)isoxazole-5-carboxamido)-3-methylbutanoate The title compound was prepared according to the procedure as set forth in example 151, except that 1-fluoro-3-isothiocyanatobenzene was used in place of 1-fluoro-3-isocyanatobenzene to yield 66% of the title compound. MS: ES (+) m/z 471(M+1);
¹HNMR (DMSO-d₆, 300 MHz): δ 10.176 (s, 1H), 10.130 (s, 1H), 9.222 (d, 1H), 7.890 (d, 2H), 7.705 (d, 2H), 7.656 (s, 1H), 7.547 (d, 1H), 7.373 (m, 1H), 7.273 (d, 1H), 6.975 (t, 1H), 4.324 (t, 1H), 3.665 (s, 3H), 2.255 (m, 1H), 0.978 (d, 3H), 0.939 (d, 3H).

Example 268

(S)-2-(3-(4-(3-(3-fluorophenyl)thioureido)phenyl) isoxazole-5-carboxamido)-3-methylbutanoic acid The title compound was prepared from (S)-methyl 2-(3-(4-(3-(3-fluorophenyl) thioureido)phenyl)isoxazole-5-carboxamido)-3-methylbutanoate as set forth in example 152 and was obtained in 76% yield. MS: ES (+) m/z 457(M+1); ¹HNMR (DMSO-d₆, 300 MHz): δ 12.715 (s, 1H), 10.172 (s, 1H), 10.125 (s, 1H), 8.980 (d, 1H), 7.923 (d, 2H), 7.733 (s, 1H), 7.713 (d, 2H), 7.556 (d, 1H), 7.398 (m, 1H), 7.368 (d, 1H), 6.973 (t, 1H), 4.294 (t, 1H), 2.490 (m, 1H), 1.000 (d, 3H(×2)).

Example 269

(S)-methyl 2-(3-(4-(3-(2-fluorophenyl)thioureido) phenyl)isoxazole-5-carboxamido)-3-methylbutanoate The title compound was prepared according to the procedure as set forth in example 151, except that 1-fluoro-2-isothiocyanatobenzene was used in place of 1-fluoro-3-isocyanatobenzene to yield 66% of the title compound. MS: ES (+) m/z 471(M+1); ¹HNMR (DMSO-d₆, 300 MHz): δ 10.204 (s, 1H), 9.66 (s, 1H), 9.220 (d, 1H), 7.891 (d, 2H), 7.727 (d, 3H), 7.585 (t, 1H), 7.281 (m, 2H), 7.241 (m, 1H), 4.324 (t, 1H), 3.748 (s, 3H), 2.255 (m, 1H), 1.222 (d, 3H), 1.061 (d, 3H).

Example 270

(S)-2-(3-(4-(3-(2-fluorophenyl)thioureido)phenyl) isoxazole-5-carboxamido)-3-methylbutanoic acid The title compound was prepared from (S)-methyl 2-(3-(4-(3-(2-fluorophenyl) thioureido)phenyl)isoxazole-5-carboxamido)-3-methylbutanoate as set forth in example 152 and was obtained in 58% yield. MS: ES (+) m/z 457(M+1), ¹HNMR (DMSO-d₆, 300 MHz): δ 12.839 (s, 1H), 10.191 (s, 1H), 9.653 (s, 1H), 8.977 (d, 1H), 7.923 (d, 2H), 7.725 (m, 3H), 7.585 (t, 1H), 7.281 (m, 3H); 4295 (t, 1H), 2.257 (m, 1H), 1.891 (d, 3H(×2)).

Example 271

(S)-Methyl 3-methyl-2-(3-(4-(3-p-tolylthioureido) phenyl)isoxazole-5-carboxamido)butanoate The title compound was prepared according to the procedure as set forth in example 151, except that 1-isothiocyanato-4-methylbenzene was used in place of 1-fluoro-3-isocyanatobenzene to yield 38% of the title compound. MS: ES (+) m/z 467(M+1); ¹HNMR (DMSO-d₆, 300 MHz): δ 9.919 (s, 1H), 9.875 (s, 1H), 9.208 (d, 1H), 7.869 (d, 2H), 7.693 (d, 3H), 7.352 (d, 2H), 7.152 (d, 2H), 4.327 (m, 1H), 3.664 (s, 3H), 2270 (s, 3H), 2.212 (m, 1H), 0.978 (s, 3H), 0.939 (s, 3H).

Example 272

(S)-Methyl 3-(4-hydroxyphenyl)-2-(3-(4-(3-p-tolylureido)phenyl) isoxazole-5-carboxamido)propanoate The title compound was prepared according to the procedure as set forth in example 151, except that 1-isocyanato-4-methylbenzene was used in place of 1-fluoro-3-isocyanatobenzene and tyrosine methyl ester was used in place of L-valine methyl ester hydrochloride to yield 64% of the title compound. MS: ES (+) m/z 515(M+1); ¹HNMR (DMSO-d₆, 300 MHz): δ 9.352 (d, 1H), 9.276 (s, 1H), 8.994 (s, 1H), 8.479 (s, 1H), 8.089 (d, 2H), 7.798 (s, 1H), 7.686 (d, 2H), 7.322(d, 2H); 7.176(t, 4H); 6.970(d, 2H); 4.639(m, 1H); 3.721(s, 3H); 2.979 (m, 2H); 1.756(s, 3H).

Example 273

(S)-3-(4-Hydroxyphenyl)-2-(3-(4-(3-p-tolylureido) phenyl)isoxazole-5-carboxamido)propanoic acid The title compound was prepared from (S)-methyl 3-(4-hydroxyphenyl)-2-(3-(4-(3-p-tolylureido)phenyl)isoxazole-5-carboxamido)propanoate as set forth in example 152 and was obtained in 77% yield. MS: ES (−) m/z 499(M−1), ES (+) m/z 501(M+1); ¹HNMR (DMSO-d₆, 300 MHz): δ 12.908 (bs, 1H), 9.202 (s, 1H), 9.176 (d, 1H), 9.006 (s, 1H), 8.729 (s, 1H), 7.822 (d, 2H), 7.603 (s, 1H), 7.657 (d, 2H), 7.349 (d, 2H), 7.084 (d, 4H), 6.648 (d, 2H), 4.536 (s, 1H), 3.351 (m, 2H), 2.228 (s, 3H).

Example 274

(S)-Methyl 2-(3-(4-(3-(2-fluorophenyl)ureido)phenyl)isoxazole-5-carboxamido)-3-(4-hydroxyphenyl) propanoate The title compound was prepared according to the procedure as set forth in example 151, except that 1-fluoro-2-isocyanatobenzene was used in place of 1-fluoro-3-isocyanatobenzene and tyrosine methyl ester was used in place of L-valine methyl ester hydrochloride to yield 60% of the title compound. MS: ES (−) m/z 517(M−1), ¹HNMR (DMSO-d₆, 300 MHz): δ 9.354 (s, 1H), 9.222 (s, 1H), 8.635 (s, 1H), 8.159 (s, 1H), 7.848 (d, 2H), 7.715(m, 3H), 7.264 (t, 2H), 7.233 (m, 3H), 6.652 (d, 2H), 4.607 (bs, 1H), 3.639 (s, 1H), 2.583 (m, 2H).

Example 275

Methyl 3-methyl-2-(3-(4-(3-(4-(trifluoromethyl) phenyl)ureido) phenyl)isoxazole-5-carboxamido) butanoate To Methyl 2-(3-(4-aminophenyl)isoxazole-5-carboxamido)-3-methylbutanoate (example 151, step 3, 500 mg) dissolved in THF (10 ml) were added 4-(trifluoromethyl)aniline (254 mg) and carbonyl diimidazole (283 mg) and heated to reflux at 65° C. overnight. THF was removed completely under reduced pressure to get pale brown residue which was purified by silica gel column chromatography in 3:7 EtOAc:CHCl$_3$ to get off white solid which was crystallized from methylene chloride to yield 375 mg (47%) off white solid. MS (ES+): m/z 505 (M+1); $^1$HNMR (DMSO-d$_6$, 300 MHz): δ 9.19 (s, 1H), 9.18 (d, 1H), 9.09 (s, 1H), 7.85 (d, 2H), 7.67 (s, 1H), 7.65 (d, 2H), 7.63 (d, 2H), 7.6 (d, 2H), 4.29 (m, 1H), 3.66 (s, 3H), 2.2 (m, 1H), 0.95 (d, 6H).

Example 276

3-Methyl-2-(3-(4-(3-(4-(trifluoromethyl)phenyl) ureido)phenyl) isoxazole-5-carboxamido)butanoic acid To Methyl 3-methyl-2-(3-(4-(3-(4-(trifluoromethyl)phenyl)ureido)phenyl)isoxazole-5-carboxamido)butanoate (250 mg) dissolved in THF (5 ml) was added 1 M aqueous solution of Lithium hydroxide monohydrate (1 ml) and stirred at RT for 14 h. The reaction mixture was acidified with dilute HCl and extracted with EtOAc. Organic layer was separated, dried over. Na$_2$SO$_4$ and concentrated under reduced pressure to get off white solid which was crystallized from EtOAc to yield 185 mg (76%) white solid. MS (ES+): m/z 491 (M+1); $^1$H NMR (DMSO-d$_6$, 300 MHz): δ 12.82 (bs, 1H), 9.22 (s, 1H), 9.12 (s, 1H), 8.93 (d, 1H), 7.85 (d, 2H), 7.68 (s, 1H), 7.65 (d, 2H), 7.61 (d, 2H), 7.56 (d, 2H), 4.26 (m, 1H), 2.21 (m, 1H), 0.95 (d, 6H).

Example 277

Methyl 3-methyl-2-(3-(4-(3-(3-(trifluoromethyl) phenyl)ureido) phenyl)isoxazole-5-carboxamido) butanoate The title compound was prepared according to the procedure as set forth in example 275, except that 3-(trifluoromethyl)aniline was used in place of 4-(trifluoromethyl)aniline to yield 47% of the title compound. MS (ES+): m/z 505 (M+1); $^1$HNMR (DMSO-d$_6$, 300 MHz): δ 9.19 (d, 1H), 9.13 (s, 1H), 9.09 (s, 1H), 8.0 (m, 1H), 7.85 (d, 2H), 7.68 (s, 1H), 7.61 (d, 2H), 7.56 (m, 1H), 7.51 (m, 1H), 7.33 (m, 1H), 4.29 (m, 1H), 3.66 (s, 3H), 2.2 (m, 1H), 0.95 (d, 6H).

Example 278

3-Methyl-2-(3-(4-(3-(3-(trifluoromethyl)phenyl) ureido)phenyl) isoxazole-5-carboxamido)butanoic acid The title compound was prepared from methyl 3-methyl-2-(3-(4-(3-(3-(trifluoromethyl) phenyl)ureido)phenyl)isoxazole-5-carboxamido)butanoate as set forth in example 276 and was obtained in 54% yield. MS (ES+): m/z 491 (M+1); $^1$HNMR (DMSO-d$_6$, 300 MHz): δ 12.84 (bs, 1H), 9.15 (s, 1H), 9.11 (s, 1H), 8.94 (d, 1H), 8.02 (m, 1H), 7.85 (d, 2H), 7.69 (s, 1H), 7.64 (d, 2H), 7.56 (m, 1H), 7.51 (m, 1H), 7.32 (m, 1H), 4.26 (m, 1H), 2.21 (m, 1H), 0.96 (d, 6H).

Example 279

Methyl 3-methyl-2-(3-(4-(3-pyridin-2-ylureido)phenyl)isoxazole-5-carboxamido)butanoate The title compound was prepared according to the procedure as set forth in example 275, except that pyridin-2-amine was used in place of 4-(trifluoromethyl)aniline to yield 47% of the title compound. MS (ES+): m/z 438 (M+1); $^1$HNMR (DMSO-d$_6$, 300 MHz): δ 10.77 (s, 1H), 9.54 (s, 1H), 9.19 (d, 1H), 8.29 (m, 1H), 7.87 (d, 2H); 7.75 (m, 1H), 7.72 (s, 1H), 7.69 (d, 2H), 7.5 (m, 1H), 7.02 (m, 1H). 4.3 (m, 1H), 3.66 (s, 3H), 2.2 (m, 1H), 0.95 (d, 6H).

Example 280

3-methyl-2-(3-(4-(3-pyridin-2-ylureido)phenyl)isoxazole-5-carboxamido)butanoic acid The title compound was prepared from methyl 3-methyl-2-(3-(4-(3-pyridin-2-ylureido)phenyl)isoxazole-5-carboxamido)butanoate as set forth in example 276 and was obtained in 49% yield. MS (ES+): m/z 424 (M+1); $^1$HNMR (DMSO-d$_6$, 300 MHz): δ 12.84 (bs, 1H), 10.77 (s, 1H), 9.54 (s, 1H), 8.94 (d, 1H), 8.29 (m, 1H), 7.87 (d, 2H), 7.75 (m, 1H), 7.7 (s, 1H), 7.69 (d, 2H), 7.5 (m, 1H), 7.05 (m, 1H), 4.26 (m, 1H), 2.21 (m, 1H), 0.95 (d, 6H).

Example 281

2-({3-[4-(3-{4-[5-(1-Methoxycarbonyl-2-methyl-propylcarbamoyl)-isoxazol-3-yl]-phenyl}-ureido)-phenyl]-isoxazol-5-carbonyl}-amino)-3-methyl-butyric acid methyl ester The title compound was prepared according to the procedure as set forth in example 275, except that methyl 2-(3-(4-aminophenyl)isoxazole-5-carboxamido)-3-methylbutanoate was used in place of 4-(trifluoromethyl)aniline to yield 32% of the title compound. MS (ES+): m/z 661 (M+1); $^1$HNMR (DMSO-d$_6$, 300 MHz): δ 9.19 (d, 1H), 9.07 (s, 1H), 7.86 (d, 4H), 7.68 (s, 2H), 7.64 (d, 4H), 4.3 (m, 2H), 3.66 (s, 6H), 2.21 (m, 2H), 0.95 (d, 12H).

Example 282

2-({3-[4-(3-{4-[5-(1-Carboxy-2-methyl-propylcarbamoyl)-isoxazol-3-yl]-phenyl}-ureido)-phenyl]-isoxazol-5-carbonyl}-amino)-3-methyl-butyric acid The title compound was prepared from 2-({3-[4-(3-{4-[5-(1-Methoxycarbonyl-2-methyl-propylcarbamoyl)-isoxazol-3-yl]-phenyl}-ureido)-phenyl]-isoxazol-5-carbonyl}-amino)-3-methyl-butyric acid methyl ester as set forth in example 276 and was obtained in 73% yield. MS (ES+): m/z 631 (M−1); $^1$HNMR (DMSO-d$_6$, 300 MHz): δ 12.83 (bs, 1H), 9.08 (s, 1H), 8.95 (d, 1H), 7.89 (d, 4H), 7.69 (s, 2H), 7.64 (d, 4H), 4.26 (m, 2H), 2.21 (m, 2H), 0.96 (d, 12H).

Example 283

Methyl 4-(3-(4-(5-(1-methoxy-3-methyl-1-oxobutan-2-ylcarbamoyl) isoxazol-3-yl)phenyl)ureido)benzoate The title compound was prepared according to the procedure as set forth in example 275, except that methyl 4-aminobenzoate was used in place of 4-(trifluoromethyl)aniline to yield 25% of the title compound. MS (ES+): m/z 495 (M+1); $^1$H NMR (DMSO-$d_6$, 300 MHz): δ 9.21 (s, 1H), 9.20 (d, 1H), 9.11 (s, 1H), 7.92 (d, 2H), 7.87 (d, 2H), 7.69 (s, 1H), 7.65 (d, 2H), 7.62 (d, 2H), 4.31 (m, 1H), 3.82 (s, 3H), 3.68 (s, 3H), 2.22 (m, 1H), 0.97 (d, 6H).

Example 284

Methyl 2-(3-(4-(3-(4-fluoro-2-methylphenyl)ureido) phenyl)isoxazole-5-carboxamido)-3-methylbutanoate The title compound was prepared according to the procedure as set forth in example 275, except that 4-fluoro-2-methylaniline was used in place of 4-(trifluoromethyl)aniline to yield 46% of the title compound. MS (ESI): m/z 469.2 (M+H)$^+$; $^1$HNMR (DMSO-$d_6$, 300 MHz): δ 9.23 (s, 1H), 9.18 (d, 1H), 8.01 (s, 1H), 7.83 (d, 2H), 7.74 (m, 1H), 7.66 (s, 1H), 7.61 (d, 2H), 7.08 (dd, 1H), 7.01 (dt, 1H), 4.32 (t, 1H), 3.66 (s, 3H), 2.23 (s, 3H), 2.20 (m, 1H), 1.21 (d, 1H), 1.05 (dd, 6H).

Example 285

2-(3-(4-(3-(4-fluoro-2-methylphenyl)ureido)phenyl) isoxazole-5-carboxamido)-3-methylbutanoic acid The title compound was prepared from methyl 2-(3-(4-(3-(4-fluoro-2-methylphenyl)ureido)phenyl)isoxazole-5-carboxamido)-3-methylbutanoate as set forth in example 273 and was obtained in 89% yield. MS (ESI): m/z 453.2 (M–H); $^1$HNMR (DMSO-$d_6$, 300 MHz): δ 12.81 (bs, 1H), 9.26 (s, 1H), 8.92 (d, 1H), 8.04 (s, 1H), 7.83 (d, 2H), 7.73 (m, 1H), 7.67 (s, 1H), 7.62 (d, 2H), 7.07 (dd, 1H), 7.00 (dt, 1H), 4.29 (t, 1H), 2.23 (s, 3H), 2.21 (m, 1H), 1.33 (d, 1H), 0.97 (dd, 6H).

Example 286

Methyl 2-(3-(4-(3-(2-chloro-4-(trifluoromethoxy) phenyl)ureido) phenyl)isoxazole-5-carboxamido)-3-methylbutanoate The title compound was prepared according to the procedure as set forth in example 275, except that 2-chloro-4-(trifluoromethoxy)aniline was used in place of 4-(trifluoromethyl) aniline to yield 44% of the title compound. MS (ESI): m/z 552.9 (M–H)$^+$; $^1$HNMR (DMSO-$d_6$, 300 MHz): δ 9.73 (s, 1H), 9.21 (d, 1H), 8.54 (s, 1H), 8.30 (d, 1H), 7.89 (d, 2H), 7.70 (s, 1H), 7.65 (m, 3H), 7.41 (dd, 1H), 4.34 (t, 1H), 3.68 (s, 3H), 2.27 (m, 1H), 0.99 (dd, 6H).

Example 287

2-(3-(4-(3-(2-chloro-4-(trifluoromethoxy)phenyl) ureido)phenyl) isoxazole-5-carboxamido)-3-methylbutanoic acid The title compound was prepared from Methyl 2-(3-(4-(3-(2-chloro-4-(trifluoromethoxy)phenyl)ureido)phenyl)isoxazole-5-carboxamido)-3-methylbutanoate as set forth in example 273 and was obtained in 84% yield. MS (ESI): m/z 541.1(M+H)$^+$; $^1$H NMR (DMSO-$d_6$, 300 MHz): δ 12.85 (bs, 1H), 9.74 (s, 1H), 8.97 (d, 1H), 8.54 (s, 1H), 8.29 (d, 1H), 7.89 (d, 2H), 7.71 (s, 1H), 7.65 (m, 3H), 7.41 (dd, 1H), 4.31 (t, 1H), 2.25 (m, 1H), 0.99 (dd, 6H).

Example 288

Ethyl 2-(3-(4-(3-(3-chloro-4-(trifluoromethoxy)phenyl)ureido) phenyl)isoxazole-5-carboxamido)-3-methylbutanoate The title compound was prepared according to the procedure as set forth in example 275, except that 3-chloro-4-(trifluoromethoxy)aniline was used in place of 4-(trifluoromethyl) aniline to yield 29% of the title compound. MS (ESI): m/z 555.1 (M+H)$^+$; $^1$HNMR (DMSO-$d_6$, 300 MHz): δ 9.21 (d, 1H), 9.17 (s, 1H), 9.15 (s, 1H), 7.92 (d, 1H), 7.87 (d, 2H), 7.70 (s, 1H), 7.65 (m, 2H), 7.52 (d, 1H), 7.45 (dd, 1H), 4.34 (t, 1H), 3.68 (s, 3H), 2.27 (m, 1H), 0.99 (dd, 6H).

Example 289

(3-(4-(3-(3-chloro-4-(trifluoromethoxy)phenyl)ureido)phenyl) isoxazole-5-carboxamido)-3-methylbutanoic acid The title compound was prepared from Ethyl 2-(3-(4-(3-(3-chloro-4-(trifluoromethoxy) phenyl)ureido)phenyl)isoxazole-5-carboxamido)-3-methylbutanoate as set forth in example 273 and was obtained in 85% yield. MS (ESI): m/z 539.1 (M–H)$^+$; $^1$HNMR (DMSO-$d_6$, 300 MHz): δ 12.86 (bs, 1H), 9.20 (s, 1H), 9.18 (s, 1H), 8.97(d, 1H), 7.92 (d, 1H), 7.87 (d, 2H), 7.71 (s, 1H), 7.65 (m, 2H), 7.52 (d, 1H), 7.45 (dd, 1H), 4.31(t, 1H), 2.28 (m, 1H), 0.99 (dd, 6H).

Example 290

Methyl 2-(3-(4-(3-biphenyl-2-ylureido)phenyl)isoxazole-5-carboxamido)-3-methylbutanoate The title compound was prepared according to the procedure as set forth in example 275, except that biphenyl-2-amine was used in place of 4-(trifluoromethyl) aniline to yield 41% yield of the title compound. MS (ESI): m/z 513.2 (M+H)$^+$; $^1$HNMR (DMSO-$d_6$, 300 MHz): δ 9.30 (s, 1H), 9.20(d, 1H), 7.94 (d, 1H), 7.84 (d, 2H), 7.76 (s, 1H), 7.68 (s, 1H), 7.58 (d, 2H), 7.52 (d, 2H), 7.44 (m, 3H), 7.38 (t, 1H), 7.25 (d, 1H), 7.19(t, 1H), 4.34 (t, 1H), 3.68 (s, 3H), 2.23 (m, 1H), 0.99 (dd, 6H).

Example 291

2-(3-(4-(3-Biphenyl-2-ylureido)phenyl)isoxazole-5-carboxamido)-3-methylbutanoic acid The title compound was prepared from methyl 2-(3-(4-(3-biphenyl-2-ylureido)phenyl) isoxazole-5-carboxamido)-3-methylbutanoate as set forth in example 273 and was obtained in 80% yield. MS (ESI): m/z 499.2(M+H)$^+$; $^1$HNMR (DMSO-$d_6$, 300 MHz): δ 12.85 (bs, 1H), 9.32 (s, 1H), 8.93 (d, 1H), 7.94 (d, 1H), 7.83 (d, 2H), 7.78 (s, 1H), 7.69 (s, 1H), 7.58 (d, 2H), 7.52 (d, 2H), 7.44 (m, 3H), 7.38 (t, 1H), 7.25 (d, 1H), 7.19 (t, 1H), 4.30 (t, 1H), 2.27 (m, 1H), 0.99 (dd, 6H).

Example 292

Methyl 2-(3-(4-(3-(4-cyclohexylphenyl)ureido)phenyl)isoxazole-5-carboxamido)-3-methylbutanoate The title compound was prepared according to the procedure as set forth in example 275, except that 4-cyclohexylaniline was used in place of 4-(trifluoromethyl)aniline to yield 60% of the title compound. MS (ESI): m/z 513.2(M+H)+; ¹HNMR (DMSO-d₆, 300 MHz): δ 9.20 (d, 1H), 9.93 (d, 1H), 8.66 (s, 1H), 7.85 (d, 2H), 7.68 (s, 1H), 7.63 (d, 2H), 7.38 (d, 2H), 7.15 (d, 2H), 4.34 (t, 1H), 3.68 (s, 3H), 2.44 (m, 1H), 2.25 (m, 1H), 1.79 (m, 5H), 1.40 (m, 5H), 0.99 (dd, 6H).

Example 293

2-(3-(4-(3-(4-cyclohexylphenyl)ureido)phenyl)isoxazole-5-carboxamido)-3-methylbutanoic acid The title compound was prepared from methyl 2-(3-(4-(3-(4-cyclohexylphenyl)ureido) phenyl)isoxazole-5-carboxamido)-3-methylbutanoate as set forth in example 273 and was obtained in 82% yield. MS (ESI): m/z 527.1 (M+Na)+; ¹H NMR (DMSO-d₆, 300 MHz): δ 12.85 (bs, 1H), 8.96 (s, 2H), 8.68 (s, 1H), 7.84 (d, 2H), 7.69 (s, 1H), 7.63 (d, 2H), 7.38 (d, 2H), 7.15 (d, 2H), 4.28 (s, 1H), 2.23 (d, 1H), 1.76 (m, 5H), 1.36 (m, 6H), 0.99 (s, 6H).

Example 294

Methyl 3-methyl-2-(3-(4-(3-(2-methyl-4-(trifluoromethoxy)phenyl) ureido)phenyl)isoxazole-5-carboxamido)butanoate The title compound was prepared according to the procedure as set forth in example 275, except that 2-methyl-4-(trifluoromethoxy)aniline was used in place of 4-(trifluoromethyl) aniline to yield 58% of the title compound. MS (ESI): m/z 535.2(M+H)+; ¹HNMR (DMSO-d₆, 300 MHz): δ 9.36 (s, 1H), 9.20 (d, 1H), 8.13 (s, 1H), 7.96 (d, 2H), 7.86 (d, 2H), 7.68 (s, 1H), 7.64 (d, 2H), 7.23 (s, 1H), 7.18 (d, 1H), 4.31 (t, 1H), 3.68 (s, 3H), 2.29 (s, 3H), 2.22 (m, 1H), 0.99 (dd, 6H).

Example 295

3-methyl-2-(3-(4-(3-(2-methyl-4-(trifluoromethoxy)phenyl)ureido) phenyl)isoxazole-5-carboxamido) butanoic acid The title compound was prepared from methyl 3-methyl-2-(3-(4-(3-(2-methyl-4-(trifluoromethoxy)phenyl)ureido)phenyl)isoxazole-5-carboxamido)butanoate as set forth in example 273 and was obtained in 74% yield. MS (ESI): m/z 521.1(M+H)+; ¹HNMR (DMSO-d₆, 300 MHz): δ 12.85 (bs, 1H), 9.39 (s, 1H), 8.96 (d, 1H), 8.16 (s; 1H), 7.96 (d, 2H), 7.87 (d, 2H), 7.70 (s, 1H), 7.65 (d, 2H), 7.24 (s, 1H), 7.19 (d, 1H), 4.28 (t, 1H), 2.29 (s, 3H), 2.23 (m, 1H), 0.97 (s, 6H).

Example 296

Methyl 2-(3-(4-(4-tert-butylbenzamido)phenyl)isoxazole-5-carboxamido)-3-methylbutanoate The title compound was prepared according to the procedure as set forth in example 275, except that 4-tert-butylbenzamide was used in place of 4-(trifluoromethyl) aniline to yield 79% of the title compound. MS (ESI): m/z 527.1 (M+Na)+; ¹HNMR (DMSO-d₆, 300 MHz): δ 10.41 (s, 1H), 9.21 (d, 1H), 7.95 (m, 6H), 7.72 (s, 1H), 7.58 (d, 2H), 4.32 (s, 1H), 3.68 (s, 3H), 2.22 (m, 1H), 1.33 (s, 9H), 0.99 (dd, 6H).

Example 297

2-(3-(4-(4-tert-butylbenzamido)phenyl)isoxazole-5-carboxamido)-3-methylbutanoic acid The title compound was prepared from methyl 2-(3-(4-(4-tert-butylbenzamido)phenyl) isoxazole-5-carboxamido)-3-methylbutanoate as set forth in example 273 and was obtained in 87% yield. MS (ESI): m/z 464.1 (M+Na)+; ¹HNMR (DMSO-d₆, 300 MHz): δ 12.85 (bs, 1H), 10.41 (s, 1H), 8.96 (d, 1H), 7.95 (m, 6H), 7.73 (s, 1H), 7.57 (d, 2H), 4.28 (s, 1H), 2.20 (s, 1H), 1.32 (s, 9H), 0.97 (dd, 6H).

Example 298

(S)-Methyl 2-(3-(4-(3-(2-fluorophenyl)ureido)phenyl)isoxazole-5-carboxamido)-3-hydroxypropanoate 3-(4-(3-(2-fluorophenyl)ureido)phenyl)isoxazole-5-carboxylic acid (example 105, step 2, 1 g, 293 mmol) was dissolved in DMF (20 ml) and, to it N,N'-Dicyclohexyl carbodiimide (724 mg, 3.51 mmol) and 1-Hydroxy benzotriazole (593 mg, 4.39 mmol) were added. Reaction mixture was stirred RT for 10 minutes followed by the addition of L-serine methyl ester hydrochloride (683 mg, 4.39 mmol) dissolved in DMF (5 ml) neutralized with triethylamine (0.6 ml, 4.39 mmol). The above reaction mixture was stirred at RT for 8 hours. DMF was distilled off under reduced pressure to give pale brown solid, which was taken in THF. DCU precipitated out and was filtered off. Water was added and the aqueous layer was extracted with EtOAc. Organic layer was dried over Na₂SO₄ and concentrated under vacuum. Crude compound was purified through precipitation using DCM and petroleum ether to yield 500 mg (39%) of the required compound as white solid. MS: ES (−): m/z 441(M−1); ES (+): m/z 443 (M+1); ¹HNMR (DMSO-d₆; 300 MHz): δ 9.342 (s, 1H), 9.109 (d; 1H), 8.633 (s, 1H), 8.161 (t, 1H), 7.369 (d, 2H), 7.676 (s, 1H), 7.619 (d, 2H), 7.242 (m, 1H), 7.066 (t, 1H), 7.024 (m, 1H), 5.149 (t, 1H), 4.575 (m, 1H), 3.821 (t, 2H), 3.657 (s, 3H).

Example 299

(S)-2-(3-(4-(3-(2-Fluorophenyl)ureido)phenyl)isoxazole-5-carboxamido)-3-hydroxypropanoic acid (S)-methyl 2-(3-(4-(3-(2-fluorophenyl)ureido)phenyl) isoxazole-5-carboxamido)-3-hydroxypropanoate (compound of Example 275, 200 mg, 0.452 mmol) was dissolved in THF and water in 2:1 ratio. Lithium hydroxide monohydrate (29 mg, 0.678 mmol) was added and the reaction mixture was stirred at RT for 4 hours. The reaction mixture was acidified with dilute HCl and extracted with EtOAc. Organic layer was separated, dried over Na₂SO₄ and concentrated under reduced pressure. Crude compound was purified by washing with methanol to get 85 mg (44%) of the title compound. MS: ES (−): m/z 427 (M−1); ES (+): m/z 429(M+1); ¹HNMR (DMSO-d₆, 300 MHz): δ 9.377 (s, 1H), 8.885 (d, 1H), 8.701 (s, 1H), 8.178 (t, 1H), 7.892 (d, 2H), 7.692 (s, 1H), 7.641 (d, 2H), 7.289 (m, 1H), 7.188 (t, 1H), 7.066 (m, 1H), 4.492 (m, 1H), 3.868 (m, 2H), 3.554 (m, 1H), 3.087 (s, 3H).

Example 300

(S)-tert-butyl 2-(3-(4-(3-(2-fluorophenyl)ureido) phenyl)isoxazole-5-carboxamido)-3-methylbutanoate 3-(4-(3-(2-fluorophenyl)ureido)phenyl)isoxazole-5-carboxylic acid (300 g, 0.879 mmol) was dissolved in DMF (20 ml) and to it N,N'-Dicyclohexyl carbodiimide (217 mg, 1.05 mmol) and 1-Hydroxy benzotriazole (176 mg, 1.31 mmol) were added. Reaction mixture was stirred at RT for 10 minutes followed by the addition of L-serine methyl ester hydrochloride (253 mg, 1.31 mmol) dissolved in DMF (5 ml) neutralized with Et₃N (0.18 ml, 1.31 mmol). The above reaction mixture was stirred at RT for 8 hours. DMF was distilled off under reduced pressure to give pale brown solid, which was taken in THF. DCU precipitated out and was filtered off. Water was added and the aqueous layer was extracted with EtOAc. Organic layer was dried over Na₂SO₄ and concentrated under vacuum. Crude compound was purified through precipitation using DCM and petroleum ether to yield 165 mg (38%) of the title compound as white solid. MS: ES (−): m/z 495 (M−1); ES(+): m/z 497(M+1); ¹HNMR (DMSO-d₆, 300 MHz) δ: 9.337(s, 1H), 8.979 (d, 1H), 8.630 (s, 1H), 8.165 (m, 1H), 7.854 (d, 2H), 7.685 (s, 1H), 7.623 (d, 2H), 7.270 (m, 1H), 7.167 (t, 1H), 7.047 (m, 1H), 4.212 (t, 1H), 2.211 (m, 1H), 1.141 (s, 9H), 1.034 (d, 3H), 0.954 (d, 1H).

Example 301

Methyl 2-(3-(4-(3-(2-fluorophenyl)ureido)phenyl) isoxazole-5-carboxamido)acrylate (S)-methyl 2-(3-(4-(3-(2-fluorophenyl)ureido)phenyl) isoxazole-5-carboxamido)-3-hydroxypropanoate (compound of Example 275, 500 mg, 1.13 mmol) was taken in DCM and mesyl chloride (0.13 ml, 1.69 mmol) and Et₃N (0.24, 1.69 mmol) were added and the reaction mixture was stirred at RT for half an hour. Water was added to quench the reaction and the organic layer was extracted with DCM. Organic layer was dried over Na₂SO₄ and concentrated under vacuum. Crude compound was purified by precipitation using DCM and petroleum ether to yield 140 mg (30%) of the required compound as white solid. MS: ES (+) m/z 425(M+1); ¹HNMR (DMSO-d₆, 300 MHz) δ: 10.241 (s, 1H), 8.367 (s, 1H), 8.656 (d, 1H), 8.180 (t, 1H), 7.907 (d, 2H), 7.769 (s, 1H), 7.645 (d, 2H), 7.290 (m, 1H), 7.189 (t, 1H), 7.067 (m, 1H), 6.046 (s, 1H), 5.918 (s, 1H), 3.782 (s, 3H).

Example 302

2-(3-(4-(3-(2-Fluorophenyl)ureido)phenyl)isoxazole-5-carboxamido) acrylic acid

Methyl 2-(3-(4-(3-(2-fluorophenyl)ureido)phenyl)isoxazole-5-carboxamido)acrylate (compound of Example 278, 100 mg, 0.235 mmol) was dissolved in solvent mixture of THF and water (2:1). Lithium hydroxide monohydrate (30 mg, 0707 mmol) was added and the reaction mixture was stirred at RT for 4 hours. The reaction mixture was acidified with dilute HCl and extracted with EtOAc. Organic layer was separated, dried over Na₂SO₄ and concentrated under reduced pressure. Crude compound was, purified by washing with methanol to get 60 mg (63%) of the title compound as white solid. MS: ES (−): m/z 409 (M−1); ES(+): m/z 411(M+1); ¹HNMR (DMSO-d₆, 300 MHz): δ 9.725 (s, 1H), 9.366 (s, 1H), 8.655 (d, 1H), 8.182 (t, 1H), 7.912 (d, 2H), 7.792 (s, 1H), 7.642 (d, 2H), 7.289 (m, 1H), 7.187 (t, 1H), 7.072 (m, 1H), 6.230 (s, 1H), 5.926 (s, 1H).

Example 303

Methyl 2-(3-(4-(3-p-tolylureido)phenyl)isoxazole-5-carboxamido) acrylate

Step 1: (S)-methyl 3-hydroxy-2-(3-(4-nitrophenyl) isoxazole-5-carboxamido) propanoate 3-(4-nitrophenyl)isoxazole-5-carboxylic acid (5 g, 21.36 mmol) was dissolved in DMF (25 ml) and to it N,N'-Dicyclohexyl carbodiimide (5.2 g, 25.64 mmol) and 1-Hydroxy benzotriazole (4.3 g, 32.05 mmol) were added. Reaction mixture was stirred at RT for 10 mins followed by the addition of L-serine methyl ester hydrochloride (6.2 g, 32.05 mmol) dissolved in DMF (5 ml) neutralized with triethylamine (4.4 ml, 32.05 mmol). The above reaction mixture was stirred at RT for 24 hours. DMF was distilled off under reduced pressure to give pale brown solid, which was taken in THF. DCU precipitated out and was filtered off. Water was added and the aqueous layer was extracted with EtOAc. Organic layer was dried over Na₂SO₄ and concentrated under vacuum. Crude compound was purified through precipitation using DCM and petroleum ether to yield 500 mg (49%) of the title compound as brown solid. MS: ES (−): m/z 334 (M−1); ¹HNMR (300 MHz, DMSO-d₆) δ: 9.252 (d, 1H), 8.414 (d, 2H), 8.248 (d, 2H), 7.931 (s, 1H), 5.175 (t, 1H), 4.611 (q, 1H), 3.847 (t, 2H), 3.337 (s, 3H).

Step 2: Methyl 2-(3-(4-nitrophenyl)isoxazole-5-carboxamido) acrylate

To (S)-methyl 3-hydroxy-2-(3-(4-nitrophenyl)isoxazole-5-carboxamido)propanoate (3.5 g, 10.44 mmol) in DCM, mesyl chloride (15.67 mmol) and Et₃N (15.67 mmol) were added and reaction mixture was stirred for 0.5 hours. Water was added to quench the reaction and the organic layer was extracted with DCM followed by purification of the crude by washing with petroleum ether to yield 1.2 g (36%) of the title compound. MS: ES (+): m/z 318(M+1); ¹HNMR (DMSO-d₆, 300 MHz) δ: 10.352 (s, 1H), 8.414 (d, 2H), 8.263 (d, 2H), 7.997 (s, 1H), 6.057 (s, 1H), 5.942 (s, 1H), 3.242 (s, 3H).

Step 3: Methyl 2-(3-(4-aminophenyl)isoxazole-5-carboxamido)acrylate

Methyl 2-(3-(4-nitrophenyl)isoxazole-5-carboxamido) acrylate (1.2 g, 3.78) was dissolved in EtOH (20 ml), THF (8 ml) and water (8 ml). Then ammonium chloride (601 mg, 11.34 mmol)) and iron (529 mg, 9.45) were added and refluxed at 80° C. for 1.5 hours. Reaction mixture was cooled and filtered through celite and solvent was removed under reduced pressure to get dark brown residue. Residue was taken in water and extracted with EtOAc. The organic layer was separated, dried over Na₂SO₄ and concentrated to get dark brown residue, which was purified by column chromatography using EtOAc and petroleum ether to yield 200 mg (18%) of the title compound. MS: ES (+): m/z 288 (M+1); ¹HNMR (DMSO-d₆, 300 MHz) δ: 10.115 (s, 1H), 7.577 (d, 2H), 7.558 (s, 1H), 6.640 (d, 2H), 6.011 (s, 1H), 5.873 (s, 1H), 5.642 (s, 2H), 3.753 (s, 3H).

Step 3: Methyl 2-(3-(4-(3-p-tolylureido)phenyl)isoxazole-5-carboxamido) acrylate Methyl 2-(3-(4-aminophenyl)isoxazole-5-carboxamido) acrylate (120 mg. 0.418 mmol)
Was dissolved in THF (10 ml) and to it 2-fluoro phenylisocyanate (83.41 mg. 0.627 mmol) was added. Reaction mixture was stirred at RT for 24 hours. THF was removed under reduced pressure to get pale brown residue which was purified by column chromatography using EtOAc and CHCl₃ to get 87 mg (50%) of the title product. MS: ES (−): m/z 419 (M−1); ¹HNMR (DMSO-d₆, 300 MHz) δ: 7.848 (s, 1H), 7.804 (s, 1H), 7.781 (s, 1H), 7.620 (m, 3H), 7.331 (s, 1H), 7.310 (s, 1H), 7.097 (s, 2H), 7.087 (s, 2H), 5.903 (d, 2H), 3.760 (s, 3H), 2.239 (s, 3H).

Example 304

2-(3-(4-(3-p-tolylureido)phenyl)isoxazole-5-carboxamido)acrylic acid

Methyl 2-(3-(4-(3-p-tolylureido)phenyl)isoxazole-5-carboxamido)acrylate (125 mg, 0.298 mmol) was dissolved in THF and water in 2:1 ratio. Lithium hydroxide monohydrate (19 mg, 0.447 mmol) was added and the reaction mixture was stirred at room temperature for 1 hour. The reaction mixture was acidified with dilute HCl and extracted with EtOAc. Organic layer was separated, dried over $Na_2SO_4$ and concentrated under reduced pressure. Crude compound was purified by washing with methanol to get 60 mg (50%) white solid as the required compound. MS: ES (+): m/z 407(M+1); $^1$HNMR (DMSO-$d_6$, 300 MHz) δ: 9.732 (s, 1H), 8.989 (s, 1H), 8.714 (s, 1H), 7.894 (d, 2H), 7.784 (s, 1H), 7.638 (d, 2H), 7.377 (d, 2H), 7.121 (d, 2H), 6.232 (s, 1H), 5.921 (s, 1H), 5.918 (s, 3H).

Example 305

(S)-Methyl 2-(3-(4-(3-(2-fluorophenyl)ureido)phenyl)-N-methylisoxazole-5-carboxamido)-3-methylbutanoate

Step 1: (S)-methyl 3-methyl-2-(N-methyl-3-(4-nitrophenyl)isoxazole-5-carboxamido) butanoate To the slurry of sodium hydride (2.17 m mol) in N,N-Dimethylformamide cooled to 0° C., (S)-methyl 3-methyl-2-(3-(4-nitrophenyl)isoxazole-5-carboxamido)butanoate (0.63 g, 1.81 mmol) was added and reaction mixture was stirred for 90 minutes followed by the addition of methyl iodide (2.71 mmol). Reaction mixture was stirred overnight at RT. Water was added to quench the reaction and the organic layer was extracted with EtOAc. Product was purified through column chromatography to yield 360 mg (55%) of the title compound. MS: ES (+): m/z 362(M+1), 384 (M+Na); $^1$HNMR (DMSO-$d_6$, 300 MHz) δ: 8.418 (d, 2H), 8.262 (d, 2H), 7.883-7.672 (s 1H), 4.742-4.146 (d, 1H), 3.736-3.703 (s, 3H), 3.172-2.973 (s, 3H), 2.347 (m, 1H), 1:033-0.853 (d, 3H(×2)).

Step 2: (S)-methyl 2-(3-(4-aminophenyl)-N-methylisoxazole-5-carboxamido)-3-methylbutanoate (S)-methyl 3-methyl-2-(N-methyl-3-(4-nitrophenyl)isoxazole-5-carboxamido)butanoate (compound of step 1, 1.4 g, 3.87) was dissolved in EtOH (20 ml), THF (8 ml) and water (8 ml). Then ammonium chloride (615 mg, 11.61 mmol) and iron (543 mg, 9.69) were added and refluxed at 80° C. for 5 hours. Reaction mixture was cooled and filtered through celite and solvent was removed under reduced pressure to get dark brown residue. Residue was taken in water and extracted with EtOAc. The organic layer was separated, dried over $Na_2SO_4$ and concentrated to get dark brown residue, which was purified by column chromatography using EtOAc and petroleum ether to yield 850 mg (66%). MS: ES (+): m/z 332(M+1); $^1$HNMR (DMSO-$d_6$, 300 MHz) δ: 7.607 (d, 2H), 7.435-7.279 (s 1H), 6.652 (d, 2H), 5.638 (s, 2H), 4.751-4.122 (d, 1H), 3.709-3.691 (s, 3H), 3.183-2.942 (s, 3H), 2.507 (m, 1H), 1.177-2.618 (d, 3H(×2)).

Step 3: (S)-methyl 2-(3-(4-(3-(2-fluorophenyl)ureido)phenyl)-N-methylisoxazole-5-carboxamido)-3-methylbutanoate ((S)-Methyl 2-(3-(4-aminophenyl)-N-methylisoxazole-5-carboxamido)-3-methylbutanoate (170 mg. 0.513 mmol) was dissolved in THF (10 ml) and to it 2-fluorophenylisocyanate (105 mg. 0.770 mmol) was added. Reaction mixture was stirred at RT for 24 hours. THF was removed under reduced pressure to get pale brown residue, which was purified by column chromatography using EtOAc and $CHCl_3$ as the solvent system to yield 160 mg (67%) of the title compound. MS: ES (−): m/z 467 (M−1); ES (+): m/z 469(M+1); $^1$HNMR (DMSO-$d_6$, 300 MHz) δ: 9.356 (s, 1H), 8.648 (d, 1H), 8.176 (t, 1H), 7.906 (d, 2H), 7.631-7.448 (s, 1H+d, 2H), 7.287 (m, 1H), 7.185 (t, 1H), 7.065 (m, 1H), 4.738-4.164 (d, 1H), 3.734-3.702 (s, 3H), 3.151-2.963 (s, 3H), 2.339 (m, 1H), 1.030-0.877 (d, 3H(×2)).

Example 306

(S)-2-(3-(4-(3-(2-fluorophenyl)ureido)phenyl)-N-methylisoxazole-5-carboxamido)-3-methylbutanoic acid

(S)-methyl 2-(3-(4-(3-(2-fluorophenyl)ureido)phenyl)-N-methylisoxazole-5-carboxamido)-3-methylbutanoate (80 mg, 0.17 mmol) was dissolved in THF and water in 2:1 ratio. Lithium hydroxide monohydrate (14 mg, 0.341 mmol) was added and the reaction mixture was stirred at room temperature for 6 hours. The reaction mixture was acidified with dilute HCl and extracted with EtOAc. Organic layer was separated, dried over $Na_2SO_4$ and concentrated under reduced pressure to yield 30 mg (39%) of the title compound. MS: ES (−): m/z 453 (M−1); ES (+): m/z 455(M+1); $^1$HNMR (DMSO-$d_6$, 300 MHz) δ: 9.427(s, 1H), 8.713 (d, 1H), 8.171 (m, 1H), 7.905-7.851 (d, 2H), 7.677-7.524 (m, 3H), 7.283 (m, 1H), 7.183 (t, 1H), 7.068 (m, 1H), 4.661-3.949 (d, 1H), 3.161-2.977 (s, 3H), 2.314 (m, 1H), 1.335-1.065 (d, 3H(×2)).

Example 307

(S)-methyl 2-(3-(4-(3-(4-fluorophenyl)ureido)phenyl)-N-methylisoxazole-5-carboxamido)-3-methylbutanoate

The title compound was prepared according to the procedure as set forth in example 305, except that 1-fluoro-4-isocyanatobenzene was used in place of 2-fluorophenylisocyanate to yield 53% of the title compound. MS: ES (−): m/z 467 (M−1); ES (+): m/z 469 (M+1); $^1$HNMR (DMSO-$d_6$, 300 MHz) δ: 8.976 (s, 1H), 8.807 (s, 1H), 7.886 (d, 2H), 7.623 (d, 3H), 7.503 (m, 2H), 7.168 (t, 2H), 4.736-4.143 (d, 1H), 3.732-3.681 (s, 3H), 3.148-2.961 (s, 3H), 2.358 (m, 1H), 1.028-0.900 (d, 3H(×2)).

Example 308

(S)-2-(3-(4-(3-(4-fluorophenyl)ureido)phenyl)-N-methylisoxazole-5-carboxamido)-3-methylbutanoic acid

The title compound was prepared from (S)-methyl 2-(3-(4-(3-(4-fluorophenyl)ureido) phenyl)-N-methylisoxazole-5-carboxamido)-3-methylbutanoate as set forth in example 306 and was obtained in 36% yield. MS: ES (+): m/z 455(M+1); $^1$HNMR (300 MHz, DMSO-$d_6$, 300 MHz) δ: 8.972 (s, 1H), 8.805 (s, 1H), 7.888(d, 2H), 7.626 (m, 3H), 7.504 (m, 2H), 7.168 (t, 2H), 4.667-3.993 (d, 1H), 3.135-2.962 (s, 3H), 2.3342 (m, 1H), 2.428-2.263 (d, 3H(×2)).

Example 309

(S)-methyl 3-methyl-2-(N-methyl-3-(4-(3-(3-(trifluoromethyl)phenyl) ureido)phenyl)isoxazole-5-carboxamido)butanoate The title compound was prepared according to the procedure as set forth in example 305, except that 1-isocyanato-3-(trifluoromethyl)benzene was used in place of 2-fluorophenylisocyanate to yield 42% of the title compound. MS: ES (−): m/z 517 (M−1), ES (+): m/z 519(M+1); $^1$HNMR (DMSO-d$_6$, 300 MHz): δ 9.154 (s, 1H), 8.111 (d, 1H), 8.035 (s, 1H), 7.903 (d, 2H), 7.652-7.455 (m, 5H), 7.350 (d, 1H), 4.737-4.144 (d, 1H), 3.733-3.686 (s, 3H), 3.151-2.962 (s, 3H), 2.338 (m, 1H), 1.030-0.942 (d, 3H(×2)).

Example 310

(S)-3-methyl-2-(N-methyl-3-(4-(3-(3-(trifluoromethyl)phenyl)ureido) phenyl)isoxazole-5-carboxamido)butanoic acid The title compound was prepared from (S)-methyl 3-methyl-2-(N-methyl-3-(4-(3-(3-(trifluoromethyl)phenyl)ureido)phenyl)isoxazole-5-carboxamido)butanoate as set forth in example 306 and was obtained in 31% yield. MS: ES (−): m/z 503 (M−1); ES(+): m/z 505 (M+1); $^1$HNMR (DMSO-d$_6$, 300 MHz): δ 9.180 (s, 1H), 9.133 d, 1H), 8.036 (s, 1H), 7.904 (d, 2H), 7.652-7.444(m, 5H), 7.347(d, 1H), 4.668-4.007 (d, 1H), 3.138-2.970 (s, 3H), 2.320 (m, 1H), 1.059-0.878 (d, 3H(×2)).

Example 311

(S)-methyl 2-(3-(4-(3-cyclohexylureido)phenyl)-N-methylisoxazole-5-carboxamido)-3-methylbutanoate The title compound was prepared according to the procedure as set forth in example 305, except that isocyanatocyclohexane was used in place of 2-fluorophenylisocyanate to yield 51% of the title compound. MS: ES (+) m/z 457(M+1); $^1$HNMR (DMSO-(d$_6$, 300 MHz): δ 8.602 (s, 1H), 7.817(d, 2H), 7.580 (s, 1H), 7.538 (d, 2H), 6.202 (s, 1H), 4.731-4.135 (d, 1H), 3.728-1698 (s, 3H), 3.139-2.956 (s, 3H), 2.333 (m, 1H), 1.827(m, 2H), 1.685 (m, 2H), 1.566 (s, 1H), 1.398-1.337 (s, 2H), 1.299-1.124 (m, 4H), 1.026-0.835 (d, 3H(×2)).

Example 312

(S)-2-(3-(4-(3-cyclohexylureido)phenyl)-N-methylisoxazole-5-carboxamido)-3-methylbutanoic acid The title compound was prepared from (S)-methyl 2-(3-(4-(3-cyclohexylureido)phenyl)-N-methylisoxazole-5-carboxamido)-3-methylbutanoate as set forth in example 306 and was obtained in 34% yield. MS: ES (+) m/z 442.8(M+1); $^1$HNMR (DMSO-d$_6$, 300 MHz): δ 8.686 (s, 1H), 7.816 (m, 2H), 7.621 (d, 2H), 7.546 (m, 3H), 4.647-3.861 (m, 1H), 3.119-2.984 (s, 3H), 2.515 (m, 1H), 1.823 (m, 2H), 1.688 (m, 2H), 1.563 (s, 1H), 1.474 (s, 2H), 1.398-1.336 (m, 4H), 1.286-1.195 (d, 3H(×2)).

Example 313

(S)-methyl 2-(3-(4-(3-(2-chlorophenyl)ureido)phenyl)-N-methylisoxazole-5-carboxamido)-3-methylbutanoate The title compound was prepared according to the procedure as set forth in example 305, except that 1-chloro-2-isocyanatobenzene was used in place of 2-fluorophenylisocyanate to yield 49% of the title compound. MS: ES(−): m/z 483 (M−1), ES(+): m/z 485(M+1); $^1$HNMR (DMSO-d$_6$, 300 MHz): δ 9.696 (s, 1H), 8.408 (s, 1H), 8.182 (dd, 1H), 7.915 (d, 2H), 7.694-7.618 (m, 3H), 7.351 (m, 1H), 7351(t, 1H), 7.089 (t, 1H), 4.740-4.148 (d, 1H), 3.736-3.684 (s, 3H), 3.211-2.965 (s, 3H), 2.516 (m, 1H), 1.032-0.879 (d, 3H(×2)).

Example 314

(S)-2-(3-(4-(3-(2-chlorophenyl)ureido)phenyl)-N-methylisoxazole-5-carboxamido)-3-methylbutanoic acid The title compound was prepared from (S)-methyl 2-(3-(4-(3-(2-chlorophenyl)ureido) phenyl)-N-methylisoxazole-5-carboxamido)-3-methylbutanoate as set forth in example 306 and was obtained in 42% yield. MS: ES (−): m/z 469(M−1), ES(+): m/z 471(M+1); $^1$HNMR (DMSO-d$_6$, 300 MHz): δ 9.764 (s, 1H), 8.469 (s, 1H); 8.166 (d, 1H), 7.912 (m, 2H), 7.709 (d, 1H), 7.648 (d, 2H), 7.487 (d, 1H), 7.344 (t, 1H), 7.084 (m, 1H), 4.654-3.881 (d, 1H), 3.180-2.983 (s, 3H), 2.273 (m, 1H), 1.056-0.817 (d, 3H(×2)).

Example 315

(R)-methyl 2-(3-(4-(2-fluorophenylsulfonamido) phenyl)isoxazole-5-carboxamido)-3-methylbutanoate To a solution of 500 mg (1.57 mmol) of (R)-methyl 2-(3-(4-aminophenyl)isoxazole-5-carboxamido)-3-methylbutanoate (example 151, step 3) in DCM, 1.2 eq of pyridine was added and stirred for 10 minutes, then 368 mg (1.89 mmol) 2-fluorobenzene-1-sulfonyl chloride was added and the reaction mixture was stirred for 3 hours. DCM was removed under vacuum, the reaction mixture was washed with 1NHCl and extracted with EtOAc. The organic layer was concentrated and purified by precipitation using DCM and petroleum ether to yield 410 mg (86%) of title compound. MS (ESI): m/z 476(M+H)$^+$; $^1$HNMR (DMSO-d$_6$, 300 MHz): δ 11.039 (s, 1H), 9.215 (d, 1H), 7.942 (m, 1H), 7.805 (d, 2H), 7.718 (m, 1H), 7.625 (s, 1H), 7.465 (m, 2H), 7.271(d, 2H), 4.314 (t, 1H), 3.690 (s, 3H), 2.228 (m, 1H), 0.971 (d, 6H).

Example 316

(R)-Methyl 2-(3-(4-(2,6-difluorophenylsulfonamido) phenyl) isoxazole-5-carboxamido)-3-methylbutanoate The title compound was prepared according to the procedure as set forth in example 315, except that 2,6-difluorobenzene-1-sulfonyl chloride was used in place of 2-fluorobenzene-1-sulfonyl chloride to yield 82% of the title compound. MS (ESI: m/z 494 (M+H)$^+$; $^1$HNMR (DMSO-d$_6$, 300 MHz): δ 11.311 (s, 1H), 9.224 (d, 1H), 7.851 (d, 2H), 7.771 (m, 1H), 7.639 (s, 1H), 7.330 (t, 4H), 4.317 (t, 1H), 3.667 (s, 3H), 2.254 (m, 1H), 0.974 (d, 6H).

Example 317

(R)-2-(3-(4-(2,6-Difluorophenylsulfonamido)phenyl) isoxazole-5-carboxamido)-3-methylbutanoic acid The title compound was prepared from (R)-methyl 2-(3-(4-(2,6-difluorophenyl sulfonamido)phenyl)isoxazole-5-carboxamido)-3-methylbutanoate as set forth in example 306 and was obtained in 56% yield. MS (ESI): m/z 480(M+H)+; $^1$HNMR (DMSO-d$_6$, 300 MHz): δ 12.856 (bs, 1H), 11.305 (s, 1H), 8.988 (d, 1H), 7.880 (d, 2H), 7.769 (m, 1H), 7.650 (s, 1H), 7.329 (m, 4H), 4.287 (t, 1H), 2.256 (m, 1H), 0.972 (d, 6H).

Example 318

(R)-methyl 3-methyl-2-(3-(4-(4-(trifluoromethyl) phenylsulfonamido) phenyl)isoxazole-5-carboxamido)butanoate The title compound was prepared according to the procedure as set forth in example 315, except that 4-(trifluoromethyl)benzene-1-sulfonyl chloride was used in place of 2-fluorobenzene-1-sulfonyl chloride to yield 80% of the title compound. MS (ESI): m/z 526(M+H)+; $^1$HNMR (DMSO-d$_6$, 300 MHz): δ 10.929 (s, 1H), 9.223 (d, 1H), 8.041 (m, 4H), 7.864(d, 2H), 7.644 (s, 1H), 7.283 (d, 2H), 4.318 (t, 1H), 3.690 (s, 3H), 2.356 (m, 1H), 1.006(d, 6H).

Example 319

(R)-3-methyl-2-(3-(4-(4-(trifluoromethyl)phenylsulfonamido)phenyl) isoxazole-5-carboxamido)butanoic acid The title compound was prepared from (R)-methyl 3-methyl-2-(3-(4-(4-(trifluoromethyl)phenylsulfonamido)phenyl)isoxazole-5-carboxamido)butanoate as set forth in example 306 and was obtained in 53% yield. MS (ESI): m/z 512(M+H)+; $^1$HNMR (DMSO-d$_6$, 300 MHz): δ 12.867 (bs, 1H), 10.934 (s, 1H), 8.989 (d, 1H), 8.041 (m, 4H), 7.831 (d, 2H), 7.656 (s, 1H), 7.285 (d, 2H), 4.289 (t, 1H), 2.257 (m, 1H), 1.194 (d, 6H).

Example 320

(R)-2-(3-(4-(3,5-Difluorophenylsulfonamido)phenyl) isoxazole-5-carboxamido)-3-methylbutanoic acid The title compound was prepared from (R)-methyl 2-(3-(4-(3,5-difluorophenyl sulfonamido)phenyl)isoxazole-5-carboxamido)-3-methylbutanoate as set forth in example 306 and was obtained in 48% yield. MS (ESI): m/z 480 (M+H)+; $^1$HNMR (DMSO-d$_6$, 300 MHz): δ 11.750 (bs, 1H), 8.975(d, 1H), 7.836 (d, 2H), 7.669 (s, 1H), 7.641 (m, 1H), 7.552 (s, 1H), 7.294 (d, 2H), 4.289 (t, 1H), 2.238 (m, 1H), 0.975 (d, 6H).

Example 321

Methyl 2-(3-(4-(benzyloxy)phenyl)isoxazole-5-carboxamido)-3-methylbutanoate

Step 1: 4-(benzyloxy)benzaldehyde

To 4-Hydroxy benzaldehyde (10 g) in acetone (200 ml), potassium carbonate (16.96 g) was added and stirred. To this, benzyl bromide (12.67 ml) was added and the reaction mixture was refluxed for 3 hours and then cooled. The reaction mixture was filtered and the filtrate was concentrated to obtain pale brown colored oil which got solidified at room temperature. Solid was crystallized from DCM-Petroleum ether to obtain the title compound as pale yellow solid. Yield: 13 g (74%); $^1$HNMR (CDCl$_3$; 300 MHz): δ 9.91 (s, 1H), 7.87 (d, 2H), 7.33-7.43 (m, 5H), 7.12 (d, 21-1) 5.17 (s, 2H).

Step 2: (Z)-4-(benzyloxy)benzaldehyde oxime

To 4-(benzyloxy)benzaldehyde (12.9 g) in MeOH (129 ml), Hydroxylamine hydrochloride (6.34 g) was added and the reaction mixture was refluxed for 3 hours and then cooled. The reaction mixture was concentrated to obtain pale brown residue. To this residue, water was added and it was extracted with EtOAc. Organic layer was collected, dried over Na$_2$SO$_4$ and concentrated to obtain off white solid, which was crystallized from DCM-Petroleum ether to obtain the title compound as white solid. Yield: 11.5 g (83%); $^1$HNMR (DMSO-d$_6$; 300 MHz): δ 10.98 (s, 1H), 8.06 (s, 1H), 7.53 (d, 2H), 7.33-7.46 (m, 5H), 7.05 (d, 2H), 5.13 (s, 2H).

Step 3: (E)-4-(benzyloxy)-N-hydroxybenzimidoyl chloride

To (Z)-4-(benzyloxy)benzaldehyde oxime (11.3 g) in N,N'-Dimethyl formamide (57 ml), N-Chlorosuccinimide (7.98 g) was added and the reaction mixture was stirred for 3 hours and then solvent was evaporated to dark brown residue. To this residue water was added and extracted with Ethyl acetate. Organic layer was collected and dried over Na$_2$SO$_4$ and concentrated to obtain pale brown solid, which was crystallized from DCM-Petroleum ether to obtain the title compound as white solid. Yield: 7.9 g (60%); $^1$HNMR (DMSO-d$_6$; 300 MHz): δ 12.17 (s, 1H), 7.73 (d, 2H), 7.33-7.47 (m, 5H), 7.11 (d, 2H) 5.16 (s, 2H).

Step 4. Ethyl 3-(4-(benzyloxy)phenyl)isoxazole-5-carboxylate

To (E)-4-(benzyloxy)-N-hydroxybenzimidoyl chloride (7.8 g) in Toluene (78 ml), Ethyl propiolate (7.25 ml) was added and stirred. To this, Et$_3$N (4.58 ml) was added dropwise since reaction was exothermic and the reaction mixture was then heated to 80° C. for 2 hours. The reaction mixture was cooled, diluted with Ethyl acetate and washed successively with 0.1M Aqueous HCl, water and brine. Organic layer was collected and concentrated to obtain dark brown residue which was purified by column chromatography (silica gel, DCM) to obtain pale brown solid which was crystallized from DCM-Petroleum ether to obtain the title compound as off white solid. Yield: 2.83 g (29%); MS (ES+): m/z 324 (M+1); $^1$HNMR (CDCl$_3$; 300 MHz): δ 7.8 (d, 2H), 7.36-7.47 (m, 5H), 7.28 (s, 1H), 7.1 (d, 2H), 5.14 (s, 2H), 4.48 (q, 2H), 1.45 (t, 3H).

Step 5: 3-(4-(benzyloxy)phenyl)isoxazole-5-carboxylic acid

To Ethyl 3-(4-(benzyloxy)phenyl)isoxazole-5-carboxylate (900 mg) in THF (18 ml), 1M aqueous solution of NaOH (13.9 ml) was added and the reaction mixture was stirred for 20 minutes. It was acidified with 1 Molar hydrochloric acid and extracted with ethyl acetate. Organic layer was collected and dried over Na$_2$SO$_4$ and concentrated to obtain pale yellow solid, which was crystallized using EtOAc—petroleum ether to obtain the title compound as off white solid. Yield: 765 mg (93%); MS (ES+): m/z 296 (M+1); $^1$H NMR (DMSO-d$_6$; 300 MHz): δ 7.91 (d, 2H), 7.73 (s, 1H), 7:34-7.48 (m, 5H), 7.17 (d, 2H), 5.19 (s, 2H).

Step 6: Methyl 2-(3-(4-(benzyloxy)phenyl)isoxazole-5-carboxamido)-3-methylbutanoate To 3-(4-(benzyloxy)phenyl)isoxazole-5-carboxylic acid (300 mg) in THF (10 ml), N-methyl morpholine (0.111 ml) was added and reaction mixture was stirred for 10 minutes at RT. Reaction mixture was cooled to −20° C., isobutyl chloroformate (0.132 ml) was added and stirred for 15-20 minutes at −20 to −30° C. L-valine methyl ester hydrochloride (238 mg) neutralized with $Et_3N$ (0.198 ml) in THF (5 ml) and added to the above reaction mixture and stirred at −20 to −30° C. for 5 minutes. Then the reaction mixture was gradually allowed to warm to RT over a period of 1 hour. Solvent was evaporated to obtain pale brown solid, which was purified by column chromatography (silica gel, EtOAc—Chloroform) to obtain off white solid, which was crystallized using EtOAc—petroleum ether to obtain the title compound as white solid. Yield: 232 mg (55%); MS (ES+): m/z 409 (M+1); $^1$H NMR (DMSO-$d_6$; 300 MHz): δ 9.19 (d, 1H), 7.87 (d, 2H), 7.68 (s, 1H), 7.32-7.49 (m, 5H), 7.19 (d, 2H), 5.19 (s, 2H), 4.31 (m, 1H), 3.67 (s, 3H), 2.22 (m, 1H), 0.96 (d, 6H).

Example 322

2-(3-(4-(Benzyloxy)phenyl)isoxazole-5-carboxamido)-3-methylbutanoic acid

To Methyl 2-(3-(4-(benzyloxy)phenyl)isoxazole-5-carboxamido)-3-methylbutanoate (150 mg) in THF (3 ml), 1 M aqueous solution of Lithium hydroxide monohydrate (0.735 ml) was added and reaction mixture was stirred at RT for 6 hours. The reaction mixture was acidified with dilute HCl and extracted with EtOAc. Organic layer was collected and dried over $Na_2SO_4$ and concentrated to obtain off white solid, which was crystallized from EtOAc to obtain the title compound as white solid. Yield: 80 mg (55%); MS (ES+): m/z 395 (M+1); $^1$HNMR (DMSO-$d_6$; 300 MHz): δ 12.91 (bs, 1H), 8.94 (d, 1H), 7.87 (d, 2H), 7.69 (s, 1H), 7.32-7.49 (m, 5H), 7.19 (d, 2H), 5.19 (s, 2H), 4.28 (m, 1H), 2.22 (m, 1H), 0.96 (d, 6H).

Example 323

Methyl 2-(3-(4-(4-fluorobenzyloxy)phenyl)isoxazole-5-carboxamido)-3-methylbutanoate Step 1: Methyl 2-(3-(4-hydroxyphenyl)isoxazole-5-carboxamido)-3-methylbutanoate To Methyl 2-(3-(4-(benzyloxy)phenyl)isoxazole-5-carboxamido)-3-methylbutanoate (6 g) in THF (120 ml), 10% Palladium on carbon (Wet, 600 mg) was added and hydrogenated at 50 psi for 3 hours. Reaction mixture was filtered through Celite and filtrate was concentrated to obtain yellow residue. This residue was purified by column chromatography (silica gel, EtOAc—$CHCl_3$) to obtain yellow solid, which was crystallized using DCM—Petroleum ether to obtain the title compound as pale yellow solid. Yield: 2.25 g (48%); MS (ES+): m/z−319 (M+1); $^1$HNMR (DMSO-$d_6$; 300 MHz): δ 10.01 (bs, 1H), 9.16 (d, 1H), 7.75 (d, 2H), 7.61 (s, 1H), 6.91 (d, 2H), 4.3 (m, 1H), 3.67 (s, 3H), 2.21 (m, 1H), 0.96 (d, 6H);

Step 2: Methyl 2-(3-(4-(4-fluorobenzyloxy)phenyl) isoxazole-5-carboxamido)-3-methylbutanoate To methyl 2-(3-(4-hydroxyphenyl)isoxazole-5-carboxamido)-3-methylbutanoate (150 mg) in, acetone (3 ml), potassium carbonate (78 mg) was added and stirred. To this 1-(bromomethyl)-4-fluorobenzene (0.07 ml) was added and the reaction mixture was refluxed for 2 hours and then cooled reaction. The mixture was filtered and filtrate was concentrated to obtain pale brown residue. To this residue, water was added and extracted with EtOAc. Organic layer was collected and dried over $Na_2SO_4$ and concentrated to obtain off white solid, which was crystallized using DCM-Petroleum ether to obtain the title compound as white solid. Yield: 170 (84%); MS (ES+): m/z 427 (M+1); $^1$HNMR (DMSO-$d_6$; 300 MHz): δ 9.18 (d, 1H), 7.88 (d, 2H), 7.68 (s, 1H), 7.53 (m, 2H), 7.23 (m, 2H), 7.18 (d, 2H), 5.17 (s, 2H), 4.31 (m, 1H), 3.67 (s, 3H), 2.22 (m, 1H), 0.96 (d, 6H).

Example 324

2-(3-(4-(Benzyloxy)phenyl)isoxazole-5-carboxamido)-3-methylbutanoic acid

The title compound was prepared from methyl 2-(3-(4-(4-fluorobenzyloxy)phenyl) isoxazole-5-carboxamido)-3-methylbutanoate as set forth in example 322 and was obtained in 56% yield. MS (ES+): m/z 413 (M+1); $^1$H NMR (DMSO-$d_6$; 300 MHz): δ 12.81 (bs, 1H), 8.95 (d, 1H), 7.87 (d, 2H), 7.69 (s, 1H), 7.53 (m, 2H), 7.23 (m, 2H) 7.18 (d, 2H), 5.17 (s, 2H), 4.27 (m, 1H), 2.22 (m, 1H), 0.97 (d, 6H).

Example 325

Methyl 3-methyl-2-(3-(4-(3-(trifluoromethyl)benzyloxy)phenyl) isoxazole-5-carboxamido)butanoate The title compound was prepared according to the procedure as set forth in example 323, except that 1-(bromomethyl)-3-(trifluoromethyl)benzene was used in place of 1-(bromomethyl)-4-fluorobenzene to yield 97% of the title compound. MS (ES+): m/z 477 (M+1); $^1$HNMR (DMSO-$d_6$, 300 MHz): δ 9.19 (d, 1H), 7.89 (d, 2H), 7.85 (m, 1H), 7.78 (m, 1H), 7.71 (m, 1H), 7.69 (s, 1H), 7.66 (m, 1H), 7.21 (d, 2H), 5.31 (s, 2H), 4.31 (m, 1H), 3.67 (s, 3H), 2.22 (m, 1H), 0.96 (d, 6H).

Example 326

3-Methyl-2-(3-(4-(3-(trifluoromethyl)benzyloxy) phenyl)isoxazole-5-carboxamido)butanoic acid The title compound was prepared from methyl 3-methyl-2-(3-(4-(3-(trifluoromethyl) benzyloxy)phenyl)isoxazole-5-carboxamido)butanoate as set forth in example 322 and was obtained in 75% yield. MS (ES+): m/z 463 (M+1); $^1$HNMR (DMSO-$d_6$, 300 MHz): δ 12.85 (bs, 1H), 8.94 (d, 1H), 7.89 (d, 2H), 7.85 (m, 1H), 7.78 (m, 1H), 7.7 (m, 1H), 7.68 (s, 1H), 7.66 (m, 1H), 7.22 (d, 2H), 5.31 (s, 2H), 4.28 (m, 1H), 2.22 (m, 1H), 0.97 (d, 6H).

Example 327

Methyl 3-methyl-2-(3-(4-(4-(trifluoromethyl)benzyloxy)phenyl) isoxazole-5-carboxamido)butanoate The title compound was prepared according to the procedure as set forth in example 323, except that 1-(bromomethyl)-4-(trifluoromethyl)benzene was used in place of 1-(bromomethyl)-4-fluorobenzene to yield 93% of the title compound. MS (ES+): m/z 477 (M+1); $^1$HNMR (DMSO-$d_6$, 300 MHz): δ 9.18 (d, 1H), 7.89 (d, 2H), 7.8 (d, 2H), 7.71 (d, 2H), 7.68 (s, 1H), 7.2 (d, 2H), 5.32 (s, 2H), 4.31 (m, 1H), 3.67 (s, 3H), 2.22 (m, 1H), 0.96 (d, 6H).

Example 328

3-methyl-2-(3-(4-(4-(trifluoromethyl)benzyloxy) phenyl)isoxazole-5-carboxamido)butanoic acid The title compound was prepared from methyl 3-methyl-2-(3-(4-(4-(trifluoromethyl) benzyloxy)phenyl)isoxazole-5-carboxamido)butanoate as set forth in example 322 and was obtained in 86% yield. MS (ES+): m/z 463 (M+1); $^1$HNMR (DMSO-$d_6$, 300 MHz): δ 12.8 (bs, 1H), 8.95 (d, 1H), 7.89 (d, 2H), 7.79 (d, 2H), 7.71 (d, 2H), 7.7 (s, 1H), 7.2 (d, 2H), 5.32 (s, 2H), 4.28 (m, 1H), 2.22 (m, 1H), 0.97 (d, 6H).

Example 329

Methyl 3-methyl-2-(3-(4-(2-(trifluoromethyl)benzyloxy)phenyl) isoxazole-5-carboxamido)butanoate The title compound was prepared according to the procedure as set forth in example 323, except that 1-(bromomethyl)-2-(trifluoromethyl)benzene was used in place of 1-(bromomethyl)-4-fluorobenzene to yield 97% of the title compound. MS (ES+): m/z 477 (M+1); $^1$HNMR (DMSO-$d_6$, 300 MHz): δ 9.2 (d, 1H), 7.9 (d, 2H), 7.81 (m, 1H), 7.78 (m, 1H), 7.74 (m, 1H), 7.69 (s, 1H), 7.61 (m, 1H), 7.19 (d, 2H), 5.32 (s, 2H), 4.31 (m, 1H), 3.68 (s, 3H), 2.22 (m, 1H), 0.97 (d, 6H).

Example 330

3-Methyl-2-(3-(4-(2-(trifluoromethyl)benzyloxy) phenyl)isoxazole-5-carboxamido)butanoic acid The title compound was prepared from methyl 3-methyl-2-(3-(4-(2-(trifluoromethyl) benzyloxy)phenyl)isoxazole-5-carboxamido)butanoate as set forth in example 322 and was obtained in 90% yield. MS (ES+): m/z 463 (M+1); $^1$HNMR (DMSO-$d_6$, 300 MHz): δ 12.82 (bs, 1H), 8.96 (d, 1H), 7.9 (d, 2H), 7.83 (m, 1H), 7.78 (m, 1H), 7.74 (m, 1H), 7.7 (s, 1H), 7.61 (m, 1H), 7.19 (d, 2H), 5.32 (s, 2H), 4.28 (m, 1H), 2.22 (m, 1H), 0.97 (d, 6H).

Example 331

Methyl 2-(3-(4-(2,4-difluorobenzyloxy)phenyl)isoxazole-5-carboxamido)-3-methylbutanoate The title compound was prepared according to the procedure as set forth in example 323, except that 1-(bromomethyl)-2,4-difluorobenzene was used in place of 1-(bromomethyl)-4-fluorobenzene to yield 93% of the title compound. MS (ES+): m/z 445 (M+1); $^1$HNMR (DMSO-$d_6$, 300 MHz): δ 9.19 (d, 1H), 7.89 (d, 2H), 7.67 (s, 1H), 7.64 (m, 1H), 7.33 (m, 1H), 7.18 (d, 2H), 7.15 (m, 1H), 5.19 (s, 2H), 4.31 (m, 1H), 3.67 (s, 3H), 2.22 (m, 1H), 0.96 (d, 6H).

Example 332

2-(3-(4-(2,4-Difluorobenzyloxy)phenyl)isoxazole-5-carboxamido-3-methylbutanoic acid The title compound was prepared from methyl 2-(3-(4-(2,4-difluorobenzyloxy)phenyl) isoxazole-5-carboxamido)-3-methylbutanoate as set forth in example 322 and was obtained in 84% yield. MS (ES+): m/z 431 (M+1); $^1$HNMR (DMSO-$d_6$, 300 MHz): δ 12.84 (bs, 1H), 8.95 (d, 1H), 7.89 (d, 2H), 7.7 (s, 1H), 7.64 (m, 1H), 7.32 (m, 1H), 7.18 (d, 2H), 7.15 (m, 1H), 5.19 (s, 2H), 4.28 (m, 1H), 2.22 (m, 1H), 0.97 (d, 6H).

Example 333

Methyl 1-(3-(4-(benzyloxy)phenyl)isoxazole-5-carbonyl)pyrrolidine-2-carboxylate

The title compound was prepared according to the procedure as set forth in example 321, except that L-Proline was used in place of L-valine methyl ester hydrochloride.

Yield: 41%; MS (ESI): m/z 429 (M+Na)$^+$; $^1$HNMR (DMSO-$d_6$, 300 MHz): δ 7.9 (d, 2H), 7.66 (s, 1H), 7.46-7.32 (m, 5H), 7.16 (d, 2H), 5.19 (s, 2H), 3.91 (t, 1H), 3.67 (s, 3H), 3.6 (t, 1H), 2.27 (m, 1H), 2.02-1.9 (m, 4H).

Example 334

Methyl 2-(3-(4-(6-fluorobenzo[d]thiazol-2-yloxy) phenyl)isoxazole-5-carboxamido)-3-methylbutanoate To methyl 2-(3-(4-hydroxyphenyl)isoxazole-5-carboxamido)-3-methylbutanoate (200 mg) in N,N'-Dimethyl formamide (4 ml), cesium carbonate (245 mg) was added and stirred for 15-20 minutes. To this 2-chloro-6-fluorobenzo[d] thiazole (141 mg) was added and the reaction mixture was stirred at RT for 18 hours. Solvent was evaporated to obtain pale brown solid, which was purified by column chromatography (silica gel, EtOAc—CHCl$_3$) to obtain off white solid, which was crystallized using DCM-Petroleum ether to obtain the title compound as white solid. Yield: 240 mg (81%); MS (ES+): m/z 470 (M+1); $^1$HNMR (DMSO-$d_6$, 300 MHz): δ 9.27 (d, 1H), 8.08 (d, 2H), 7.93 (dd, 1H), 7.8 (s, 1H), 7.74 (dd, 1H), 7.67 (d, 2H), 7.31 (m, 1H), 4.33 (m, 1H), 3.69 (s, 3H), 2.23 (m, 1H), 0.98 (d, 6H).

Example 335

2-(3-(4-(6-fluorobenzo[d]thiazol-2-yloxy)phenyl) isoxazole-5-carboxamido)-3-methylbutanoic acid To Methyl 2-(3-(4-(6-fluorobenzo[d]thiazol-2-yloxy)phenyl)isoxazole-5-carboxamido)-3-methylbutanoate (160 mg) in THF (4 ml), 1 M aqueous solution of Lithium hydroxide monohydrate (0.68 ml) was added and reaction mixture was stirred at RT for 6 hours. The reaction mixture was acidified with dilute HCl and extracted with EtOAc. Organic layer was collected and dried over Na$_2$SO$_4$ and concentrated to obtain off white solid, which was crystallized from EtOAc to yield 82 mg (52%) of the title compound as white solid. MS (ES+): m/z 456 (M+1); $^1$HNMR (DMSO-$d_6$, 300 MHz): δ 12.9 (bs, 1H), 9.04 (d, 1H), 8.08 (d, 2H), 7.93 (dd, 1H), 7.81 (s, 1H), 7.75 (dd, 1H), 7.67 (d, 2H), 7.3 (m, 1H), 4.29 (m, 1H), 2.23 (m, 1H), 0.96 (d, 6H).

Example 336

Methyl 3-methyl-2-(3-(4-(2-oxo-2-(3-(trifluoromethyl)phenylamino) acetamido)phenyl)isoxazole-5-carboxamido)butanoate To 3-(trifluoromethyl)aniline (0.117 ml), methyl 2-(3-(4-aminophenyl)isoxazole-5-carboxamido)-3-methylbutanoate (300 mg, example 151, step 3) in EtOAc (6 ml), oxalyl chloride was added and stirred at RT for 3 hours. To this water was added and organic layer was collected and dried over Na$_2$SO$_4$ and concentrated to obtain brown solid which was purified by column chromatography (silica gel, EtOAc—CHCl$_3$ to obtain pale brown solid which was crystallized from DCM-Petroleum ether to yield 150 mg (29%) of the title compound as off white solid. MS (ES+): m/z 533 (M+1); $^1$HNMR (DMSO-d$_6$; 300 MHz): δ 11.24 (s, 1H), 11.14 (s, 1H), 9.25 (d, 1H), 8.35 (dd, 1H), 8.16 (dd, 1H), 8.06 (d, 2H), 7.96 (d, 2H), 7.72 (s, 1H), 7.64 (m, 1H), 7.54 (dd, 1H), 4.31 (m, 1H), 3.68 (s, 3H), 2.23 (m, 1H), 0.97 (d, 6H).

Example 337

3-Methyl-2-(3-(4-(2-oxo-2-(3-(trifluoromethyl)phenylamino) acetamido)phenyl)isoxazole-5-carboxamido)butanoic acid To methyl 3-methyl-2-(3-(4-(2-oxo-2-(3-(trifluoromethyl)phenylamino)acetamido) phenyl)isoxazole-5-carboxamido) butanoate (100 mg) in THF (2 ml) 1 M aqueous solution of Lithium hydroxide monohydrate (0.375 ml) was added and reaction mixture was stirred at RT for 6 hours. The reaction mixture was acidified with dilute HCl and extracted with EtOAc. Organic layer was collected and dried over Na$_2$SO$_4$ and concentrated to obtain off white solid, which was crystallized from EtOAc to yield 22 mg (22%) of the title compound as white solid. MS (ES+): m/z 519 (M+1); $^1$HNMR (DMSO-d$_6$; 300 MHz): δ 11.24 (s, 1H), 11.13 (s, 1H), 9.01 (d, 1H), 8.35 (dd, 1H), 8.16 (dd, 1H), 8.06 (d, 2H), 7.96 (d, 2H), 7.73 (s, 1H), 7.64 (m, 1H), 7.54 (dd, 1H), 4.28 (m, 1H), 2.23 (m, 1H), 0.98 (d, 6H).

Example 338

Methyl 2-(3-(4-(2-(2,4-difluorophenylamino)-2-oxoacetamido)phenyl)isoxazole-5-carboxamido)-3-methylbutanoate The title compound was prepared according to the procedure as set forth in example 336, except that 2,4-difluoroaniline was used in place of 3-(trifluoromethyl)aniline to yield 27% of the title compound. MS (ES+): m/z 501 (M+1); $^1$HNMR (DMSO-d$_6$; 300 MHz): δ 11.12 (s, 1H), 10.62 (s, 1H), 9.24 (d, 1H), 8.05 (d, 2H), 7.96 (d, 2H), 7.12 (s, 1H), 7.64 (m, 1H), 7.45 (m, 1H), 7.39 (m, 1H), 4.31 (m, 1H), 3.68 (s, 3H), 2.23 (m, 1H), 0.97 (d, 6H).

Example 339

2-(3-(4-(2-(2,4-difluorophenylamino)-2-oxoacetamido)phenyl) isoxazole-5-carboxamido)-3-methylbutanoic acid The title compound was prepared from methyl 2-(3-(4-(2-(2,4-difluorophenylamino)-2-oxoacetamido)phenyl)isoxazole-5-carboxamido)-3-methylbutanoate as set forth in example 333 and was obtained in 60% yield. MS (ES+): m/z 487 (M+1); $^1$HNMR (DMSO-d$_6$; 300 MHz): δ 12.88 (bs, 1H), 11.11 (s, 1H), 10.61 (s, 1H), 8.99 (d, 1H), 8.05 (d, 2H), 7.95 (d, 2H), 7.73 (s, 1H), 7.64 (m, 1H), 7.42 (m, 1H), 7.16 (m, 1H), 4.28 (m, 1H), 2.23 (m, 1H), 0.98 (d, 6H).

Example 340

Methyl 2-(3-(4-((R)-2-hydroxy-2-phenylacetamido) phenyl) isoxazole-5-carboxamido)-3-methylbutanoate To (R)-2-hydroxy-2-phenylacetic acid (200 mg), methyl 2-(3-(4-aminophenyl) isoxazole-5-carboxamido)-3-methylbutanoate (417 mg), in N,N'-Dimethyl formamide (5 ml), DCC (406 mg) and HOBT (177 mg) were added and stirred at RT for 16 hours. The reaction mixture was filtered and concentrated to obtain brown oil which was purified by column chromatography (silica gel, EtOAc—CHCl$_3$) to obtain pale brown solid which was crystallized from DCM-Petroleum ether to yield 235 mg (39%) of the title compound as off white solid. MS (ES+): m/z 452 (M+1); $^1$H NMR (DMSO-d$_6$; 300 MHz): δ 10.19 (s, 1H), 9.2 (d, 1H), 7.88 (d, 4H), 7.69 (s, 1H), 7.54 (m, 2H), 7.39-7.27 (m, 3H), 6.51 (d, 1H), 5.13 (d, 1H), 4.3 (m, 1H), 3.67 (s, 3H), 2.24 (m, 1H), 0.96 (d, 6H).

Example 341

2-(3-(4-((R)-2-hydroxy-2-phenylacetamido)phenyl) isoxazole-5-carboxamido)-3-methylbutanoic acid To Methyl 2-(3-(4-((R)-2-hydroxy-2-phenylacetamido) phenyl)isoxazole-5-carboxamido)-3-methylbutanoate (135 mg) in THF (4 ml) 1 M aqueous solution of Lithium hydroxide monohydrate (0.6 ml) was added and reaction mixture was stirred at RT for 6 hours. The reaction mixture was acidified with dilute HCl and extracted with EtOAc. Organic layer was collected and dried over Na$_2$SO$_4$ and concentrated to obtain off white solid, which was crystallized from EtOAc to obtain the title compound as white solid. Yield: 80 mg (61%); MS (ES+): m/z 438 (M+1); $^1$HNMR (DMSO-d$_6$; 300 MHz): δ 12.86 (bs, 1H), 10.2 (s, NH), 8.97 (d, 1H), 7.88 (d, 4H), 7.7 (s, 1H), 7.54 (m, 2H), 7.39-7.29 (m, 3H), 6.51 (d, 1H), 5.13 (d, 1H), 4.27 (m, 1H), 2.19 (m, 1H), 0.97 (d, 6H).

Example 342

(S)-Methyl 2-(3-(4-(3-(4-fluorophenyl)ureido)phenyl)-1,2,4-oxadiazole-5-carboxamido)-3-methylbutanoate The title compound was prepared according to the procedure as set forth in example 104, step 5 except that 1-fluoro-4-isocyanatobenzene was used in place of 2,4-difluoro-1-isocyanatobenzene to yield 67% of the title compound. MS (ESI) m/z: 454(M−H)$^{−1}$; HNMR (DMSO-d$_6$, 300 MHz): δ 9.697 (d, 1H), 9.088 (s, 1H), 8.837 (s, 1H), 8.015 (d, 2H), 7.695 (d, 2H), 7.504 (t, 2H), 7.161 (t, 2H), 4.317 (t, 1H), 3.704 (s, 3H), 2.282 (m, 1H), 0.988 (dd, 6H).

Example 343

(S)-2-(3-(4-(3-(4-Fluorophenyl)ureido)phenyl)-1,2,4-oxadiazole-5-carboxamido)-3-methylbutanoic acid The title compound was prepared from (S)-methyl 2-(3-(4-(3-(4-fluorophenyl)ureido) phenyl)-1,2,4-oxadiazole-5-carboxamido)-3-methylbutanoate as set forth in example 104, step 6 and was obtained in 58% yield. MS (ESI) m/z: 440(M−H)$^−$; $^1$HNMR (DMSO-d$_6$, 300 MHz): δ 13.021 (s, 1H), 9.401

(d, 1H), 9.233 (s, 1H), 8.867 (d, 1H), 8.015 (d, 2H), 7.694 (d, 2H), 7.505 (t, 2H), 7.162 (t, 2H), 4.327 (t, 1H), 2.279 (m, 2H), 0.975 (dd, 6H).

Example 344

(S)-Methyl 2-(3-(4-(3-(4-methoxyphenyl)ureido)phenyl)-1,2,4-oxadiazole-5-carboxamido)-3-methylbutanoate The title compound was prepared according to the procedure as set forth in example 104, step 5 except that 1-isocyanato-4-methoxybenzene was used in place of 2,4-difluoro-1-isocyanatobenzene to yield 96% of the title compound. MS (ESI) m/z: 468(M+H)$^+$; $^1$HNMR (DMSO-d$_6$, 300 MHz): δ 9.691 (d, 1H), 8.991 (s, 1H), 8.592 (s, 1H), 7.990 (d, 2H), 7.670 (d, 2H), 7.376 (d, 2H), 6.882 (d, 2H), 4.358 (t, 1H), 3.704 (s, 3H), 3.681 (s, 3H), 2.273 (m, 1H), 0.970 (t, 6H).

Example 345

(S)-2-(3-(4-(3-(4-methoxyphenyl)ureido)phenyl)-1,2,4-oxadiazole-5-carboxamido)-3-methylbutanoic acid The title compound was prepared from (S)-Methyl 2-(3-(4-(3-(4-methoxyphenyl)ureido)phenyl)-1,2,4-oxadiazole-5-carboxamido)-3-methylbutanoate as set forth in example 104, step 6 and was obtained in 78% yield. MS (ESI) m/z: 452(M−H)$^-$; $^1$HNMR (DMSO-d$_6$, 300 MHz): δ 12.636 (s, 1H), 9.383 (d, 1H), 9.037 (s, 1H), 8.636 (d, 1H), 7.990 (d, 2H), 7.671 (d, 2H), 7.378 (d, 2H), 6.879 (d, 2H), 4.293 (t, 1H), 3.702 (s, 3H), 2.272 (m, 1H), 0.970 (d, 6H).

Example 346

(S)-Methyl 3-methyl-2-(3-(4-(3-p-tolylureido)phenyl)-1,2,4-oxadiazole-5-carboxamido)butanoate The title compound was prepared according to the procedure as set forth in example 104, step 5 except that 1-isocyanato-4-methylbenzene was used in place of 2,4-difluoro-1-isocyanatobenzene to yield 92% of the title compound. $^1$HNMR (DMSO-d$_6$, 300 MHz): δ 9.688 (d, 1H), 9.020 (s, 1H), 8.670 (s, 1H), 7.995 (d, 2H), 7.673 (d, 2H), 7.354 (d, 2H), 7.069 (d, 2H), 4.360 (t, 1H), 3.681 (s, 3H), 2.230 (m, 1H), 0.970 (dd, 6H); MS (ESI) m/z: 452(M+H)$^+$.

Example 347

(S)-3-Methyl-2-(3-(4-(3-p-tolylureido)phenyl)-1,2,4-oxadiazole-5-carboxamido)butanoic acid The title compound was prepared from (S)-methyl 3-methyl-2-(3-(4-(3-p-tolylureido)phenyl)-1,2,4-oxadiazole-5-carboxamido)butanoate as set forth in example 104, step 6 and was obtained in 68% yield. MS (ESI) m/z: 436(M−H)$^-$; $^1$HNMR (DMSO-d$_6$, 300 MHz): δ 13.0454 (s, 1H), 9.3889 (d, 1H), 9.035 (s, 1H), 8.683 (d, 1H), 7.995 (d, 2H), 7.672 (d, 2H), 7.355 (d, 2H), 7.097 (d, 2H), 4.318 (dd, 1H), 2.231 (s, 3H), 2.271 (m, 1H), 0.971 (d, 6H).

Example 348

(S)-methyl 2-(3-(4-(3-(2-fluorophenyl)ureido)phenyl)-1,2,4-oxadiazole-5-carboxamido)-3-methylbutanoate The title compound was prepared according to the procedure as set forth in example 104, step 5 except that 1-fluoro-2-isocyanatobenzene was used in place of 2,4-difluoro-1-isocyanatobenzene to yield 92% of the title compound. MS (ESI) m/z: 456(M+H)$^+$; $^1$HNMR (DMSO-d$_6$, 300 MHz): δ 9.677 (d, 1H), 9.435 (s, 1H), 8.654 (s, 1H), 8.162 (t, 1H), 8.017 (d, 2H), 7.685 (d, 2H), 7.272 (dd, 1H), 7.168 (t, 1H), 7.055 (m, 1H), 4.361 (t, 1H), 3.682 (s, 3H), 2.275 (m, 1H), 0.971 (dd, 6H).

Example 349

(S)-2-(3-(4-(3-(2-Fluorophenyl)ureido)phenyl)-1,2,4-oxadiazole-5-carboxamido)-3-methylbutanoic acid The title compound was prepared from (S)-methyl 2-(3-(4-(3-(2-fluorophenyl)ureido)phenyl)-1,2,4-oxadiazole-5-carboxamido)-3-methylbutanoate as set forth in example 104, step 6 and was obtained in 57% yield. MS (ESI) m/z: 442(M+H)$^+$; $^1$HNMR (DMSO-d$_6$, 300 MHz): δ 9.436 (s, 1H), 9.382 (d, 1H), 8.656 (s, 1H), 8.147 (t, 1H), 8.015 (d, 2H), 7.680 (d, 2H), 7.265 (dd, 1H), 7.166 (t, 1H), 7.050 (m, 1H), 4.315 (t, 1H), 1268 (m, 1H), 0.968 (dd, 6H).

Example 350

(S)-methyl 2-(3-(4-(2,4-difluorophenylsulfonamido)phenyl)-1,2,4-oxadiazole-5-carboxamido)-3-methylbutanoate The title compound was prepared according to the procedure as set forth in example 104, step 5 except that 2,4-difluorobenzene-1-sulfonyl chloride was used in place of 2,4-difluoro-1-isocyanatobenzene to yield 91% of the title compound. MS (ESI) m/z: 495(M+H)$^+$; $^1$HNMR (DMSO-d$_6$, 300 MHz): δ 11.204 (s, 1H), 9.662 (s, 1H), 8.025 (m, 1H), 7.955 (d, 2H), 7.562 (d, 1H), 7.313 (d, 3H), 4.314 (t, 1H), 3.666 (s, 3H), 2.274 (m, 1H), 0.948 (d, 6H).

Example 351

(S)-Methyl 3-methyl-2-(3-(4-(3-phenylureido)phenyl)-1,2,4-oxadiazole-5-carboxamido)butanoate The title compound was prepared according to the procedure as set forth in example 104, step 5 except that isocyanatobenzene was used in place of 2,4-difluoro-1-isocyanatobenzene to yield 81% of the title compound. MS (ESI) m/z: 438(M+H)$^+$;

$^1$HNMR (DMSO-d$_6$, 300 MHz): δ 9.688 (d, 1H), 9.066 (s, 1H), 8.780 (s, 1H), 8.055 (d, 2H), 7.686 (d, 2H), 7.680 (d, 2H), 7.308 (t, 2H), 7.003 (t, 1H), 4.337 (t, 1H), 3.682 (s, 3H), 2.321 (m, 1H), 0.968 (dd, 6H).

Example 352

(S)-methyl 2-(3-(4-(3-benzylureido)phenyl)-1,2,4-oxadiazole-5-carboxamido)-3-methylbutanoate The title compound was prepared according to the procedure as set forth in example 104, step 5 except that benzyl isocyanate was used, in place of 2,4-difluoro-1-isocyanatobenzene to yield 56% of the title compound. MS (ESI) m/z: 450(M−H)$^-$; $^1$HNMR (DMSO-d$_6$, 300 MHz): δ 9.680 (d, 1H), 9.002 (s, 1H), 7.948 (d, 2H), 7.632 (d, 2H), 7.351 (m, 5H), 6.802 (t, 1H), 4.351 (m, 3H), 3.677 (s, 3H), 2.268 (m, 1H), 0.965 (dd, 6H).

Example 353

(S)-Methyl 2-(3-(4-(3-(3-fluorophenyl)thioureido)phenyl)-1,2,4-oxadiazole-5-carboxamido)-3-methylbutanoate The title compound was prepared according to the procedure as set forth in example 104, step 5 except that 1-fluoro-3-isothiocyanatobenzene was used in place of 2,4-difluoro-1-isocyanatobenzene to yield 88% of the title compound. MS (ESI) m/z: 472(M+H)$^+$; $^1$HNMR (DMSO-d$_6$, 300 MHz): δ 10.388 (s, 1H), 10.311 (s, 1H), 9.766 (d, 1H), 8.078 (d, 2H), 7.855 (d, 2H), 7.586 (d, 1H), 7.480 (d, 1H), 7.308 (d, 1H), 7.003 (t, 1H), 4.495 (t, 1H), 3.812 (s, 3H), 2.351(m, 1H), 0.968 (dd, 6H).

Example 354

(S)-Methyl 2-(3-(4-(3-(4-fluorophenyl)thioureido)phenyl)-1,2,4-oxadiazole-5-carboxamido)-3-methylbutanoate The title compound was prepared according to the procedure as set forth in example 104, step 5 except that 1-fluoro-4-isothiocyanatobenzene was used in place of 2,4-difluoro-1-isocyanatobenzene to yield 54% of the title compound. MS (ESI) m/z: 472 (M+H)$^+$; $^1$HNMR (DMSO-d$_6$, 300 MHz): δ 10.136 (s, 1H), 10.011 (s, 1H), 9.754 (d, NH), 8.078 (d, 2H), 7.855(d, 2H), 7.562 (m, 2H), 7.280 (t, 2H), 4.469 (t, 1H), 3.813 (s, 3H), 2.428 (m, 1H), 1.067 (dd, 6H).

Example 355

(S)-methyl 2-(3-(4-(3-(2-fluorophenyl)thioureido)phenyl)-1,2,4-oxadiazole-5-carboxamido)-3-methylbutanoate The title compound was prepared according to the procedure as set forth in example 104, step 5 except that 1-fluoro-2-isothiocyanatobenzene was used in place of 2,4-difluoro-1-isocyanatobenzene to yield 75% of the title compound. MS (ESI) m/z: 472(M+H)$^+$.

$^1$HNMR (DMSO-d$_6$, 300 MHz): δ 10.306 (s, 1H), 9.811 (s, 1H), 9.754 (d, 1H), 8.088 (d, 2H), 7.860 (d, 2H), 7.662 (t, 1H), 7.380 (m, 3H), 4.469 (t, 1H), 3.813 (s, 3H), 2.428 (m, 1H), 1.0037 (dd, 6H).

Example 356

(S)-methyl 2-(3-(4-(3-benzylthioureido)phenyl)-1,2,4-oxadiazole-5-carboxamido)-3-methylbutanoate The title compound was prepared according to the procedure as set forth in example 104, step 5 except that (isothiocyanatomethyl)benzene was used in place of 2,4-difluoro-1-isocyanatobenzene to yield 61% of the title compound. MS (ESI) m/z: 468(M+H)$^+$; $^1$HNMR (DMSO-d$_6$, 300 MHz): δ 9.933 (s, 1H), 9.689 (d, 1H), 8.440 (s, 1H), 8.013 (d, 2H), 7.773 (d, 2H), 7.353 (m, 5H), 4.755 (d, 1H), 4.360 (t, 1H), 3.681 (s, 3H), 2.295 (m, 1H), 0.970 (dd, 6H).

Example 357

(S)-methyl 3-methyl-2-(3-(4-(3-phenylthioureido)phenyl)-1,2,4-oxadiazole-5-carboxamido)butanoate The title compound was prepared according to the procedure as set forth in example 104, step 5 except that isothiocyanatobenzene was used in place of 2,4-difluoro-1-isocyanatobenzene to yield 56% of the title compound. MS (ESI) m/z: 454(M+H)$^+$; $^1$HNMR (DMSO-d$_6$): δ 10.104 (s, 1H), 10.035 (s, 1H), 8.032 (d, 2H), 7.781 (d, 2H), 7.497 (d, 2H), 7.369 (t, 2H), 7.166 (t, 1H), 4.370 (t, 1H), 3.688 (s, 3H), 2.280 (m, 1H), 0.978 (dd, 6H).

Example 358

(S)-methyl 2-(2-(4-(3-(2,4-difluorophenyl)ureido)phenyl)thiazole-4-carboxamido)-3-methylbutanoate Step 1: Ethyl 2-(4-nitrophenyl)thiazole-4-carboxylate Ethyl 2-(4-nitrophenyl)thiazole-4-carboxylate was synthesized by following the procedure mentioned in Bioorg. Med. chem. Lett. 17, 4670-4677, 2007.

Step 2: 2-(4-nitrophenyl)thiazole-4-carboxylic acid

To a solution of Ethyl 2-(4-nitrophenyl)thiazole-4-carboxylate in THF, 1N LiOH was added at RT and stirred for 2-3 hr. After completion of reaction THF was removed under reduced pressure. Obtained material was dissolved in water acidified with 1N HCl and white solid precipitated out. It was filtered and dried. Yield 4.4 gm (97%). MS (ESI) m/z: 249 (M−H)$^−$; $^1$HNMR (DMSO-d$_6$, 300 MHz): δ 13.233 (s, 1H), 8.658 (s, 1H), 8.358 (d, 2H), 8.269 (d, 2H).

Step 3: (S)-methyl 3-methyl-2-(2-(4-nitrophenyl)thiazole-4-carboxamido) butanoate 2-(4-nitrophenyl)thiazole-4-carboxylic acid (4.4 gm, 0.0176 mol) was taken in dry THF and to this N-methyl morpholine (1.78 gm, 0.0176) was added at RT and then cooled to −20° C. At this temperature, isobutyl chloroformate (2.4 gm, 0.0176) was added and stirred for ½ hr. Then to this reaction mixture, a solution of L-valine methyl ester Hydrochloride salt (4.12 gm, 0.0246 mol) neutralized with Et$_3$N (2.489 gm, 0.0246 mol) was added at −20° C. and stirred for ½ hr at that temperature and then stirred at RT for 2-3 hr. After completion of reaction, EtOAc was added and layers were separated. The aqueous layer was washed with EtOAc and all organic layers were mixed together and washed with water, brine, dried by sodium sulphate and concentrated to give solid material. Then it was purified by column chromatography. Column was eluted with 20% EtOAc Pet Ether. Yield: 6.2 gm (98%). MS (ESI) m/z: 364 (M+H)$^+$; $^1$HNMR (DMSO-d$_6$, 300 MHz): δ 8.537(s, 1H), 8.375(m, 4H), 4.427(t, 1H), 3.692(s, 3H), 2.305 (m, 1H), 0.981 (t, 6H).

Step 4: (S)-methyl 2-(2-(4-aminophenyl)thiazole-4-carboxamido)-3-methylbutanoate (S)-methyl 3-methyl-2-(2-(4-nitrophenyl)thiazole-4-carboxamido) butanoate (6 gm, 0.016 mol) was taken solution of EtOH:Water (60 mL:30 mL), to this Fe (2.16 gm, 0.0388 mol) and Ammonium chloride (2.567, 0.048 mole) was added and reflux for 2 hr. After completion of reaction, reaction mass was filtered through bed of celite. Filtrate was concentrated and dissolved in EtOAc and washed with water, brine, dried by sodium sulphate and concentrated. Obtained crude material purified by column chromatography. Column was eluted with 20% Ethyl acetate Pet Ether. Yield: 4.5 gm (82%); MS (ESI) m/z: 334 (M+H)$^+$; $^1$HNMR (DMSO-d$_6$, 300 MHz): δ

8.110 (s, 1H), 7.731 (d, 2H), 6.660 (d, 2H), 5.790 (s, NH$_2$), 4.418 (t, 1H), 3.690 (s, 3H), 2.284 (m, 1H), 0.968 (t, 6H).

Step 5: (S)-methyl 2-(2-(4-(3-(2,4-difluorophenyl)ureido)phenyl)thiazole-4-carboxamido)-3-methylbutanoate (S)-methyl 2-(2-(4-aminophenyl)thiazole-4-carboxamido)-3-methylbutanoate (150 mg, 0.450 mmol) was taken in 3 mL THF, to this 2,4-difluoro-1-isocyanatobenzene (76.8 mg, 0.495 mol) was added and stirred at RT for 3-4 hr. After completion of reaction solvent was removed under reduced pressure and the residue purified by column chromatography. Yield: 200 mg (91%). MS (ESI) m/z: 487(M−H)$^-$; $^1$HNMR (DMSO-d$_6$, 300 MHz): δ 9.369 (s, 1H), 8.594 (d, 1H), 8.316 (s, 1H), 8.291 (s, 1H), 8.126 (m, 1H), 8.023 (d, 2H), 7.640 (d, 2H), 7.372 (m, 1H), 7.106 (m, 1H), 4.431 (dd, 1H), 3.696 (s, 3H), 2.300 (m, 1H), 0.981 (dd, 6H).

Example 359

(S)-2-(2-(4-(3-(2,4-difluorophenyl)ureido)phenyl)thiazole-4-carboxamido)-3-methylbutanoic acid To a solution of (S)-methyl 2-(2-(4-(3-(2,4-difluorophenyl)ureido)phenyl)thiazole-4-carboxamido)-3-methylbutanoate (100 mg, 0.204 mmol) in THF (4 mL)+MeOH (1 ml), 1 ml of 1N LiOH (42.99 mg, 1.024 mmol) was added at RT and stirred for 2-3 hr. After completion of reaction, THF was removed under reduced pressure. Obtained material was dissolved in water, acidified with 1N HCl and white solid precipitated out. It was filtered and dried.
Yield: 85 mg (97%); MS (ESI) m/z: 473(M−H)$^-$; $^1$HNMR (DMSO-d$_6$, 300 MHz): δ 9.398(s, NH), 8.606 (s, 1H), 8.287 (s, 1H), 8.110 (m, 2H), 8.001 (d, 2H), 7.640 (d, 2H), 7.356 (m, 1H), 7.089 (m, 1H), 4.412 (t, 1H), 2.288 (m, 1H), 0.978 (dd, 6H).

Example 360

(S)-methyl 2-(2-(4-(3-(2,3-dihydro-1H-inden-5-yl)ureido)phenyl) thiazole-4-carboxamido)-3-methylbutanoate The title compound was prepared according to the procedure as set forth in example 358, except that 5-isocyanato-2,3-dihydro-1H-indene was used in place of 2,4-difluoro-1-isocyanatobenzene to yield 90% of the title compound. MS (ESI) m/z: 492(M−H)$^-$; $^1$HNMR (DMSO-d$_6$, 300 MHz): δ 8.987(s, 1H), 8.620 (s, 1H), 8.317(d, 2H), 8.002 (d, 2H), 7.634 (d, 2H), 7.339 (d, 1H), 7.178 (dd, 2H), 4.429 (t, 1H), 3.696 (s, 3H), 2.865(m, 4H), 2.300 (m, 1H), 2.055 (m, 1H), 0.984 (dd, 6H).

Example 361

(S)-2-(2-(4-(3-(2,3-dihydro-1H-inden-5-yl)ureido)phenyl)thiazole-4-carboxamido)-3-methylbutanoic acid The title compound was prepared from (S)-methyl 2-(2-(4-(3-(2,3-dihydro-1H-inden-5-yl)ureido)phenyl)thiazole-4-carboxamido)-3-methylbutanoate as set forth in example 359 and was obtained in 98% yield. MS (ESI) m/z: 477(M−H)$^-$; $^1$HNMR (DMSO-d$_6$): δ 8.995 (s, 1H), 8.625 (s, 1H), 8.278 (s, 1H), 8.109 (d, 1H), 7.981 (d, 2H), 7.634 (d, 2H), 7.392 (s, 1H), 7.143 (m, 2H), 4.413 (t, 1H), 2.862 (m, 4H), 2.267 (m, 1H), 2.028 (m, 1H), 0.979 (dd, 6H).

Example 362

(S)-methyl 2-(2-(4-(3-(3,4-dimethylphenyl)ureido)phenyl)thiazole-4-carboxamido)-3-methylbutanoate The title compound was prepared according to the procedure as set forth in example 358, except that 4-isocyanato-1,2-dimethylbenzene was used in place of 2,4-difluoro-1-isocyanatobenzene to yield 92% of the title compound. MS (ESI) m/z: 479(M−H)$^-$; $^1$HNMR (DMSO-d$_6$): δ 8.985 (s, 1H), 8.576 (s, 1H), 8.318 (d, 1H), 8.282 (s, 1H), 8.00 (d, 2H), 7.633 (d, 2H), 7.247 (s, 1H), 7.202 (dd, 1H), 7.056 (d, 1H), 4.429 (dd, 1H), 3.696 (s, 3H), 2.279 (m, 1H), 2.201 (s, 3H), 2.164 (s, 3H), 0.985(dd, 6H).

Example 363

(S)-2-(2-(4-(3-(3,4-dimethylphenyl)ureido)phenyl)thiazole-4-carboxamido)-3-methylbutanoic acid The title compound was prepared from (S)-methyl 2-(2-(4-(3-(3,4-dimethylphenyl)ureido)phenyl)thiazole-4-carboxamido)-3-methylbutanoate as set forth in example 359 and was obtained in 92% yield. MS (ESI) m/z: 465(M−H)$^-$. $^1$HNMR (DMSO-d$_6$, 300 MHz): δ 12.986 (s, 1H), 9.005 (s, 1H), 8.591 (s, 1H), 8.284 (s, 1H), 8.117 (d, 1H), 7.983 (d, 2H), 7.638 (d, 2H), 7.251 (s, 1H), 7.203 (d, 2H), 7.057 (d, 2H), 4.416 (t, 1H), 2.295 (m, 1H), 2.202 (s, 3H), 2.165 (s, 3H), 0.983(dd, 6H).

Example 364

(S)-methyl 2-(2-(4-(3-(4-chloro-2-phenoxyphenyl)ureido)phenyl) thiazole-4-carboxamido)-3-methylbutanoate The title compound was prepared according to the procedure as set forth in example 358, except that 4-chloro-1-isocyanato-2-phenoxybenzene was used in place of 2,4-difluoro-1-isocyanatobenzene to yield 84% of the title compound. MS (ESI) m/z: 577(M−H)$^-$; $^1$HNMR (DMSO-d$_6$, 300 MHz): δ 9.690 (s, 1H), 8.761(s, 1H), 8.407(d, 1H), 8.321 (d, 2H), 8.026 (d, 2H), 7.627 (d, 2H), 7.473 (t, 2H), 7.229 (t, 1H), 7.113 (d, 2H), 7.039 (dd, 1H), 6.865 (d, 1H), 6.862 (d, 1H), 4.427 (t, 1H), 3.693 (s, 3H), 2.297 (m, 1H), 0.981 (dd, 6H).

Example 365

(S)-2-(2-(4-(3-(4-chloro-2-phenoxyphenyl)ureido)phenyl)thiazole-4-carboxamido)-3-methylbutanoic acid The title compound was prepared from (S)-methyl 2-(2-(4-(3-(4-chloro-2-phenoxyphenyl)ureido)phenyl) thiazole-4-carboxamido)-3-methylbutanoate as set forth in example 359 and was obtained in 75% yield. MS (ESI) m/z: 563 (M−H)$^-$; $^1$HNMR (DMSO-d$_6$, 300 MHz): δ 9.694 (s, 1H), 8.761 (s, 1H), 8.404 (d, 1H), 8.290 (s, 1H), 8.113 (d, 1H), 8.005 (d, 2H), 7.625 (s, 1H), 7.471 (t, 2H), 7.227 (d, 1H), 7.085 (d, 2H), 7.038 (dd, 2H), 6.862 (d, 1H), 4.412 (t, 1H), 2.286 (m, 1H), 0.976 (dd, 6H).

Example 366

(S)-methyl 3-methyl-2-(2-(4-(3-(3-(trifluoromethyl) phenyl)ureido) phenyl) thiazole-4-carboxamido) butanoate The title compound was prepared according to the procedure as set forth in example 358, except that 1-isocyanato-3-(trifluoromethyl)benzene was used in place of 2,4-difluoro-1-isocyanatobenzene to yield 94% of the title compound. MS (ESI) m/z: 519(M−H)$^-$; $^1$HNMR (DMSO-d$_6$): δ 9.172 (s, 1H), 9.136 (s, 1H), 8.320 (s, 1H), 8.294 (s, 1H), 8.024 (d, 3H), 7.665 (d, 2H), 7.627 (m, 2H), 7.354 (d, 1H), 4.431 (dd, 1H), 3.697 (s, 3H), 2.279 (m, 1H), 0.986 (dd, 6H).

Example 367

(S)-3-Methyl-2-(2-(4-(3-(3-(trifluoromethyl)phenyl) ureido)phenyl) thiazole-4-carboxamido)butanoic acid The title compound was prepared from (S)-methyl 3-methyl-2-(2-(4-(3-(3-(trifluoromethyl)phenyl)ureido)phenyl) thiazole-4-carboxamido)butanoate as set forth in example 359 and was obtained in 82% yield. MS (ESI) m/z: 505(M−H)$^-$; $^1$HNMR (DMSO-d$_6$, 300 MHz): δ 12.975 (s, 1H), 9.192 (s, 1H), 9.152 (s, 1H), 8.294 (s, 1H), 8.117 (d, 1H), 8.027 (d, 3H), 7.666 (d, 2H), 7.625 (m, 2H), 7.353 (d, 1H), 4.415 (dd, 1H), 2.271 (m, 1H), 0.981 (dd, 6H).

Example 368

(S)-Methyl 2-(2-(4-(3-(2-chlorophenyl)ureido)phenyl)thiazole-4-carboxamido)-3-methylbutanoate The title compound was prepared according to the procedure as set forth in example 358, except that 1-chloro-2-isocyanatobenzene was used in place of 2,4-difluoro-1-isocyanatobenzene to yield 94% of the title compound. MS (ESI) m/z: 485 (M−H)$^-$; $^1$HNMR, (DMSO-d$_6$): δ 9.756 (s, 1H), 8.408 (s, 1H), 8.319 (d, 1H), 8.295 (s, 1H), 8.037 (d, 2H), 7.660 (d, 2H), 7.497 (dd, 1H), 7.325 (m, 1H), 7.065 (m, 1H), 4.412 (dd, 1H), 3.698 (s, 3H), 2.302 (m, 1H); 1.009 (dd, 6H).

Example 369

(S)-2-(2-(4-(3-(2-Chlorophenyl)ureido)phenyl)thiazole-4-carboxamido)-3-methylbutanoic acid The title compound was prepared from (S)-methyl 2-(2-(4-(3-(2-chlorophenyl)ureido) phenyl)thiazole-4-carboxamido)-3-methylbutanoate as set forth in example 359 and was obtained in 92% yield. MS (ESI) m/z: 471(M−H)$^-$; $^1$HNMR (DMSO-d$_6$, 300 MHz): δ 9.805 (s, 1H), 8.429 (s, 1H), 8.294 (s, 1H), 8.182 (d, 1H), 8.114 (d, 1H), 8.017(d, 2H), 7.663 (d, 2H), 7.494 (dd, 1H), 7.347 (m, 1H), 7.089 (m, 1H), 4.399 (dd, 1H), 2.292 (m, 1H), 0.981 (dd, 6H).

Example 370

(S)-Methyl 2-(2-(4-(3-(3,4-difluorophenyl)ureido) phenyl)thiazole-4-carboxamido)-3-methylbutanoate The title compound was prepared according to the procedure as set forth in example 358, except that 1,2-difluoro-4-isocyanatobenzene was used in place of 2,4-difluoro-1-isocyanatobenzene to yield 91% of the title compound. MS (ESI) m/z: 487(M−H)$^-$; $^1$HNMR (DMSO-d$_6$, 300 MHz): δ 9.134 (s, 1H), 8.995 (s, 1H), 8.317(d, 1H), 8.291 (s, 1H), 8.018 (d, 2H), 7.721 (m, 1H), 7.643 (d, 2H), 7.414 (dd, 1H), 7.170 (m, 1H), 4.428 (dd, 1H), 3.696 (s, 3H), 2.300 (m, 1H), 0.984 (dd, 6H).

Example 371

(S)-2-(2-(4-(3-(3,4-Difluorophenyl)ureido)phenyl) thiazole-4-carboxamido)-3-methylbutanoic acid The title compound was prepared from (S)-methyl 2-(2-(4-(3-(3,4-difluorophenyl)ureido)phenyl)thiazole-4-carboxamido)-3-methylbutanoate as set forth in example 359 and was obtained in 77% yield. MS (ESI) m/z: 475(M+H)$^+$; $^1$HNMR (DMSO-d$_6$, 300 MHz): δ 12.973 (s, 1H), 8.242 (s, 1H), 8.166 (d, 1H), 7.972 (d, 2H), 7.758 (m, 3H), 7.390 (dd, 1H), 7.252 (m, 1H), 7.414 (dd, 1H), 7.170 (m, 1H), 4.356 (dd, 1H), 2.271 (m, 1H), 0.983 (dd, 6H).

PHARMACOLOGICAL DATA

The efficacy of the compounds of the present invention can be determined by a number of pharmacological assays well known in the art, such as described below. The exemplified pharmacological assays, which follow herein below, have been carried out with the compounds of the present invention.

Materials:
Tissue culture materials, (Nunc)
Tissue culture media, (Gibco)
Fetal bovine serum (FBS), (Hyclone)
Bovine serum albumin (BSA), (Sigma)
sn-1,2-dioleoylglycerol (Sigma)
Sucrose (Sigma)
2-propanol (Qualigens)
Heptane (Qualigens)
$^{14}$C Oleoyl CoA (GE Healthcare)
Sf9 cells were obtained from American Type Culture Collection (ATCC)
Bradford (Sigma)
Cellfectin (Invitrogen)

Abbreviations:
FBS Fetal Bovine serum
ORF Open Reading Frame
DAB DGAT Assay Buffer
AESSM Alkaline Ethanol Stop Solution Mix
KH$_2$PO$_4$ Potassium Dihydrogen Phosphate
EDTA Ethylene Diamine Tetraacetic Acid
LB Luria Bertani
BSA Bovine serum albumin
PPO 2,5-Diphenyloxazole
POPOP 1,4-bis(5-phenyloxazol-2-yl)benzene
EDTA Ethylene Diamine Tetraacetic Acid

Example 372

In-vitro Protocol for DGAT1 Assay

Sf9 Culture and Treatment

Sf9 cells were grown in T25 flasks containing Graces's Insect media with 10% FBS with antibiotic (100 units/mL penicillin, 100 μg/mL streptomycin sulphate, 0.25 μg/mL Amptotericin B as Fungizone) grown in a 27° C. incubator:

Viral Stock Preparation hDGAT1ORF expression clone (RZPDo839C09146 in pDEST vector) was obtained from RZPD, Germany. hDGAT1 bacmid DNA was obtained by transformation of the hDGAT expression clone into DH10Bac E. coli competent cells. Approximately 1 μg of hDGAT1 bacmid DNA was infected into Sf9 cells with Cellfectin (Invitrogen) reagent. Following infection, Sf9 cells were incubated at 27° C. for 30 minutes. Five hours after infection, the media was replaced with growth media containing antibiotic (100 units/mL penicillin, 100 μg/mL streptomycin sulphate, 0.25 μg/mL Amptotericin B as Fungizone) and incubated at 27° C. for 72 hours. The supernatant containing the virus was centrifuged at 1500×g for 5 minutes, passed through 0.22 μm filter, and subsequently stored at 4° C. The virus was further amplified three more times by re-infection of Sf9 cells and the viral titer was determined by plaque assay.

Preparation of DGAT1 Microsomes from Sf9 Cells

Sf9 cells were seeded in spinner flasks on day 0 at a cell density of 1×10$^6$ and infected on day 1 with hDGAT1 baculovirus at a multiplicity of infection (MOI) of 5 and a cell density of 2×10$^6$. On day 3 (or 66-72 hours), cells were harvested and centrifuged at 2500×g for 10 minutes. Pellet was resuspended in lysis buffer (100 mM sucrose, 50 mM KCl, 40 mM KH$_2$PO$_4$, 30 mM EDTA, pH 7.2) and passed through 21-gauge needle approximately 10 times. The mixture was centrifuged at 12,000 rpm in a Sigma 12158-H rotor at 4° C. for 30 minutes. The supernatant was subjected to centrifugation at 35,000 rpm in a Beckman Ti-45 rotor at 4° C. for 1 hour. The resultant pellet containing the microsomes were resuspended overnight in 1 mL of lysis buffer and total protein concentration was estimated using Bradford Reagent. Microsomes were aliquoted and stored at −20° C.

Measurement of DGAT1 Activity

Frozen aliquots of hDGAT1 containing microsomes were thawed (5-10 mg/mL total protein) on ice and diluted to a working stock of 1 mg/mL with DGAT Assay Buffer (DAB). The DGAT reaction assay was performed by following the procedure described in U.S. Pat. No. 6,607,893 with some modifications that are described below.

Preparation of DGAT1 substrate mixture: 1 mL stock solution of DGAT1 substrate mixture contains (i) 5.6 μL of $^{14}$C oleoyl CoA (16.8 nCi) and 35 μL 1,2-dioleoyl-sn-glycerol (409.5 μM) or (ii) 5.6 μL of $^{14}$C oleoyl CoA (16.8 nCi) and 105 μL 1,2-dioleoyl-sn-glycerol (1228.5 μM) or (iii) 5.6 μL of $^{14}$C oleoyl CoA (16.8 nCi) and 140 μL 1,2-dioleoyl-sn-glycerol (1638 μM).

1,2-sn-dioleoylglycerol substrate concentration in the 1 mL stock solution of DGAT1 substrate mixture was varied depending on the microsome concentration used in the assay reaction. 1,2-dioleoyl-sn-glycerol stock (19.5 mM) was prepared by dissolving 25 mg of 1,2-dioleoyl-sn-glycerol (Sigma, US) in 2060 μL of acetone. The assay was performed in duplicates in a reaction volume of 100 μL. The reaction volume consisted of:

(i) 27.5 μL of DGAT assay buffer (0.25M Sucrose, 1 mM EDTA (pH 8.0), 150 mM Tris-HCl, pH 7.4, 1.25 mg/mL, fatty acid free BSA),
(ii) 10 μL of compound, of present invention or standard (dissolved in DMSO and diluted to 10× with DAB and screened at 10 μM, 5 μM and 1 μM),
(iii) 60 μL DGAT1 substrate mixture taken from a 1 mL stock (16.8 nCi of $^{14}$C oleoyl CoA and 409.5 μM or 1228.5 μM or 1638 μM of 1,2-dioleyl-sn-glycerol),
(iv) 2.5-10 μL of 1 mg/mL of microsomes (the amount of assay buffer was varied depending upon the concentration of microsome to make up the volume to 100 μL).

Procedure:

The reaction was started by the addition of 2.5-10 μL of 1 mg/mL of microsomes (iv) to a mixture of (i), (ii) and (iii), vortexed and incubated at 37° C. for 10 minutes. The reaction was stopped by the addition of 300 μL of Alkaline Ethanol Stop Solution Mix (AESSM; 12.5% of 100% non-denatured ethanol, 10% deionized water, 2.5% 1N NaOH, 75% stop solution (78.4% isopropanol, 19.6% n-heptane, 2% deionized water)) followed by addition of 600 μL of n-heptane. The mixture was vortexed and the triglycerides formed were extracted into the organic heptane phase. 250 μL of the heptane phase was added into 4 mL scintillation cocktail (66.72% toluene, 33.3% TritonX-100, 0.5% PPO, 0.02% POPOP) and counted on a liquid scintillation counter for 1 minute. Data was collected and plotted as a function of concentration in μM versus percentage inhibition of hDGAT1 by the compounds of present invention. Inhibitor concentration at 50% (IC$_{50}$) was determined using 8 point concentration values.

The following table displays the % Inhibition of hDGAT1 by representative examples of the present invention at 10 μM, 5 μM and 1 μM.

| Example No. | % inhibition of hDGAT1 | Example No. | % inhibition of hDGAT1 | Example No. | % inhibition of hDGAT1 |
|---|---|---|---|---|---|
| At 10 μM | | | | | |
| 1 | ++ | 2 | + | 3 | + |
| 4 | + | 5 | ++ | 6 | + |
| 7 | ++ | 8 | ++ | 9 | + |
| 10 | ++ | 11 | + | 12 | ++ |
| 13 | +++ | 14 | + | 15 | ++ |
| 16 | ++ | 17 | + | 18 | ++ |
| 19 | ++ | 20 | + | 21 | + |
| 22 | + | 23 | + | 24 | + |
| 25 | + | 26 | + | 27 | + |
| 28 | + | 29 | + | 30 | + |
| 31 | + | 32 | + | 33 | + |
| 34 | + | 35 | + | 36 | ++ |
| 37 | + | 38 | ++ | 39 | + |
| 40 | + | 41 | + | 42 | ++ |
| 43 | ++ | 44 | +++ | 45 | ++ |
| 46 | + | 47 | +++ | 48 | + |
| 49 | ++ | 50 | + | 51 | + |
| 52 | + | 53 | +++ | 54 | + |
| 55 | ++ | 56 | + | 57 | + |
| 59 | + | 60 | + | 61 | + |
| 62 | + | 63 | + | 65 | + |
| 66 | + | 67 | +++ | 68 | + |
| 69 | + | 70 | + | 72 | + |
| 74 | + | 76 | ++ | 77 | +++ |
| 78 | + | 79 | +++ | 80 | ++ |
| 81 | +++ | 82 | + | 83 | ++ |
| 84 | ++ | 85 | +++ | 86 | + |
| 87 | +++ | 88 | + | 89 | + |
| 90 | + | 91 | + | 92 | + |
| 93 | + | 94 | + | 95 | + |
| 96 | ++ | 97 | +++ | 98 | ++ |
| 100 | + | 101 | + | 102 | + |
| 103 | +++ | 104 | +++ | 105 | ++ |
| 106 | +++ | 107 | + | 108 | ++ |
| 109 | + | 110 | + | 111 | ++ |
| 112 | +++ | 113 | + | 114 | +++ |
| 115 | + | 116 | +++ | 117 | ++ |
| 118 | ++ | 119 | ++ | 120 | ++ |
| 121 | ++ | 122 | +++ | 123 | ++ |
| 124 | +++ | 125 | ++ | 126 | +++ |
| 127 | + | 128 | +++ | 131 | + |
| 132 | + | 133 | ++ | 134 | +++ |
| 137 | + | 138 | +++ | 139 | + |
| 140 | +++ | 147 | ++ | 148 | +++ |
| 150 | +++ | | | | |
| At 5 μM | | | | | |
| 135 | + | 136 | +++ | 141 | + |
| 142 | +++ | 143 | ++ | 144 | +++ |
| 145 | ++ | 151 | ++ | 152 | +++ |
| 153 | + | 154 | +++ | 222 | ++ |
| 241 | + | 242 | ++ | 243 | + |

-continued

| Example No. | % inhibition of hDGAT1 | Example No. | % inhibition of hDGAT1 | Example No. | % inhibition of hDGAT1 |
|---|---|---|---|---|---|
| 244 | ++ | 245 | + | 246 | ++ |
| 253 | + | 254 | ++ | 255 | + |
| 256 | ++ | 263 | + | 264 | + |
| 265 | ++ | 266 | +++ | 267 | + |
| 268 | ++ | 269 | + | 270 | ++ |
| 271 | + | 272 | + | 273 | ++ |
| 274 | + | 275 | + | 276 | +++ |
| 277 | + | 278 | +++ | 279 | + |
| 280 | ++ | 281 | + | 282 | + |
| 284 | ++ | 285 | +++ | 298 | ++ |
| 299 | ++ | 300 | ++ | 301 | ++ |
| 343 | ++ | 344 | + | 345 | ++ |
| 346 | ++ | 347 | ++ | 348 | + |
| 349 | ++ | 350 | + | 351 | + |
| 352 | + | 353 | + | 354 | + |
| 355 | ++ | 356 | ++ | 357 | + |
| At 1 µM | | | | | |
| 129 | ++ | 130 | +++ | 146 | ++ |
| 156 | +++ | 158 | +++ | 160 | +++ |
| 162 | +++ | 164 | +++ | 166 | ++ |
| 167 | +++ | 169 | ++ | 171 | +++ |
| 173 | +++ | 175 | + | 177 | +++ |
| 179 | +++ | 181 | +++ | 183 | +++ |
| 185 | +++ | 187 | +++ | 189 | +++ |
| 191 | +++ | 193 | +++ | 195 | +++ |
| 197 | +++ | 199 | +++ | 201 | +++ |
| 203 | +++ | 205 | ++ | 207 | + |
| 209 | +++ | 211 | +++ | 213 | ++ |
| 215 | +++ | 216 | + | 217 | ++ |
| 218 | + | 219 | ++ | 220 | + |
| 221 | +++ | 223 | + | 224 | + |
| 225 | + | 226 | + | 228 | +++ |
| 230 | + | 232 | +++ | 234 | + |
| 236 | +++ | 238 | +++ | 240 | +++ |
| 248 | +++ | 250 | +++ | 252 | +++ |
| 257 | + | 258 | ++ | 259 | ++ |
| 260 | ++ | 261 | ++ | 262 | ++ |
| 283 | + | 287 | +++ | 289 | +++ |
| 291 | +++ | 293 | +++ | 295 | +++ |
| 297 | +++ | 302 | ++ | 303 | + |
| 304 | ++ | 305 | ++ | 306 | ++ |
| 307 | ++ | 308 | ++ | 309 | ++ |
| 310 | ++ | 311 | ++ | 312 | + |
| 314 | ++ | 315 | + | 316 | + |
| 317 | + | 318 | + | 319 | + |
| 320 | + | 322 | + | 324 | + |
| 326 | + | 329 | + | 330 | + |
| 332 | + | 335 | + | 337 | + |
| 339 | + | 341 | + | 359 | + |
| 361 | + | 363 | + | 365 | ++ |
| 367 | + | 369 | + | 371 | + |

% Inhibition Ranges
+ >0% Inhibition ≤50
++ >50% Inhibition ≤75
+++ >75% Inhibition ≤100

In-Vivo Protocol

Animals were housed and cared for in accordance with the Guidelines in force published by CPCSEA (Committee for the Purpose of Control and Supervision of Experiments on Animals), Tamil Nadu, India. Procedures using laboratory animals were approved by the IAEC (Institutional Animal Ethics Committee) of the Research Centre of Piramal Life Sciences Limited, Mumbai, India.

Example 373

Study Protocol for Screening of Compounds for Fat Tolerance Test (ftt) in mice

Swiss mice of age 4-5 weeks and body weight between 25-30 g were selected for study. After overnight fasting, animals were divided into three groups based on plasma triglyceride level with same mean and variation. Animals were administered with either vehicle (1% Tween 80 in 0.5% carboxy methylcellulose) or compounds of the present invention ((100, 75, 30 mg/kg, or 3 mg/kg, p.o). Compounds of the present invention were prepared as suspension in 0.5% carboxy methylcellulose (cmc) with 1% tween 80 (25 µl). One hour or 30 minutes after the treatment, olive oil load (10 ml/kg, p.o.) was given. Blood samples were collected at 1, 2, 3 and 4 hours after the fat (olive oil) load. Plasma was separated and triglyceride level was measured using commercially available kits (Diasys, Germany). Percentage reduction in area under curve ($AUC_{0-4h}$) of the compounds of the present invention was calculated by taking $AUC_{0-4h}$ of the vehicle group as 100%.

| Example No. | % Reduction (Plasma triglyceride) |
|---|---|
| 8 | + |
| 13 | + |
| 15 | + |
| 18 | + |
| 19 | + |
| 44 | ++ |
| 45 | + |
| 105 | ++ |
| 106 | ++ |
| 142 | + |
| 172 | ++ |
| 173 | ++ |
| 200 | ++ |
| 201 | + |
| 266 | + |
| 278 | + |
| 112 | ++ |

% Reduction (Plasma triglyceride) Scoring Details
+ >0% Reduction ≤50
++ >50% Reduction ≤100

REFERENCES

1. Koji Ueshima, Hitomi Akihisa-Umeno, Akira Nagayoshi, Shoji Takakura, Masahiko Matsuo, Seitaro Mutoh. A gastrointestinal lipase inhibitor reduces progression of atherosclerosis in mice fed a western-type diet. European Journal of Pharmacology (2004), 501, 137-142.
2. L-K Han et al. "Anti-obesity effects in rodents of dietary teasaponin, a lipase inhibitor" International Journal of Obesity (2001), 25, 1459-1464.
3. Katherine J. D. Ashbourne Excoffon et al. "Correction of Hypertriglyceridemia and Impaired Fat Tolerance in Lipoprotein Lipase—Deficient Mice by Adenovirus-Mediated Expression of Human Lipoprotein Lipase" Arteriosclerosis, Thrombosis, and Vascular Biology (1997), 17, 2532-2539.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense, including "and/or" unless the content clearly dictates otherwise.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

The invention claimed is:

1. A compound of formula (I),

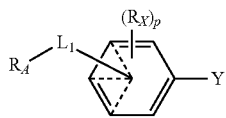

wherein,
--- dotted line represents the variable attachment of -L$_1$-R$_A$ to the specified carbon atoms of the phenyl ring,
R$_A$ is cycloalkyl, alkylaryl, aryl, heteroaryl or heterocycle; wherein each of cycloalkyl, alkylaryl, aryl, heteroaryl and heterocycle is optionally substituted;
R$_x$ is H, halogen or alkyl;
R$_1$ and R$_2$ are independently selected from H, alkyl, alkenyl, alkynyl, cycloalkyl, alkylcycloalkyl, aryl, alkylaryl, alkylheteroaryl, heterocycle and heteroaryl;
L$_1$ is —O—, —NR$_3$(CR$_4$R$_5$)$_a$NR$_3$—, —(CR$_4$R$_5$)$_b$NR$_3$—, —SO$_2$NH— or —SO$_2$NHCONH—;
R$_3$ is H, —COR$_1$, —COOR$_1$, —CONR$_1$R$_2$, alkyl, alkenyl, alkynyl, cycloalkyl or alkylcycloalkyl;
R$_4$ and R$_5$ are independently selected from H, —OR$_6$, —COOR$_6$, —CONR$_6$R$_7$, alkyl, alkenyl, alkynyl, cycloalkyl, alkylcycloalkyl, aryl, heteroaryl, alkylaryl, alkylheteroaryl and alkytheterocycle;
or R$_4$ and R$_5$ together are =O, =S or =NR$_8$;
R$_6$ and R$_7$ are independently selected from H, alkyl, cycloalkyl and heterocycle;
Y is

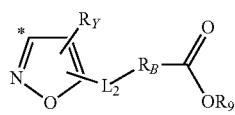

wherein,
L$_2$ is —C(=O)—NR$_Z$—, —C(=S)—NR$_Z$—, —C(=NR$_8$)—NR$_Z$—, —C(SR$_9$)=N—, —C(=O), —C(=S) or —SO$_2$NR$_Z$—;
R$_Z$ is H, or alkyl;
R$_8$ is H, —OR$_9$, —COR$_9$, —COOR$_9$, —CONR$_6$R$_7$, —SO$_2$R$_9$ or —SO$_2$NR$_6$R$_7$;
R$_9$ is absent or is selected from H or alkyl;
R$_B$ is —(CR$_{10}$R$_{11}$)$_c$— or —(NR$_{12}$)(CR$_{10}$R$_{11}$)$_c$; wherein c is an integer from 1 to 3;
or OR$_9$, C(O), R$_B$ and L$_2$; or R$_B$ and L$_2$; or R$_B$, C(O) and OR$_9$ together form a 5 to 7-membered ring selected from heteroaryl and heterocycle;
R$_{10}$, R$_{11}$, and R$_{12}$ are independently selected from: H, aryl, C$_1$-C$_6$ alkyl optionally substituted with OH or C$_1$-C$_4$alkoxy; or (C$_1$-C$_6$)alkylaryl optionally substituted with OH;
or R$_{12}$ and R$_{10}$ or R$_{11}$ together with the respective N and C atoms to which they are attached, form a 3 to 6 membered heterocyclic or heteroaryl ring;
or R$_{12}$ and R$_{11}$ of —(CR$_{10}$R$_{11}$)$_c$ wherein c is an integer 1 together with the C atom to which they are attached form a 3 to 6-membered cycloalkyl ring;
or R$_{10}$ and R$_{11}$ of —(CR$_{10}$R$_{11}$)$_c$ wherein c is an integer 1 together with the C atom to which they are attached form alkenylene;
R$_Y$ is —H, halogen, —CN, OH, alkyl or unsubstituted aryl;
with the proviso that when L$_1$ is —(CR$_4$R$_5$)$_b$NR$_3$—, L$_2$ is —C(=O)—NR$_Z$— is and R$_B$ is —(CR$_{10}$R$_{11}$)$_c$—, then (a) c is the integer 1; and (b) R$_A$ is heteroaryl or heterocycle, wherein the heteroaryl or heterocycle is selected from indolyl, isoindolyl, indolizinyl, benzofuranyl, benzothienyl, quinolinyl, isoquinolinyl, benzopyranyl, indazolyl, benzimidazolyl, benzothiazolyl, coumarinyl, benzoisothiazolyl, benzodioxolyl, benzoxazolyl, benzoisoxazolyl, quinoxalinyl, quinazolinyl, phthalazinyl, pteridinyl, cinnolinyl, chromonyl, pyrrolopyridyl, furopyridinyl, purinyl, benzothiadiazolyl, benzooxadiazolyl, benzotriazolyl, acridinyl, benzothiadiazolyl, benzotriazinyl, carbazolyl, dibenzofuranyl, dibenzothienyl, phenanthridinyl and xanthenyl; and wherein the heteroaryl or heterocycle is optionally substituted with one or more groups selected from halogen, oxo, thio, nitro, —CN, —OR$_1$, —S(=O)$_m$R$_1$, —S(=O)$_{1-2}$NR$_1$R$_2$, —OCOR$_1$, —SCOR$_1$, —NR$_1$R$_2$, —NR$_1$COR$_2$, —NR$_1$COOR$_2$, —NR$_1$SOR$_2$, —NR$_1$SO$_2$R$_2$, —NR$_1$CONR$_1$R$_2$, —COR$_1$, —COOR$_1$, —CONR$_1$R$_2$, alkyl, alkenyl, alkynyl, cycloalkyl, alkylcycloalkyl, aryl, alkylaryl, heterocyclyl, alkylheterocyclyl, heteroaryl and alkylheteroaryl; wherein R$_1$ and R$_2$ are independently selected from H, alkyl, alkenyl, alkynyl, cycloalkyl, alkylcycloalkyl, aryl, alkylaryl, heterocyclyl, alkytheterocyclyl, heteroaryl and alkylheteroaryl;
a is an integer from 1 to 5;
b is 0 or an integer from 1 to 5;
m is 0 or an integer from 1 to 2;
p is an integer from 1 to 4;
* indicates the point of attachment;
or a stereoisomer, a tautomer or a pharmaceutically acceptable salt thereof.

2. A compound according to claim 1 having formula (Iaa),

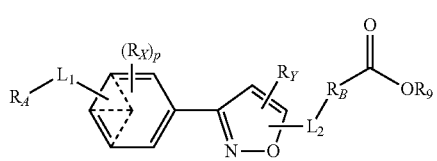

wherein,
--- dotted line represents the variable attachment of -L$_1$-R$_A$ to the specified carbon atoms of the phenyl ring,
R$_A$ is cycloalkyl, aryl, alkylaryl, heteroaryl or heterocycle; wherein each of cycloalkyl, aryl, alkylaryl, heteroaryl and heterocycle is optionally substituted;
R$_X$ is H, halogen or alkyl;
R$_Y$ is selected from H, halogen, —CN, OH, alkyl or unsubstituted aryl;
L$_1$ is —O—, —NR$_3$(CR$_4$R$_5$)$_a$NR$_3$—, —(CR$_4$R$_5$)$_b$NR$_3$—, —SO$_2$NH—, or —SO$_2$NHCONH—;
L$_2$ is —C(=O), —C(=O)—NR$_Z$—, —C(=S)—NR$_Z$—, —C(=NR$_8$)—NR$_Z$—, —C(SR$_9$)=N— or —SO$_2$NR$_Z$—;
R$_B$ is —(CR$_{10}$R$_{11}$)$_c$— or —(NR$_{12}$)(CR$_{10}$R$_{11}$)$_c$, wherein c is an integer from 1 to 3;

$R_9$ is absent or is selected from H or alkyl;
or $R_B$, C(O), $OR_9$ and $L_2$; or $R_B$ and $L_2$; or $R_B$, C(O) and $OR_9$ together form a 5 to 7-membered ring selected from heteroaryl and heterocycle;

$R_1$ and $R_2$ are independently selected from H, alkyl, alkenyl, alkynyl, cycloalkyl, alkylcycloalkyl, aryl, alkylaryl, alkylheteroaryl, heterocycle and heteroaryl;

$R_3$ is —H, —$COR_1$, —$COOR_1$, —$CONR_1R_2$, alkyl, alkenyl, alkynyl, cycloalkyl or alkylcycloalkyl;

$R_4$ and $R_5$ are independently selected from —H, —$OR_6$, —$COOR_6$, —$CONR_6R_7$, alkyl, alkenyl, alkynyl, cycloalkyl, alkylcycloalkyl, aryl, heteroaryl, alkylaryl, alkylheteroaryl and alkyltheterocycle;

or $R_4$ and $R_5$ together are =O, =S or =$NR_8$;

$R_6$ and $R_7$ are independently selected from H, alkyl, cycloalkyl and heterocycle;

$R_Z$ is —H, or alkyl;

$R_8$ is —H, —$OR_9$, —$COR_9$, —$COOR_9$, —$CONR_6R_7$, —$SO_2R_9$ or —$SO_2NR_6R_7$;

$R_{10}$, $R_{11}$ and $R_{12}$ are independently selected from H, aryl, $C_1$-$C_6$ alkyl optionally substituted with OH or $C_1$-$C_4$alkoxy; or ($C_1$-$C_6$)alkylaryl optionally substituted with OH;

or $R_{12}$ and $R_{10}$ or $R_{11}$ together with the respective N and C atoms to which they are attached, form a 3 to 6-membered, heteroaryl or heterocyclic ring;

or $R_{10}$ and $R_{11}$ of —$(CR_{10}R_{11})_c$ wherein c is the integer 1, together with the C atom to which they are attached form a 3 to 6-membered cycloalkyl ring;

or $R_{10}$ and $R_{11}$ of —$(CR_{10}R_{11})_c$ wherein c is the integer 1 together with the C atom to which they are attached form alkenylene;

a is an integer from 1 to 5;
b is 0 or an integer from 1 to 5;
m is 0 or an integer from 1 to 2;
p is an integer from 1 to 4;

with the proviso that When $L_2$ is —C(=O)—$NR_Z$—, $L_1$ is —$(CR_4R_5)_bNR_3$—, and $R_B$ is —$(CR_{10}R_{11})_c$ then (a) c is the integer 1; and (b) $R_4$ is heteroaryl or heterocycle, wherein the heteroaryl or heterocycle is selected from indolyl, isoindolyl, indolizinyl, benzofuranyl, benzothienyl, quinolinyl, isoquinolinyl, benzopyranyl, indazolyl, benzimidazolyl, benzothiazolyl, benzoisothiazolyl, benzodioxolyl, benzoxazolyl, benzoisoxazolyl, quinoxalinyl, quinazolinyl, phthalazinyl, pteridinyl, cinnolinyl, chromonyl, coumarinyl, pyrrolopyridyl, furopyridinyl, purinyl, benzothiadiazolyl, benzooxadiazolyl, benzotriazolyl, benzothiadiazolyl, benzotriazinyl, carbazolyl, dibenzofuranyl, dibenzothienyl, acridinyl, phenanthridinyl and xanthenyl; and wherein the heteroaryl or heterocycle is optionally substituted with one or more groups selected from halogen, oxo, thio, nitro, —CN, —$OR_1$, —$S(=O)_mR_1$, —$S(=O)_{1-2}NR_1R_2$, —$OCOR_1$, —$SCOR_1$, —$NR_1R_2$, —$NR_1COR_2$, —$NR_1COOR_2$, —$NR_1SOR_2$, —$NR_1SO_2R_2$, —$NR_1CONR_1R_2$, —$COR_1$, —$COOR_1$, —$CONR_1R_2$, alkyl, alkenyl, alkynyl, cycloalkyl, alkylcycloalkyl, aryl, alkylaryl, heterocyelyl, alkylheterocyclyl, heteroaryl and alkylheteroaryl; wherein $R_1$ and $R_2$ are independently selected from H, alkyl, alkenyl, alkynyl, cycloalkyl, alkylcycloalkyl, aryl, alkylaryl, heterocyclyl, alkylheterocyclyl, heteroaryl and alkylheteroaryl;

or a stereoisomer, a tautomer or a pharmaceutically acceptable salt thereof.

3. A compound according to claim 2, having formula (Iab),

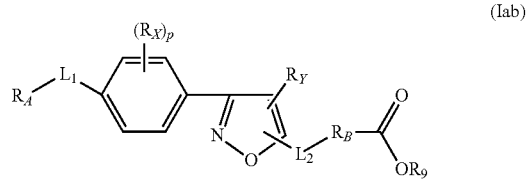

wherein, $R_A$ is cycloalkyl, alkylaryl, aryl, heteroaryl or heterocycle; wherein each of cycloalkyl, alkylaryl, aryl, heteroaryl and heterocycle is optionally substituted;

$R_X$ is H, halogen or alkyl;

$R_Y$ is selected from H, halogen, —CN, OH, alkyl, or unsubstituted aryl;

$R_1$ and $R_2$ are independently selected from H, alkyl, alkenyl, alkynyl, cycloalkyl, alkylcycloalkyl, aryl, alkylaryl, alkylheteroaryl, heterocycle and heteroaryl;

$L_1$ is —O—, —$NR_3(CR_4R_5)_aNR_3$—, —$(CR_4R_5)_bNR_3$—, —$SO_2NH$— or —$SO_2NHCONH$—;

$R_3$ is H, —$COR_1$, —$COOR_1$, —$CONR_1R_2$, alkyl, alkenyl, alkynyl, cycloalkyl or alkylcycloalkyl;

$R_4$ and $R_5$ are independently selected from H, —$OR_6$, —$COOR_6$, —$CONR_6R_7$, alkyl, alkenyl, alkynyl, cycloalkyl, alkylcycloalkyl, aryl, heteroaryl, alkylaryl, alkylheteroaryl and alkyltheterocycle;

or $R_4$ and $R_5$ together are =O or =S or =$NR_8$;

$R_6$ and $R_7$ are independently selected from H, alkyl, cycloalkyl and heterocycle;

$L_2$ is —C(=O)—, —C(=O)—$NR_Z$—, —C(=S)—$NR_Z$—, —C(=$NR_8$)—$NR_Z$, —C($SR_9$)=N— or —$SO_2NR_Z$—, $R_Z$ is H or alkyl;

$R_8$ is H, —$OR_9$, —$COR_9$, —$COOR_9$, —$CONR_6R_7$, —$SO_2R_9$ or —$SO_2NR_6R_7$;

$R_9$ is absent or is selected from H or alkyl;

$R_B$ is —$(CR_{10}R_{11})_c$— or —$(NR_{12})(CR_{10}R_{11})_c$; wherein c is an integer from 1 to 3;

or $R_B$, C(O), $OR_9$ and $L_2$; or $R_B$ and $L_2$; or $R_B$, C(O) and $OR_9$, together form a 5 to 7-membered ring selected from heteroaryl or heterocycle;

$R_{10}$, $R_{11}$ and $R_{12}$ are independently selected from: H, aryl, $C_1$-$C_6$ alkyl optionally substituted with OH or $C_1$-$C_4$alkoxy; or ($C_1$-$C_6$)alkylaryl optionally substituted with OH;

or $R_{12}$ and $R_{10}$ or $R_{11}$, together with the respective N and C atoms to which they are attached, form a 3 to 6-membered heteroaryl or heterocyclic ring;

or $R_{10}$ and $R_{11}$ of —$(CR_{10}R_{11})_c$ wherein c is the integer 1, together with the C atony to which they are attached form a 3 to 6-membered cycloalkyl ring;

or $R_{10}$ and $R_{11}$ of —$(CR_{10}R_{11})_c$ wherein c is the integer 1 together with the C atom to which they are attached form alkenylene;

a is the integer 1;
b is 0 or an integer from 1 to 5;
m is 0 or the integer 1 or 2;
p is an integer from 1 to 4;

with the proviso that when $L_2$ is —C(=O)—$NR_Z$—, $L_1$ is —$(CR_4R_5)_bNR_3$—, and $R_B$ is —$(CR_{10}R_{11})_c$, then (a) c is the integer 1 and (b) $R_A$ is heteroaryl or heterocycle, wherein the heteroaryl or heterocycle is selected from indolyl, isoindolyl, indolizinyl, benzofuranyl, benzothienyl, quinolinyl, isoquinolinyl, benzopyranyl, indazolyl, benzimidazolyl, benzothiazolyl, benzoisothiazolyl, benzodioxolyl, benzoxazolyl, benzoisoxazolyl, quinoxalinyl, quinazolinyl, phthalazinyl, pteridinyl, cinnolinyl, chromonyl, coumarinyl, pyrrolopyridyl, furopyridinyl, purinyl, benzothiadiazolyl, benzooxadiazolyl, benzotriazolyl, benzothiadiazolyl, benzotriazinyl, carbazolyl, dibenzofuranyl, dibenzothienyl, acridinyl, phenanthridinyl and xanthenyl; and wherein the heteroaryl or heterocycle is optionally substituted with one or more groups selected from halogen, oxo, thio, nitro, —CN, —OR$_1$, —S(=O)$_m$R$_1$, —S(=O)$_{1-2}$NR$_1$R$_2$, —OCOR$_1$, —SCOR$_1$, —NR$_1$R$_2$, —NR$_1$COR$_2$, —NR$_1$COOR$_2$, —NR$_1$SOR$_2$, —NR$_1$SO$_2$R$_2$, —NR$_1$CONR$_1$R$_2$, —COR$_1$, —COOR$_1$, —CONR$_1$R$_2$, alkyl, alkenyl, alkynyl, cycloalkyl, alkylcycloalkyl, aryl, alkylaryl, heterocyclyl, alkylheterocyclyl, heteroaryl and alkylheteroaryl; wherein R$_1$ and R$_2$ are independently selected from H, alkyl, alkenyl, alkynyl, cycloalkyl, alkylcycloalkyl, aryl, alkylaryl, heterocyclyl, alkylheterocyclyl, heteroaryl and alkylheteroaryl;

or a stereoisomer, a tautomer or a pharmaceutically acceptable salt thereof.

4. A compound according to claim 2, having formula (Iac),

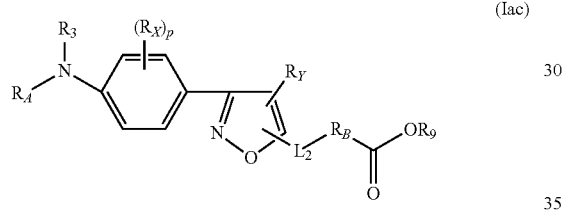

(Iac)

wherein,

R$_A$ is cycloalkyl, aryl, heteroaryl or heterocycle; wherein each of cycloalkyl, aryl, heteroaryl and heterocycle is optionally substituted;

R$_X$ and R$_Y$ are independently selected from H, halogen, —CN, —OR$_1$, —S(=O)$_m$R$_1$, —OCOR$_1$, —SCOR$_1$, —NR$_1$R$_2$, —NR$_1$COR$_2$, —NR$_1$COOR$_2$, —NR$_1$SO$_2$R$_2$, —NR$_1$CONR$_2$, —COR$_1$, —COOR$_1$, —CONR$_1$R$_2$, alkyl, alkenyl, alkynyl, cycloalkyl, alkylcycloalkyl, aryl, alkylaryl, alkylheteroaryl or heteroaryl;

R$_1$ and R$_2$ are independently selected from H, alkyl, alkenyl, alkynyl, cycloalkyl, alkylcycloalkyl, aryl, alkylaryl, alkylheteroaryl, heterocycle and heteroaryl;

L$_2$ is —C(=O)—NR$_Z$—, —C(=S)—NR$_Z$—, —C(=NR$_8$)—NR$_Z$— or —SO$_2$NR$_Z$—;

R$_Z$ is —H, —COR$_1$, —COOR$_1$, —CONR$_1$R$_2$, alkyl, alkenyl, alkynyl, cycloalkyl or alkylcycloalkyl;

R$_8$ is H, —OR$_9$, —COR$_9$, —COOR$_9$, —CONR$_6$R$_7$, —SO$_2$R$_9$ or —SO$_2$NR$_6$R$_7$;

R$_6$ and R$_7$ are independently selected from H, alkyl, cycloalkyl and heterocycle;

R$_3$ is H, —COR$_1$, —COOR$_1$, —CONR$_1$R$_2$, alkyl, alkenyl, alkynyl, cycloalkyl or alkylcycloalkyl;

R$_9$ is absent or is selected from H, alkyl, alkenyl, alkynyl, cycloalkyl, aryl, alkylcycloalkyl, alkylaryl, alkylheteroaryl, heterocycle and heteroaryl;

R$_B$ is —(CR$_{10}$R$_{11}$)$_c$— or —(NR$_{12}$)(CR$_{10}$R$_{11}$)$_c$; wherein c is an integer from 1 to 3;

or R$_B$, C(O), OR$_9$ and L$_2$; or R$_B$ and L$_2$; or R$_B$ C(O) and OR$_9$, together form a 5 to 7-membered ring selected from cycloalkyl, aryl, heteroaryl and heterocycle;

R$_{10}$, R$_{11}$ and R$_{12}$ are independently selected from H or the groups alkyl, alkenyl, alkynyl, cycloalkyl, alkylcycloalkyl, aryl, alkylaryl, alkylheteroaryl, heterocycle and heteroaryl;

or R$_{12}$ and R$_{10}$ or R$_{11}$ together with the respective N and C atoms to which they are attached, form a 3 to 6 membered heterocyclic or heteroaryl ring;

or R$_{10}$ and R$_{11}$ of —(CR$_{10}$R$_{11}$)$_c$ wherein c is the integer 1, together with the C atom to which they are attached form a 3 to 6-membered cycloalkyl ring;

m is 0 or an integer from 1 to 2;

p is an integer from 1 to 4;

with the proviso that when L$_2$ is —C(=O)—NR$_Z$— and R$_B$ is —(CR$_{10}$R$_{11}$)$_c$, then (i) c is the integer 1 and (ii) R$_A$ is heteroaryl or heterocycle, wherein the heteroaryl or heterocycle is selected from indolyl, isoindolyl, indolizinyl, benzofuranyl, benzothienyl, quinolinyl, isoquinolinyl, benzopyranyl, indazolyl, benzimidazolyl, benzothiazolyl, benzoisothiazolyl, benzodioxolyl, benzoxazolyl, benzoisoxazolyl, quinoxalinyl, quinazolinyl, phthalazinyl, pteridinyl, cinnolinyl, chromonyl, coumarinyl, pyrrolopyridyl, furopyridinyl, purinyl, benzothiadiazolyl, benzooxadiazolyl, benzotriazolyl, benzothiadiazolyl, benzotriazinyl, carbazolyl, dibenzofuranyl, dibenzothienyl, acridinyl, phenanthridinyl and xanthenyl; and wherein the heteroaryl or heterocycle is optionally substituted with one or more groups selected from halogen, oxo, thio, nitro, —CN, —OR$_1$, —S(=O)$_m$R$_1$, —S(=O)$_{1-2}$NR$_1$R$_2$, —OCOR$_1$, —SCOR$_1$, —NR$_1$R$_2$, —NR$_1$COR$_2$, —NR$_1$COOR$_2$, —NR$_1$SOR$_2$, —NR$_1$SO$_2$R$_2$, —NR$_1$CONR$_2$R$_2$, —COR$_1$, —COOR$_1$, —CONR$_1$R$_2$, alkyl, alkenyl, alkynyl, cycloalkyl, alkylcycloalkyl, aryl, alkylaryl, heterocyclyl, alkylheterocyclyl, heteroaryl and alkylheteroaryl; Wherein R$_1$ and R$_2$ are independently selected from H, alkyl, alkenyl, alkynyl, cycloalkyl, alkylcycloalkyl, aryl, alkylaryl, heterocyclyl, alkylheterocyclyl, heteroaryl and alkylheteroaryl;

or a stereoisomer or a tautomer thereof or a pharmaceutically acceptable salt or a pharmaceutically acceptable solvate thereof.

5. A compound according to claim 2 having formula (Iae),

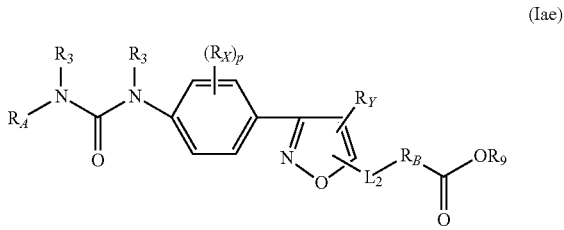

(Iae)

wherein,

R$_A$ is cycloalkyl, alkylaryl, aryl, heteroaryl or heterocycle; wherein each of cycloalkyl, alkylaryl, aryl, heteroaryl and heterocycle is optionally substituted;

R$_X$ is H, halogen or alkyl;

R$_Y$ is selected from H, halogen, —CN, OH, alkyl, or unsubstituted aryl;

R$_1$ and R$_2$ are independently selected from H, alkyl, alkenyl, alkynyl, cycloalkyl, alkylcycloalkyl, aryl, alkylaryl, alkylheteroaryl, heterocycle and heteroaryl;

R$_3$ is H, —COR$_1$, —COOR$_1$, —CONR$_1$R$_2$, alkyl, alkenyl, alkynyl, cycloalkyl or alkylcycloalkyl;

$L_2$ is —C(=O)—, —C(=O)—$NR_Z$—, —C(=S)—$NR_Z$—, —C(=$NR_8$)—$NR_Z$—, —C($SR_9$)=N— or —$SO_2NR_Z$—;

$R_Z$ is H;

$R_8$ is H, —$OR_9$, —$COR_9$, —$COOR_9$, —$CONR_6R_7$, —$SO_2R_9$ or —$SO_2NR_6R_7$;

$R_6$ and $R_7$ are independently selected from H, alkyl, cycloalkyl and heterocycle;

$R_9$ is H or alkyl;

$R_B$ is —$(CR_{10}R_{11})_c$— or —$(NR_{12})(CR_{10}R_{11})_c$; wherein c is an integer from 1 to 3;

$R_{10}$, $R_{11}$ and $R_{12}$ are independently selected from
H,
aryl,
$C_1$-$C_6$ alkyl optionally substituted With OH or $C_1$-$C_4$alkoxy, or
($C_1$-$C_6$)alkylaryl optionally substituted with OH;

or $R_{12}$ and $R_{10}$ or $R_{11}$ together with the respective N and C atoms to which they are attached, form a 3 to 6 membered heterocyclic or heteroaryl ring;

or $R_{10}$ and $R_{11}$ of —$(CR_{10}R_{11})_c$ wherein c is the integer 1, together with the C atom to which they are attached form a 3 to 6-membered cycloalkyl ring;

or $R_{10}$ and $R_{11}$ of —$(CR_{10}R_{11})_c$ wherein c is the integer 1 together with the C atom to which they are attached form alkenylene;

m is 0 or the integer 1 or 2;

p is an integer from 1 to 4;

or a stereoisomer, a tautomer or a pharmaceutically acceptable salt thereof.

6. A compound according to claim 2, having formula (Iaf),

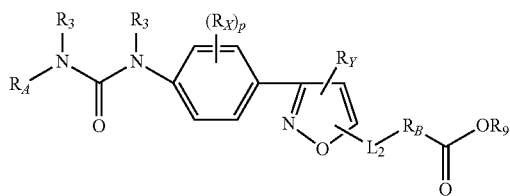

(Iaf)

wherein, $R_A$ is cycloalkyl, alkylaryl, aryl, heteroaryl or heterocycle; wherein the cycloalkyl, alkylaryl, aryl, heteroaryl or heterocyclyl is optionally substituted with one or more groups, which may be the same or different, selected from halogen, —CN, —$COOR_1$, —$OR_1$, —S(=O)$_m$$R_1$, alkyl, haloalkyl, cycloalkyl, aryl and heteroaryl;

$R_X$ is H, halogen or alkyl;

$R_Y$ is selected from H, halogen, —CN, OH or alkyl;

$R_1$ and $R_2$ are independently selected from H, alkyl, alkenyl, alkynyl, cycloalkyl or aryl;

$R_3$ is H or alkyl;

$L_2$ is —C(=O)—, —C(=O)—$NR_Z$, —C(=S)—$NR_Z$—, —C(=$NR_8$—$NR_Z$—, —C($SR_9$)=N— or —$SO_2NR_Z$—;

$R_Z$ is H or alkyl;

$R_8$ is H, —$OR_9$, —$COR_9$, —$COOR_9$, —$CONR_6R_7$, —$SO_2R_9$ or —$SO_2NR_6R_7$;

$R_6$ and $R_7$ are independently selected from H, alkyl, cycloalkyl and heterocycle;

$R_9$ is H or alkyl;

$R_B$ is —$(CR_{10}R_{11})_c$— or —$(NR_{12})(CR_{10}R_{11})_c$; wherein c is an integer from 1 to 3;

$R_{10}$, $R_{11}$ and $R_{12}$ are independently selected from
H,
aryl,
$C_1$-$C_6$ alkyl optionally substituted with OH or $C_1$-$C_4$alkoxy, or
($C_1$-$C_6$)alkylaryl optionally substituted with OH;

or $R_{12}$ and $R_{10}$ or $R_{11}$ together with the respective N and C atoms to which they are attached, form a 3 to 6 membered heterocyclic or heteroaryl ring;

or $R_{10}$ and $R_{11}$ of —$(CR_{10}R_{11})_c$ wherein c is an integer 1, together with the C atom to which they are attached form a 3 to 6-membered cycloalkyl ring;

or $R_{10}$ and $R_{11}$ of —$(CR_{10}R_{11})_c$ wherein c is the integer 1 together with the C atom to which they are attached form alkenylene;

m is 0 or the integer 1 or 2;

p is an integer from 1 to 4;

or a stereoisomer, a tautomer or a pharmaceutically acceptable salt thereof.

7. A compound according claim 2, having formula (Iah),

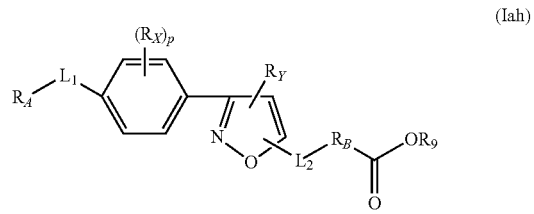

(Iah)

wherein, $R_A$ is cycloalkyl, alkylaryl, aryl, heteroaryl or heterocycle; wherein the cycloalkyl, alkylaryl, aryl, heteroaryl or heterocycle is optionally substituted with one or more groups, which may be the same or different, selected from halogen, cyano, —$COOR_1$, —$OR_1$, —S(=O)$_m$$R_1$, alkyl, haloalkyl, cycloalkyl, aryl and heteroaryl; wherein $R_1$ is hydrogen, alkyl, alkenyl, alkynyl, cycloalkyl or aryl;

$R_X$ is H, halogen or alkyl;

$R_Y$ is selected from H, halogen, —CN, OH, alkyl or unsubstituted aryl;

$L_1$ is —NH(C=O)NH—, —NH— or —(CO)$NR_3$; wherein $R_3$ is H or alkyl;

$L_2$ is —C(=O), —C(=O)—$NR_Z$—, —C(=S)—$NR_Z$—, —C(=$NR_8$)—$NR_Z$—, —C($SR_9$)=N— or —$SO_2NR_Z$—;

$R_Z$ is H or alkyl; $R_8$ is —$OR_9$; wherein $R_9$ is absent or is selected from H and alkyl;

$R_B$ is —$(CR_{10}R_{11})_c$; or —$(NR_{12})(CR_{10}R_{11})_c$; wherein c is an integer from 1 to 3;

or $R_B$, C(O), $OR_9$ and $L_2$; or $R_B$ and $L_2$; or $R_B$, C(O) and $OR_9$, together form a 5 to 7-membered ring selected from heteroaryl or heterocycle; wherein the heteroaryl or heterocycle is optionally substituted with one or more groups selected from halogen, —CN, —$OR_1$, —S(=O)$_m$ $R_1$, —$OCOR_1$, —$SCOR_1$, —$NR_1NR_2$, —$NR_1COR_2$, —$NR_1COOR_2$, —$NR_1SO_2R_2$, —$NR_1CONR_2$, —$COR_1$, —$COOR_1$, —$CONR_1R_2$, alkyl, alkenyl, alkynyl, cycloalkyl and alkylcycloalkyl; wherein $R_2$ is selected from hydrogen, alkyl, alkenyl, alkynyl, cycloalkyl or aryl;

$R_{10}$, $R_{11}$ and $R_{12}$ are independently selected from H, alkyl, and aryl, wherein the alkyl or aryl is optionally substituted with OH or —$C_1$-$C_4$alkoxy;

or $R_{12}$ and $R_{10}$ or $R_{11}$ together with the respective N and C atoms to which they are attached, together form a heterocyclic ring such as pyrrolidine ring;

or $R_{10}$ and $R_{11}$ of —$CR_{10}R_{11}$ together with the C atom to which they are attached form a 3 to 6-membered cycloalkyl ring such as cyclopentyl ring;

or $R_{10}$ and $R_{11}$ of —$(CR_{10}R_{11})_c$ wherein c is the integer 1 together with the C atom to which they are attached form alkenylene;

m is 0 or the integer 1 or 2;

p is an integer from 1 to 4;

with the proviso that when $L_1$ is —NH—, $L_2$ is —C(=O)—$NR_Z$— and $R_B$ is —$CR_{10}R_{11}$ then $R_A$ is heteroaryl or heterocycle selected from indolyl, isoindolyl, indolizinyl, benzofuranyl, benzothienyl, quinolinyl, isoquinolinyl, benzopyranyl, indazolyl, benzimidazolyl, benzothiazolyl, benzoisothiazolyl, benzodioxolyl, benzoxazolyl, benzoisoxazolyl, quinoxalinyl, quinazolinyl, phthalazinyl, pteridinyl, cinnolinyl, chromonyl, coumarinyl, pyrrolopyridyl, furopyridinyl, purinyl, benzothiadiazolyl, benzooxadiazolyl, benzotriazolyl, benzothiadiazolyl, benzotriazinyl, carbazolyl, dibenzoluranyl, dibenzothienyl, acridinyl, phenanthridinyl and xanthenyl; and wherein the heteroaryl or heterocycle is optionally substituted with one or more groups selected from halogen, oxo, thio, nitro, —CN, —$OR_1$, —$S(=O)_mR_1$, —$S(=O)_{1-2}NR_1R_2$, —$OCOR_1$, —$SCOR_1$, —$NR_1R_2$, —$NR_1COR_2$, —$NR_1COOR_2$, —$NR_1SOR_2$, —$NR_1SO_2R_2$, —$NR_1CONR_1R_2$, —$COR_1$, —$COOR_1$, —$CONR_1R_2$, alkyl, alkenyl, alkynyl, cycloalkyl, alkylcycloalkyl, aryl, alkylaryl, heterocyclyl, alkylheterocyclyl, heteroaryl and alkylheteroaryl; wherein $R_1$ and $R_2$ are independently selected from H, alkyl, alkenyl, alkynyl, cycloalkyl, alkylcycloalkyl, aryl, alkylaryl, heterocyclyl, alkylheterocyclyl, heteroaryl and alkylheteroaryl;

or a stereoisomer, a tautomer or a pharmaceutically acceptable salt thereof.

8. A compound according claim 2, having formula (Iai),

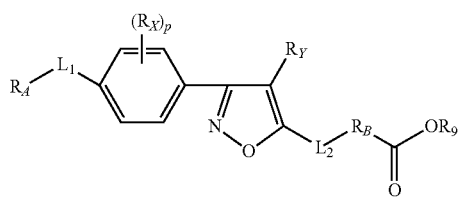

(Iai)

wherein, $R_A$ is cycloalkyl, alkylaryl, aryl, heteroaryl or heterocycle; wherein the cycloalkyl, alkylaryl, aryl, heteroaryl or heterocycle are optionally substituted with one or more groups, which may be the same or different, selected from cyano, halogen, —$OR_1$, —$COOR_1$, —$S(=O)_mR_1$, alkyl, haloalkyl, cycloalkyl, aryl and heteroaryl; $R_1$ is hydrogen, alkyl, alkenyl, alkynyl, cycloalkyl or aryl;

$R_X$ is H, halogen or alkyl;

$R_Y$ is H, halogen, —CN, OH, alkyl or unsubstituted aryl;

$L_1$ is —NH(C=O)NH—, —NH— or —(CO)$NR_3$—, wherein $R_3$ is H or alkyl;

$L_2$ is —C(=O)—, —C(=O)—$NR_Z$—, —C(=S)—$NR_Z$—, —C(=$NR_8$)—$NR_Z$—, —C($SR_9$)=N— or —$SO_2NR_Z$—;

$R_Z$ is H or alkyl; $R_8$ is —$OR_9$; wherein $R_9$ is absent or is selected from H or alkyl;

$R_B$ is —$(CR_{10}R_{11})_c$ or —$(NR_{12})(CR_{10}R_{11})_c$; wherein c is an integer from 1 to 3;

or $R_B$, C(O), $OR_9$ and $L_2$; or $R_B$ and $L_2$; or $R_B$, C(O) and $OR_9$, together form a 5 to 7-membered ring selected from heteroaryl or heterocycle; wherein the cycloalkyl, aryl, heteroaryl or heterocycle is optionally substituted with one or more groups selected from halogen, —CN, —$OR_1$, —$S(=O)_mR_1$, —$OCOR_1$, —$SCOR_1$, —$NR_1R_2$, —$NR_1COR_2$, —$NR_1COOR_2$, —$NR_1SO_2R_2$, —$NR_1CONR_2$, —$COR_1$, —$COOR_1$, —$CONR_1R_2$, alkyl, alkenyl, alkynyl, cycloalkyl and alkylcycloalkyl;

wherein $R_2$ is hydrogen, alkyl, alkenyl, alkynyl, cycloalkyl or aryl;

$R_{10}$, $R_{11}$ and $R_{12}$ are independently selected from H, alkyl and aryl, wherein the alkyl or aryl is optionally substituted with OH or $C_1$-$C_4$alkoxy;

or $R_{12}$ and $R_{10}$ or $R_{11}$ together with the respective N and C atoms to which they are attached, together form a heterocyclic ring such as pyrrolidine ring;

or $R_{10}$ and $R_{11}$ of —$CR_{10}R_{11}$ together with the C atom to which they are attached form a 3 to 6-membered cycloalkyl ring such as cyclopentyl ring;

or $R_{10}$ and $R_{11}$ of —$(CR_{10}R_{11})_c$ wherein c is the integer 1 together with the C atom to which they are attached form alkenylene;

m is 0 or the integer 1 or 2;

p is an integer from 1 to 4;

with the proviso that when $L_1$ is —NH—, $L_2$ is —C(=O)—$NR_Z$— and $R_B$ is —$CR_{10}R_{11}$ then $R_A$ is heteroaryl or heterocycle selected from indolyl, isoindolyl, indolizinyl, benzofuranyl, benzothienyl, quinolinyl, isoquinolinyl, benzopyranyl, indazolyl, benzimidazolyl, benzothiazolyl, benzoisothiazolyl, benzodioxolyl, benzoxazolyl, benzoisoxazolyl, quinoxalinyl, quinazolinyl, phthalazinyl, pteridinyl, cinnolinyl, chromonyl, coumarinyl, pyrrolopyridyl, furopyridinyl, purinyl, benzothiadiazolyl, benzooxadiazolyl, benzotriazolyl, benzothiadiazolyl, benzotriazinyl, carbazolyl, dibenzofuranyl, dibenzothienyl, acridinyl, phenanthridinyl and xanthenyl: and wherein the heteroaryl or heterocycle is optionally substituted with one or more groupS selected from halogen, oxo, thio, nitro, —CN, —$OR_1$, —$S(=O)_mR_1$, —$S(=O)_{1-2}NR_1R_2$, —$OCOR_1$, —$SCOR_1$, —$NR_1R_2$, —$NR_1COR_2$, —$NR_1COOR_2$, —$NR_1SOR_2$, —$NR_1SO_2R_2$, —$NR_1CONR_1R_2$, —$COR_1$, —$COOR_1$, —$CONR_1R_2$, alkyl, alkenyl, alkynyl, cycloalkyl, alkylcycloalkyl, aryl, alkylaryl, heterocyclyl, alkylheterocyclyl, heteroaryl and alkylheteroaryl; wherein $R_1$ and $R_2$ are independently selected from H, alkyl, alkenyl, alkynyl, cycloalkyl, alkylcycloalkyl, aryl, alkylaryl, heterocyclyl, alkylheterocyclyl, heteroaryl and alkylheteroaryl;

or a stereoisomer, a tautomer or a pharmaceutically acceptable salt thereof.

9. A compound according to claim 2, having formula (Iaj),

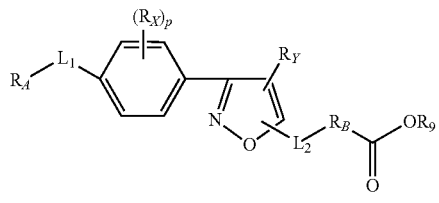

(Iaj)

wherein
R$_A$ is alkylaryl, aryl or heteroaryl; wherein the alkylaryl, aryl or heteroaryl is optionally substituted with one or more groups, which may be the same or different, selected from halogen, OR$_1$, alkyl and haloalkyl; wherein R$_1$ is hydrogen or alkyl;
R$_X$ and R$_Y$ are hydrogen;
L$_1$ is —O—, —NR$_3$(C=S)NR$_3$—, —SO$_2$NHCONH, —SO$_2$NH—, —NR$_3$(CO)$_2$NR$_3$—, wherein R$_3$ is H or alkyl;
L$_2$ is —C(=O)—, —C(=O)—NR$_Z$—, —C(=S)—NR$_Z$—, —C(=NR$_8$)—NR$_Z$—SO$_2$NR$_Z$—;
R$_Z$ is H; R$_8$ is —OR$_9$, wherein R$_9$ is H or alkyl;
R$_B$ is —CR$_{10}$R$_{11}$; or —(NR$_{12}$)(CR$_{10}$R$_{11}$)$_c$; wherein c is an integer from 1 to 3;
R$_{10}$, R$_{11}$ and R$_{12}$ are independently selected from H and alkyl;
or R$_{12}$ and R$_{10}$ or R$_{11}$ together with the respective N and C atoms to which they are attached, together form a heterocyclic ring such as pyrrolidine ring;
m is 0 or the integer 1 or 2;
p is an integer from 1 to 4;
or a stereoisomer or a tautomer thereof or a pharmaceutically acceptable salt or a pharmaceutically acceptable solvate thereof.

10. A compound according to claim 1 selected from:
(S)-2-({3-[4-(6-Fluoro-benzothiazol-2-ylamino)-phenyl]-isoxazole-5-carbonyl}-amino)-3-methyl-butyric acid methyl ester;
(S)-2-({3-[4-(6-Fluoro-benzothiazol-2-ylamino)-phenyl]-isoxazole-5-carbothioyl}-amino)-3-methyl-butyric acid methyl ester;
(S)-2-({3-[4-(6-Fluoro-benzothiazol-2-ylamino)-phenyl]-N-hydroxy-isoxazole-5-carboximidoyl}-amino)-3-methyl-butyric acid methyl ester;
(S)-2-({3-[4-(6-Fluoro-benzothiazol-2-ylamino)-phenyl]-N-hydroxy-isoxazole-5-carboximidoyl}-amino)-3-methyl-butyric acid;
(S)-2-({3[4-(6-Fluoro-benzothiazol-2-ylamino)-phenyl]-isoxazole-5-carbonyl}-amino)-3-hydroxy-propionic acid methyl ester;
(S)-2-({3-[4-(6-Fluoro-benzothiazol-2-ylamino)-phenyl]-isoxazole-5-carbonyl}-amino)-3-hydroxy-propionic acid;
(S)-2-{3-[4-(6-Fluoro-benzothiazol-2-ylamino)-phenyl]-isoxazol-5-yl}-4,5-dihydro-thiazole-4-carboxylic acid methyl ester;
(S)-2-({3-[4-(6-Fluoro-benzothiazol-2-ylamino)-phenyl]-isoxazole-5-carbonyl}amino)-3-methoxy-propionic acid methyl ester;
(S)-2-({3-[4-(6-Fluoro-benzothiazol-2-ylamino)-phenyl]-isoxazole-5-carbonyl}-amino)-3-methoxy-propionic acid;
(S)-2-({3-[4-(6-Fluoro-benzothiazol-2-ylamino)-phenyl]-isoxazole-5-carbothioyl}-amino)-3-methoxy-propionic acid methyl ester;
(S)-2-({3-[4-(6-Fluoro-benzothiazol-2-ylamino)-phenyl]-isoxazole-5-carbothioyl}-amino)-3-methoxy-propionic acid;
(S)-2-({3-[4-(6-Fluoro-benzothiazol-2-ylamino)-phenyl]-N-hydroxy-isoxazole-5-carboximidoyl}-amino)-3-methoxy-propionic acid methyl ester;
(S)-2-({3-[4-(6-Fluoro-benzothiazol-2-ylamino)-phenyl]-N-hydroxy-isoxazole-5-carboximidoyl}-amino)-3-methoxy-propionic acid;
(S)-1-{3-[4-(6-Fluoro-benzothiazol-2-ylamino)-phenyl]-isoxazole-5-carbonyl}-pyrrolidine-2-carboxylic acid methyl ester;
(S)-1-{3-[4-(6-Fluoro-benzothiazol-2-ylamino)-phenyl]-isoxazole-5-carbonyl}-pyrrolidine-2-carboxylic acid;
(S)-2-({3-[3-(6-Fluoro-berizothiazol-2-ylamino)-phenyl]-isoxazole-5-carbonyl}-amino)-3-methyl-butyric acid methyl ester;
(S)-2-({3-[3-(6-Fluoro-benzothiazol-2-ylamino)-phenyl]-isoxazole-5-carbonyl}-amino)-3-methyl-butyric acid;
(S)-2-({3-[3-(6-Fluoro-benzothiazol-2-ylamino)-phenyl]-isoxazole-5-carbothioyl}-amino)-3-methyl-butyric acid methyl ester;
(S)-2-({3-[3-(6-Fluoro-benzothiazol-2-ylamino)-phenyl]-isoxazole-5-carbothioyl}-amino)-3-methyl-butyric acid;
(S)-2-({3-[3-(6-Fluoro-benzothiazol-2-ylamino)-phenyl]-N-hydroxy-isoxazole-5-carboximidoyl}-amino)-3-methyl-butyric acid methyl ester;
(S)-2-({3-[3-(6-Fluoro-benzothiazol-2-ylamino)-phenyl]-N-hydroxy-isoxazole-5-carboximidoyl}-amino)-3-methyl-butyric acid;
(S)-2-({3-[3-(6-Fluoro-benzothiazol-2-ylamino)-phenyl]-isoxazole-5-carbonyl}-amino)-3-methoxy-propionic acid methyl ester;
(S)-2-({3-[3-(6-Fluoro-benzothiazol-2-ylamino)-phenyl] isoxazole-5-carbonyl}-amino)-3-methoxy-propionic acid;
(S)-2-({3-[3-(6-Fluoro-benzothiazol-2-ylamino)-phenyl]-isoxazole-5-carbothioyl}-amino)-3-methoxy-propionic acid methyl ester;
(S)-2-({3-[3-(6-Fluoro-benzothiazol-2-ylamino)-phenyl] isoxazole-5-carbothioyl}-amino)-3-methoxy-propionic acid;
(S)-2-({3-[3-(6-Fluoro-benzothiazol-2-ylamino)-phenyl]-N-hydroxy-isoxazole-5-carboximidoyl}-amino)-3-methoxy-propionic acid methyl ester;
(S)-2-({3-[3-(6-Fluoro-benzothiazol-2-ylamino)-phenyl]-N-hydroxy-isoxazole-5-carboximidoyl}-amino)-3-methoxy-propionic acid;
(S)-1-{3-[3-(6-Fluoro-benzothiazol-2-ylamino)-phenyl]-isoxazole-5-carbonyl}-pyrrolidine-2-carboxylic acid methyl ester;
(S)-1-{3-[3-(6-Fluoro-benzothiazol-2-ylamino)-phenyl]-isoxazole-5-carbonyl}-pyrrolidine-2-carboxylic acid;
(S)-1-{3-[3-(6-Fluoro-benzothiazol-2-ylamino)-phenyl]-isoxazole-5-carbothioyl}-pyrrolidine-2-carboxylic acid methyl ester;
(S)-1-{3-[3-(6-Fluoro-benzothiazol-2-ylamino)-phenyl]-isoxazole-5-carbothioyl}-pyrrolidine-2-carboxylic acid;
(R)-2-({3-[4-(6-Fluoro-benzothiazol-2-ylamino)-phenyl]-isoxazole-5-carbonyl}-amino)-3-methyl-butyric acid methyl ester;
(R)-2-({3-[4-(6-Fluoro-benzothiazol-2-ylamino)-phenyl]-isoxazole-5-carbothioyl}-amino)-3-methyl-butyric acid methyl ester;
(R)-2-({3-[4-(6-Fluoro-benzothiazol-2-ylamino)-phenyl]-N-hydroxy-isoxazole-5-carboximidoyl}-amino)-3-methyl-butyric acid methyl ester;
(R)-2-({3-[4-(6-Fluoro-benzothiazol-2-ylamino)-phenyl]-N-hydroxy-isoxazole-5-carboximidoyl}-amino)-3-methyl-butyric acid;
(R)-2-({3-[4-(6-Fluoro-benzothiazol-2-ylamino)-phenyl]-isoxazole-5-carbonyl}-amino)-3-methyl-butyric acid;

(R)-2-({3-[4-(6-Fluoro-benzothiazol-2-ylamino)-phenyl]-isoxazole-5-carbothioy}-amino)-3-methyl-butyric acid;
(S)-2-({3-[4-(6-Fluoro-benzothiazol-2-ylamino)-phenyl]-isoxazole-5-carbonyl}-amino)-3-methyl-butyric acid;
(S)-2-({3-[4-(6-Fluoro-benzothiazol-2-ylamino)-phenyl]-isoxazole-5-carbothioyl}-amino)-3-methyl-butyric acid;
(S)-2-({3-[4-(6-Fluoro-benzothiazol-2-ylamino)-phenyl]-isoxazole-5-carbonyl}-amino)-4-methyl-pentanoic acid methyl ester;
(S)-2-({3-[4-(6-Fluoro-benzothiazol-2-ylamino)-phenyl]-isoxazole-5-carbonyl}-amino)-4-methyl-pentanoic acid;
(S)-2-({3-[4-(6-Fluoro-benzothiazol-2-ylamino)-phenyl]-isoxazole-5-carbothioyl}-amino)-4-methyl-pentanoic acid methyl ester;
(S)-2-({3-[4-(6-Fluoro-benzothiazol-2-ylamino)-phenyl]-isoxazole-5-carbothioyl}-amino)-4-methyl-pentanoic acid;
(S)-2-({3-[4-(6-Fluoro-benzothiazol-2-ylamino)-phenyl]-N-hydroxy-isoxazole-5-carboximidoyl}-amino)-4-methyl-pentanoic acid methyl ester;
(S)-2-({3-[4-(6-Fluoro-benzothiazol-2-ylamino)-phenyl]-N-hydroxy-isoxazole-5-carboximidoyl}-amino)-4-methyl-pentanoic acid;
(S)-({3-[4-(6-Fluoro-benzothiazol-2-ylamino)-phenyl]-isoxazole-5-carbonyl}-amino)-phenyl-acetic acid methyl ester;
(S)-({3-[4-(6-Fluoro-benzothiazol-2-ylamino)-phenyl]-isoxazole-5-carbonyl}-amino)-phenyl-acetic acid;
(S)-({3-[4-(6-Fluoro-benzothiazol-2-ylamino)-phenyl]-isoxazole-5-carbothioyl}amino)-phenyl-acetic acid methyl ester;
(S)-({3-[4-(6-Fluoro-benzothiazol-2-ylamino)-phenyl]-isoxazole-5-carbothioyl}-amino)-phenyl-acetic acid;
(S)-({3-[4-(6-Fluoro-benzothiazol-2-ylamino)-phenyl]-N-hydroxy-isoxazole-5-carboximidoyl}-amino)-phenyl-acetic acid methyl ester;
(S)-({3-[4-(6-Fluoro-benzothiazol-2-ylamino)-phenyl]-N-hydroxy-isoxazole-5-carboximidoyl}-amino)-phenyl-acetic acid;
({3-[4-(6-Fluoro-benzothiazol-2-ylamino)-phenyl]-isoxazole-5-carbonyl}-amino)-acetic acid methyl ester;
({3-[4-(6-Fluoro-benzothiazol-2-ylamino)-phenyl]-isoxazole-5-carbonyl}-amino)-acetic acid;
({3-[4-(6-Fluoro-benzothiazol-2-ylamino)-phenyl]-isoxazole-5-carbothioyl}-amino)-acetic acid methyl ester:
({3-[4-(6-Fluoro-benzothiazol-2-ylamino)-phenyl]-isoxazole-5-carbothioyl}-amino)-acetic acid;
1-({3-[4-(6-Fluoro-benzothiazol-2-ylamino)-phenyl]-isoxazole-5-carbonyl}-amino)-cyclopentanecarboxylic acid methyl ester;
1-({3-[4-(6-Fluoro-benzothiazol-2-ylamino)-phenyl]-isaxazole-5-carbonyl}-amino)-cyclopentanecarboxylic acid;
1-({3-[4-(6-Fluoro-benzothiazol-2-ylamino)-phenyl]-isaxazole-5-carbothioyl}-amino)-cyclopentanecarboxylic acid methyl ester;
1-({3-[4-(6-Fluoro-benzothiazol-2-ylamino)-phenyl]-isoxazole-5-carbothioyl}-amino)-cyclopentanecarboxylic acid;
1-({3-[4-(6-Fluoro-benzothiazol-2-ylamino)-phenyl]-N-hydroxy-isoxazole-5-carboximidoyl}-amino)-cyclopentanecarboxylic acid;
7-{3-[4-(6-Fluoro-benzothiazol-2-ylamino)-phenyl]-isoxazole-5-yl}-9-oxa-6,8-diaza-spiro[4,5]dec-7-en-10-one;
(S)-2-({3-[4-(6-Fluoro-benzothiazol-2-ylamino)-phenyl]-5-phenyl-isoxazole-4-carbonyl}-amino)-3-methyl-butyric acid methyl ester;
(S)-2-({3-[4-(6-Fluoro-benzothiazol-2-ylamino)-phenyl]-5-phenyl-isaxazole-4-carbonyl}-amino)-3-methyl-butyric acid;
(S)-2-({3-[4-(6-Fluoro-benzothiazol-2-ylamino)-phenyl]-5-phenyl-isoxazole-4-carbonyl}-amino)-3-methoxy-propionic acid methyl ester;
(S)-2-({3-[4-(6-Fluoro-benzothiazol-2-ylamino)-phenyl]-5-phenyl-isoxazole-4-carbonyl}-amino)-3-methoxy-propionic acid;
(S)-2-({3-[4-(6-Fluoro-benzothiazol-2-ylamino)-phenyl]-5-phenyl-isoxazole-4-carbothioyl}-amino)-3-methyl-butyric acid methyl ester;
(S)-2-({3-[4-(6-Fluoro-benzothiazol-2-ylamino)-phenyl]-5-phenyl-isoxazole-4-carbothioyl}-amino)-3-methyl-butyric acid;
(S)-2-({3-[4-(6-Fluoro-benzothiazol-2-ylamino)-phenyl]-5-phenyl-isoxazole-4-carbothioyl}-amino)-3-methoxy-propionic acid methyl ester;
(S)-2-({3-[4-(6-Fluoro-benzothiazol-2-ylamino)-phenyl]-5-phenyl-isoxazole-4-carbothioyl}-amino)-3-methoxy-propionic acid;
(S)-3-Methyl-2-({3-[4-(3-phenyl-ureido)-phenyl]-isoxazole-5-carbonyl}-amino)-butyric acid methyl ester;
(S)-3-Methyl-2-({3[4-(3-phenyl-ureido)-phenyl]-isoxazole-5-carbonyl}-amino)-butyric acid;
(S)-3-Methyl-2-({3-[4-(3-phenyl-ureido)-phenyl]-isoxazole-5-carbonyl}-amino)-pentanoic acid methyl ester;
(S)-3-Methyl-2-({3-[4-(3-phenyl-ureido)-phenyl]-isoxazole-5-carbonyl}-amino)-pentanoic acid;
(S)-2-({3-[4-(3-cyclohexyl-ureido)-phenyl]-isoxazole-5-carbonyl}-amino)-3-methyl-butyric acid methyl ester;
(S)-2-({3-[4-(3-cyclohexyl-ureido)-phenyl]-isoxazole-5-carbonyl}-amino-3-methyl-butyric acid;
(S)-2-({3-[4-(3-cyclohexyl-ureido)-phenyl]-isoxazole-5-carbonyl}amino)-4-methyl-pentanoic acid methyl ester;
(S)-2-({3-[4-(3-cyclohexyl-ureido)-phenyl]-isoxazole-5-carbonyl}-amino)-4-methyl-pentanoic acid;
(S)-2-[(3-{4-[3-(4-Fluoro-phenyl)-ureido]-phenyl}-isoxazole-5-carbonyl}-amino]-3-methyl-butyric acid methyl ester:
(S)-2-[(3-{4-[3-(4-Fluoro-phenyl)-ureido]-phenyl}-isoxazole-5-carbonyl)-amino]-3-methyl-butyric acid;
(S)-2-[3-{4-[3-(4-Fluoro-phenyl)-ureido]-phenyl}-isoxazole-5-carbonyl)-amino]-4-methyl-pentanoic acid methyl ester;
(S)-2-[(3-{4-[3-(4-Fluoro-phenyl)-ureido]-phenyl}-isoxazole-5-carbonyl)-amino]-4-methyl-pentanoic acid;
(S)-3-Methyl-2-({4-phenyl-3-[4-(3-phenyl-ureido)-phenyl]-isoxazole-5-carbonyl}-amino)-butyric acid methyl ester;
(S)-3-Methyl-2-({4-phenyl-3-[4-(3-phenyl-ureido)-phenyl]-isoxazole-5-carbonyl}-amino)-butyric acid;
(S)-4-Methyl-2-({4-phenyl-3-[4-(3-phenyl-ureido)-phenyl]-isoxazole-5-carbonyl}-amino)-pentanoic acid methyl ester;
(S)-4-Methyl-2-({4-phenyl-3-[4-(3-phenyl-ureido)-phenyl]-isoxazole-5-carbonyl}-amino)-pentanoic acid;
(S)-2-[(3-{4-[3-(4-Fluoro-phenyl)-ureido]-phenyl}-4-phenyl-isoxazole-5-carbonyl)-amino]-3-methyl-butyric acid methyl ester;

(S)-2-[(3-{4-[3-(4-Fluoro-phenyl)-ureido]-phenyl}-4-phenyl-isoxazole-5-carbonyl)-amino]-3-methyl-butyric acid;
(S)-2-({3-[4-(6-Fluoro-benzothiazol-2-ylamino)-phenyl]-4-phenyl-isoxazole-5-carbonyl}-amino)-4-methyl-pentanoic acid methyl ester;
(S)-2-({3-[4-(6-Fluoro-benzothiazol-2-ylamino)-phenyl]-4-phenyl-isoxazole-5-carbonyl}-amino)-4-methyl-pentanoic acid;
(S)-2-[3-{3-Fluoro-4-[3-(4-fluoro-phenyl)-ureido]-phenyl}-isoxazole-5-carbonyl)-amino]-3-methyl-butyric acid methyl ester;
(S)-2-[3-{3-Fluoro-4-[3-(4-fluoro-phenyl)-ureido]-phenyl}-isoxazole-5-carbonyl)-amino]-3-methyl-butyric acid;
2-(3-(4-(3(2,6-Difluorophenyl)ureido)-3-methylphenyl)isoxazole-5-carboxamido)-3-methylbutanoic acid:
Methyl 2-(3(4-(3-(2,6-difluorophenyl)ureido)-3-methylphenyl)isoxazole-5-carboxamido)-4-methylpentanoate;
2-(3-(4-(3-(2,6-Difluorophenyl)ureido)-3-methylphenyl)isoxazole-5-carboxamido)-4-methylpentanoic acid;
Methyl 2-(3-(4-(3-(2,6-dfluorophenyl)ureido)-3-methylphenyl)isoxazole-5-carboxamido)propanoate;
2-(3-(4-(3-(2,6-Difluorophenyl)ureido)-3-methylphenyl)isoxazole-5-carboxamido)propanoic acid:
2-(3-(4-(3-(2,4-Difluorophenyl)ureido)-3-methylphenyl)isoxazole-5-carboxamido)-3-methylbutanoic acid; and
2-[(3-{4-[3-(2-Fluoro-phenyl)ureido]-phenyl}-isoxazole-5-carbonyl)-amino]-3-methyl-butyric acid methyl ester:
2-(3-(4-(3-(2-Fluorophenyl)ureido)phenyl)isoxazole-5-carboxamido)-3-methylbutanoic acid;
Methyl 2-(3-(4-(3-benzylureido)phenyl)isoxazole-5-carboxamido)-3-methylbutanoate;
2-(3-(4-(3-Benzylureido)phenyl)isoxazole-5-carboxamido)-3-methylbutanoic acid:
Methyl 2-(3-(4-(3-benzylureido)phenyl)isoxazole-5-carboxamido)-4-methylpentanoate;
2-(3-(4-(3-Benzylureido)phenyl)isoxazole-5-carboxamido)-4-methyl pentanoic acid;
Methyl 2-(3-(4-(3-(2,4-difluorophenyl)ureido)phenyl)isoxazole-5-carboxamido)-3-methylbutanoate;
2-(3-(3-(2,4-Difluorophenyl)ureido)phenyl)isoxazole-5-carboxamido)-3-methylbutanoic acid;
Methyl 2-(3-(4-(3-(2,4-difluorophenyl)ureido)phenyl)isoxazole-5-carboxamido)-4-methylpentanoate;
2-(3-(4-(3-(2,4-Difluorophenyl)ureido)phenyl)isoxazole-5-carboxamido)-4-methylpentanoic acid;
Methyl 2-(3-(4-(3-(4-fluorophenyl)ureido)phenyl)isoxazole-5-carboxamido)propanoate;
2-(3-(4-(3-(4-Fluorophenyl)ureido)phenyl)isoxazole-5-carboxamido)propanoic acid ;
Methyl 2-(3-(4-(3-(4-fluorophenyl)ureido)phenyl)isoxazole-5-carboxamido)-2-methylpropanoate;
2-(3-(4-(3-(4-fluorophenyl)ureido)phenyl)isoxazole-5-carboxamido)-2-methylpropnoic acid;
Methyl 1-(3-(4-(3-(4-fluorophenyl)ureido)phenyl)isoxazole-5-carboxamido)cyclopentanecarboxylate;
1-(3-(4-(3-(4-Fluorophenyl)ureido)phenyl)isoxazole-5-carboxamido)cyelopentanecarboxylic acid:
Methyl 2-methyl-2-(3-(4-(3-phenylureido)phenyl)isoxazole-5-carboxamido)propanoate;
2-methyl-2-(3-(4-(3-phenylureido)phenyl)isoxazole-5-carboxamido) propanoic acid;
Methyl 2-(3-(4-(3-(2,6-difluorophenyl)ureido)phenyl)isoxazole-5-carboxamido)-3-methylbutanoate;
2-(3-(4-(3-(2,6-difluorophenyl)ureido)phenyl)isoxazole-5-carboxamido 3-methylbutanoic acid;
Methyl 3-methyl-2-(3-(4-(3-p-tolylureido)phenyl)isoxazole-5-carboxamido)butanoate;
3-Methyl-2-(3-(4-(3-p-tolylureido)phenyl)isoxazole-5-carboxamido)butanoic acid;
Methyl 2-(3-(4-(3-(4-methoxyphenyl)ureido)phenyl)isoxazole-5-carboxamido)-3-methylbutanoate;
2-(3-(4-(3-(4-methoxyphenyl)ureido)phenyl)isoxazole-5-carboxamido)-3-methylbutanoic acid;
(S)-methyl 2-(3-(4-(3-(3,4-difluorophenyl)ureido)phenyl)isoxazole-5-carboxamido)-3-methylbutanoate;
(S)-2-(3-(4-(3-(3,4-difluorophenyl)ureido)phenyl)isoxazole-5-carboxamido)-3-methylbutanoic acid;
Methyl 2-(3-(5-(3-(4-fluorophenyl)ureido)-2-methylphenyl)isoxazole-5-carboxamido)-4-methylpentanoate;
2-(3-(5-(3-(4-fluorophenyl)ureido)-2-methylphenyl)isoxazole-5-carboxamido)-4-methylpentanoic acid;
Methyl 2-(3-(4-(3-(4-fluorophenyl)ureido)-2-methylphenyl)isoxazole-5-carboxamido)-3-methylbutanoate;
2-(3-(4-(3-(4-fluorophenyl)ureido)-2-methylphenyl)isoxazote-5-carboxamido)-3-methylbutanoic acid;
Methyl 2-(3-(4-(3-(2-fluorophenyl)ureido)-2-methylphenyl)isoxazole-5-carboxamido)-3-methylbutanoate;
2-(3-(4-(3-(2-Fluorophenyl)ureido)-2-methylphenyl)isoxazole-5-carboxamido)-3-methylbutanoic acid;
Methyl 2-(3-(4-(3-(2,4-difluorophenyl)ureido)-2-methylphenyl)isoxazole-5-carboxamido)-3-methylbutanoate;
2-(3-(4-(3-(2,4-difluorophenyl)ureido)-2-methylphenyl)isoxazole-5-carboxamido)-3-methylbutanoic acid;
Methyl 2-(3-(4-(3-(2,4-difluorophenyl)ureido)-2-methylphenyl)isoxazole-5-carboxamido)-4-methylpentanoate;
2-(3-(4-(3-(2,4-difluorophenyl)ureido)-2-methylphenyl)isoxazole-5-carboxamido)-4-methylpentanoic acid;
(S)-Methyl 2-(3-(4-(3-(2,4-Difluorophenyl)ureido)-2-fluorophenyl)isoxazole-5-carboxamido)-3-methylbutanoate;
(S)-2-(3-(4-(3-(2,4-difluorophenyl)ureido)-2-fluorophenyl)isoxazole-5-carboxamido)-3-methylbutanoic acid;
(S)-methyl 2-(3-(2-fluoro-4-(3-(2-fluorophenyl)ureido)phenyl)isoxazole-5-carboxamido)-3-methylbutanoate;
(S)-2-(3-(2-Fluoro-4-(3-(2-fluorophenyl)ureido)phenyl)isoxazole-5-carboxamido)-3-methylbutanoic acid;
(S)-Methyl 2-(3-(2-fluoro-4-(3-(4-fluorophenyl)ureido)phenyl)isoxazole-5-carboxamido)-3-methylbutanoate;
(S)-2-(3-(2-fluoro-4-(3-(4-fluorophenyl)ureido)phenyl)isoxazole-5-carboxamido)-3-methylbutanoic acid;
Methyl 2-(3-(3-fluoro-4-(3-(2-fluorophenyl)ureido)phenyl)isoxazole-5-carboxamido)-3-methylbutanoate;
2-(3-(3-fluoro-4-(3-(2-fluorophenyl)ureido)phenyl)isoxazole-5-carboxamido)-3-methylbutanoic acid;
Methyl 2-(3-(4-(3-(2,4-difluorophenyl)ureido)-3-fluorophenyl)isoxazole-5-carboxamido)-3-ethylbutanoate;
2-(3-(4-(3-(2,4-Difluorophenyl)ureido) 3 fluorophenyl) isoxazole 5 -carboxamido)-3-methylbutanoic acid:
Methyl 2-(3-(4-(3-(3-fluorophenyl)ureido)phenyl)isoxazole-5-carboxamido)-3-methylbutanoate;
2-(3-(4-(3-(3-fluorophenyl)ureido)phenyl)isoxazole-5-carboxamido)-3-methylbutanoic acid;
Methyl 3-methyl-2-(3-(4-(3-o-tolylureido)phenyl)isoxazole-5-carboxamido)butanoate;
3-methyl-2-(3-(4-(3-o-tolylureido)phenyl)isoxazole-5-carboxamido)butanoic acid;
Methyl 2-(3-(4-(3-(2-fluoro-5-methylphenyl)ureido)phenyl)isoxazole-5-carboxamido)-3-methylbutanoate;

2-(3-(4-(3-(2-fluoro-5-methylphenyl)ureido)phenyl)isoxazole-5-carboxamido)-3-methylbutanoic acid;
Methyl 2-(3-(4-(3-(4-butylphenyl)ureido)phenyl)isoxazole-5-carboxamido)-3-methylbutanoate;
2-(3-(4-(3-(4-butylphenyl)ureido)phenyl)isoxazole-5-carboxamido)-3-methylbutanoic acid;
Methyl 2-(3-(4-(3-(3,5-difluorophenyl)ureido)phenyl)isoxazole-5-carboxamido)-3-methylbutanoate;
2-(3-(4-(3 (3,5-difluorophenyl)ureido)phenyl)isoxazole-5-carboxamido)-3-methylbutanoic acid:
Methyl 2-(3-(4-(3-(3-chloro-4-fluorophenyl)ureido)phenyl)isoxazole-5-carboxamido)-3-methylbutanoate;
2-(3-(4-(3-(3-chloro-4-fluorophenyl)ureido)phenyl)isoxazole-5-carboxamido)-3-methylbutanoic acid:
(S)-methyl 3-methyl-2-(3-(4-(3-(2-(trifluoromethyl)phenyl)ureido)phenyl)isoxazole-5-carboxamido)butanoate;
(S)-3-methyl-2-(3-(4-(3-(2-(trifluoromethyl)ureido)phenyl)isoxazole-5-carboxamido)butanoic acid;
(S)-Methyl 2-(3-(4-(3-(2,5-dimethoxyphenyl)ureido)phenyl)isoxazole-5-carboxamido)-3-methylbutanoate;
(S)-2-(3-(4-(3-(2,5-Dimethoxyphenyl)ureido)phenyl)isoxazole-5-carboxamido)-3-methylbutanoic acid;
(S)-2-(3-(4-(3-(3,5-difluorophenyl)ureido)phenyl)isoxazole-5-carboxamido)-3-methylbutanoic acid;
(S)-methyl 2-(3-(4-(3-(2,4-dimethoxyphenyl)ureido)phenyl)isoxazole-5-carboxamido)-3-methylbutanoate;
(S)-2-(3-(4-(3-(2,4-dimethoxyphenyl)ureido)phenyl)isoxazole-5-carboxamido)-3-methylbutanoic acid;
(S)-methyl 2-(3-(4-(3-(2,4-dimethylphenyl)ureido)phenyl)isoxazole-5-carboxamido)-3-methylbutanoate;
(S)-2-(3-(4-(3-(2,4-dimethylphenyl)ureido)phenyl)isoxazole-5-carboxamido)-3-methylbutanoic acid;
(S)-methyl 2-(3-(4-(3-(3,4-dimethylphenyl)ureido)phenyl)isoxazole-5-carboxamido)-3-methylbutanoate;
(S)-2-(3-(4-(3-(3,4-dimethylphenyl)ureido)phenyl)isoxazole-5-carboxamido)-3-methylbutanoic acid:
(S)-Methyl 2-(3-(4-(3-(2-chloro-6-methylphenyl)ureido)phenyl)isoxazole-5-carboxamido)-3-methylbutanoate;
(S)-2-(3-(4-(3-(2-Chloro-6-methylphenyl)ureido)phenyl)isoxazole-5-carboxamido)-3-methylbutanoic acid;
(S)-Methyl 2-(3-(4-(3-benzo[d][1,3]dioxol-5-ylureido)phenyl)isoxazole-5-carboxamido)-3-methylbutanoate;
(S)-2-(3-(4-(3-benzo[d][1.3]dioxol-5-ylureido)phenyl)isoxazole-5-carboxamido)-3-methylbutanoic acid;
(S)-methyl 2-(3-(4-(3-(4-chlorophenyl)ureido)phenyl)isoxazole-5-carboxamido)-3-methylbutanoate;
(S)-2-(3-(4-(3-(4-Chlorophenyl)ureido)phenyl)isoxazole-5-carboxamido)-3-methylbutanoic acid;
(S)-methyl 2-(3-(4-(3-(2,3-dihydro-1H-inden-5-yl)ureido)phenyl)isoxazole-5-carboxamido)-3-methylbutanoate;
(S)-2-(3-(4-(3-(2,3-dihydro-1H-inden-5-yl)ureido)phenyl)isoxazole-5-carboxamido)-3-methylbutanoic acid;
(S)-methyl 2-(3-(4-(3-(3-chloro-2-fluorophenyl)ureido)phenyl)isoxazole-5-carboxamido)-3-methylbutanoate;
(S)-2-(3-(4-(3-(3-chloro-2-fluorophenyl)ureido)phenyl)isoxazole-5-carboxamido)-3-methylbutanoic acid;
(S)-methyl 2-(3-(4-(3-(2-methoxyphenyl)ureido)phenyl)isoxazole-5-carboxamido)-3-methylbutanoate;
(S)-2-(3-(4-(3-(2-methoxyphenyl)ureido)phenyl)isoxazole-5-carboxamido)-3-methylbutanoic acid;
(S)-methyl 3-methyl-2-(3-(4-(3-(4-(trifluoromethoxy)phenyl)ureido)phenyl)isoxazole-5-carboxamido)butanoate;
(S)-3-methyl-2-(3-(4-(3-(4-trifluoromethoxy)phenyl)ureido)phenyl)isoxazole-5-carboxamido)butanoic acid;
(S)-methyl 2-(3-(4-(3-(2-chloro-5-methylphenyl)ureido)phenyl)isoxazole-5-carboxamido)-3-methylbutanoate;
(S)-2-(3-(4-(3-(2-chloro-5-methylphenyl)ureido)phenyl)isoxazole-5-carboxamido)-3-methylbutanoic acid;
(S)-Methyl 3-methyl-2-(3-(4-(3-(2,3,4-trifluorophenyl)ureido)pbenyl)isoxazole-5-carboxamido)butanoate;
(S)-3-Methyl-2-(3-(4-(3-(2,3,4-trifluorophenyl)ureido)phenyl)isoxazole-5-carboxamido)butanoic acid;
(S)-methyl 2-(3-(4-(3-(4-chloro-2-fluorophenyl)ureido)phenyl)isoxazole-5-carboxamido)-3-methylbutanoate;
(S)-2-(3-(4-(3-(4-chloro-2-fluorophenyl)ureido)phenyl)isoxazole-5-carboxamido)-3-methylbutanoic acid;
(S)-methyl 2-(3-(4-(3-(5-chloro-2-methylphenyl)ureido)phenyl)isoxazole-5-carboxamido)-3-methylbutanoate;
(S)-2-(3-(4-(3-(5-chloro-2-methylphenyl)ureido)phenyl)isoxazole-5-carboxamido)-3-methylbutanoic acid;
(S)-Methyl 3-methyl-2-(3-(4-(3-(4-(methylthio)phenyl)ureido)phenyl)isoxazole-5-carboxamido)butanoate;
(S)-3-methyl-2-(3-(4-(3-(4-(methylthio)phenyl)ureido)phenyl)isoxazole-5-carboxamido)butanoic acid;
(S)-methyl 2-(3 -(4(3 -(2,5 -difluorophenyl)ureido)phenyl)isoxazole-5-carboxamido)-3-methylbutanoate;
(S)-2-(3-(4-(3-(2,5-difluorophenyl)ureido)phenyl)isoxazole-5-carboxamido)-3-methylbutanoic acid;
(S)-methyl 2-(3-(4-(3-(4-chloro-2-phenoxyphenyl)ureido)phenyl)isoxazole-5-carboxamido)-3-methylbutanoate;
(S)-2-(3-(4-(3-(4-chloro-2-phenoxyphenyl)ureido)phenyl)isoxazole-5-carboxamido)-3-methylbutanoic acid;
(S)-methyl 3-methyl-2-(3-(4-(3-(2-(trifluoromethoxy)phenyl)ureido)phenyl)isoxazole-5-carboxamido)butanoate;
(S)-3-methyl-2-(3-(4-(3-(2-(trifluoromethoxy)phenyl)ureido)phenyl)isoxazole-5-carboxamido)butanoic acid;
(S)-methyl 2-(3-(4-(3-(3,5-dimethylphenyl)ureido)phenyl)isoxazole-5-carboxamido)-3-methylbutanoate;
(S)-2-(3-(4-(3-(3,5-dimethylphenyl)ureido)phenyl)isoxazole-5-carboxamido)-3-methylbutanoic acid;
(S)-methyl 2-(3-(4-(3-(6-chloropyridin-3-yl)ureido)phenyl)isoxazole-5-carboxamido)-3-methylbutanoate;
(S)-2-(3-(4-(3-(6-chloropyridin-3-yl)ureido)phenyl)isoxazole-5-carboxamido)-3-methylbutanoic acid;
(S)-methyl 2-(3-(4-(3-(3-chlorophenyl)ureido)phenyl)isoxazole-5-carboxamido)-3-methylbutanoate;
(S)-2-(3-(4-(3-(3-chlorphenyl)ureido)phenyl)isoxazole-5-carboxamido)-3-methylbutanoic acid;
(S)-methyl 2-(3-(4-(3-(2-chloro-5-(trifluoromethyl)phenyl)ureido)phenyl)isoxazole-5-carboxamido)-3-methylbutanoate;
(S)-2-(3-(4-(3-(2-chloro-5-(trifluoromethyl)phenyl)ureido)phenyl)isoxazole-5-carboxamido)-3-methylbutanoic acid;
(S)-Methyl 2-(3-(4-(3-(4-fluoro-2-(trifluoromethyl)phenyl)ureido)phenyl)isoxazole-5-carboxamido)-3-methylbutanoate;
(S)-2-(3-(4-(3-(4-fluoro-2-(trifluoromethyl)phenyl)ureido)phenyl)isoxazole-5-carboxamido)-3-methylbutanoic acid;
(S)-methyl 2-(3-(4-(3-(4-chloro-2-(trifluoromethyl)phenyl)ureido)phenyl)isoxazole-5-carboxamido)-3-methylbutanoate;
(S)-2-(3-(4-(3-(4-chloro-2-(trifluoromethyl)phenyl)ureido)phenyl)isoxazole-5-carboxamido)-3-methylbutanoic acid;
(R)-methyl 2-(3-(4-(3-(2-cyanophenyl)ureido)phenyl)isoxazole-5-carboxamido)-3-methylbutanoate;

(R)-2-(3-(4-(3-(3-cyanophenyl)ureido)phenyl)isoxazole-5-carboxamido)-3-methylbutanoic acid;
(R)-methyl 2-(3-(4-(3-(4-cyanophenyl)ureido)phenyl)isoxazole-5-carboxamido)-3-methylbutanoate;
(R)-2-(3-(4-(3-(4-Cyanophenyl)ureido)phenyl)isoxazole-5-carboxamido-3-methylbutanoic acid;
(R)-Methyl 2-(3-(4-(3-(2-chlorophenyl)ureido)phenyl)isoxazole-5-carboxamido)-3-methylbutanoate;
(R)-2-(3-(4-(3-(2-Chlorophenyl)ureido)phenyl)isoxazole-5-carboxamido)-3-methylbutanoic acid;
(R)-Methyl 2-(3-(4-(3-(2-fluorophenyl)ureido)phenyl)isoxazole-5-carbothioamido)-3-methylbutanoate;
(R)-Methyl 3-methyl-2-(3-(4-(3-p-tolylureido)phenyl)isoxazole-5-carbothioamido) butanoate;
(R,Z)-Methyl 2-(ethylthio(3-(4-(3-(2-fluorophenyl)ureido)phenyl)isoxazol-5-yl)methyleneamino)-3-methylbutanoate;
(R,Z)-Methyl 2-(ethylthio(3-(4-(3-p-tolylureido)phenyl)isoxazol-5- methyleneamimo)-3-methylbutanoate;
(R,E)-2-(3-(4-(3-(2-Fluorophenyl)ureido)phenyl)-N'-hydroxyisoxazole-5-caboximidamido)-3-methylbutanoic acid;
(S)-Methyl 2-(3-(4-(3-(4-isopropylphenyl)ureido)phenyl)isoxazole-5-carboxamide)-3-methylbutanoate;
(S)-2-(3-(4-(3-(4-Isopropylphenyl)ureido)phenyl)isoxazole-5-carboxamido)-3-methylbutanoic acid;
(S)-Methyl 2-(3-(4-(3-(2-fluoro-6-(trifluoromethyl)phenyl)ureido)phenyl)isoxazole-5-carboxamido)-3-methylbutanoate;
(S)-2-(3-(4-(3-(2-Fluoro-6-(trifluoromethyl)phenyl)ureido)phenyl)ismazole-5-carboxamido)-3-methylbutanoic acid;
(S)-Methyl 2-(3-(4-(3-(2-chloro-4-(trifluoromethyl)phenyl)ureido)phenyl)isoxazole-5-carboxamido)-3-methylbutanoate;
(S)-2-(3-(4-(3-(2-Chloro-4-(trifluoromethyl)phenyl)ureido)phenyl)isoxazole-5-carboxamido)-3-methylbutanoic acid;
(S)-Methyl 2-(3-(4-(3-(2-chloro-6-(trifluoromethyl)phenyl)ureido)phenyl)isoxazole-5-carboxamido)-3-methylbutanoate;
(S)-2-(3-(4-(3-(2-Chloro-6-(trifluoromethyl)phenyl)ureido)phenyl)isoxazole-5-carboxamido)-3-methylbutanoic acid;
(S)-Methyl 2-(3-(4-(3-(5-chloro-2-phenoxyphenyl)ureido)phenyl)isoxazole-5-carboxamido)-3-methylbutanoate;
(S)-2-(3-(4-(3-(5-Chloro-2-phenoxyphenyl)ureido)phenyl)isoxazole-5-carboxamido)-3-methylbutanoic acid;
(S)-Methyl 3-methyl-2-(3-(4-(3-(2-phenoxyphenyl)ureido)phenyl)isoxazole-5-carboxamido)butanoate;
(S)-3-Methyl-2-(3-(4-(3-(2-phenoxyphenyl)ureido)phenyl)isoxazole-5-carboxamido)butanoic acid;
(S)-Methyl 3-methyl-2-(3-(4-(3(4-phenoxyphenyl)ureido)phenyl)isoxazole-5-carboxamido)butanoate;
(S)-3-Methyl-2-(3-(4-(3-(4-phenoxyphenyl)ureido)phenyl)isoxazole-5-carboxamido)butanoic acid;
Methyl 2-(3-(3-(4-(3-(2-fluorophenyl)ureido)phenyl)isoxazole-5-carboxamido)-3-phenyl propanoate;
2-(3-(4-(3-(2-Fluorophenyl)ureido)phenyl)isoxazole-5-carboxamido)-3-phenylpropanoic acid;
Methyl 3-phenyl-2-(3-(4-(3-p-tolylureido)phenyl)isoxazole-5-carboxamido)propanoate;
3-Phenyl-2-(3-(4-(3-p-tolylureido)phenyl)isoxazole-5-carboxamido)propanoic acid;
Methyl 2-(3-(4-(3-(2,4-difluorophenyl)ureido)phenyl)isoxazole-5-carboxamido)-3-phenylpropanoate;
2-(3-(4-(3-(2,4-Difluorophenyl)ureido)phenyl)isoxazole-5-carboxamido)-3-phenylpropanoic acid;
Methyl 2-(3-(4-(3-(3-chloro4-methylphenyl)ureido)phenyl)isoxazole-5-carboxamido)-3-methylbutanoate;
2-(3-(4-(3-(3-Chloro-4-methylphenyl)ureido)phenyl)isoxazole-5-carboxamido)-3-methylbutanoic acid;
Ethyl 2-(3-(4-(3-(3-fluoro-4-methylphenyl)ureido)phenyl)isoxazole-5-carboxamido-3-methylbutanoate;
2-(3-(4-(3-(3-Fluoro-4-methylphenyl)ureido)phenyl)pisoxazole-5-carboxamido)-3-methylbutanoic acid;
Methyl 2-(3-(4-(3-(5-fluoro-2-methylphenyl)ureido)phenyl)isoxazole-5-carboxamido)-3-methylbutanoate;
2-(3-(4-(3-(5-Fluoro-2-methylphenyl)ureido)phenyl)isoxazole-5-carboxamido)-3-methylbutanoic acid;
Methyl 4-(3-(4-(3-(2-fluorophenyl)ureido)phenyl)isoxazole-5-carboxamido)butanoate;
4-(3-(4-(3-(2-Fluorophenyl)ureido)phenyl)isoxazole-5-carboxamido)butanoic acid;
Methyl 4-(3-(4-(3-p-tolylureido)phenyl)isoxazole-5-carboxamido)butanoate;
4-(3-(4-(3-p-Tolylureido)phenyl)isoxazole-5-carboxamido)butanoic acid;
(R)-Methyl 2-(3-(4-(3-(2-fluorophenyl)ureido)phenyl)isoxazole-5-carboxamido)-3-methylbutanoate;
(R)-2-(3-(4-(3-(2-Fluorophenyl)ureido)phenyl)isoxazole-5-carboxamido)-3-methylbutanoic acid;
(R)-Methyl 1-(3-(4-(3-(2-fluorophenyl)ureido)phenyl)isoxazole-5-carbonyl)pyrrolidine-2-carboxylate;
(R)-1-(3-(4-(3-(2-Fluorophenyl)ureido)phenyl)isoxazole-5-carbonyl)pyrrolidine-2-carboxylic acid;
(S)-Methyl 1-(3-(4-(3-(2-fluorophenyl)ureido)phenyl)isoxazole-5-carbonyl)pyrrolidine-2-carboxylate;
(S)-1-(3-(4-(3-(2-Fluorophenyl)ureido)phenyl)isoxazole-5-carbonyl)pyrrolidine-2-carboxylic acid;
Methyl 3-methyl-2-(3-(4-(3-(o-tolylsultbnyl)ureido)phenyl)isoxazole-5-carboxamido)butanoate;
3-Methyl-2-(3-(4-(3-(o-tolylsulfonyl)ureido)phenyl)isoxazole-5-carboxamido)butanoic acid;
(S)-Methyl 3-methyl-2-(3-(4-(3-m-tolylureido)phenyl)isoxazole-5-carboxamido)butanoate;
(S)-3-Methyl-2-(3-(4-(3-m-tolylureido)phenyl)isoxazole-5-carboxamido)butanoic acid;
(S)-methyl 2-(3-(4-(3-(3-fluorophenyl)thioureido)phenyl)isoxazole-5-carboxamido)-3-methylbutanoate;
(S)-2-(3-(4-(3-(3-Fluorophenyl)thioureido)phenyl)isoxazole-5-carboxamido)-3-methylbutanoic acid;
(S)-Methyl 2-(3-(4-(3-(2-fluorophenyl)thioureido)phenyl)isoxazole-5-carboxamido)-3-methylbutanoate;
(S)-2-(3-(4-(3-(2-Fluorophenyl)thioureido)phenyl)isoxazole-5-carboxamido)-3-methylbutanoic acid;
(S)-Methyl 3-methyl-2-(3-(4-(3-p-tolylthioureido)phenyl)isoxazole-5-carboxamido)butanoate;
(S)-Methyl 3-(4-hydroxyphenyl)-2-(3-(4-(3-p-tolylureido)phenyl)isoxazole-5-carboxamido)propanoate;
(S)-3-(4-Hydroxyphenyl)-2-(3-(4-(3-p-tolylureido)phenyl)isoxazole-5-carboxamido)propanoic acid;
(S)-Methyl 2-(3-(4-(3-(2-fluorophenyl)ureido)phenyl)isoxazole-5-carboxamido)-3-(4-hydroxyphenyl)propanoate;
Methyl 3-methyl-2-(3-(4-(3-(4-(trifluoromethyl)phenyl)ureido)phenyl)isoxazole-5-carboxamido)butanoate;
3-Methyl-2-(3-(4-(3-(4-(trifluoromethyl)phenyl)ureido)phenyl)isoxazole-5-carboxamido)butanoie acid;
Methyl 3-methyl-2-(3-(4-(3-(3-(trifluoromethyl)phenyl)ureido)phenyl)isoxazole-5-carboxamido)butanoate;
3-Methyl-2-(3-(4-(3-(3-(trifluoromethyl)phenyl)ureido)phenyl)isaxazole-5-carboxamido)butanoic acid;

Methyl 3-methyl-2-(3-(4-(3-pyridin-2-ylureido)phenyl)isoxazole-5-carboxamido)butanoate;
3-methyl-2-(3-(4-(3-pyridin-2-ylureido)phenyl)isoxazole-5-carboxamido)butanoic acid;
2-({3-[4-(3-{4-[5-(1-Methoxycarbonyl-2-methy-propyl-carbamoyl)-isoxazol-3-yl]-phenyl}-ureido)-phenyl]-isoxazol-5-carbonyl}-amino)-3-methyl-butyric acid methyl ester;
2-({3-[4-(3-{4-[5-(1-Carboxy-2-methyl-propylcarbamoyl)-isoxazol-3-yl]-phenyl}-ureido)-phenyl]-isoxazol-5-carbonyl}-amino)-3-methyl-butyric acid;
Methyl 4-(3-(4-(5-(1-methoxy-3-methyl-1-oxobutan-2-ylcarbamoyl)isoxazol-3-yl)phenyl)ureido)benzoate;
Methyl 2-(3-(4-(3-(4-fluoro-2-methylphenyl)ureido)phenyl)isoxazole-5-carboxamido)-3-methylbutanoate;
2-(3-(4-(3-(4-fluoro-2-methylphenyl)ureido)phenyl)isoxazole-5-carboxamido)-3-methylbutanoic acid;
Methyl 2-(3-(4-(3-(2-chloro-4-(trifluoromehoxy)phenyl)ureido)phenyl)isoxazole-5-carboxamido)-3-methylbutanoate;
2-(3-(4-(3-(2-chloro-4-(trifluoromethoxy)phenyl)ureido)phenyl)isoxazole-5-carboxamido)-3-methylbutanoic acid;
Ethyl 2-(3-(4-(3-(3-chloro-4-(trifluoromethoxy)phenyl)ureido)phenyl)isoxazole-5-carboxamido)-3-methylbutanoate;
(3-(4-(3-(3-chloro-4-(trifluoromethoxy)phenyl)ureido)phenyl)isoxazole-5-carboxamido)-3-methylbutanoic acid;
Methyl 2-(3-(4-(3-biphenyl-2-ylureido)phenyl)isoxazole-5-carboxamido)-3-methylbutanoate;
2-(3-(4-(3-biphenyl-2-ylureido)phenyl)isoxazole-5-carboxamido)-3-methylbutanoic acid;
Methyl 2-(3-(4-(3-(4-cyclohexylphenyl)ureido)phenyl)isoxazole-5-carboxamido)-3-methylbutanoate;
2-(3-(4-(3-(4-cyclohexylphenyl)ureido)phenyl)isoxazole-5-carboxamido)-3-methylbutanoic acid;
Methyl 3-methyl-2-(3-(4-(3-(2-methyl-4-(trifluoromethoxy)phenyl)ureido)phenyl)isoxazole-5-carboxamido)butanoate;
3-methyl-2-(3-(4-(3-(2-methyl-4-(trifluoromethoxy)phenyl)ureido)phenyl)isoxazole-5-carboxamido)butanoic acid;
Methyl 2-(3-(4-(4-tert-butylbenzamido)phenyl)isoxazole-5-carboxamido)-3-methylbutanoate;
2-(3-(4-(4-tert-butylbenzamido)phenyl)isoxazole-5-carboxamido)-3-methylbutanoic acid;
(S)-Methyl 2-(3-(4-(3-(2-fluorophenyl)ureido)phenyl)isoxazole-5-carbamido)-3-hydroxypropanoate;
(S)-2-(3-(4-(3-(2-Fluorophenyl)ureido)phenyl)isoxazole-5-carboxamido)-3-hydroxypropanoic acid;
(S)-tert-butyl 2-(3-(4-(3-(2-fluorophenyl)ureido)phenyl)isoxazole-5-carboxamido)-3-methylbutanoate;
Methyl 2-(3-(4-(3-(2-fluorophenyl)ureido)phenyl)isoxazole-5-carboxamido)acrylate;
2-(3-(4-(3-(2-Fluorophenyl)ureido)phenyl)isoxazole-5-carboxamido)acrylic acid;
Methyl 2-(3-(4-(3-p-tolylureido)phenyl)isoxazole-5-carboxamido)acrylate;
2-(3-(4-(3-p-tolylureido)phenyl)isoxazole-5-carboxamido)acrylic acid;
(S)-Methyl 2-(3-(4-(3-(2-fluorophenyl)ureido)phenyl)-N-methylisoxazole-5-carboxamido)-3-methylbutanoate;
(S)-2-(3-(4-(3-(2-fluorophenyl)ureido)phenyl)-N-methylisoxazole-5-carboxamido)-3-methylbutanoic acid;
(S)-methyl 2-(3-(4-(3-(4-fluorophenyl)ureido)phenyl)-N-methylisoxazole-5-carboxamido-3-methylbutanoate;
(S)-2-(3-(4-(3-(4-fluorophenyl)ureido)phenyl)-N-methylisoxazole-5-carboxamido)-3-methylbutanoic acid;
(S)-Methyl 3-methyl-2-(N-methyl-3-(4-(3-(3-(trifluoromethyl)phenyl)ureido)phenyl)isoxazole-5-carboxamido)butanoate;
(S)-3-methyl-2-(N-methyl-3-(4-(3-(3-(trifluoromethyl)phenyl)ureido)phenyl)isoxazole-5-carboxamido)butanoic acid;
(S)-methyl 2-(3-(4-(3-cyclohexylureido)phenyl)-N-methylisoxazole-5-carboxamido)-3-methylbutanoate;
(S)-2-(3-(4-(3-cyclohexylureido)phenyl)-N-methylisoxazole-5-carboxamido)-3-methylbutanoic acid;
(S)-methyl 2-(3-(4-(3-(2-chlorophenyl)ureido)phenyl)-N-mcthylisoxazole-5-carboxamido)-3-methylbutanoate;
(S)-2-(3-(4-(3-(2-chlorophenyl)ureido)phenyl)-N-methylisoxazole-5-carboxamido)-3-methylbutanoic acid:
(R)-methyl 2-(3-(4-(2-fluorophenylsulfonamido)phenyl)isoxazole-5-carboxamido)-3-Methylbutanoate;
(R)-Methyl 2-(3-(4-(2,6-difluorophenylsulfonamido)phenyl)isoxazole-5-carboxamido)-3-methylbutanoate;
(R)-Methyl 3-methyl-2-(3-(4-(4-(trifluoromethyl)phenylsulfonamido)phenyl)isoxazole-5-carboxamido)butanoate;
(R)-3-Methyl-2-(3-(4-(4-(trifluoromethyl)phenylsulfonamido)phenyl)isoxazole-5-carboxamido)butanoic acid;
(R)-2-(3 -(4-(2,6-Difluorophenylsulfonamido)phenyl)isoxazole-5-carboxamido)-3-methyibutanoic acid;
(R)-2-(3-(4-(3,5-Difluorophenylsulfonamido)phenyl)isoxazole-5-carboxamido)-3-methylbutanoic acid;
Methyl 2-(3-(4-(benzyloxy)phenyl)isoxazole-5-carboxamido)-3-methylbutanoate;
2-(3-(4-(Benzyloxy)phenyl)isoxazole-5-carboxamido)-3-methylbutanoic acid;
Methyl 2-(3-(4-(4-fluorobenzyloxy)phenyl)isoxazole-5-carboxamido)-3-methylbutanoate;
2-(3-(4-(Benzyloxy)phenyl)isoxazole-5-carboxamido)-3-methylbutanoic acid;
Methyl 3-methyl-2-(3-(4-(3-(trifluoromethyl)benzyloxy)phenyl)isoxazole-5-carboxamido)butanoate;
3-Methyl-2-(3-(4-(3-(trifluoromethyl)benzyloxy)phenyl)isoxazole-5-carboxamido)butanoic acid;
Methyl 3-methyl-2-(3-(4-(4-(trifluoromethyl)benzyloxy)phenyl)isoxazole-5-carboxamido)butanoate;
3-methyl-2-(3-(4-(4-(trifluoromethyl)benzyloxy)phenyl)isoxazole-5-carboxamido)butanoic acid;
Methyl 3-methyl-2-(3-(4-(2-(trifluoromethyl)benzyloxy)phenyl)isoxazole-5-carboxamido)butanoate;
3-methyl-2-(3-(4-(2-(trifluoromethyl)benzyloxy)phenyl)isoxazole-5-carboxamido)butanoic acid;
Methyl 2-(3-(4-(2,4-difluorobenzyloxy)phenyl)isoxazole-5-carboxamido)-3-methylbutanoate;
2-(3-(4-(2,4-Difluorobenzyloxy)phenyl)isoxazole-5-carboxamido)-3-methylbutanoic acid;
Methyl 1-(3-(4-(benzyloxy)phenyl)isoxazole-5-carbonyl)pyrrolidine-2-carboxylate;
Methyl 2-(3-(4-(6-fluorobenzo[d]thiazol-2-yloxy)phenyl)isoxazole-5-carboxamido)-3-methylbutanoate;
2-(3-(4-(6-fluorobenzo[d]thiazol-2-yloxy)phenyl)isoxazole-5-carboxamido)-3-methylbutanoic acid;
Methyl 3-methyl-2-(3-(4-(2-oxo-2-(3-(trifluoromethyl)phenylamino)acetamido)phenyl)isoxazole-5-carboxamido)butanoate;
3-Methyl-2-(3-(4-(2-oxo-2-(3-(trifluoromethyl)phenylamino)acetamido)phenyl)isoxazole-5-carboxamido)butanoic acid;

Methyl 2-(3-(4-(2-(2,4-difluorophenylamino)-2-oxoacetamido)phenyl)isoxazole-5-carboxamido)-3-methylbutanoate;

2-(3-(4-(2-(2,4-difluorophenylamino)-2-oxoacetamido)phenyl)isoxazole-5-carboxamido)-3-methylbutanoic acid;

Methyl 2-(3-(4-((R)-2-hydroxy-2-phenylacetamido)phenyl)isoxazole-5-carboxamido)-3-methylbutanoate;

2-(3-(4-((R)-2-hydroxy-2-phenylacetamido)phenyl)isoxazole-5-carboxamido)-3-methyl butanoic acid; or a stereoisomer, a tautomer or a pharmaceutically acceptable salt thereof.

11. A pharmaceutical composition, comprising a therapeutically effective amount of a compound of formula (I) according to claim 1 or a pharmaceutically acceptable salt thereof, and a pharmaceutically acceptable excipient or carrier.

12. A method for the treatment of diseases mediated by DGAT-1, comprising administering to a mammal in need thereof a therapeutically effective amount of a compound of formula (I) according to claim 1 or a pharmaceutically acceptable salt or a pharmaceutically acceptable solvate thereof.

13. A process for the preparation of a compound of formula (Ivi),

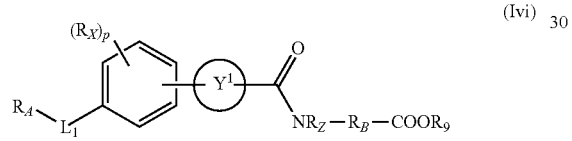

(Ivi)

which comprises,
reacting a compound of formula (Iv)

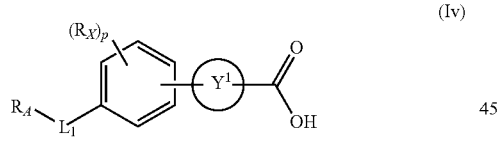

(Iv)

with a compound of formula $R_Z NH-R_B-COOR_9$ in a solvent such as dimethyl formamide and in presence of a base such as triethylamine and a coupling agent such as N-Hydroxybenzotriazole and N,N'-dicyclohexylcarbodiimide, wherein $Y^1$ is selected from

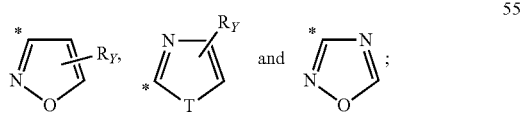

$R_A$, $L_1$, $R_X$, $R_Y$, $R_Z$, $R_B$, $R_9$ and p are as defined for formula (I) according to claims 1, T is —O— or —S— and * indicates point of attachment to phenyl ring;

optionally, converting the resulting compound into a pharmaceutically acceptable salt.

14. A process for the preparation of a compound of formula (Ixix)

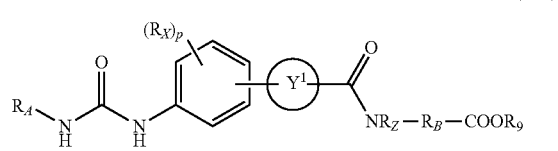

(Ixix)

which comprises
reacting a compound of formula (Ixviii)

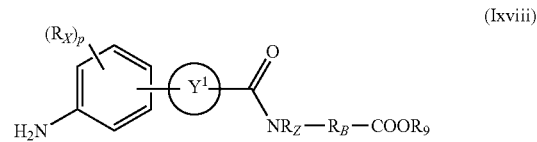

(Ixviii)

with a compound of formula $R_A-N=C=O$ or with a compound of formula $R_A-NH_2$ in presence of a coupling agent such as carbonyl diimidazole, wherein $R_A$, $R_X$, $R_Z$, $R_B$, $R_9$, and p are as defined for formula (I) according to claim 1 and $Y^1$ is selected from

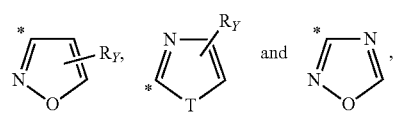

wherein $R_Y$ is as defined for formula (I) in claim 1 and * indicates point of attachment to phenyl ring;

optionally, converting the resulting compound into a pharmaceutically acceptable salt.

15. A process for the preparation of a compound of formula (Iiii)

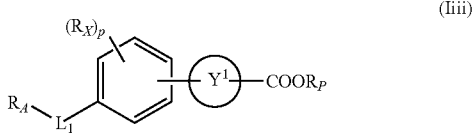

(Iiii)

which comprises,
reacting a compound formula 2a

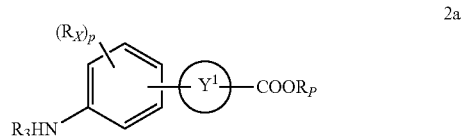

2a i) with a compound of formula $R_A(CR_4R_5)_b$-$L_g$ or ii) by reductive alkylation of a compound of formula (2a) using a compound of formula $R_A(CR_4R_5)_{b-1}$—CHO, wherein $R_A$, $L_1$, $R_X$ and p are as defined for formula (I) according to claim 1; $R_p$ is a suitable protecting group selected from methyl, ethyl, tert-butyl, benzyl, p-methoxybenzyl and $Y^1$ is selected from
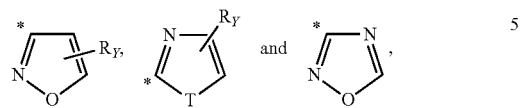
wherein $R_Y$ is as defined for formula (I) in claim 1 and * indicates point of attachment to phenyl ring.
* * * * *